(12) United States Patent
Alves et al.

(10) Patent No.: US 7,636,668 B1
(45) Date of Patent: Dec. 22, 2009

(54) METHOD AND APPARATUS FOR ACCOUNTING AND CONTRACTING FOR CLINICAL TRIAL STUDIES

(75) Inventors: Fernando F. Alves, Philadelphia, PA (US); Ann S. Vurimindi, Philadelphia, PA (US); Ieda A. Mancini, Philadelphia, PA (US); Mirela Meka, Philadelphia, PA (US)

(73) Assignee: Numoda Technologies, Inc., Philadelphia, PA (US)

( * ) Notice: Subject to any disclaimer, the term of this patent is extended or adjusted under 35 U.S.C. 154(b) by 0 days.

(21) Appl. No.: 12/431,508

(22) Filed: Apr. 28, 2009

Related U.S. Application Data

(63) Continuation of application No. 12/165,982, filed on Jul. 1, 2008.

(51) Int. Cl.
*G06Q 50/00* (2006.01)
(52) U.S. Cl. .......................................................... 705/2
(58) Field of Classification Search ...................... 705/2
See application file for complete search history.

(56) References Cited

U.S. PATENT DOCUMENTS

| | | | |
|---|---|---|---|
| 7,054,823 | B1 | 5/2006 | Briegs et al. |
| 7,401,028 | B2 * | 7/2008 | Deakter .......................... 705/3 |
| 2005/0010451 | A1 | 1/2005 | Marks et al. |
| 2005/0171918 | A1 | 8/2005 | Eden et al. |
| 2005/0182657 | A1 * | 8/2005 | Abraham-Fuchs et al. ...... 705/2 |
| 2005/0182658 | A1 * | 8/2005 | Abraham-Fuchs et al. ...... 705/2 |
| 2005/0182663 | A1 * | 8/2005 | Abraham-Fuchs et al. ...... 705/3 |
| 2005/0273360 | A1 * | 12/2005 | Drucker et al. .................. 705/2 |
| 2006/0143047 | A1 * | 6/2006 | Briegs et al. .................... 705/2 |
| 2006/0282287 | A1 * | 12/2006 | McKinley et al. ............... 705/2 |
| 2007/0067189 | A1 | 3/2007 | Boris et al. |

(Continued)

OTHER PUBLICATIONS

"Third-Party Audit Firm Confirms Lilly Has Kept Its Promise to Disclose Clinical Trial Data." PR Newswire. PR Newswire Association LLC. 2006. HighBeam Research. Oct. 21, 2009.*

(Continued)

*Primary Examiner*—C. Luke Gilligan
*Assistant Examiner*—Robert Sorey
(74) *Attorney, Agent, or Firm*—Panitch Schwarze Belisario & Nadel LLP

(57) ABSTRACT

A clinical trial study is modeled for automatically generating business intelligence information regarding the clinical trial study. The clinical trial study has a total budget amount and a total amount of deliverables. A software application program is provided that has equations and business rules that together define a process, a timeline, and deliverables associated with the clinical trial study. The program is populated with items including entities that have been contracted to provide the deliverables to the clinical trial study, budget items and amounts related to the deliverables for the respective entities that have been contracted to provide the deliverables, and for at least some of the budget items, a time frame in which the budget item is expected to be incurred or paid. Business intelligence information is then automatically generated using the equations and business rules in the program, and the items entered into the program. The business intelligence information includes appropriate invoice payments for the deliverables for the respective entities that have been contracted to provide the deliverables at a specific time frame, an accounting for the clinical trial study, and cash flow needs for the clinical trial study.

12 Claims, 142 Drawing Sheets

| | |
|---|---|
| Contract signature payment | 233,590 |
| Level Monthly Payment Schedule: | |
| 06-15-2008 | 181,410 |
| 07-15-2008 | 181,410 |
| 08-15-2008 | 181,410 |
| 09-15-2008 | 181,410 |
| 10-15-2008 | 181,410 |
| 11-15-2008 | 181,410 |
| 12-15-2008 | 181,410 |
| 01-15-2009 | 181,410 |
| 02-15-2009 | 181,410 |
| 03-15-2009 | 181,410 |
| 04-15-2009 | 181,407 |
| Total Project Budget | $ 2,229,09 |

NOTES:
(A) Monthly payments are due on the first of each month.
(B) We shall mail and/or email invoices to XXXXXXX per XXXXXXX instructions.
(C) XXXXXXX shall make all payments payable to us. By wire transfer, EFT or ACH, XXXXXXX shall send funds to XXXXXXX National Bank, as follows:
  Bank:            XXXXXXX Bank
  ABA Number   XXXXXXXX
  Account Name  XXXXXX Corporation
  Account Number XXXXXXXXXXXXX
  or such other bank account as is specified by us.
(D) Upon written request, we will forward to XXXXXX within 12 months after conclusion of the Project all invoices it received from any supplier for this Project, other than our Affiliate. If we are able to obtain any reductions in fees from such suppliers that are not attributable to reduced specifications and/or scope of work, then we will provide those fee reductions to XXXXXXX Pharma at the conclusion of the Project through a credit against any monies owed by XXXXXXX Pharma to us pursuant to this agreement or a check if no monies are due.

U.S. PATENT DOCUMENTS

2007/0255587 A1    11/2007    Chien et al.
2008/0177573 A1*    7/2008    Brescia et al. .................. 705/2
2008/0194921 A1*    8/2008    Schmidt et al. ............. 600/300
2008/0288285 A1    11/2008    Mancini et al.
2009/0089098 A1*    4/2009    Schoenberg .................... 705/3
2009/0112619 A1*    4/2009    Owens et al. .................. 705/2

OTHER PUBLICATIONS

"Accrual Accounting" definition, Investopedia®, printout from website: http://www.investopedia.com/terms/a/accrualaccounting.asp, Copyright ™ 2009 Investopedia ULC, printout date: Apr. 27, 2009, original posting date: unknown, 3 pages.

* cited by examiner

Figure 1A

| | B | C |
|---|---|---|
| | Budget Summary | Clinical Project Accounting |
| 1 | | |
| 2 | | Entity #1 - Corporation |
| 3 | SERVICE TYPE | |
| 4 | (2 integrations) | |
| 5 | Portal | |
| 6 | Ongoing Consolidation and Reconciliation | |
| 7 | Vendor Management | |
| 8 | CLINICAL PROFESSIONAL SERVICES: | |
| 9 | Start up, Regulatory, and Site Management Activities | |
| 10 | Monitoring Activities | |
| 11 | Project Management Activities (PM) | |
| 12 | Data Management Activities (DM) | |
| 13 | Safety, Medical & Scientific Services Activities | |
| 14 | Biostatistics & Medical Writing Activities | |
| 15 | SUBTOTAL PROFESSIONAL FEES | |
| 16 | | |
| 17 | SYSTEMS AND REPORTING TOOLS: | |
| 18 | Screening and Enrollment Tools | |
| 19 | Site Compliance Tools | |
| 20 | Reporting Systems | |
| 21 | Monitoring System | |
| 22 | Safety System | |
| 23 | Supplies and Re-Supply System | |
| 24 | IVRS System | |
| 25 | SUBTOTAL SYSTEMS AND REPORTING TOOLS | |
| 26 | | |

Figure 1B

| | B | C |
|---|---|---|
| 27 | TOTAL PRODUCTS AND SERVICES | |
| 28 | | |
| 29 | | |
| 30 | VALUE ADDED SUPPLIER ITEMS | |
| 31 | Drug Labeling | |
| 32 | Diagnostic Services: | |
| 33 | Labs | |
| 34 | ECG | |
| 35 | Investigator Grants | |
| 36 | Investigator Meeting Travel | |
| 37 | Monitor Travel | |
| 38 | Other Meals and Travel | |
| 39 | Meetings and Teleconferences | |
| 40 | IVRS Expenses | |
| 41 | Shipping, Printing, and Other | |
| 42 | Weight Scales | |
| 43 | Other (contingencies) | |
| 44 | Central IRB Cost | |
| 45 | TOTAL ESTIMATED PASS THROUGH COSTS | |
| 46 | | |
| 47 | | |
| 48 | TOTAL PROJECT BUDGET | |

Figure 1C

| | E | G | I | K | M |
|---|---|---|---|---|---|
| | Management Services | Systems and Tools | Sites, Monitoring, Safety, and Biostats | Supply | Lab |
| 1 | Entity #2 Supplier 1 | Entity #3 Supplier 2 | Entity #4 Supplier 3 (CRO) | Entity #5 Supplier 4 (Supplies) | Entity #6 Supplier 5 (Lab) |
| 2 | | | | | |
| 3 | | | | | |
| 4 | | | | | |
| 5 | | | | | |
| 6 | | | | | |
| 7 | | | | | |
| 8 | | | | | |
| 9 | | | | | |
| 10 | | | | | |
| 11 | | | | | |
| 12 | | | | | |
| 13 | | | | | |
| 14 | | | | | |
| 15 | | | | | |
| 16 | | | | | |
| 17 | | | | | |
| 18 | | | | | |
| 19 | | | | | |
| 20 | | | | | |
| 21 | | | | | |
| 22 | | | | | |
| 23 | | | | | |
| 24 | | | | | |
| 25 | | | | | |
| 26 | | | | | |

| | O | Q |
|---|---|---|
| | Central EKG | Contract |
| 1 | | |
| 2 | Entity #7 Supplier 6 (EKG) | Contract Value |
| 3 | | |
| 4 | | |
| 5 | | |
| 6 | | |
| 7 | | |
| 8 | | |
| 9 | | |
| 10 | | |
| 11 | | |
| 12 | | |
| 13 | | |
| 14 | | |
| 15 | | |
| 16 | | |
| 17 | | |
| 18 | | |
| 19 | | |
| 20 | | |
| 21 | | |
| 22 | | |
| 23 | | |
| 24 | | |
| 25 | | |
| 26 | | |

Figure 1F

| | O | | Q | |
|---|---|---|---|---|
| 27 28 29 | 30 31 32 33 34 35 36 37 38 39 40 41 42 43 44 | 45 46 47 48 | | |

Figure 2A

| | B | C |
|---|---|---|
| | | Clinical Project Accounting |
| 1 | | Corporation |
| 2 | Budget Summary | |
| 3 | SERVICE TYPE | |
| 4 | (2 integrations) | ='Change Order Tracking '!AZ96 |
| 5 | Portal | ='Change Order Tracking '!AZ97 |
| 6 | Ongoing Consolidation and Reconciliation | ='Change Order Tracking '!AZ98 |
| 7 | Vendor Management | ='Change Order Tracking '!AZ99 |
| 8 | CLINICAL PROFESSIONAL SERVICES: | |
| 9 | Start up, Regulatory, and Site Management Activities | |
| 10 | Monitoring Activities | |
| 11 | Project Management Activities (PM) | |
| 12 | Data Management Activities (DM) | |
| 13 | Safety, Medical & Scientific Services Activities | |
| 14 | Biostatistics & Medical Writing Activities | |
| 15 | SUBTOTAL PROFESSIONAL FEES | =SUM(C3:C14) |
| 16 | | |
| 17 | SYSTEMS AND REPORTING TOOLS: | |
| 18 | Screening and Enrollment Tools | |
| 19 | Site Compliance Tools | |
| 20 | Reporting Systems | |
| 21 | Monitoring System | |
| 22 | Safety System | |
| 23 | Supplies and Re-Supply System | |
| 24 | IVRS System | |
| 25 | SUBTOTAL SYSTEMS AND REPORTING TOOLS | =SUM(C18:C24) |
| 26 | | |

Figure 2B

| | B | C |
|---|---|---|
| | | |
| 27 | TOTAL PRODUCTS AND SERVICES | =C15+C25 |
| 28 | | |
| 29 | | |
| 30 | VALUE ADDED SUPPLIER ITEMS | |
| 31 | Drug Labeling | |
| 32 | Diagnostic Services: | |
| 33 | Labs | |
| 34 | ECG | |
| 35 | Investigator Grants | |
| 36 | Investigator Meeting Travel | |
| 37 | Monitor Travel | |
| 38 | Other Meals and Travel | |
| 39 | Meetings and Teleconferences | ='Change Order Tracking '!AZ150 |
| 40 | IVRS Expenses | |
| 41 | Shipping, Printing, and Other | |
| 42 | Weight Scales | |
| 43 | Other (contingencies) | |
| 44 | Central IRB Cost | |
| 45 | TOTAL ESTIMATED PASS THROUGH COSTS | =SUM(C31:C44) |
| 46 | | |
| 47 | | |
| 48 | TOTAL PROJECT BUDGET | =C27+C45 |

Figure 2C

| | E | G | I | K | M |
|---|---|---|---|---|---|
| | Management Services | Systems and Tools | Sites, Monitoring, Safety, and Biostats | Supply | Lab |
| 1 | Supplier 1 | Supplier 2 | Supplier 3 (CRO) | Supplier 4 (Supplies) | Supplier 5 (Lab) |
| 2 | | | | | |
| 3 | | | | | |
| 4 | | | | | |
| 5 | | | | | |
| 6 | | | | | |
| 7 | | | | | |
| 8 | | | ='Change Order Tracking'!AZ4+'Change Order Tracking'!AZ22 | | |
| 9 | | | ='Change Order Tracking'!AZ14+'Change Order Tracking'!AZ105 | | |
| 10 | ='Change Order Tracking'!AZ105 | | | | |
| 11 | ='Change Order Tracking'!AZ106 | | | | |
| 12 | ='Change Order Tracking'!AZ108 | | | | |
| 13 | | | ='Change Order Tracking'!AZ37 | | |
| 14 | | | | | |
| 15 | =SUM(E3:E14) | =SUM(G3:G14) | =SUM(I3:I14) | =SUM(K3:K14) | =SUM(M3:M14) |
| 16 | | | | | |
| 17 | | | | | |
| 18 | | ='Change Order Tracking'!AZ112 | | | |
| 19 | | ='Change Order Tracking'!AZ113 | | | |
| 20 | | ='Change Order Tracking'!AZ114 | | | |
| 21 | | ='Change Order Tracking'!AZ115 | | | |
| 22 | | ='Change Order Tracking'!AZ116 | | | |
| 23 | | ='Change Order Tracking'!AZ117 | | | |
| 24 | | ='Change Order Tracking'!AZ118 | | | |
| 25 | =SUM(E18:E24) | =SUM(G18:G24) | =SUM(I18:I24) | =SUM(K18:K24) | =SUM(M18:M24) |

Figure 2D

| | E | G | I | K | M |
|---|---|---|---|---|---|
| 27 | =E15+E25 | =G15+G25 | =I15+I25 | =K15+K25 | =M15+M25 |
| 28 | | | | | |
| 29 | | | | | |
| 30 | | | | | |
| 31 | | | | ='Change Order Tracking '!AZ48 | |
| 32 | | | | | |
| 33 | | | | | ='Change Order Tracking '!AZ59 |
| 34 | | | | | |
| 35 | | | ='Change Order Tracking '!AZ124 | | |
| 36 | | | ='Change Order Tracking '!AZ122 | | |
| 37 | | | ='Change Order Tracking '!AZ125 | | |
| 38 | ='Change Order Tracking '!AZ148 | | | | |
| 39 | | | | | |
| 40 | | 1968 | | | |
| 41 | | | | ='Change Order Tracking '!AZ133 | |
| 42 | | | ='Change Order Tracking '!AZ130 | | |
| 43 | ='Change Order Tracking '!AZ155 | | ='Change Order Tracking '!AZ123 | | |
| 44 | | | | | ='Change Order Tracking '!AZ137 |
| 45 | =SUM(E31:E44) | =SUM(G31:G44) | =SUM(I31:I44) | =SUM(K31:K44) | =SUM(M31:M44) |
| 46 | | | | | |
| 47 | | | | | |
| 48 | =E27+E45 | =G27+G45 | =I27+I45 | =K27+K45 | =M27+M45 |

Figure 2E

| | O | Q |
|---|---|---|
| 1 | Central EKG | Contract |
| 2 | Supplier 6 (EKG) | Contract Value |
| 3 | | |
| 4 | | =SUM(C4:P4) |
| 5 | | =SUM(C5:P5) |
| 6 | | =SUM(C6:P6) |
| 7 | | =SUM(C7:P7) |
| 8 | | =SUM(C8:P8) |
| 9 | | =SUM(C9:P9) |
| 10 | | =SUM(C10:P10) |
| 11 | | =SUM(C11:P11) |
| 12 | | =SUM(C12:P12) |
| 13 | | =SUM(C13:P13) |
| 14 | | =SUM(C14:P14) |
| 15 | =SUM(O3:O14) | =SUM(Q3:Q14) |
| 16 | | |
| 17 | | |
| 18 | | =SUM(C18:P18) |
| 19 | | =SUM(C19:P19) |
| 20 | | =SUM(C20:P20) |
| 21 | | =SUM(C21:P21) |
| 22 | | =SUM(C22:P22) |
| 23 | | =SUM(C23:P23) |
| 24 | | =SUM(C24:P24) |
| 25 | =SUM(O18:O24) | =SUM(Q18:Q24) |
| 26 | | |

Figure 2F

| | O | Q |
|---|---|---|
| 27 | =O15+O25 | =SUM(Q15+Q25) |
| 28 | | |
| 29 | | |
| 30 | | |
| 31 | | =SUM(C31:P31) |
| 32 | | =SUM(C32:P32) |
| 33 | | =SUM(C33:P33) |
| 34 | ='Change Order Tracking '!AZ85 | =SUM(C34:P34) |
| 35 | | =SUM(C35:P35) |
| 36 | | =SUM(C36:P36) |
| 37 | | =SUM(C37:P37) |
| 38 | | =SUM(C38:P38) |
| 39 | | =SUM(C39:P39) |
| 40 | | =SUM(C40:P40) |
| 41 | ='Change Order Tracking '!AZ144 | =SUM(C41:P41) |
| 42 | | =SUM(C42:P42) |
| 43 | | =SUM(C43:P43) |
| 44 | | =SUM(C44:P44) |
| 45 | =SUM(O31:O44) | =SUM(Q31:Q44) |
| 46 | | |
| 47 | | |
| 48 | =O27+O45 | =Q45+Q27 |

Figure 3A

| | B | C |
|---|---|---|
| 1 | Budget Summary | Clinical Project Accounting Corporation |
| 2 | | |
| 3 | SERVICE TYPE | |
| 4 | 2 integrations | 29,364 |
| 5 | Portal | 28,459 |
| 6 | Ongoing Consolidation and Reconciliation | 38,010 |
| 7 | Vendor Management | 59,000 |
| 8 | CLINICAL PROFESSIONAL SERVICES: | |
| 9 | Start up, Regulatory, and Site Management Activities | |
| 10 | Monitoring Activities | |
| 11 | Project Management Activities (PM) | |
| 12 | Data Management Activities (DM) | |
| 13 | Safety, Medical & Scientific Services Activities | |
| 14 | Biostatistics & Medical Writing Activities | |
| 15 | SUBTOTAL PROFESSIONAL FEES | $154,833 |
| 16 | | |
| 17 | SYSTEMS AND REPORTING TOOLS: | |
| 18 | Screening and Enrollment Tools | |
| 19 | Site Compliance Tools | |
| 20 | Reporting System | |
| 21 | Monitoring System | |
| 22 | Safety System | |
| 23 | Supplies and Re-Supply System | |
| 24 | IVRS System | |
| 25 | SUBTOTAL SYSTEMS AND REPORTING TOOLS | $ |
| 26 | | |

Figure 3B

| | B | | C |
|---|---|---|---|
| 27 | TOTAL PRODUCTS AND SERVICES | $ | 154,833 |
| 28 | | | |
| 29 | | | |
| 30 | VALUE ADDED SUPPLIER ITEMS | | |
| 31 | Drug Labeling | | |
| 32 | Diagnostic Services: | | |
| 33 | Labs | | |
| 34 | ECG | | |
| 35 | Investigator Grants | | |
| 36 | Investigator Meeting Travel | | |
| 37 | Monitor Travel | | |
| 38 | Other Meals and Travel | | |
| 39 | Meetings and Teleconferences | | 8,064 |
| 40 | IVRS Expenses | | |
| 41 | Shipping, Printing, and Other | | |
| 42 | Weight Scales | | |
| 43 | Other (contingencies) | | |
| 44 | Central IRB Cost | | |
| 45 | TOTAL ESTIMATED PASS THROUGH COSTS | $ | 8,064 |
| 46 | | | |
| 47 | | | |
| 48 | TOTAL PROJECT BUDGET | $ | 162,897 |

Figure 3C

| | E | G | I | K | M |
|---|---|---|---|---|---|
| | Management Services | Systems and Tools | Sites, Monitoring, Safety, and Biostats | Supply | Lab |
| 1 | Supplier 1 | Supplier 2 | Supplier 3 (CRO) | Supplier 4 (Supplies) | Supplier 5 (Lab) |
| 2 | | | | | |
| 3 | | | | | |
| 4 | | | | | |
| 5 | | | | | |
| 6 | | | | | |
| 7 | | | | | |
| 8 | | | 90,588 | | |
| 9 | | | 249,764 | | |
| 10 | 68,776 | | 105,462 | | |
| 11 | 216,585 | | | | |
| 12 | 32,313 | | | | |
| 13 | | | 84,073 | | |
| 14 | $ 317,674 | $ - | $ 529,887 | $ - | $ - |
| 15 | | | | | |
| 16 | | | | | |
| 17 | | 23,671 | | | |
| 18 | | 28,047 | | | |
| 19 | | 27,222 | | | |
| 20 | | 28,809 | | | |
| 21 | | 28,715 | | | |
| 22 | | 17,378 | | | |
| 23 | | 65,119 | | | |
| 24 | $ - | $ 218,961 | $ - | $ - | $ - |
| 25 | | | | | |

Figure 3D

| | E | | G | | I | | K | | M |
|---|---|---|---|---|---|---|---|---|---|
| 27 | $ | 317,674 | $ | 218,961 | $ | 529,887 | $ | - | $ | - |
| 28 | | | | | | | | | | |
| 29 | | | | | | | | | | |
| 30 | | | | | | | | | | |
| 31 | | | | | | | | | 31,900 | | |
| 32 | | | | | | | | | | | 53,386 |
| 33 | | | | | | | | | | | |
| 34 | | | | | | | | | | | |
| 35 | | | | | | | 627,300 | | | | |
| 36 | | | | | | | 57,600 | | | | |
| 37 | | | | | | | 83,400 | | | | |
| 38 | | 3,000 | | | | | | | | | |
| 39 | | | | | | | | | | | |
| 40 | | | | 1,968 | | | | | | | |
| 41 | | | | | | | | | 8,400 | | 871 |
| 42 | | | | | | | 28,800 | | | | |
| 43 | | 25,000 | | | | | 10,005 | | | | |
| 44 | | | | | | | 24,000 | | | | |
| 45 | $ | 28,000 | $ | 1,968 | $ | 831,105 | $ | 40,300 | $ | 54,257 |
| 46 | | | | | | | | | | | |
| 47 | | | | | | | | | | | |
| 48 | $ | 345,674 | $ | 220,929 | $ | 1,360,992 | $ | 40,300 | $ | 54,257 |

Figure 3E

| | O | Q |
|---|---|---|
| | Central EKG | Contract |
| 1 | | |
| 2 | Supplier 6 (EKG) | Contract Value |
| 3 | | |
| 4 | | $ 29,364 |
| 5 | | 28,459 |
| 6 | | 38,010 |
| 7 | | 59,000 |
| 8 | | - |
| 9 | | 90,588 |
| 10 | | 249,764 |
| 11 | | 174,238 |
| 12 | | 216,585 |
| 13 | | 32,313 |
| 14 | | 84,073 |
| 15 | $ - | $ 1,002,394 |
| 16 | | |
| 17 | | |
| 18 | | 23,671 |
| 19 | | 28,047 |
| 20 | | 27,222 |
| 21 | | 28,809 |
| 22 | | 28,715 |
| 23 | | 17,378 |
| 24 | | 65,119 |
| 25 | $ - | $ 218,961 |
| 26 | | |

Figure 3F

|    | O  |        | Q  |           |
|----|----|--------|----|-----------|
| 27 | $  | -      | $  | 1,221,355 |
| 28 |    |        |    |           |
| 29 |    |        |    |           |
| 30 |    |        |    |           |
| 31 |    |        |    | 31,900    |
| 32 |    |        |    | -         |
| 33 |    |        |    | 53,386    |
| 34 |    | 42,896 |    | 42,896    |
| 35 |    |        |    | 627,300   |
| 36 |    |        |    | 57,600    |
| 37 |    |        |    | 83,400    |
| 38 |    |        |    | 3,000     |
| 39 |    |        |    | 8,064     |
| 40 |    |        |    | 1,968     |
| 41 |    | 1,152  |    | 10,423    |
| 42 |    |        |    | 28,800    |
| 43 |    |        |    | 35,005    |
| 44 |    |        |    | 24,000    |
| 45 | $  | 44,048 | $  | 1,007,742 |
| 46 |    |        |    |           |
| 47 |    |        |    |           |
| 48 | $  | 44,048 | $  | 2,229,097 |

Figure 3G

| A | B |
|---|---|
| Overall Assumptions | |
| Type of Clinical Trial | Phase III |
| Compound | XXXXXX |
| Sites | 12 |
| Patients Screened | 246 |
| Patients Enrolled | 123 |
| Patients Completed | 100 |
| Startup (Months) | 2 |
| Recruitment (Months) | 6 |
| Treatment (Months) | 3 |
| Closeout (Months) | 1 |
| Total Project Duration (Months) | 12 |
| Integration Assumptions | |
| Number of Integrations | 2 |
| Custom Integration | 2 |
| Single Portal | 1 |
| Consolidation and Reconciliation | 2 |
| Vendor Management (Integration, Negotiation, Documentation, Monitoring, and Reconciliation) | 2-Apr |
| Clinical Project Accounting and Contracting (CPAC) | YES |
| Systems and Tools | |
| Screening and Enrollment Tools | 6 tool sets |
|     Executive Summary | |
|     Enrollment Status | |
|     Subject Status | |
|     Site Info | |
|     Enrollment By Site | |
|     Team Contact Info | |
| Site Compliance Tools | 4 tool sets |
|     Newsletters | |
|     CRFs | |
|     Assessment schedule | |
|     Inclusion/Exclusion calculator | |
| Real Time Reporting Tools | 7 tool sets |
|     Study Visit Summary | |
|     Protocol and Amendments | |
|     Newsletters | |
|     Training Materials | |

Figure 3H

| A | B |
|---|---|
| Project Management | |
|    Upload | |
|    Remove File | |
| Monitoring System | 12 tool sets |
|    Data View | |
|    Monitoring Summary | |
|    Query Tracking | |
|    Comments | |
|    Positive Pregnancy Report | |
|    Unsigned Items | |
|    Unlocked Forms | |
|    Supplies Status For Monitors | |
|    Sync Status Report | |
|    Subject Status | |
|    Missing eCRF Report | |
|    Pending eCRF Report | |
| Safety System | 6 tool sets |
|    AE/SAE | |
|    Subject Safety Reports | |
|    Positive Pregnancy Report | |
|    Subject Status | |
|    Early Terminators | |
|    Site Info | |
| Supplies Management | |
| IVRS System | 3 tool sets |
|    Shipment Address Management | |
|    IVRS Reconciliation Report | |
|    Materials Dispensed | |

Figure 3I

| A | B |
|---|---|
| Project Management Assumptions | |
| Status Reports | Unlimited |
| Number of Kick-off Meetings | 1 |
| Number of Investigator Meetings | 1 |
| Monitoring Assumptions | |
| Qualification Visits | 12 |
| Initiation Visits | 12 |
| Interim Visits | 72 |
| Closeout Visits | 12 |
| Total Monitoring Visits | 108 |
| Data Management Assumptions | |
| Total CFR Pages per Patient | 61 |
| Unique CFR Pages per Patient | 20 |
| Total CFR Pages per Patient | 8,612 |
| Total Number of Queries (no charge for queries) | Unlimited |
| Total Number of Users | 24 |
| Total Number of | 14 |
| Interim Analysis | N/A |
| SAS Transfers | 3 |
| Con Meds per Patient | 10 |
| Disease per Patient | 10 |
| AE's per Patient | 10 |
| SAE Reconciliation | 10 |
| Total Number of Edit Checks | Unlimited in 2 Iterations |
| Central Lab Transfers | YES |
| Echo Lab Transfers | N/A |
| Biomarker Transfers | N/A |
| ECG Transfers | YES |
| Database Lock | 1 |

Figure 3J

| A | B |
|---|---|
| Diagnostic Assumptions | |
| Number of ECGs per Patient | 3 |
| Total ECG units per site | 1 |
| Number of Central Labs per Patient | 3 |
| Number of Echo Labs per Patient | N/A |
| Number of Biomarkers per Patient | N/A |
| Biostats Assumptions (Interim and Final) | |
| Statistical Analysis Plan | YES |
| Tables | 35 |
| Listings | 25 |
| Figures | 5 |
| Table Analysis | YES |
| Final Study Report | NA |
| Safety Assumptions | |
| SAE's | 10 |
| Safety Database | 1 |

| Timeline: | |
|---|---|
| Contract Signed | May 2008 |
| First Patient Enrolled | July 2008 |
| Last Patient Enrolled | October 2008 |
| Last Patient Last Visit | February 2009 |
| Delivery of Final Clinical Study Report | June 2009 |

Figure 3K

| | |
|---|---:|
| Contract signature payment | 233,590 |
| Level Monthly Payment Schedule: | |
| 06-15-2008 | 181,410 |
| 07-15-2008 | 181,410 |
| 08-15-2008 | 181,410 |
| 09-15-2008 | 181,410 |
| 10-15-2008 | 181,410 |
| 11-15-2008 | 181,410 |
| 12-15-2008 | 181,410 |
| 01-15-2009 | 181,410 |
| 02-15-2009 | 181,410 |
| 03-15-2009 | 181,410 |
| 04-15-2009 | 181,407 |
| Total Project Budget | $ 2,229,09 |

NOTES:
(A) Monthly payments are due on the first of each month.
(B) We shall mail and/or email invoices to XXXXXXX per XXXXXXX instructions.
(C) XXXXXXX shall make all payments payable to us. By wire transfer, EFT or ACH, XXXXXXX shall send funds to XXXXXXX National Bank, as follows:
   Bank: XXXXXXX Bank
   ABA Number XXXXXXXX
   Account Name XXXXXX Corporation
   Account Number XXXXXXXXXXXXX
   or such other bank account as is specified by us.
(D) Upon written request, we will forward to XXXXXXX within 12 months after conclusion of the Project all invoices it received from any supplier for this Project, other than our Affiliate. If we are able to obtain any reductions in fees from such suppliers that are not attributable to reduced specifications and/or scope of work, then we will provide those fee reductions to XXXXXXX Pharma at the conclusion of the Project through a credit against any monies owed by XXXXXXX Pharma to us pursuant to this agreement or a check if no monies are due.

Figure 3L

| A | B |
|---|---|
| Overall Assumptions | |
| Type of Clinical Trial | Phase III |
| Compound | XXXXXX |
| Number of Sites Monitored | 12 |
| Number of Subjects Screened | 246 |
| Number of Subjects Enrolled | 130 |
| Number of Subjects Complete | 130 |
| Startup (Months) | 2 |
| Enrollment Period (months) | 6 |
| Treatment Period (months) | 3 |
| Total Duration of CRO Activities (months) | 12 |
| Project Management Assumptions | |
| Number of Kick-Off Meetings | 1 |
| Number of Investigator Meetings | 1 |
| Number of Client Project Meetings | 2 |
| Monthly Teleconferences | 24 |
| Monitoring Specifications | |
| Qualification Visits | 12 |
| Number of Initiation Visits | 12 |
| Interim Visits | Pool of 72 Visits (6 visits per site = 4 one-day & 2 two-day visits per site) |
| Number of Closeout Visits | 12 |
| Total Monitoring Visits | 108 |
| Biostats Assumptions | |
| Statistical Analysis Plan | YES |
| Number of Tables | 35 |
| Number of Listings | 25 |
| Number of Figures | 5 |
| Table Analysis | YES |
| Quality Assurance Specifications | |
| Number of Sites to be Audited | N/A |

| Timeline: | |
|---|---|
| Contract Signed | May 2008 |
| First Patient Enrolled | July 2008 |
| Last Patient Enrolled | October 2008 |
| Last Patient Last Visit | February 2009 |

Figure 3M

| | B | C | D | E |
|---|---|---|---|---|
| 3 | Protocol: XXXXXXXXX | | For Billing : | XXXX |
| 4 | Inv. No. XXXXXXXX | | Invoice Date: | XXXXXX |
| 5 | | | Due Date: | XXXXXXXX |
| 6 | | | | |
| 7 | | | | |
| 8 | PROFESSIONAL FEE | | | |
| 9 | | Unit | Unit Price | Total Price |
| 10 | PROJECT AGREEMENT EXECUTION | 1 | 53,000.00 | 53,000.00 |
| 11 | | | | |
| 12 | STUDY SETUP | | | 88,142.00 |
| 13 | INVESTIGATOR SELECTION | 12.0 | 945.0 | 11,340.0 |
| 14 | QUALIFICATION SITE ASSESSMENT VISITS | 12.00 | 1,421.00 | 17,052.00 |
| 15 | COLLECTION AND PROCESSING OF REGULATORY DOCUMENTATION | 12.00 | 1,539.00 | 18,468.00 |
| 16 | INVESTIGATORS MEETING (ATTENDANCE & PARTICIPATION) | 1.00 | 26,514.00 | 26,514.00 |
| 17 | TRAINING MEETING | 1.00 | 4,328.00 | 4,328.00 |
| 18 | NEGOTIATION & ADMINISTRATION OF INVESTIGATOR GRANTS | 1.00 | 10,440.00 | 10,440.00 |
| 19 | | | | |
| 20 | PROJECT MANAGEMENT | | | 107,906.00 |
| 21 | PROJECT COORDINATION (12 months) | 12.00 | 7,065.00 | 84,780.00 |
| 22 | PROJECT MEETINGS | 12.00 | 744.33 | 8,932.00 |
| 23 | CONFERENCE CALLS | 15.00 | 687.80 | 10,317.00 |
| 24 | NEWSLETTERS | 12.00 | 323.08 | 3,877.00 |
| 25 | | | | |

Figure 3N

|    | B | C | D | E |
|----|---|---|---|---|
| 26 | MONITORING ACTIVITIES | | | 249,764.00 |
| 27 | INITIATION VISITS | 12.00 | 1,527.33 | 18,328.00 |
| 28 | INTERIM MONITORING VISITS (pool of 300 monitoring days) | 72.00 | 2,129.68 | 153,337.00 |
| 29 | CLOSEOUT VISITS | 12.00 | 1,580.42 | 18,965.00 |
| 30 | STATUS REPORTS | 12.00 | 283.50 | 3,402.00 |
| 31 | IN-HOUSE MEDICAL SUPPORT | 12.00 | 585.00 | 7,020.00 |
| 32 | SITE MANAGEMENT | 12.00 | 3,087.33 | 37,048.00 |
| 33 | ADMINISTRATION | 12.00 | 972.00 | 11,664.00 |
| 34 | | | | |
| 35 | BIOSTATISTICAL SERVICES | | | 84,072.00 |
| 36 | PROJECT TEAM AND CLIENT INTERACTION | 12.00 | 738.00 | 8,856.00 |
| 37 | STATISTICAL ANALYSIS PLAN | 1.00 | 12,160.00 | 12,160.00 |
| 38 | STATISTICAL TABLES, LISTINGS, FIGURES, OUTPUTS & PROGRAMMING | 1.00 | 54,888.00 | 54,888.00 |
| 39 | ANALYSIS PRODUCTION | 1.00 | 6,732.00 | 6,732.00 |
| 40 | RESULTS REVIEW MEETING | 1.00 | 1,436.00 | 1,436.00 |
| 41 | | | | |
| 42 | TOTAL PROFESSIONAL FEE | | | 529,884.00 |
| 43 | TOTAL PROFESSIONAL FEE CURRENT | | | - |

Figure 30

| | A | B | C | D | E | F | G |
|---|---|---|---|---|---|---|---|
| 47 | | | | | | | |
| 48 | | Protocol: | | For Billing : | | | |
| 49 | | | | | | | |
| 50 | | | | Invoice Date: | | | |
| 51 | | | | Due Date: | | | |
| 52 | | | | | | | |
| 53 | | PASS-THROUGH EXPENSES | | | | Units Completed to Date | % of Work Completed to Date |
| 54 | | | | | | | |
| 55 | | | Unit | Unit Price | Total Price | | |
| 56 | | | | | | | |
| 57 | | INVESTIGATOR MEETING (Travel and expenses) | | | 57,600.00 | | |
| 58 | | | | | | | |
| 59 | | CLINICAL TRIAL MATERIAL COORDINATION | | | 10,005.00 | | |
| 60 | | | | | | | |
| 61 | | GRANTS | | | 627,300.00 | | |
| 62 | | | | | | | |
| 63 | | TRAVEL MONITOR | | | 83,400.00 | | |
| 64 | | Airfare | | | | | |
| 65 | | Meals, Lodging, etc | | | | | |
| 66 | | REGULATORY | | | | | |
| 67 | | CENTRAL IRB COSTS | | | 24,000.00 | | |
| 68 | | | | | | | |
| 69 | | LEGAL WORK (Investigators Contracts) | | | | | |
| 70 | | | | | | | |
| 71 | | CREDIT | | | | | |
| 72 | | | | | | | |
| 73 | | TOTAL PASS-THROUGH EXPENSES | | | 802,305.00 | | |
| 75 | | TOTAL PASS-THROUGH EXPENSES CURRENT | | | - | | |
| 76 | | CREDIT | | | | | |
| 77 | | TOTAL INVOICE | | | - | | . |
| 78 | | | | | | | |

Figure 3P

| | H | I | J | K |
|---|---|---|---|---|
| 47 | | | | |
| 48 | | | | |
| 49 | | | | |
| 50 | | | | |
| 51 | | | | |
| 52 | | | | |
| 53 | Units Billed | Amount Billed Current | Life to Date Units Billed | Life to Date Amount Billed |
| 54 | | | | |
| 55 | | | | |
| 56 | | | | |
| 57 | | | | |
| 58 | | | | |
| 59 | | | | |
| 60 | | | | |
| 61 | | | | |
| 62 | | | | |
| 63 | | | | |
| 64 | | | | |
| 65 | | | | |
| 66 | | | | |
| 67 | | | | |
| 68 | | | | |
| 69 | | | | |
| 70 | | | | |
| 71 | | | | |
| 72 | | | | |
| 73 | | | | |
| 75 | | | | |
| 76 | | | | |
| 77 | | | | |
| 78 | | | | |

Figure 3Q

The terms and conditions of the Master Clinical Trials Laboratory Services Agreement between COMPANY and XXXXX dated 05/24/2008 apply to this Study Protocol.

| Test Name | Price per Sample |
|---|---|
| Chemistry Panel | $12.00 |
| Panel (SGOT, SGPT, albumin, alkaline phosphatase, total bilirubin, amylase, calcium, creatinine, GGT, glucose, potassium, total protein, sodium, BUN., uric acid) | |
| Hematology Panel | $9.00 |
| (WBC, RBC, hemoglobin, hematocrit, platelet differential) | |
| Urinalysis | $9.00 |
| (appearance, bilirubin, color, glucose, ketones, leukocytes, nitrite, occult blood, protein, pH, specific gravity, urobilinogen) | |
| PSA | $19.98 |
| Serum Pregnancy | $15.00 |
| Hemoglobin A1C | $18.62 |
| Kits-Safety | $7.00 |
| Kits-PSA | $5.00 |
| Urine Pregnancy Kits | $5.00 |
| Outbound transportation of kits to sites | actual +15% |
| Inbound Transportation | actual +15% |
| Project Set Up Fee | $4,000.00 |
| Data Management Fee | $3,000.00 |
| Monthly Management Fee | $170.00/month |

If COMPANY initiates any changes to the study which directly or indirectly results in XXXXXXXXX amending the instructional materials or necessitates the resupply of new shipping or sample collection materials, XXXXXX will charge COMPANY and COMPANY will pay for all materials shipped and labor costs associated with each change. These charges will be in addition to any charges currently allowed for in the Agreement.

A facsimile, telecopy or other reproduction of this Agreement may be executed by one or more parties hereto, and an executed copy of this Agreement may be delivered by one or more parties hereto by facsimile or similar electronic transmission device pursuant to which the signature of or on behalf of such party can be seen, and such execution and delivery shall be considered valid, binding and effective for all purposes. At the request of any party hereto, all parties hereto agree to execute an original of this Agreement as well as any facsimile, telecopy or other reproduction hereof.

IN WITNESS WHEREOF, the parties have caused this Agreement to be executed in their names as their official acts by their respective representatives, each of whom is duly authorized to execute the same.

Figure 3R

Site #
XXXXXXXXXXX
Protocol XXXXXXX

Attachment A

"A Double-Blind, Randomized, Parallel, Placebo-Controlled, Multicenter Study Evaluating the Effect of Treatment with Topically Administered xxxxxxxxxxxx in Patients with Urinary Frequency, and Urge and Mixed Urinary Incontinence with a Predominance of Urge Incontinence Episodes"

Protocol #

Sponsor: xxxxxxxxxxx

The total maximum grant is $5,100 per Completed, Evaluable Case (as defined in Section 5 of this Agreement) patient.

Upon execution of this Agreement, xxxxxxxx agrees to pay the INSTITUTION a pre-payment of $10,200, equivalent to two (2) Completed, Evaluable patients. xxxxxxxx expects that all funds from this pre-payment not earned by the INSTITUTION/INVESTIGATOR per the payment schedule below will be remitted to stated in Section 5 of this Agreement.

Enrollment for this Study is competitive. The INVESTIGATOR/INSTITUTION agrees to recruit a minimum of 11 patients. Enrollment of these patients will take place during the period between xxxxxxxx xxxxxxxx xxxxxxxx xxxxxxxx Enrollment will end when a total of 123 subjects have been enrolled in the Study, or upon the decision of the Sponsor.

The INSTITUTION will be reimbursed $600 per documented Screen Failure; up to five (5) Screen Failures based on every five (5) Study subjects enrolled. The parties agree that a Screen Failure is defined as a Study subject who signs an Informed Consent, but does not meet the inclusion/exclusion criteria. This reimbursement will be included in the final payment Each INSTITUTION will be paid at monthly intervals during the Study. The amount of each payment will be based on subject enrollment/visit log verification, monitored source data verified electronic Case Report Forms (eCRFs) and queries by during the applicable month.

Investigator Grant

| Visit | Week | |
|---|---|---|
| 1 | -2 | 1219 |
| 2 | -1 | 344 |
| 3 | 0 | 594 |
| 4 | 2 | 563 |
| 5 | 4 | 563 |
| 6 | 8 | 563 |
| 7 | 12 | 1254 |
| | | 5100 |

Figure 3S

CHANGE ORDER FORM (COF)

COF # 0 2

| | | | |
|---|---|---|---|
| Date Requested/Identified: | 12-Jul-08 | Numoda Contact: | XXXXXXXX |
| Customer Name: | XXXXXXXXXXX | Customer Contact: | XXXXXXXX |
| Project Code: | XXXXX | Project Name: | XXXXXX |

Description and/or Date of Original Agreement:    Project Agreement Dated:    5/17/2008

Comment: With the most recent FDA issues about Safety, a Medical Monitor will alleviate Medical Monitor concerns.

CHANGE DESCRIPTION:

| | |
|---|---|
| Medical Monitoring Services, and Medical Monitor attending Investigator's Meeting and Training Meeting - (2) Project Meetings | $ 34,100 |
| Ongoing Medical Monitoring Support Services | |

$ 34,100

BUDGET SUMMARY:

| Item | Effective Date | Amount |
|---|---|---|
| Change Order Number 02 | 7/12/2008 | $34,100 |

AGREED TO, ACKNOWLEDGED, AND ACCEPTED

XXXXXXXXX                                          XXXXXXXXX

| | |
|---|---|
| Signature | Signature |
| | XXXXXX |
| Name (print) | Name (print) |
| Title | Title |
| Date | Date |

Figure 3T

| | E | G | I | K | M |
|---|---|---|---|---|---|
| | Management Services | Systems and Tools | Sites, Monitoring, Safety, and Biostats | Supply | Lab |
| | Entity #2 Supplier 1 | Entity #3 Supplier 2 | Entity #4 Supplier 3 (CRO) | Entity #5 Supplier 4(Supplies) | Entity #6 Supplier 5 (Lab) |
| 1 | | | | | |
| 2 | | | | | |
| 3 | | | | | |
| 4 | | | | | |
| 5 | | | | | |
| 6 | | | | | |
| 7 | | | | | |
| 8 | | | 90,588 | | |
| 9 | | | 249,764 | | |
| 10 | 68,776 | | 105,462 | | |
| 11 | 216,585 | | | | |
| 12 | 32,313 | | 34,100 | | |
| 13 | | | 84,073 | | |
| 14 | $ 317,674 | $ - | $ 563,987 | $ - | $ - |
| 15 | | | | | |
| 16 | | 23,671 | | | |
| 17 | | 28,047 | | | |
| 18 | | 27,222 | | | |
| 19 | | 28,809 | | | |
| 20 | | 28,715 | | | |
| 21 | | 17,378 | | | |
| 22 | | 65,119 | | | |
| 23 | $ - | $ 218,961 | $ - | $ - | $ - |
| 24 | | | | | |

Figure 3U

| | O | Q |
|---|---|---|
| 1 | Central EKG | Contract |
| 2 | Entity #7 Supplier 6 (EKG) | Contract Value |
| 3 | | |
| 4 | | $ 29,364 |
| 5 | | 28,459 |
| 6 | | 38,010 |
| 7 | | 59,000 |
| 8 | | - |
| 9 | | 90,588 |
| 10 | | 249,764 |
| 11 | | 174,238 |
| 12 | | 216,585 |
| 13 | | 66,413 |
| 14 | | 84,073 |
| 15 | - | $ 1,036,494 |
| 16 | | |
| 17 | | |
| 18 | | 23,671 |
| 19 | | 28,047 |
| 20 | | 27,222 |
| 21 | | 28,809 |
| 22 | | 28,715 |
| 23 | | 17,378 |
| 24 | | 65,119 |
| 25 | - | $ 218,961 |
| 26 | | |

Figure 3V

| | O | | Q | |
|---|---|---|---|---|
| 27 | $ | - | $ | 1,255,455 |
| 28 | | | | |
| 29 | | | | |
| 30 | | | | |
| 31 | | | | 31,900 |
| 32 | | | | - |
| 33 | | | | 53,386 |
| 34 | | 42,896 | | 42,896 |
| 35 | | | | 627,300 |
| 36 | | | | 57,600 |
| 37 | | | | 83,400 |
| 38 | | | | 3,000 |
| 39 | | | | 8,064 |
| 40 | | | | 1,968 |
| 41 | | 1,152 | | 10,423 |
| 42 | | | | 28,800 |
| 43 | | | | 35,005 |
| 44 | | | | 24,000 |
| 45 | $ | 44,048 | $ | 1,007,742 |
| 46 | | | | |
| 47 | | | | |
| 48 | $ | 44,048 | $ | 2,263,197 |

Figure 4A

| | A | B | C | D | E | F | G | H | I | J | K | L | M | N |
|---|---|---|---|---|---|---|---|---|---|---|---|---|---|---|
| 1 | Protocol: | | Units | Unit Price | | | Unit | Unit Price | CO # 01 | | Unit | Unit Price | CO # 02 | |
| | | | Units | Unit Price | Original Contract | | Unit | Unit Price | CO # 01 | | Unit | Unit Price | CO # 02 | |
| 3 | | ENTITY #4 - Professional Fees | | | 529,883.92 | | | | 0.00 | | | | 0.00 | |
| 4 | | STUDY SETUP | | | 90,586.00 | | | | 0.00 | | | | 0.00 | |
| 5 | | Investigator Selection | 12.0 | 945.00 | 11,340.00 | | | | 0.00 | | | | 0.00 | |
| 6 | | Qualification Site Assessment Visits | 12.0 | 1,421.00 | 17,052.00 | | | | 0.00 | | | | 0.00 | |
| 7 | | Collection and Processing of Regulatory Documentation | 12.0 | 1,539.00 | 18,468.00 | | | | 0.00 | | | | 0.00 | |
| 8 | | Kick of Meeting | | | | | | | | | | | | |
| 9 | | Investigators Meeting (Attendance & Participation) | 1.0 | 26,514.00 | 26,514.00 | | | | 0.00 | | | | 0.00 | |
| 10 | | Investigators Meeting (Coordination) | 0.0 | 0.00 | 0.00 | | | | 0.00 | | | | 0.00 | |
| 11 | | Training Meeting | 1.0 | 4,328.00 | 4,328.00 | | | | 0.00 | | | | 0.00 | |
| 12 | | Negotiation & Administration of Investigator Grants | 1.0 | 12,884.00 | 12,884.00 | | | | 0.00 | | | | 0.00 | |
| 13 | | Negotiation of Investigator Contracts (Legal Counsel) | 0.0 | 0.00 | 0.00 | | | | 0.00 | | | | 0.00 | |
| 14 | | PROJECT MANAGEMENT | | | 105,462.00 | | | | 0.00 | | | | 0.00 | |
| 15 | | Project Coordination (12 Months) | 12.0 | 7,065.00 | 84,780.00 | | | | 0.00 | | | | 0.00 | |
| 16 | | Project Meeting | 12.0 | 744.34 | 8,932.08 | | | | 0.00 | | | | 0.00 | |
| 17 | | Conference Calls | 24.0 | 328.04 | 7,872.96 | | | | 0.00 | | | | 0.00 | |
| 18 | | Newsletters | 12.0 | 323.08 | 3,876.96 | | | | 0.00 | | | | 0.00 | |
| 19 | | Status Report | 0.0 | 0.00 | 0.00 | | | | 0.00 | | | | 0.00 | |
| 20 | | Scale and Calibration Weight Coordination | 0.0 | 0.00 | 0.00 | | | | 0.00 | | | | 0.00 | |
| 21 | | Protocol Amendment # 01 Review | 0.0 | 0.00 | 0.00 | | | | 0.00 | | | | 0.00 | |
| 22 | | MONITORING ACTIVITIES | | | 205,695.96 | | | | 0.00 | | | | 0.00 | |
| 23 | | Initiation Visits | 12.0 | 1,527.33 | 18,327.96 | | | | 0.00 | | | | 0.00 | |
| 24 | | Interim Monitoring Visits | 72.0 | 2,129.68 | 153,336.96 | | | | 0.00 | | | | 0.00 | |
| 25 | | Closeout Visits | 12.0 | 1,580.42 | 18,965.04 | | | | 0.00 | | | | 0.00 | |
| 26 | | Status Reports | 12.0 | 283.50 | 3,402.00 | | | | 0.00 | | | | 0.00 | |
| 27 | | Administration | 12.0 | 972.00 | 11,664.00 | | | | 0.00 | | | | 0.00 | |
| 28 | | Protocol Amendment # 01 Coordination (for 12 Sites) | 0.0 | 0.00 | 0.00 | | | | 0.00 | | | | 0.00 | |
| 29 | | Medical Management | 0.0 | 0.00 | 0.00 | | | | 0.00 | | | | 0.00 | |
| 30 | | SAE Management (SET-UP) | 0.0 | 0.00 | 0.00 | | | | 0.00 | | | | 0.00 | |
| 31 | | SAE Management (01 SAE) | 0.0 | 0.00 | 0.00 | | | | 0.00 | | | | 0.00 | |
| 32 | | SAE Narratives (01 Narrative) | 0.0 | 0.00 | 0.00 | | | | 0.00 | | | | 0.00 | |
| 33 | | SITE MANAGEMENT | | | 37,047.96 | | | | 0.00 | | | | 0.00 | |
| 34 | | SITE MANAGEMENT | 12.0 | 3,087.33 | 37,047.96 | | | | 0.00 | | | | 0.00 | |
| 35 | | PROJECT MEETINGS | 0.0 | 3,087.33 | 0.00 | | | | 0.00 | | | | 0.00 | |
| 36 | | STATUS REPORTS | 0.0 | 0.00 | 0.00 | | | | 0.00 | | | | 0.00 | |
| 37 | | BIOSTATISTICAL SERVICES | | | 84,072.00 | | | | 0.00 | | | | 0.00 | |
| 38 | | Project Team and Client interaction | 12.0 | 738.00 | 8,856.00 | | | | 0.00 | | | | 0.00 | |
| 39 | | Statistical Analysis Plan | 1.0 | 12,160.00 | 12,160.00 | | | | 0.00 | | | | 0.00 | |
| 40 | | Statistical Tables, Listings, Figures, Output &Programming | 1.0 | 54,888.00 | 54,888.00 | | | | 0.00 | | | | 0.00 | |
| 41 | | Final Programming & Analysis | 1.0 | 6,732.00 | 6,732.00 | | | | 0.00 | | | | 0.00 | |
| 42 | | Results Review Meeting | 1.0 | 1,436.00 | 1,436.00 | | | | 0.00 | | | | 0.00 | |

Figure 4B

| | A | B | C | D | E | F | G | H | I | J | K | L | M | N |
|---|---|---|---|---|---|---|---|---|---|---|---|---|---|---|
| 43 | | | | | | | | | | | | | | |
| 44 | | SAFETY MEDICAL & SCIENTIFIC SERVICES | | | 7,020.00 | | | | 0.00 | | | | 0.00 | 0.00 |
| 45 | | SAFETY MEDICAL & SCIENTIFIC SERVICES (SCIENTIF | 12.0 | 0.00 | 0.00 | | | | 0.00 | | | | 0.00 | 0.00 |
| 46 | | IN HOUSE MEDICAL SUPPORT | 12.0 | 585.00 | 7,020.00 | | | | 0.00 | | | | 0.00 | 0.00 |
| 47 | | | | | | | | | | | | | | |
| 48 | | PharmaForm - Professional Fees | | | 31,902.20 | | | | 0.00 | | | | 0.00 | 0.00 |
| 49 | | STUDY SETUP | | | 31,902.20 | | | | 0.00 | | | | 0.00 | 0.00 |
| 50 | | Generation / Revision of Labeling Record | 1 | 500.00 | 500.00 | | | | 0.00 | | | | 0.00 | |
| 51 | | Generation of Randomization Code | 1 | 3,000.00 | 3,000.00 | | | | 0.00 | | | | 0.00 | |
| 52 | | Acquisition of single Panel Labels to be applied to the bott | 2,000 | 1.25 | 2,500.00 | | | | 0.00 | | | | 0.00 | |
| 53 | | Acquisition of three panel labels to be applied to the boxes | 3 | 1,167.00 | 3,501.00 | | | | 0.00 | | | | 0.00 | |
| 54 | | Acquisiton of boxes (667 units) | 667 | 3.60 | 2,401.20 | | | | 0.00 | | | | 0.00 | |
| 55 | | Approvals of labels according to the Randomization Code | 1 | 2,500.00 | 2,500.00 | | | | 0.00 | | | | 0.00 | |
| 56 | | Labeling of Bottled Gels and Packaging into boxes | 1 | 17,500.00 | 17,500.00 | | | | 0.00 | | | | 0.00 | |
| 57 | | Release of Clinically Labeled Product ( Included) | 0 | | 0.00 | | | | 0.00 | | | | 0.00 | |
| 58 | | | | | | | | | | | | | | |
| 59 | | ENTITY #6 - Professional Fees | | | 48,149.00 | | | | 0.00 | | | | 0.00 | 0.00 |
| 60 | | Testing: Screen | | | 15,280.04 | | | | 0.00 | | | | 0.00 | 0.00 |
| 61 | | Chemistry Panel(1) | 246.0 | 12.00 | 2,952.00 | | | | 0.00 | | | | 0.00 | |
| 62 | | Hematology Panel(2) | 246.0 | 9.00 | 2,214.00 | | | | 0.00 | | | | 0.00 | |
| 63 | | Urinalysis | 246.0 | 9.00 | 2,214.00 | | | | 0.00 | | | | 0.00 | |
| 64 | | PSA( cooled) | 73.8 | 19.98 | 1,474.52 | | | | 0.00 | | | | 0.00 | |
| 65 | | Hemoglobin A1C | 246.0 | 18.62 | 4,580.52 | | | | 0.00 | | | | 0.00 | |
| 66 | | Serum Pregnancy (5) | 123.0 | 15.00 | 1,845.00 | | | | 0.00 | | | | 0.00 | |
| 67 | | Testin: Enrolled - Visit 7 | | | 4,428.00 | | | | 0.00 | | | | 0.00 | 0.00 |
| 68 | | Chemistry Panel (1) | 98.4 | 12.00 | 1,180.80 | | | | 0.00 | | | | 0.00 | |
| 69 | | Hematology Panel (2) | 98.4 | 9.00 | 885.60 | | | | 0.00 | | | | 0.00 | |
| 70 | | Urinalysis (3) | 98.4 | 9.00 | 885.60 | | | | 0.00 | | | | 0.00 | |
| 71 | | Serum Pregnancy (5) | 98.4 | 15.00 | 1,476.00 | | | | 0.00 | | | | 0.00 | |
| 72 | | Materials: | | | 3,419.40 | | | | 0.00 | | | | 0.00 | 0.00 |
| 73 | | Kits - Screen (6) | 246.0 | 7.00 | 1,722.00 | | | | 0.00 | | | | 0.00 | |
| 74 | | Kits - Screen PSA (6) | 98.4 | 5.00 | 492.00 | | | | 0.00 | | | | 0.00 | |
| 75 | | Kits - Enrolled Visit 7 (6) | 98.4 | 7.00 | 688.80 | | | | 0.00 | | | | 0.00 | |
| 76 | | Urine Pregnancy Kits (Visit 3) | 73.8 | 7.00 | 516.60 | | | | 0.00 | | | | 0.00 | |
| 77 | | Project Set Up fee | 1.0 | 4,000.00 | 4,000.00 | | | | 0.00 | | | | 0.00 | 0.00 |
| 78 | | Data Management Fee | 1.0 | 3,000.00 | 3,000.00 | | | | 0.00 | | | | 0.00 | 0.00 |
| 79 | | Monthly Management Fee | 10.0 | 170.00 | 1,700.00 | | | | 0.00 | | | | 0.00 | 0.00 |
| 80 | | Other Contingencies | 1.0 | 16,321.5 | 16,321.5 | | | | 0.00 | | | | 0.00 | 0.00 |
| 81 | | PK Lab | | | 0.00 | | | | 0.00 | | | | 0.00 | |
| 82 | | PK Lab | 0.0 | | 0.00 | | | | 0.00 | | | | 0.00 | |
| 83 | | PK Lab | 0.0 | | 0.00 | | | | 0.00 | | | | 0.00 | |
| 84 | | | | | | | | | | | | | | |
| 85 | | ERT - Professional Fees | | | 42,896.00 | | | | 0.00 | | | | 0.00 | |

Figure 4C

|    | A | B | C | D | E | F | G | H | I | J | K | L | M | N |
|----|---|---|---|---|---|---|---|---|---|---|---|---|---|---|
| 86 | | Project Assurance Services Fee, Project Management, Site Support, Customer Care Center eReporting Services | 10.0 | 347.85 | 3,478.50 | | | | 0.00 | | | | 0.00 | |
| 87 | | 12 Lead ECG Analysis Methodology | | | 16,605.00 | | | | 0.00 | | | | 0.00 | |
| 88 | | Manual Adjudication | 369.0 | 45.00 | 16,605.00 | | | | 0.00 | | | | 0.00 | |
| 89 | | 12 Lead ECG Collection and Delivery Equipment | | | 22,812.50 | | | | 0.00 | | | | 0.00 | |
| 90 | | Mortara ELI -150/200/250 or MAC1200 12-Lead ECG Dev | 108.0 | 150.00 | 16,200.00 | | | | 0.00 | | | | 0.00 | |
| 91 | | Standard Electrodes | 4,200.0 | 0.40 | 1,680.00 | | | | 0.00 | | | | 0.00 | |
| 92 | | ECG Paper | 12.0 | 25.00 | 300.00 | | | | 0.00 | | | | 0.00 | |
| 93 | | Other Contingencies | 1.0 | 4,632.50 | 4,632.50 | | | | 0.00 | | | | 0.00 | |
| 94 | | ENTITY #1 - Professional Fees | | | 691,468.00 | | | | 0.00 | | | | 0.00 | |
| 95 | | ENTITY #1 SERVICES: | | | 154,833.00 | | | | 0.00 | | | | 0.00 | |
| 96 | | Integrations (3 integrations) | 12.0 | 2,447.00 | 29,364.00 | | | | 0.00 | | | | 0.00 | |
| 97 | | Portal | 12.0 | 2,371.58 | 28,459.00 | | | | 0.00 | | | | 0.00 | |
| 98 | | Consolidation and Reconciliation | 12.0 | 3,167.50 | 38,010.00 | | | | 0.00 | | | | 0.00 | |
| 99 | | Vendor Management | 12.0 | 4,916.67 | 59,000.00 | | | | 0.00 | | | | 0.00 | |
| 100 | | Medical Monitoring Support Services | | | 0.00 | | | | 0.00 | | | | 0.00 | |
| 101 | | Patient Diaries - Printing Shipping, QC and Logistics tracking | | | 0.00 | | | | 0.00 | | | | 0.00 | |
| 102 | | CLINICAL PROFESSIONAL SERVICES: | | | 317,674.00 | | | | 0.00 | | | | 0.00 | |
| 103 | | Startup Regulatory, and Site Management Activities | | | 0.00 | | | | 0.00 | | | | 0.00 | |
| 104 | | Monitoring Activities | | | 0.00 | | | | 0.00 | | | | 0.00 | |
| 105 | | Project Management Activities (PM) | 12.0 | 5,731.33 | 68,776.00 | | | | 0.00 | | | | 0.00 | |
| 106 | | Data Management Activities (DM) | 8,612.0 | 25.15 | 216,585.00 | | | | 0.00 | | | | 0.00 | |
| 107 | | Monthly Management Fee | | | 0.00 | | | | 0.00 | | | | 0.00 | |
| 108 | | Safety, Medical &Scientific Activities | 12.0 | 2,692.75 | 32,313.00 | | | | 0.00 | | | | 0.00 | |
| 109 | | Biostatistics & Medical Writing Activities | | | 0.00 | | | | 0.00 | | | | 0.00 | |
| 110 | | Labeling Regulatory Input | | | 0.00 | | | | 0.00 | | | | 0.00 | |
| 111 | | SYSTEMS AND REPORTING TOOLS: | | | 218,961.00 | | | | 0.00 | | | | 0.00 | |
| 112 | | Screening and Enrollment Tools | 12.0 | 1,972.58 | 23,671.00 | | | | 0.00 | | | | 0.00 | |
| 113 | | Site Compliance Tools | 12.0 | 2,337.25 | 28,047.00 | | | | 0.00 | | | | 0.00 | |
| 114 | | Real Time Reporting Tools | 12.0 | 2,268.50 | 27,222.00 | | | | 0.00 | | | | 0.00 | |
| 115 | | Monitoring System | 12.0 | 2,400.75 | 28,809.00 | | | | 0.00 | | | | 0.00 | |
| 116 | | Safety System | 12.0 | 2,392.92 | 28,715.00 | | | | 0.00 | | | | 0.00 | |
| 117 | | Supplies System | 12.0 | 1,448.17 | 17,378.00 | | | | 0.00 | | | | 0.00 | |
| 118 | | IVRS System | 12.0 | 5,426.58 | 65,119.00 | | | | 0.00 | | | | 0.00 | |
| 119 | | Reserved | | | | | | | | | | | | |
| 120 | | TOTAL PROFESSIONAL FEES | | | 1,344,299.12 | | | | 0.00 | | | | 0.00 | |
| 121 | | ENTITY #4 | | | 831,105.00 | | | | 0.00 | | | | 0.00 | |
| 122 | | INVESTIGATOR MEETING (Travel and expenses) | 1.0 | 57,600.00 | 57,600.00 | | | | 0.00 | | | | 0.00 | |

Figure 4D

| | A | B | C | D | E | F | G | H | I | J | K | L | M | N |
|---|---|---|---|---|---|---|---|---|---|---|---|---|---|---|
| 123 | | CLINICAL TRIAL MATERIAL COORDINATION | 12.0 | 833.75 | 10,005.00 | | | | 0.00 | | | | 0.00 | 0.00 |
| 124 | | GRANTS | 123.0 | 5,100.00 | 627,300.00 | | | | 0.00 | | | | 0.00 | 0.00 |
| 125 | | TRAVEL MONITOR | 96.0 | 868.75 | 83,400.00 | | | | 0.00 | | | | 0.00 | 0.00 |
| 126 | | REGULATORY | | | 24,000.00 | | | | 0.00 | | | | 0.00 | 0.00 |
| 127 | | CENTRAL IRB COSTS | 12.0 | 2,000.00 | 24,000.00 | | | | 0.00 | | | | 0.00 | 0.00 |
| 128 | | ADVERTISING | | | 0.00 | | | | 0.00 | | | | 0.00 | 0.00 |
| 129 | | Other (Contingencies) | | | 0.00 | | | | 0.00 | | | | 0.00 | 0.00 |
| 130 | | PURCHASE OF 13 SCALES ( $ 1300 each) | 12.0 | 2,400.00 | 28,800.00 | | | | 0.00 | | | | 0.00 | 0.00 |
| 131 | | PURCHASE OF 26 CALIBRATION WEIGHTS | | | 0.00 | | | | | | | | | | |
| 133 | | PharmaForm | | | 8,400.04 | | | | 0.00 | | | | 0.00 | 0.00 |
| 134 | | Distribution to Clinical Site | 20.0 | 350.00 | 7,000.00 | | | | | | | | | |
| 135 | | Shipment | 12.0 | 116.67 | 1,400.04 | | | | 0.00 | | | | 0.00 | 0.00 |
| 137 | | ENTITY #6 | | | 6,108.00 | | | | 0.00 | | | | 0.00 | 0.00 |
| 138 | | Estimated Transportation Costs: | | | 6,108.00 | | | | 0.00 | | | | 0.00 | 0.00 |
| 139 | | Outbound (7) | 12.0 | 63.00 | 756.00 | | | | 0.00 | | | | 0.00 | 0.00 |
| 140 | | Inbound RT –Screen | 246.0 | 12.00 | 2,952.00 | | | | 0.00 | | | | 0.00 | 0.00 |
| 141 | | Inbound RT –Screen Cooled | 80.0 | 15.00 | 1,200.00 | | | | 0.00 | | | | 0.00 | 0.00 |
| 142 | | Inbound RT - Enrolled - Visit 7 | 100.0 | 12.00 | 1,200.00 | | | | 0.00 | | | | 0.00 | 0.00 |
| 144 | | ERT | | | 1,152.00 | | | | 0.00 | | | | 0.00 | 0.00 |
| 145 | | Pass Through/Courier Shipments | 24.0 | 48.00 | 1,152.00 | | | | 0.00 | | | | 0.00 | 0.00 |
| 147 | | ENTITY #1 | | | 38,032.00 | | | | 0.00 | | | | 0.00 | 0.00 |
| 148 | | Travel to Client Meetings | 3.0 | 1,000.00 | 3,000.00 | | | | 0.00 | | | | 0.00 | 0.00 |
| 149 | | Travel for Audit Visits | 1.0 | | 0.00 | | | | 0.00 | | | | 0.00 | 0.00 |
| 150 | | Meetings and Teleconferences | 53.8 | 150.00 | 8,064.00 | | | | 0.00 | | | | 0.00 | 0.00 |
| 151 | | Printing, Shipping and Other | 1.0 | | 0.00 | | | | 0.00 | | | | 0.00 | 0.00 |
| 152 | | IVRS Expenses | 12.0 | 164.00 | 1,968.00 | | | | 0.00 | | | | 0.00 | 0.00 |
| 153 | | Translation | 1.0 | | 0.00 | | | | 0.00 | | | | 0.00 | 0.00 |
| 154 | | Advertising | 1.0 | | 0.00 | | | | 0.00 | | | | 0.00 | 0.00 |
| 155 | | OTHER CONTINGENCIES | 1.0 | 25,000.00 | 25,000.00 | | | | 0.00 | | | | 0.00 | 0.00 |
| 156 | | Reserved | 1.0 | 0.00 | 0.00 | | | | 0.00 | | | | 0.00 | 0.00 |
| 157 | | TOTAL PASS-THROUGH EXPENSES | | | 884,797.04 | | | | | | | | | | |
| 159 | | TOTAL BY VENDOR | | | | | | | | | | | | |
| 160 | | ENTITY #4 | | | 1,360,988.9 | | | | 0.00 | | | | 0.00 | 0.00 |
| 161 | | Pharma Form | | | 40,302.24 | | | | 0.00 | | | | 0.00 | 0.00 |
| 162 | | ENTITY #6 | | | 54,257.00 | | | | 0.00 | | | | 0.00 | 0.00 |
| 163 | | eRT | | | 44,048.00 | | | | 0.00 | | | | 0.00 | 0.00 |
| 164 | | ENTITY #1 | | | 729,500.00 | | | | 0.00 | | | | 0.00 | 0.00 |
| 166 | | Reserved | | | 0.00 | | | | 0.00 | | | | 0.00 | 0.00 |
| 168 | | TOTAL PROJECT | | | 2,229,096.16 | | | | 0.00 | | | | 0.00 | 0.00 |

Figure 4E

| | AK | AL | AM | AN | AO | AP | AR | AS | AT | AU | AV | AW | AX | AY | AZ |
|---|---|---|---|---|---|---|---|---|---|---|---|---|---|---|---|
| | CO # 07 | | Unit | Unit Price | CO # 08 | Unit | Unit Price | CO # 09 | | Unit | Unit Price | CO # 10 | | Units | Numoda Contract Value |
| 1 | | | | | | | | | | | | | | | |
| 2 | 0.00 | | | | 0.00 | | | 0.00 | | | | 0.00 | | 0.00 | 529,883.92 |
| 3 | 0.00 | | | | 0.00 | | | 0.00 | | | | 0.00 | | | 90,586.00 |
| 4 | 0.00 | | | | 0.00 | | | 0.00 | | | | 0.00 | | 12.00 | 11,340.00 |
| 5 | 0.00 | | | | 0.00 | | | 0.00 | | | | 0.00 | | 12.00 | 17,052.00 |
| 6 | 0.00 | | | | 0.00 | | | 0.00 | | | | 0.00 | | 12.00 | 18,468.00 |
| 7 | | | | | | | | | | | | | | | |
| 8 | 0.00 | | | | 0.00 | | | 0.00 | | | | 0.00 | | 1.00 | 26,514.00 |
| 9 | 0.00 | | | | 0.00 | | | 0.00 | | | | 0.00 | | 0.00 | 0.00 |
| 10 | 0.00 | | | | 0.00 | | | 0.00 | | | | 0.00 | | 1.00 | 4,328.00 |
| 11 | 0.00 | | | | 0.00 | | | 0.00 | | | | 0.00 | | 1.00 | 12,884.00 |
| 12 | 0.00 | | | | 0.00 | | | 0.00 | | | | 0.00 | | 0.00 | 0.00 |
| 13 | 0.00 | | | | 0.00 | | | 0.00 | | | | 0.00 | | | 105,462.00 |
| 14 | 0.00 | | | | 0.00 | | | 0.00 | | | | 0.00 | | 12.00 | 84,780.00 |
| 15 | 0.00 | | | | 0.00 | | | 0.00 | | | | 0.00 | | 12.00 | 8,932.08 |
| 16 | 0.00 | | | | 0.00 | | | 0.00 | | | | 0.00 | | 24.00 | 7,872.96 |
| 17 | 0.00 | | | | 0.00 | | | 0.00 | | | | 0.00 | | 12.00 | 3,876.96 |
| 18 | 0.00 | | | | 0.00 | | | 0.00 | | | | 0.00 | | 0.00 | 0.00 |
| 19 | 0.00 | | | | 0.00 | | | 0.00 | | | | 0.00 | | 0.00 | 0.00 |
| 20 | 0.00 | | | | 0.00 | | | 0.00 | | | | 0.00 | | | 205,695.96 |
| 21 | 0.00 | | | | 0.00 | | | 0.00 | | | | 0.00 | | 12.00 | 18,327.96 |
| 22 | 0.00 | | | | 0.00 | | | 0.00 | | | | 0.00 | | 72.00 | 153,336.96 |
| 23 | 0.00 | | | | 0.00 | | | 0.00 | | | | 0.00 | | 12.00 | 18,965.04 |
| 24 | 0.00 | | | | 0.00 | | | 0.00 | | | | 0.00 | | 12.00 | 3,402.00 |
| 25 | 0.00 | | | | 0.00 | | | 0.00 | | | | 0.00 | | 12.00 | 11,664.00 |
| 26 | 0.00 | | | | 0.00 | | | 0.00 | | | | 0.00 | | 0.00 | 0.00 |
| 27 | 0.00 | | | | 0.00 | | | 0.00 | | | | 0.00 | | 0.00 | 0.00 |
| 28 | 0.00 | | | | 0.00 | | | 0.00 | | | | 0.00 | | 0.00 | 0.00 |
| 29 | 0.00 | | | | 0.00 | | | 0.00 | | | | 0.00 | | 0.00 | 0.00 |
| 30 | 0.00 | | | | 0.00 | | | 0.00 | | | | 0.00 | | 0.00 | 37,047.96 |
| 31 | 0.00 | | | | 0.00 | | | 0.00 | | | | 0.00 | | 12.00 | 37,047.96 |
| 32 | 0.00 | | | | 0.00 | | | 0.00 | | | | 0.00 | | 0.00 | 0.00 |
| 33 | 0.00 | | | | 0.00 | | | 0.00 | | | | 0.00 | | 0.00 | 0.00 |
| 34 | 0.00 | | | | 0.00 | | | 0.00 | | | | 0.00 | | | 84,072.00 |
| 35 | 0.00 | | | | 0.00 | | | 0.00 | | | | 0.00 | | 12.00 | 8,856.00 |
| 36 | 0.00 | | | | 0.00 | | | 0.00 | | | | 0.00 | | 1.00 | 12,160.00 |
| 37 | 0.00 | | | | 0.00 | | | 0.00 | | | | 0.00 | | 1.00 | 54,888.00 |
| 38 | 0.00 | | | | 0.00 | | | 0.00 | | | | 0.00 | | 1.00 | 6,732.00 |
| 39 | 0.00 | | | | 0.00 | | | 0.00 | | | | 0.00 | | 1.00 | 1,436.00 |

Figure 4F

| | AK | AL | AM | AN | AO | AP | AR | AS | AT | AU | AV | AW | AX | AY | AZ |
|---|---|---|---|---|---|---|---|---|---|---|---|---|---|---|---|
| 43 | | | | | | | | | | | | | | | |
| 44 | 0.00 | | | | 0.00 | | | 0.00 | | | | 0.00 | | | 7,020.00 |
| 45 | 0.00 | | | | 0.00 | | | 0.00 | | | | 0.00 | | 0.00 | 0.00 |
| 46 | 0.00 | | | | 0.00 | | | 0.00 | | | | 0.00 | | 12.00 | 7,020.00 |
| 48 | 0.00 | | | | 0.00 | | | 0.00 | | | | 0.00 | | | 31,902.20 |
| 49 | 0.00 | | | | 0.00 | | | 0.00 | | | | 0.00 | | | 31,902.20 |
| 50 | 0.00 | | | | 0.00 | | | 0.00 | | | | 0.00 | | 1.00 | 500.00 |
| 51 | 0.00 | | | | 0.00 | | | 0.00 | | | | 0.00 | | 1.00 | 3,000.00 |
| 52 | 0.00 | | | | 0.00 | | | 0.00 | | | | 0.00 | | 2,000.00 | 2,500.00 |
| 53 | 0.00 | | | | 0.00 | | | 0.00 | | | | 0.00 | | 3.00 | 3,501.00 |
| 54 | 0.00 | | | | 0.00 | | | 0.00 | | | | 0.00 | | 667.00 | 2,401.20 |
| 55 | 0.00 | | | | 0.00 | | | 0.00 | | | | 0.00 | | 1.00 | 2,500.00 |
| 56 | 0.00 | | | | 0.00 | | | 0.00 | | | | 0.00 | | 1.00 | 17,500.00 |
| 57 | 0.00 | | | | 0.00 | | | 0.00 | | | | 0.00 | | 0.00 | 0.00 |
| 59 | 0.00 | | | | 0.00 | | | 0.00 | | | | 0.00 | | | 48,149.00 |
| 60 | 0.00 | | | | 0.00 | | | 0.00 | | | | 0.00 | | | 15,280.04 |
| 61 | 0.00 | | | | 0.00 | | | 0.00 | | | | 0.00 | | 246.00 | 2,952.00 |
| 62 | 0.00 | | | | 0.00 | | | 0.00 | | | | 0.00 | | 246.00 | 2,214.00 |
| 63 | 0.00 | | | | 0.00 | | | 0.00 | | | | 0.00 | | 246.00 | 2,214.00 |
| 64 | 0.00 | | | | 0.00 | | | 0.00 | | | | 0.00 | | 73.80 | 1,474.52 |
| 65 | 0.00 | | | | 0.00 | | | 0.00 | | | | 0.00 | | 246.00 | 4,580.52 |
| 66 | 0.00 | | | | 0.00 | | | 0.00 | | | | 0.00 | | 123.00 | 1,845.00 |
| 67 | 0.00 | | | | 0.00 | | | 0.00 | | | | 0.00 | | | 4,428.00 |
| 68 | 0.00 | | | | 0.00 | | | 0.00 | | | | 0.00 | | 98.40 | 1,180.80 |
| 69 | 0.00 | | | | 0.00 | | | 0.00 | | | | 0.00 | | 98.40 | 885.60 |
| 70 | 0.00 | | | | 0.00 | | | 0.00 | | | | 0.00 | | 98.40 | 885.60 |
| 71 | 0.00 | | | | 0.00 | | | 0.00 | | | | 0.00 | | 98.40 | 1,476.00 |
| 72 | 0.00 | | | | 0.00 | | | 0.00 | | | | 0.00 | | | 3,419.40 |
| 73 | 0.00 | | | | 0.00 | | | 0.00 | | | | 0.00 | | 246.00 | 1,722.00 |
| 74 | 0.00 | | | | 0.00 | | | 0.00 | | | | 0.00 | | 98.40 | 492.00 |
| 75 | 0.00 | | | | 0.00 | | | 0.00 | | | | 0.00 | | 98.40 | 688.80 |
| 76 | 0.00 | | | | 0.00 | | | 0.00 | | | | 0.00 | | 73.80 | 516.60 |
| 77 | 0.00 | | | | 0.00 | | | 0.00 | | | | 0.00 | | 1.00 | 4,000.00 |
| 78 | 0.00 | | | | 0.00 | | | 0.00 | | | | 0.00 | | 1.00 | 3,000.00 |
| 79 | 0.00 | | | | 0.00 | | | 0.00 | | | | 0.00 | | 10.00 | 1,700.00 |
| 80 | 0.00 | | | | 0.00 | | | 0.00 | | | | 0.00 | | 1.00 | 16,321.56 |
| 81 | 0.00 | | | | 0.00 | | | 0.00 | | | | 0.00 | | 0.00 | 0.00 |
| 82 | 0.00 | | | | 0.00 | | | 0.00 | | | | 0.00 | | 0.00 | 0.00 |
| 83 | 0.00 | | | | 0.00 | | | 0.00 | | | | 0.00 | | 0.00 | 0.00 |
| 85 | 0.00 | | | | 0.00 | | | 0.00 | | | | 0.00 | | | 42,896.00 |

Figure 4G

| | AK | AL | AM | AN | AO | AP | AR | AS | AT | AU | AV | AW | AX | AY | AZ |
|---|---|---|---|---|---|---|---|---|---|---|---|---|---|---|---|
| 86 | 0.00 | | | | 0.00 | | | 0.00 | | | | 0.00 | | 10.00 | 3,478.50 |
| 87 | 0.00 | | | | 0.00 | | | 0.00 | | | | 0.00 | | | 16,605.00 |
| 88 | 0.00 | | | | 0.00 | | | 0.00 | | | | 0.00 | | 369.00 | 16,605.00 |
| 89 | 0.00 | | | | 0.00 | | | 0.00 | | | | 0.00 | | | 22,812.50 |
| 90 | 0.00 | | | | 0.00 | | | 0.00 | | | | 0.00 | | 108.00 | 16,200.00 |
| 91 | 0.00 | | | | 0.00 | | | 0.00 | | | | 0.00 | | 4,200.00 | 1,680.00 |
| 92 | 0.00 | | | | 0.00 | | | 0.00 | | | | 0.00 | | 12.00 | 300.00 |
| 93 | 0.00 | | | | 0.00 | | | 0.00 | | | | 0.00 | | 1.00 | 4,632.50 |
| 94 | 0.00 | | | | 0.00 | | | 0.00 | | | | 0.00 | | | 691,468.00 |
| 95 | 0.00 | | | | 0.00 | | | 0.00 | | | | 0.00 | | | 154,833.00 |
| 96 | 0.00 | | | | 0.00 | | | 0.00 | | | | 0.00 | | 12.00 | 29,364.00 |
| 97 | 0.00 | | | | 0.00 | | | 0.00 | | | | 0.00 | | 12.00 | 28,459.00 |
| 98 | 0.00 | | | | 0.00 | | | 0.00 | | | | 0.00 | | 12.00 | 38,010.00 |
| 99 | 0.00 | | | | 0.00 | | | 0.00 | | | | 0.00 | | 12.00 | 59,000.00 |
| 100 | 0.00 | | | | 0.00 | | | 0.00 | | | | 0.00 | | 0.00 | 0.00 |
| 101 | 0.00 | | | | 0.00 | | | 0.00 | | | | 0.00 | | 0.00 | 0.00 |
| 102 | 0.00 | | | | 0.00 | | | 0.00 | | | | 0.00 | | 0.00 | 317,674.00 |
| 103 | 0.00 | | | | 0.00 | | | 0.00 | | | | 0.00 | | 0.00 | 0.00 |
| 104 | 0.00 | | | | 0.00 | | | 0.00 | | | | 0.00 | | 0.00 | 0.00 |
| 105 | 0.00 | | | | 0.00 | | | 0.00 | | | | 0.00 | | 12.00 | 68,776.00 |
| 106 | 0.00 | | | | 0.00 | | | 0.00 | | | | 0.00 | | 8,612.00 | 216,585.00 |
| 107 | 0.00 | | | | 0.00 | | | 0.00 | | | | 0.00 | | 0.00 | 0.00 |
| 108 | 0.00 | | | | 0.00 | | | 0.00 | | | | 0.00 | | 12.00 | 32,313.00 |
| 109 | 0.00 | | | | 0.00 | | | 0.00 | | | | 0.00 | | 0.00 | 0.00 |
| 110 | 0.00 | | | | 0.00 | | | 0.00 | | | | 0.00 | | 0.00 | 0.00 |
| 111 | 0.00 | | | | 0.00 | | | 0.00 | | | | 0.00 | | 12.00 | 218,961.00 |
| 112 | 0.00 | | | | 0.00 | | | 0.00 | | | | 0.00 | | 12.00 | 23,671.00 |
| 113 | 0.00 | | | | 0.00 | | | 0.00 | | | | 0.00 | | 12.00 | 28,047.00 |
| 114 | 0.00 | | | | 0.00 | | | 0.00 | | | | 0.00 | | 12.00 | 27,222.00 |
| 115 | 0.00 | | | | 0.00 | | | 0.00 | | | | 0.00 | | 12.00 | 28,809.00 |
| 116 | 0.00 | | | | 0.00 | | | 0.00 | | | | 0.00 | | 12.00 | 28,715.00 |
| 117 | 0.00 | | | | 0.00 | | | 0.00 | | | | 0.00 | | 12.00 | 17,378.00 |
| 118 | 0.00 | | | | 0.00 | | | 0.00 | | | | 0.00 | | 12.00 | 65,119.00 |
| 119 | 0.00 | | | | 0.00 | | | 0.00 | | | | 0.00 | | | 0.00 |
| 120 | 0.00 | | | | 0.00 | | | 0.00 | | | | 0.00 | | | 1,344,299.12 |
| 121 | 0.00 | | | | 0.00 | | | 0.00 | | | | 0.00 | | | 831,105.00 |
| 122 | 0.00 | | | | 0.00 | | | 0.00 | | | | 0.00 | | 1.00 | 57,600.00 |

Figure 4H

| | AK | AL | AM | AN | AO | AP | AR | AS | AT | AU | AV | AW | AX | AY | AZ |
|---|---|---|---|---|---|---|---|---|---|---|---|---|---|---|---|
| 123 | 0.00 | | | | 0.00 | | | 0.00 | | | | 0.00 | | 12.00 | 10,005.00 |
| 124 | 0.00 | | | | 0.00 | | | 0.00 | | | | 0.00 | | 123.00 | 627,300.00 |
| 125 | 0.00 | | | | 0.00 | | | 0.00 | | | | 0.00 | | 96.00 | 83,400.00 |
| 126 | 0.00 | | | | 0.00 | | | 0.00 | | | | 0.00 | | | 24,000.00 |
| 127 | 0.00 | | | | 0.00 | | | 0.00 | | | | 0.00 | | 12.00 | 24,000.00 |
| 128 | 0.00 | | | | 0.00 | | | 0.00 | | | | 0.00 | | 0.00 | 0.00 |
| 129 | 0.00 | | | | 0.00 | | | 0.00 | | | | 0.00 | | 0.00 | 0.00 |
| 130 | 0.00 | | | | 0.00 | | | 0.00 | | | | 0.00 | | 12.00 | 28,800.00 |
| 131 | 0.00 | | | | 0.00 | | | 0.00 | | | | 0.00 | | 0.00 | 0.00 |
| 133 | 0.00 | | | | 0.00 | | | 0.00 | | | | 0.00 | | | 8,400.04 |
| 134 | | | | | | | | | | | | | | 20.00 | 7,000.00 |
| 135 | 0.00 | | | | 0.00 | | | 0.00 | | | | 0.00 | | 12.00 | 1,400.04 |
| 137 | 0.00 | | | | 0.00 | | | 0.00 | | | | 0.00 | | | 6,108.00 |
| 138 | 0.00 | | | | 0.00 | | | 0.00 | | | | 0.00 | | 12.00 | 6,108.00 |
| 139 | 0.00 | | | | 0.00 | | | 0.00 | | | | 0.00 | | 12.00 | 756.00 |
| 140 | 0.00 | | | | 0.00 | | | 0.00 | | | | 0.00 | | 246.00 | 2,952.00 |
| 141 | 0.00 | | | | 0.00 | | | 0.00 | | | | 0.00 | | 80.00 | 1,200.00 |
| 142 | 0.00 | | | | 0.00 | | | 0.00 | | | | 0.00 | | 100.00 | 1,200.00 |
| 144 | 0.00 | | | | 0.00 | | | 0.00 | | | | 0.00 | | | 1,152.00 |
| 145 | 0.00 | | | | 0.00 | | | 0.00 | | | | 0.00 | | 24.00 | 1,152.00 |
| 147 | 0.00 | | | | 0.00 | | | 0.00 | | | | 0.00 | | | 38,032.00 |
| 148 | 0.00 | | | | 0.00 | | | 0.00 | | | | 0.00 | | 3.00 | 3,000.00 |
| 149 | 0.00 | | | | 0.00 | | | 0.00 | | | | 0.00 | | 1.00 | 0.00 |
| 150 | 0.00 | | | | 0.00 | | | 0.00 | | | | 0.00 | | 53.76 | 8,064.00 |
| 151 | 0.00 | | | | 0.00 | | | 0.00 | | | | 0.00 | | 1.00 | 0.00 |
| 152 | 0.00 | | | | 0.00 | | | 0.00 | | | | 0.00 | | 12.00 | 1,968.00 |
| 153 | 0.00 | | | | 0.00 | | | 0.00 | | | | 0.00 | | 1.00 | 0.00 |
| 154 | 0.00 | | | | 0.00 | | | 0.00 | | | | 0.00 | | 1.00 | 0.00 |
| 155 | 0.00 | | | | 0.00 | | | 0.00 | | | | 0.00 | | 1.00 | 25,000.00 |
| 156 | 0.00 | | | | 0.00 | | | 0.00 | | | | 0.00 | | | 0.00 |
| 157 | 0.00 | | | | 0.00 | | | 0.00 | | | | 0.00 | | | 884,797.04 |
| 160 | 0.00 | | | | 0.00 | | | 0.00 | | | | 0.00 | | | 1,360,988.92 |
| 161 | 0.00 | | | | 0.00 | | | 0.00 | | | | 0.00 | | | 40,302.24 |
| 162 | 0.00 | | | | 0.00 | | | 0.00 | | | | 0.00 | | | 54,257.00 |
| 163 | 0.00 | | | | 0.00 | | | 0.00 | | | | 0.00 | | | 44,048.00 |
| 164 | 0.00 | | | | 0.00 | | | 0.00 | | | | 0.00 | | | 729,500.00 |
| 165 | | | | | | | | | | | | | | | |
| 166 | 0.00 | | | | 0.00 | | | 0.00 | | | | 0.00 | | | 0.00 |
| 167 | | | | | | | | | | | | | | | |
| 168 | 0.00 | | | | 0.00 | | | 0.00 | | | | 0.00 | | | 2,229,096.16 |

Figure 5A

| A | B | C | D | E | F | G | H | I | J | K |
|---|---|---|---|---|---|---|---|---|---|---|
| 1 |   |   | Advance |   | Screening |   | Visit 01 |   | Visit 02 |   |
| 2 |   | Investig |   |   |   |   |   |   |   |   |
| 3 |   |   |   |   |   |   |   |   |   |   |
| 4 |   |   | 12 |   | - |   | 99 |   |   |   |
| 5 |   |   |   |   |   |   |   |   |   |   |
| 6 |   |   |   |   |   |   |   |   |   |   |
| 7 |   | Per Site | Total |   |   |   |   |   |   |   |
| 8 |   | Advance | 10,200 | 122,400 |   |   |   |   |   |   |
| 9 |   |   |   |   |   |   |   |   |   |   |
| 10 |   | Enrolled | Per Patient | Total |   |   |   |   |   |   |
| 11 |   | Screening |   | - |   | - |   |   |   |   |
| 12 |   |   |   |   |   |   |   |   |   |   |
| 13 |   | Visit 1 | 1,219 | 120,681 |   |   |   | 120,681 |   |   |
| 14 |   |   |   |   |   |   |   |   |   |   |
| 15 |   | Visit 2 | 344 | 26,144 |   |   |   |   |   | 26,144 |
| 16 |   |   |   |   |   |   |   |   |   |   |
| 17 |   | Visit 3 | 594 | 33,264 |   |   |   |   |   |   |
| 18 |   |   |   |   |   |   |   |   |   |   |
| 19 |   | Visit 4 | 563 | 25,898 |   |   |   |   |   |   |
| 20 |   |   |   |   |   |   |   |   |   |   |
| 21 |   | Visit 5 | 563 | 22,520 |   |   |   |   |   |   |
| 22 |   |   |   |   |   |   |   |   |   |   |
| 23 |   | Visit 6 | 563 | 18,579 |   |   |   |   |   |   |
| 24 |   |   |   |   |   |   |   |   |   |   |
| 25 |   | Visit 7 | 1,254 | 25,080 |   |   |   |   |   |   |
| 26 |   |   |   |   |   |   |   |   |   |   |
| 27 |   | Visit 8 |   | - |   |   |   |   |   |   |
| 28 |   |   |   |   |   |   |   |   |   |   |
| 29 |   | Visit 9 |   | - |   |   |   |   |   |   |
| 30 |   |   |   |   |   |   |   |   |   |   |
| 31 |   | Visit 10 |   | - |   |   |   |   |   |   |
| 32 |   |   |   |   |   |   |   |   |   |   |
| 33 |   | Visit 11 |   | - |   |   |   |   |   |   |
| 34 |   |   |   |   |   |   |   |   |   |   |
| 35 |   |   | Per Patient | Total |   |   |   |   |   |   |
| 36 |   | Completed | 5,100 |   |   |   |   |   |   |   |
| 37 |   |   |   |   |   |   |   |   |   |   |
| 38 |   |   | Per Patient | Total |   |   |   |   |   |   |
| 39 |   | Screen | - | - |   | - |   |   |   |   |
| 40 |   |   |   |   |   |   |   |   |   |   |
| 41 |   |   | Total Investigator Grants |   |   | - |   | 120,68 |   | 26,144 |
| 42 |   |   |   |   |   |   |   |   |   |   |
| 43 |   |   |   |   |   |   |   |   |   |   |
| 44 |   |   |   |   |   |   |   |   |   |   |
| 45 |   |   |   |   |   |   |   |   |   |   |
| 46 |   |   |   |   |   |   |   |   |   |   |
| 47 |   |   |   |   |   |   |   |   |   |   |
| 48 |   |   |   |   |   |   |   |   |   |   |
| 49 |   |   |   |   |   |   |   |   |   |   |
| 50 |   |   |   |   |   |   |   |   |   |   |
| 51 |   |   |   |   |   |   |   |   |   |   |
| 52 |   |   |   |   |   |   |   |   |   |   |

Figure 5B

| | L | M | N | O | P | Q | R | S | T | U | V | W | X | Y |
|---|---|---|---|---|---|---|---|---|---|---|---|---|---|---|
| 1 | Visit 03 | | Visit 04 | | Visit 05 | | Visit 06 | | Visit 07 | | Visit 08 | | Visit 09 | |
| 2 | | | | | | | | | | | | | | |
| 3 | | | | | | | | | | | | | | |
| 4 | 56 | | 46 | | 40 | | 33 | | 20 | | | | | |
| 5 | | | | | | | | | | | | | | |
| 6 | | | | | | | | | | | | | | |
| 7 | | | | | | | | | | | | | | |
| 8 | | | | | | | | | | | | | | |
| 9 | | | | | | | | | | | | | | |
| 10 | | | | | | | | | | | | | | |
| 11 | | | | | | | | | | | | | | |
| 12 | | | | | | | | | | | | | | |
| 13 | | | | | | | | | | | | | | |
| 14 | | | | | | | | | | | | | | |
| 15 | | | | | | | | | | | | | | |
| 16 | | | | | | | | | | | | | | |
| 17 | 33,264 | | | | | | | | | | | | | |
| 18 | | | | | | | | | | | | | | |
| 19 | | | 25,898 | | | | | | | | | | | |
| 20 | | | | | | | | | | | | | | |
| 21 | | | | | 22,520 | | | | | | | | | |
| 22 | | | | | | | | | | | | | | |
| 23 | | | | | | | 18,579 | | | | | | | |
| 24 | | | | | | | | | | | | | | |
| 25 | | | | | | | | | 25,080 | | | | | |
| 26 | | | | | | | | | | | | | | |
| 27 | | | | | | | | | | | | | | |
| 28 | | | | | | | | | | | | | | |
| 29 | | | | | | | | | | | | | | |
| 30 | | | | | | | | | | | | | | |
| 31 | | | | | | | | | | | | | | |
| 32 | | | | | | | | | | | | | | |
| 33 | | | | | | | | | | | | | | |
| 34 | | | | | | | | | | | | | | |
| 35 | | | | | | | | | | | | | | |
| 36 | | | | | | | | | | | | | | |
| 37 | | | | | | | | | | | | | | |
| 38 | | | | | | | | | | | | | | |
| 39 | | | | | | | | | | | | | | |
| 40 | | | | | | | | | | | | | | |
| 41 | 33,264 | | 25,898 | | 22,520 | | 18,579 | | 25,080 | | | | | |
| 42 | | | | | | | | | | | | | | |
| 43 | | | | | | | | | | | | | | |
| 44 | | | | | | | | | | | | | | |
| 45 | | | | | | | | | | | | | | |
| 46 | | | | | | | | | | | | | | |
| 47 | | | | | | | | | | | | | | |
| 48 | | | | | | | | | | | | | | |
| 49 | | | | | | | | | | | | | | |
| 50 | | | | | | | | | | | | | | |
| 51 | | | | | | | | | | | | | | |
| 52 | | | | | | | | | | | | | | |

Figure 5C

| | Z | AA | AB | AC | AD | AE | AF | AG | AH | AI | A |
|---|---|---|---|---|---|---|---|---|---|---|---|
| 1 | Visit 10 | | Visit 11 | | Visit 12 | | Visit 13 | | Visit 14 | | Visit 15 |
| 2 | | | | | | | | | | | |
| 3 | | | | | | | | | | | |
| 4 | 0 | | 0 | | | | | | | | |
| 5 | | | | | | | | | | | |
| 6 | | | | | | | | | | | |
| 7 | | | | | | | | | | | |
| 8 | | | | | | | | | | | |
| 9 | | | | | | | | | | | |
| 10 | | | | | | | | | | | |
| 11 | | | | | | | | | | | |
| 12 | | | | | | | | | | | |
| 13 | | | | | | | | | | | |
| 14 | | | | | | | | | | | |
| 15 | | | | | | | | | | | |
| 16 | | | | | | | | | | | |
| 17 | | | | | | | | | | | |
| 18 | | | | | | | | | | | |
| 19 | | | | | | | | | | | |
| 20 | | | | | | | | | | | |
| 21 | | | | | | | | | | | |
| 22 | | | | | | | | | | | |
| 23 | | | | | | | | | | | |
| 24 | | | | | | | | | | | |
| 25 | | | | | 25,080 | | | | | | |
| 26 | | | | | | | | | | | |
| 27 | | | | | | | - | | | | |
| 28 | | | | | | | | | | | |
| 29 | | | | | | | | | - | | |
| 30 | | | | | | | | | | | |
| 31 | | - | | - | | | | | | | - |
| 32 | | | | | | | | | | | |
| 33 | | | | | | | | | | | |
| 34 | | | | | | | | | | | |
| 35 | | | | | | | | | | | |
| 36 | | | | | | | | | | | |
| 37 | | | | | | | | | | | |
| 38 | | | | | | | | | | | |
| 39 | | - | | - | | - | | - | | - | - |
| 40 | | | | | | | | | | | |
| 41 | | - | | - | | 25,080 | | - | | - | - |
| 42 | | | | | | | | | | | |
| 43 | | | | | | | | | | | |
| 44 | | | | | | | | | | | |
| 45 | | | | | | | | | | | |
| 46 | | | | | | | | | | | |
| 47 | | | | | | | | | | | |
| 48 | | | | | | | | | | | |
| 49 | | | | | | | | | | | |
| 50 | | | | | | | | | | | |
| 51 | | | | | | | | | | | |
| 52 | | | | | | | | | | | |

Figure 5D

| | AK | AL | AM | AN | AO | AP | AQ | AR | AS | AT | AU | AV |
|---|---|---|---|---|---|---|---|---|---|---|---|---|
| 1 | | Visit 16 | | Visit 17 | | Visit 18 | | Visit 19 | | Visit 20 | | Completed |
| 2 | | | | | | | | | | | | |
| 3 | | | | | | | | | | | | |
| 4 | | | | | | | | | | | | |
| 5 | | | | | | | | | | | | |
| 6 | | | | | | | | | | | | |
| 7 | | | | | | | | | | | | |
| 8 | | | | | | | | | | | | 122,400 |
| 9 | | | | | | | | | | | | |
| 10 | | | | | | | | | | | | |
| 11 | | | | | | | | | | | | - |
| 12 | | | | | | | | | | | | |
| 13 | | | | | | | | | | | | 120,681 |
| 14 | | | | | | | | | | | | |
| 15 | | | | | | | | | | | | 26,144 |
| 16 | | | | | | | | | | | | |
| 17 | | | | | | | | | | | | 33,264 |
| 18 | | | | | | | | | | | | |
| 19 | | | | | | | | | | | | 25,898 |
| 20 | | | | | | | | | | | | |
| 21 | | | | | | | | | | | | 22,520 |
| 22 | | | | | | | | | | | | |
| 23 | | | | | | | | | | | | 18,579 |
| 24 | | | | | | | | | | | | |
| 25 | | | | | 25,080 | | | | | | | 25,080 |
| 26 | | | | | | | | | | | | |
| 27 | | | | | | | | | | | | - |
| 28 | | | | | | | | | | | | |
| 29 | | | | | | | | | | | | - |
| 30 | | | | | | | | | | | | |
| 31 | | - | | | | | | | | - | | |
| 32 | | | | | | | | | | | | |
| 33 | | | | | | | | | | | | |
| 34 | | | | | | | | | | | | |
| 35 | | | | | | | | | | | | |
| 36 | | | | | | | | | | | | - |
| 37 | | | | | | | | | | | | |
| 38 | | | | | | | | | | | | |
| 39 | | - | | | | | | | | - | | - |
| 40 | | | | | | | | | | | | |
| 41 | | - | | 25,080 | | | | | | - | | 394,566 |
| 42 | | | | | | | | | | | | |
| 43 | | | | | | | | | | | | (122,400) |
| 44 | | | | | | | | | | | | |
| 45 | | | | | | | | | | | | 272,166 |
| 46 | | | | | | | | | | | | |
| 47 | | | | | | | | | | | | |
| 48 | | | | | | | | | | | | |
| 49 | | | | | | | | | | | | 394,566 |
| 50 | | | | | | | | | | | | |
| 51 | | | | | | | | | | | | |
| 52 | | | | | | | | | | | | |

Figure 6A

| | A | B | C | D | E | F | G | H |
|---|---|---|---|---|---|---|---|---|
| 1 | | | | | | | | |
| 2 | | | Current | Date | Date | Drug | | |
| 3 | PatientID | Initials | Status | Randomized/ | Disc'ned | Dispensed | | |
| 4 | | | | (Screened) | | | V1 | V2 |
| 5 | 10001 | PLR | R | 26-Nov-07 | | Y | | 11/7/2007 |
| 6 | 10002 | J-P | D | 15-Nov-07 | 11/29/2007 | Y | 10/30/2007 | 11/9/2007 |
| 7 | 10003 | LCS | R | 13-Nov-07 | | Y | 10/30/2007 | 11/7/2007 |
| 8 | 10004 | SAT | R | 21-Dec-07 | | Y | 12/7/2007 | 12/14/2007 |
| 9 | 10005 | CRK | R | 24-Jan-08 | | Y | 1/9/2008 | 1/17/2008 |
| 10 | 10006 | N-R | R | 24-Jan-08 | | Y | 1/11/2008 | 1/17/2008 |
| 11 | 10007 | TMB | R | 1-Feb-08 | | Y | 1/14/2008 | 1/24/2008 |
| 12 | 10008 | LMS | AS | (01/28/08) | | N | 1/28/2008 | 2/4/2008 |
| 13 | 10009 | BLA | AS | (02/05/08) | | N | 2/5/2008 | 2/26/2008 |
| 14 | 11001 | ELT | C | 10-Oct-07 | | Y | 9/9/2007 | 9/19/2007 |
| 15 | 11002 | C-G | IS | (09/07/07) | | N | | |
| 16 | 11003 | MAA | C | 10-Oct-07 | | Y | 9/19/2007 | 10/1/2007 |
| 17 | 11004 | C-G | IS | (11/09/07) | | N | 11/9/2007 | 11/30/2007 |
| 18 | 11005 | DLF | R | 22-Jan-08 | | Y | 1/8/2008 | 1/8/2008 |
| 19 | 11006 | EZB | SF | (01/15/08) | | N | 1/15/2008 | 1/15/2008 |
| 20 | 11007 | DJL | R | 4-Feb-08 | | Y | 1/24/2008 | 1/24/2008 |
| 21 | 11008 | J-H | W | (01/31/08) | | N | 1/31/2008 | 2/21/2008 |
| 22 | 11009 | K-R | AS | (02/05/08) | | N | 2/5/2008 | 2/5/2008 |
| 23 | 12001 | JLR | C | 30-Oct-07 | | Y | 10/11/2007 | 10/26/2007 |
| 24 | 12002 | DRG | R | 15-Jan-08 | | Y | 1/3/2008 | 1/10/2008 |
| 25 | 12003 | DCD | AS | (01/30/08) | | N | 1/30/2008 | 2/20/2008 |
| 26 | 13001 | EMM | R | 28-Dec-07 | | Y | 12/14/2007 | 12/14/2007 |
| 27 | 13002 | BJS | SF | (12/18/07) | | N | 12/18/2007 | 12/18/2007 |
| 28 | 13003 | JMR | W | (02/06/08) | | N | 2/6/2008 | 2/27/2008 |
| 29 | 14001 | CAF | C | 25-Oct-07 | | Y | 10/4/2007 | 10/17/2007 |
| 30 | 14002 | MRN | SF | (10/05/07) | | N | 10/5/2007 | |
| 31 | 14003 | RMA | C | 5-Nov-07 | | Y | 10/15/2007 | 10/29/2007 |
| 32 | 14004 | GJC | R | 6-Nov-07 | | Y | 10/16/2007 | 10/30/2007 |
| 33 | 14005 | CLF | SF | (10/17/07) | | N | 10/17/2007 | |
| 34 | 14006 | KES | R | 19-Nov-07 | | Y | 10/18/2007 | 11/9/2007 |
| 35 | 14007 | DRB | SF | (11/26/07) | | N | 11/26/2007 | |
| 36 | 14008 | KMW | IS | (11/29/07) | | N | 11/29/2007 | 12/20/2007 |
| 37 | 14009 | CMM | AS | (01/23/08) | | N | | |
| 38 | 14010 | S-W | AS | (01/24/08) | | N | | |
| 39 | 15001 | J-D | SF | (11/27/07) | | N | 11/27/2007 | |
| 40 | 15002 | D-D | SF | (11/27/07) | | N | 11/27/2007 | |
| 41 | 15004 | DGD | AS | (01/23/08) | | N | 1/23/2008 | 2/13/2008 |
| 42 | 16001 | LOC | IW | (10/25/07) | | N | 10/25/2007 | 11/15/2007 |
| 43 | 16002 | MMW | IS | (11/19/07) | | N | 11/19/2007 | 11/27/2007 |
| 44 | 16003 | AFF | D | 3-Dec-07 | 2/4/2008 | Y | 11/19/2007 | 11/26/2007 |
| 45 | 16004 | LJM | D | 3-Dec-07 | 1/28/2008 | Y | 11/19/2007 | 11/26/2007 |
| 46 | 16005 | DAD | R | 19-Dec-07 | | Y | 11/28/2007 | 12/5/2007 |
| 47 | 16006 | PAB | IS | (11/29/07) | | N | 11/29/2007 | 12/20/2007 |
| 48 | 16007 | EWD | IW | (11/30/07) | | N | 11/30/2007 | 1/23/2008 |
| 49 | 16008 | CTV | D | 2-Jan-08 | 1/8/2008 | Y | 12/19/2007 | 12/26/2007 |
| 50 | 16009 | CEB | IS | (12/12/07) | | N | 12/12/2007 | 1/25/2008 |

Figure 6B

| | I | J | K | L | M | N | O | P | Q |
|---|---|---|---|---|---|---|---|---|---|
| 1 | | | | | | | | | |
| 2 | | | Visit | | | eCRF Status | | | |
| 3 | | | | | | | | | |
| 4 | V | V | V | V6 | V7 | C | L | I/P | Q |
| 5 | 11/26/2007 | 12/12/2007 | 12/24/2007 | 1/22/2008 | 2/18/2008 | 54 | 42 | 1 | 0 |
| 6 | 11/15/2007 | | | | 11/29/2007 | 42 | 1 | 0 | 0 |
| 7 | 11/13/2007 | 11/27/2007 | 12/12/2007 | 1/11/2008 | 2/5/2008 | 53 | 1 | 1 | 0 |
| 8 | 12/21/2007 | 1/4/2008 | 1/18/2008 | 2/15/2008 | 3/14/2008 | 44 | 1 | 0 | 0 |
| 9 | 1/24/2008 | 2/7/2008 | 2/21/2008 | 3/20/2008 | 4/17/2008 | 27 | 0 | 0 | 0 |
| 10 | 1/24/2008 | 2/7/2008 | 2/21/2008 | 3/20/2008 | 4/17/2008 | 27 | 0 | 0 | 0 |
| 11 | 2/1/2008 | 2/15/2008 | 2/29/2008 | 3/28/2008 | 4/25/2008 | 26 | 0 | 1 | 0 |
| 12 | 2/11/2008 | | | | | 18 | 0 | 0 | 0 |
| 13 | | | | | | 10 | 0 | 0 | 0 |
| 14 | 10/10/2007 | 10/24/2007 | 11/7/2007 | 12/14/2007 | 1/16/2008 | 68 | 59 | 0 | 8 |
| 15 | | | | | | 0 | 0 | 10 | 0 |
| 16 | 10/10/2007 | 10/24/2007 | 11/9/2007 | 12/14/2007 | 1/7/2008 | 68 | 8 | 0 | 0 |
| 17 | | | | | | 10 | 0 | 1 | 0 |
| 18 | 1/22/2008 | 2/4/2008 | 2/19/2008 | 3/18/2008 | 4/15/2008 | 35 | 0 | 0 | 0 |
| 19 | | | | | | 18 | 0 | 0 | 0 |
| 20 | 2/4/2008 | 2/18/2008 | 3/3/2008 | 3/31/2008 | 4/28/2008 | 26 | 0 | 0 | 0 |
| 21 | | | | | | 8 | 0 | 2 | 0 |
| 22 | 2/12/2008 | | | | | 18 | 0 | 0 | 0 |
| 23 | 10/30/2007 | 11/13/2007 | 11/27/2007 | 12/26/2007 | 1/24/2008 | 68 | 58 | 0 | 9 |
| 24 | 1/15/2008 | 1/29/2008 | 2/12/2008 | 3/11/2008 | 4/8/2008 | 35 | 16 | 0 | 1 |
| 25 | | | | | | 10 | 0 | 0 | 0 |
| 26 | 12/28/2007 | 1/11/2008 | 1/24/2008 | 2/22/2008 | 3/21/2008 | 43 | 40 | 1 | 1 |
| 27 | | | | | | 18 | 16 | 8 | 3 |
| 28 | | | | | | 1 | 0 | 9 | 0 |
| 29 | 10/25/2007 | 11/8/2007 | 11/21/2007 | 12/19/2007 | 1/17/2008 | 67 | 29 | 1 | 22 |
| 30 | | | | | | 10 | 0 | 1 | 0 |
| 31 | 11/5/2007 | 11/19/2007 | 12/3/2007 | 12/31/2007 | 1/28/2008 | 68 | 26 | 1 | 13 |
| 32 | 11/6/2007 | 11/19/2007 | 12/10/2007 | 1/1/2008 | 1/29/2008 | 44 | 0 | 2 | 0 |
| 33 | | | | | | 10 | 0 | 0 | 0 |
| 34 | 11/19/2007 | 12/3/2007 | 12/17/2007 | 1/11/2008 | 2/11/2008 | 54 | 0 | 0 | 0 |
| 35 | | | | | | 2 | 0 | 8 | 0 |
| 36 | | | | | | 10 | 0 | 0 | 0 |
| 37 | | | | | | 0 | 0 | 0 | 0 |
| 38 | | | | | | 0 | 0 | 0 | 0 |
| 39 | | | | | | 2 | 0 | 8 | 0 |
| 40 | | | | | | 10 | 0 | 0 | 0 |
| 41 | | | | | | 1 | 0 | 9 | 0 |
| 42 | | | | | | 11 | 6 | 8 | 1 |
| 43 | 12/4/2007 | | | | | 19 | 12 | 0 | 6 |
| 44 | 12/3/2007 | 12/17/2007 | | | 2/4/2008 | 51 | 23 | 0 | 11 |
| 45 | 12/3/2007 | 12/17/2007 | 1/7/2008 | | 1/28/2008 | 60 | 0 | 0 | 0 |
| 46 | 12/19/2007 | 1/2/2008 | 1/16/2008 | 2/13/2008 | 3/12/2008 | 45 | 0 | 0 | 0 |
| 47 | | | | | | 11 | 0 | 0 | 0 |
| 48 | 1/30/2008 | 2/13/2008 | 2/27/2008 | 3/26/2008 | 4/23/2008 | 27 | 0 | 0 | 0 |
| 49 | 1/2/2008 | | | | 1/8/2008 | 41 | 0 | 0 | 0 |
| 50 | 2/1/2008 | | | | | 12 | 0 | 7 | 0 |

Figure 6C

| R | S | T | U | V | W | X | Y | Z | AA |
|---|---|---|---|---|---|---|---|---|---|
| 1 | 1 | | | | 1 | | | | 1 |
| 2 | 1/1/2007 | | | | 1/2/2007 | | | | 1/3/2007 |
| 3 | 6/1/2008 | 6/1/2008 | 6/1/2008 | 6/1/2008 | 6/1/2008 | 6/1/2008 | 6/1/2008 | 6/1/2008 | 6/1/2008 |
| 4 | V1 | V1 | V1 | | V2 | V2 | V2 | | V3 |
| 5 | 39600.00 | 6/1/2008 | 0 | | 207.00 | 6/1/2008 | 1 | | 188.00 |
| 6 | 215.00 | 6/1/2008 | 1 | | 205.00 | 6/1/2008 | 1 | | 199.00 |
| 7 | 215.00 | 6/1/2008 | 1 | | 207.00 | 6/1/2008 | 1 | | 201.00 |
| 8 | 177.00 | 6/1/2008 | 1 | | 170.00 | 6/1/2008 | 1 | | 163.00 |
| 9 | 144.00 | 6/1/2008 | 1 | | 136.00 | 6/1/2008 | 1 | | 129.00 |
| 10 | 142.00 | 6/1/2008 | 1 | | 136.00 | 6/1/2008 | 1 | | 129.00 |
| 11 | 139.00 | 6/1/2008 | 1 | | 129.00 | 6/1/2008 | 1 | | 121.00 |
| 12 | 125.00 | 6/1/2008 | 1 | | 118.00 | 6/1/2008 | 1 | | 111.00 |
| 13 | 117.00 | 6/1/2008 | 1 | | 96.00 | 6/1/2008 | 1 | | 39600.00 |
| 14 | 266.00 | 6/1/2008 | 1 | | 256.00 | 6/1/2008 | 1 | | 235.00 |
| 15 | 39600.00 | 6/1/2008 | 0 | | 39600.00 | 6/1/2008 | 0 | | 39600.00 |
| 16 | 256.00 | 6/1/2008 | 1 | | 244.00 | 6/1/2008 | 1 | | 235.00 |
| 17 | 205.00 | 6/1/2008 | 1 | | 184.00 | 6/1/2008 | 1 | | 39600.00 |
| 18 | 145.00 | 6/1/2008 | 1 | | 145.00 | 6/1/2008 | 1 | | 131.00 |
| 19 | 138.00 | 6/1/2008 | 1 | | 138.00 | 6/1/2008 | 1 | | 39600.00 |
| 20 | 129.00 | 6/1/2008 | 1 | | 129.00 | 6/1/2008 | 1 | | 118.00 |
| 21 | 122.00 | 6/1/2008 | 1 | | 101.00 | 6/1/2008 | 1 | | 39600.00 |
| 22 | 117.00 | 6/1/2008 | 1 | | 117.00 | 6/1/2008 | 1 | | 110.00 |
| 23 | 234.00 | 6/1/2008 | 1 | | 219.00 | 6/1/2008 | 1 | | 215.00 |
| 24 | 150.00 | 6/1/2008 | 1 | | 143.00 | 6/1/2008 | 1 | | 138.00 |
| 25 | 123.00 | 6/1/2008 | 1 | | 102.00 | 6/1/2008 | 1 | | 39600.00 |
| 26 | 170.00 | 6/1/2008 | 1 | | 170.00 | 6/1/2008 | 1 | | 156.00 |
| 27 | 166.00 | 6/1/2008 | 1 | | 166.00 | 6/1/2008 | 1 | | 39600.00 |
| 28 | 116.00 | 6/1/2008 | 1 | | 95.00 | 6/1/2008 | 1 | | 39600.00 |
| 29 | 241.00 | 6/1/2008 | 1 | | 228.00 | 6/1/2008 | 1 | | 220.00 |
| 30 | 240.00 | 6/1/2008 | 1 | | 39600.00 | 6/1/2008 | 0 | | 39600.00 |
| 31 | 230.00 | 6/1/2008 | 1 | | 216.00 | 6/1/2008 | 1 | | 209.00 |
| 32 | 229.00 | 6/1/2008 | 1 | | 215.00 | 6/1/2008 | 1 | | 208.00 |
| 33 | 228.00 | 6/1/2008 | 1 | | 39600.00 | 6/1/2008 | 0 | | 39600.00 |
| 34 | 227.00 | 6/1/2008 | 1 | | 205.00 | 6/1/2008 | 1 | | 195.00 |
| 35 | 188.00 | 6/1/2008 | 1 | | 39600.00 | 6/1/2008 | 0 | | 39600.00 |
| 36 | 185.00 | 6/1/2008 | 1 | | 164.00 | 6/1/2008 | 1 | | 39600.00 |
| 37 | 39600.00 | 6/1/2008 | 0 | | 39600.00 | 6/1/2008 | 0 | | 39600.00 |
| 38 | 39600.00 | 6/1/2008 | 0 | | 39600.00 | 6/1/2008 | 0 | | 39600.00 |
| 39 | 187.00 | 6/1/2008 | 1 | | 39600.00 | 6/1/2008 | 0 | | 39600.00 |
| 40 | 187.00 | 6/1/2008 | 1 | | 39600.00 | 6/1/2008 | 0 | | 39600.00 |
| 41 | 130.00 | 6/1/2008 | 1 | | 109.00 | 6/1/2008 | 1 | | 39600.00 |
| 42 | 220.00 | 6/1/2008 | 1 | | 199.00 | 6/1/2008 | 1 | | 39600.00 |
| 43 | 195.00 | 6/1/2008 | 1 | | 187.00 | 6/1/2008 | 1 | | 180.00 |
| 44 | 195.00 | 6/1/2008 | 1 | | 188.00 | 6/1/2008 | 1 | | 181.00 |
| 45 | 195.00 | 6/1/2008 | 1 | | 188.00 | 6/1/2008 | 1 | | 181.00 |
| 46 | 186.00 | 6/1/2008 | 1 | | 179.00 | 6/1/2008 | 1 | | 165.00 |
| 47 | 185.00 | 6/1/2008 | 1 | | 164.00 | 6/1/2008 | 1 | | 39600.00 |
| 48 | 184.00 | 6/1/2008 | 1 | | 130.00 | 6/1/2008 | 1 | | 123.00 |
| 49 | 165.00 | 6/1/2008 | 1 | | 158.00 | 6/1/2008 | 1 | | 151.00 |
| 50 | 172.00 | 6/1/2008 | 1 | | 128.00 | 6/1/2008 | 1 | | 121.00 |

Figure 6D

|     | R | S | T | U | V | W | X | Y | Z | AA |
|-----|---|---|---|---|---|---|---|---|---|---|
| 102 |   | 139.00 | 6/1/2008 | 1 |   | 123.00 | 6/1/2008 | 1 |   | 116.00 |
| 103 |   | 138.00 | 6/1/2008 | 1 |   | 39600.00 | 6/1/2008 | 0 |   | 39600.00 |
| 104 |   | 136.00 | 6/1/2008 | 1 |   | 125.00 | 6/1/2008 | 1 |   | 118.00 |
| 105 |   | 136.00 | 6/1/2008 | 1 |   | 39600.00 | 6/1/2008 | 0 |   | 39600.00 |
| 106 |   | 136.00 | 6/1/2008 | 1 |   | 125.00 | 6/1/2008 | 1 |   | 118.00 |
| 107 |   | 132.00 | 6/1/2008 | 1 |   | 122.00 | 6/1/2008 | 1 |   | 115.00 |
| 108 |   | 131.00 | 6/1/2008 | 1 |   | 39600.00 | 6/1/2008 | 0 |   | 39600.00 |
| 109 |   | 131.00 | 6/1/2008 | 1 |   | 110.00 | 6/1/2008 | 1 |   | 39600.00 |
| 110 |   | 130.00 | 6/1/2008 | 1 |   | 109.00 | 6/1/2008 | 1 |   | 39600.00 |
| 111 |   | 129.00 | 6/1/2008 | 1 |   | 39600.00 | 6/1/2008 | 0 |   | 39600.00 |
| 112 |   | 128.00 | 6/1/2008 | 1 |   | 107.00 | 6/1/2008 | 1 |   | 39600.00 |
| 113 |   | 227.00 | 6/1/2008 | 1 |   | 213.00 | 6/1/2008 | 1 |   | 206.00 |
| 114 |   | 181.00 | 6/1/2008 | 1 |   | 166.00 | 6/1/2008 | 1 |   | 156.00 |
| 115 |   | 145.00 | 6/1/2008 | 1 |   | 145.00 | 6/1/2008 | 1 |   | 138.00 |
| 116 |   | 131.00 | 6/1/2008 | 1 |   | 124.00 | 6/1/2008 | 1 |   | 118.00 |
| 117 |   | 129.00 | 6/1/2008 | 1 |   | 39600.00 | 6/1/2008 | 0 |   | 39600.00 |
| 118 |   | 122.00 | 6/1/2008 | 1 |   | 101.00 | 6/1/2008 | 1 |   | 39600.00 |
| 119 |   |   |   |   |   |   |   |   |   |   |
| 120 |   |   |   |   |   |   |   |   |   |   |
| 121 |   |   |   |   |   |   |   |   |   |   |
| 122 |   |   | 109 |   |   |   | 95 |   |   |   |

Figure 6E

| | AU |
|---|---|
| 3 | Total visits per Patient number |
| 4 | Total Visits |
| 5 | 6 |
| 6 | 4 |
| 7 | 7 |
| 8 | 7 |
| 9 | 7 |
| 10 | 7 |
| 11 | 7 |
| 12 | 3 |
| 13 | 2 |
| 14 | 7 |
| 15 | 0 |
| 16 | 7 |
| 17 | 2 |
| 18 | 7 |
| 19 | 2 |
| 20 | 7 |
| 21 | 2 |
| 22 | 3 |
| 23 | 7 |
| 24 | 7 |
| 25 | 2 |
| 26 | 7 |
| 27 | 2 |
| 28 | 2 |
| 29 | 7 |
| 30 | 1 |
| 31 | 7 |
| 32 | 7 |
| 33 | 1 |
| 34 | 7 |
| 35 | 1 |
| 36 | 2 |
| 37 | 0 |
| 38 | 0 |
| 39 | 1 |
| 40 | 1 |
| 41 | 2 |
| 42 | 2 |
| 43 | 3 |
| 44 | 5 |
| 45 | 6 |
| 46 | 7 |
| 47 | 2 |
| 48 | 7 |
| 49 | 4 |
| 50 | 3 |

Figure 6F

|     | AU |
| --- | --- |
| 51  | 2  |
| 52  | 7  |
| 53  | 7  |
| 54  | 7  |
| 55  | 7  |
| 56  | 7  |
| 57  | 2  |
| 58  | 5  |
| 59  | 7  |
| 60  | 7  |
| 61  | 7  |
| 62  | 7  |
| 63  | 7  |
| 64  | 7  |
| 65  | 7  |
| 66  | 6  |
| 67  | 0  |
| 68  | 7  |
| 69  | 7  |
| 70  | 7  |
| 71  | 3  |
| 72  | 2  |
| 73  | 1  |
| 74  | 7  |
| 75  | 7  |
| 76  | 7  |
| 77  | 7  |
| 78  | 2  |
| 79  | 7  |
| 80  | 7  |
| 81  | 2  |
| 82  | 7  |
| 83  | 7  |
| 84  | 7  |
| 85  | 7  |
| 86  | 7  |
| 87  | 7  |
| 88  | 7  |
| 89  | 1  |
| 90  | 7  |
| 91  | 7  |
| 92  | 7  |
| 93  | 1  |
| 94  | 2  |
| 95  | 7  |
| 96  | 1  |
| 97  | 7  |
| 98  | 7  |
| 99  | 7  |
| 100 | 2  |
| 101 | 1  |

Figure 6G

|     | A   |
| --- | --- |
| 102 | 3   |
| 103 | 1   |
| 104 | 3   |
| 105 | 1   |
| 106 | 3   |
| 107 | 3   |
| 108 | 1   |
| 109 | 2   |
| 110 | 2   |
| 111 | 1   |
| 112 | 2   |
| 113 | 7   |
| 114 | 3   |
| 115 | 7   |
| 116 | 7   |
| 117 | 1   |
| 118 | 2   |
| 119 |     |
| 120 |     |
| 121 |     |
| 122 | 517 |

Figure 7A

Bill-to
ACCOUNTS PAYABLE
Numoda Corporation
The Curtis Center
601 Walnut Street, 9th Floor
Philadelphia PA 19106-3323

Invoice

Page 1 of 1

Number/Date
Protocol Number
Quotation number/Date
Sold-to party / Sold-to name

Remit to:
TAX ID #:
Electronic Payments: Bank of America ... Atlanta, GA. 30384-4120

Requirements
Terms of payment   Due Net 30 Days

Currency USD

| Description March 2008 Units | |
|---|---|
| Orde... | 42,294.13 |
| Final amount | 42,294.13 |

For questions concerning this invoice, please contact Stephanie Loeper.

Figure 7B

|   | A | B | C |
|---|---|---|---|
| 1 | Invoice # XXXXXXX - PROFESSIONAL FEES | Unit | Unit Price |
| 2 | PROTOCOL AMENDMENT #1 REVIEW | 1.00 | 53,000.00 |
| 3 | STUDY SETUP | | |
| 4 | INVESTIGATOR SELECTION | 12.00 | 945.00 |
| 5 | QUALIFICATION SITE ASSESSMENT VISITS | 12.00 | 1,421.00 |
| 6 | COLLECTION AND PROCESSING OF REGULATORY | 12.00 | 1,539.00 |
| 7 | INVESTIGATOR MEETING (ATTENDANCE & PARTICIPATION) | 1.00 | 34,704.00 |
| 8 | INVESTIGATOR MEETING COORDINATION | 1.00 | 12,960.00 |
| 9 | TRAINING MEETING | 1.00 | 4,328.00 |
| 10 | NEGOTIATION AND ADMINISTRATION AF INVESTIGATOR GRANTS | 1.00 | 10,440.00 |
| 11 | NEGOTIATION OF INVESTIGATOR CONTRACTS (LEGAL COUNSEL) | 1.00 | 3,750.00 |
| 12 | PROTOCOL AMENDMENT #1 REVIEW | 1.00 | 1,374.00 |
| 13 | | | |
| 14 | PROJECT MANAGEMENT | | |
| 15 | PROJECT COORDINATION (12 months) | 12.00 | 7,065.00 |
| 16 | PROJECT MEETINGS | 12.00 | 744.34 |
| 17 | CONFERENCE CALLS (15) | 8.00 | 687.80 |
| 18 | CONFERENCE CALLS☐CORP FOR 8 BILLED @ 687.80 | 8.00 | 146.27 |
| 19 | CONFERENCE CALLS (15) Total | 15.00 | 834.07 |
| 20 | NEWSLETTERS | 12.00 | 323.08 |
| 21 | | | |
| 22 | MONITORING ACTIVITIES | | |
| 23 | INITIATION VISITS | 12.00 | 157.33 |
| 24 | INTERIM MONITORING VISITS | 72.00 | 1,846.49 |
| 25 | INTERIM MONITORING SUBSEQUENT DAY | 24.00 | 849.59 |
| 26 | CLOSEOUT VISITS | 12.00 | 1,580.42 |
| 27 | STATUS REPORTS | 12.00 | 283.50 |
| 28 | IN☐HOUSE MEDICAL SUPPORT | 12.00 | (7,020.00) |
| 29 | SITE MANAGEMENT | 12.00 | 3,087.33 |
| 30 | ADMINISTRATION | 12.00 | 972.00 |
| 31 | PROTOCOL AMENDMENT #1 COORDINATION (for 12 sites) | 1.00 | 5,103.00 |
| 32 | MEDICAL MANAGEMENT | 130.00 | 233.00 |
| 33 | SAE MANAGEMENT SETUP | 1.00 | 1,935.00 |
| 34 | SAE MANAGEMENT (1 SAE) Add'l billed per unit per PCF#2 | 1.00 | 1,530.00 |
| 35 | SAE NARRATIVES (1 NARRATIVE) Add'l billed per unit per PCF#2 | 1.00 | 349.00 |
| 36 | | | |
| 37 | BIOSTATISTICAL SERVICES | | |
| 38 | PROJECT TEAM AND CLIENT INTERACTION | 12.00 | 738.00 |
| 39 | STATISTICAL ANALYSIS PLAN | 1.00 | 12,160.00 |
| 40 | STATISTICAL TABLES, LISTINGS, FIGURES, OUTPUTS & | 1.00 | 54,888.00 |
| 41 | ANALYSIS PRODUCTION | 1.00 | 6,732.00 |
| 42 | RESULTS REVIEW MEETING | 1.00 | 1,436.00 |

Figure 7C

|    | A | B | C |
|----|---|---|---|
| 43 |   |   |   |
| 44 | SCALE AND CALIBRATION WEIGHT COORDINATION | 1.00 | 1,116.00 |
| 45 |   |   |   |
| 46 |   |   |   |
| 47 | TOTAL PROFESSIONAL |   |   |
| 48 | TOTAL PROFESSIONAL FEE |   |   |
| 49 |   |   |   |
| 50 |   |   |   |
| 51 | Invoice # XXXXXXX - PASS-THROUGH EXPENSES | Unit | Unit Price |
| 52 |   |   |   |
| 53 | INVESTIGATOR MEETING (travel and expenses) |   |   |
| 54 |   |   |   |
| 55 | GRANTS |   |   |
| 56 |   |   |   |
| 57 | TRAVEL MONITOR |   |   |
| 58 | Airfare |   |   |
| 59 | Meals, Lodging, etc. |   |   |
| 60 | REGULATORY |   |   |
| 61 | CENTRAL IRB COSTS |   |   |
| 62 |   |   |   |
| 63 | PURCHASE OF 13 SCALES ($1,300 each) |   |   |
| 64 | PURCHASE OF CALIBRATION WEIGHTS |   |   |
| 65 |   |   |   |
| 66 | CREDIT |   |   |
| 67 |   |   |   |
| 68 | TOTAL PASS☐THROUGH |   |   |
| 69 | TOTAL PASS☐THROUGH EXPENSES |   |   |
| 70 | CREDI |   |   |
| 71 | TOTAL |   |   |

Figure 7D

| | D | E | F | G | H | I | J |
|---|---|---|---|---|---|---|---|
| 1 | Total Price | Units completed to date | %of work completed to | Units Billed Curren | Amount Billed Current | Life to date units billed | Life to date amount billed |
| 2 | 53,000.00 | | 100% | | | 1.00 | 53,000.00 |
| 3 | 11,340.00 | | | | | | |
| 4 | 11,340.00 | | 100% | | - | 12.00 | 11,340.00 |
| 5 | 17,052.00 | | 100% | | - | 12.00 | 17,052.00 |
| 6 | 18,468.00 | | 100% | | - | 12.00 | 18,468.00 |
| 7 | 34,704.00 | | 100% | | - | 1.00 | 34,704.00 |
| 8 | 12,960.00 | | 100% | | - | 1.00 | 12,960.00 |
| 9 | 4,328.00 | | 100% | | - | 1.00 | 4,328.00 |
| 10 | 10,440.00 | | 100% | | - | 1.00 | 10,440.00 |
| 11 | 3,750.00 | | 100% | | - | 1.00 | 3,750.00 |
| 12 | 1,374.00 | | 100% | | - | 1.00 | 1,374.00 |
| 13 | | | | | | | |
| 14 | 110,100.09 | | | | | | |
| 15 | 84,780.00 | | 83% | 1.00 | 7,065.00 | 10.00 | 70,650.00 |
| 16 | 8,932.08 | | 33% | | - | 4.00 | 2,977.36 |
| 17 | | | | | | | 5,502.40 |
| 18 | | | | | | | 1,170.16 |
| 19 | 12,511.05 | | 100% | | - | 15.00 | 5,838.49 |
| 20 | 3,876.96 | | 100% | | - | 12.00 | 3,876.96 |
| 21 | | | | | | | |
| 22 | 281,951.40 | | | | | | |
| 23 | 18,327.96 | | 100% | | - | 12.00 | 18,327.96 |
| 24 | 132,947.28 | | 29% | 6.00 | 11,078.94 | 21.00 | 38,776.29 |
| 25 | 20,390.16 | | 42% | 4.00 | 3,398.36 | 10.00 | 8,495.90 |
| 26 | 18,965.04 | | 0% | | - | 0.00 | |
| 27 | 3,402.00 | | 83% | 1.00 | 283.50 | 10.00 | 2,835.00 |
| 28 | | | | | - | 0.00 | |
| 29 | 37,047.96 | | 83% | 1.00 | 3,087.33 | 10.00 | 30,873.30 |
| 30 | 11,664.00 | | 83% | 1.00 | 972.00 | 10.00 | 9,720.00 |
| 31 | 5,103.00 | | 100% | | - | 1.00 | 5,103.00 |
| 32 | 30,290.00 | | 42% | 35.00 | 8,155.00 | 55.00 | 12,815.00 |
| 33 | 1,935.00 | | 100% | | - | 1.00 | 1,935.00 |
| 34 | 1,530.00 | | | 4.00 | 6,120.00 | 5.00 | 7,650.00 |
| 35 | 349.00 | | | 4.00 | 1,396.00 | 5.00 | 1,745.00 |
| 36 | | | | | | | |
| 37 | 84,072.00 | | | | | | |
| 38 | 8,856.00 | | 83% | 1.00 | 738.00 | 10.00 | 7,380.00 |
| 39 | 12,160.00 | | 0% | | - | 0.00 | - |
| 40 | 54,888.00 | | 0% | | - | 0.00 | - |
| 41 | 6,732.00 | | 0% | | - | 0.00 | - |
| 42 | 1,436.00 | | 0% | | - | 0.00 | - |

Figure 7E

|    | D | E | F | G | H | I | J |
|----|---|---|---|---|---|---|---|
| 43 |   |   |   |   |   |   |   |
| 44 | 1,116.00 |   | 100% |   |   | 1.00 | 1,116.00 |
| 45 |   |   |   |   |   |   |   |
| 46 |   |   |   |   |   |   |   |
| 47 | 591,655.49 |   |   |   | 42,294.13 |   | 404,203.82 |
| 48 | 42,294.13 |   |   |   |   |   |   |
| 49 |   |   |   |   |   |   |   |
| 50 |   |   |   |   |   |   |   |
| 51 | Total Price | Units completed to date | work completed to | Units Billed Curren | Amount Billed Current | Life to date units billed | Life to date amount billed |
| 52 |   |   |   |   |   |   |   |
| 53 | 59,100.00 |   | 63% |   |   |   | 37,343.84 |
| 54 |   |   |   |   |   |   |   |
| 55 | 723,000.00 |   | 34% |   |   |   | 248,774.00 |
| 56 |   |   |   |   |   |   |   |
| 57 | 83,400.00 |   | 34% |   |   |   | 28,649.82 |
| 58 |   |   |   |   |   |   |   |
| 59 |   |   |   |   |   |   |   |
| 60 |   |   |   |   |   |   |   |
| 61 | 24,000.00 |   | 64% |   |   |   | 15,437.47 |
| 62 |   |   |   |   |   |   |   |
| 63 | 16,900.00 |   | 74% |   |   |   | 12,500.09 |
| 64 | 200.00 |   | 74% |   |   |   | 148.20 |
| 65 |   |   |   |   |   |   |   |
| 66 |   |   |   |   |   |   |   |
| 67 |   |   |   |   |   |   |   |
| 68 | 906,600.00 |   |   |   |   |   | 342,853.42 |
| 69 |   |   |   |   |   |   |   |
| 70 |   |   |   |   |   |   |   |
| 71 | 42,294.13 |   |   |   |   |   |   |

Figure 8A

| | A | B |
|---|---|---|
| 1 | XXXXX - Project XXXXX | |
| 2 | Enrolled Patients | 246 |
| 3 | Evaluable Patients | 123 |
| 4 | Sites | 12 |
| 5 | Total CRF Pages | |
| 6 | Study Duration | 12 |
| 7 | | |
| 8 | | Unit |
| 9 | ENTITY #4 (CRO) | |
| 10 | *INITIAL PAYMENT* | |
| 11 | STUDY SETUP AND REGULATORY | |
| 12 | INVESTIGATOR SELECTION | 12.00 |
| 13 | QUALIFICATION SITE ASSESSMENT VISIT | 12.00 |
| 14 | COLLECTION AND PROCESSING OF REGULATORY DOCUMENTATION | 12.00 |
| 15 | KICKOFF MEETING | 0.00 |
| 16 | INVESTIGATOR MTG (Attendance & Participation) | 1.00 |
| 17 | INVESTIGATOR MTG (Coordination) | 0.00 |
| 18 | TRAINING MTG | 1.00 |
| 19 | NEGOTIATION & ADMINISTRATION OF INVESTIGATOR CONTRACTS | 1.00 |
| 20 | NEGOTIATION OF INVESTIGATOR CONTRACTS | 0.00 |
| 21 | | |
| 22 | PROJECT MANAGEMENT | |
| 23 | PROJECT COORDINATION (12 Months) | 12.00 |
| 24 | PROJECT MEETINGS | 12.00 |
| 25 | CONFERENCE CALLS | 24.00 |
| 26 | NEWSLETTERS | 12.00 |
| 27 | STATUS REPORTS | 0.00 |
| 28 | Scale and Calibration Weight Coordination | 0.00 |
| 29 | PROTOCOL AMENDMENT # 01 (Review) | 0.00 |
| 30 | | |
| 31 | CLINICAL MONITORING AND MEDICAL SUPPORT | |
| 32 | INITIATION VISITS | 12.00 |
| 33 | INTERIM MONITORING VISITS | 72.00 |
| 34 | CLOSEOUT VISITS | 12.00 |
| 35 | STATUS REPORTS | 12.00 |
| 36 | ADMINISTRATION | 12.00 |
| 37 | PROTOCOL AMENDMENT #01 (Coordination for 12 Sites) | 0.00 |
| 38 | MEDICAL MANAGEMENT | 0.00 |
| 39 | SAE Management (SET-UP) | 0.00 |
| 40 | SAE Management (01 SAE) | 0.00 |
| 41 | SAE Narratives (01 Narrative) | 0.00 |
| 42 | | |
| 43 | SITE MANAGEMENT | |
| 44 | SITE MANAGEMENT | 12.00 |
| 45 | PROJECT MEETINGS | 0.00 |
| 46 | STATUS REPORTS | 0.00 |
| 47 | | |
| 48 | BIOSTATISTICAL SERVICES | |
| 49 | Project Team and Client interaction | 12.00 |
| 50 | Statistical Analysis Plan | 1.00 |
| 51 | Statistical Tables, Listings, Figures, Output & Programming | 1.00 |
| 52 | Final Programming & Analysis | 1.00 |

Figure 8B

| | A | B |
|---|---|---|
| 53 | Results Review Meeting | 1.00 |
| 54 | | |
| 55 | SAFETY MEDICAL & SCIENTIFIC SERVICES | |
| 56 | SAFETY MEDICAL & SCIENTIFIC SERVICES (SCIENTIFIC WRITING) | 12.00 |
| 57 | IN HOUSE MEDICAL SUPPORT | 12.00 |
| 58 | | |
| 59 | CREDIT | |
| 60 | | |
| 61 | ENTITY #5 (Supplies) | |
| 62 | *INITIAL PAYMENT* | |
| 63 | STUDY SETUP AND REGULATORY | |
| 64 | GENERATION OF RANDOMIZATION CODE | 1.00 |
| 65 | GENERATION/REVISION OF LABELING RECORD | 1.00 |
| 66 | Acquisition of single Panel Labels to be applied to the bottles (2000 units) | 2,000 |
| 67 | Acquisition of three panel labels to be applied to the boxes (667 units) | 3.00 |
| 68 | Acquisiton of boxes (667 units) | 667 |
| 69 | Approvals of labels according to the Randomization Code | 1.00 |
| 70 | Labeling of Bottled Gels and Packaging into boxes | 1.00 |
| 71 | Release of Clinically Labeled Product ( Included) | 0.00 |
| 72 | | |
| 73 | ENTITY #6 (Lab) | |
| 74 | *INITIAL PAYMENT* | |
| 75 | TESTING: SCREEN | |
| 76 | Chemistry Panel(1) | 246.00 |
| 77 | Hematology Panel(2) | 246.00 |
| 78 | Urinalysis | 246.00 |
| 79 | PSA( cooled) | 73.80 |
| 80 | Hemoglobin A1C | 246.00 |
| 81 | Serum Pregnancy (5) | 123.00 |
| 82 | | |
| 83 | TESTING: ENROLLED - VISIT 7 | |
| 84 | Chemistry Panel(1) | 98.40 |
| 85 | Hematology Panel(2) | 98.40 |
| 86 | Urinalysis | 98.40 |
| 87 | Serum Pregnancy (5) | 98.40 |
| 88 | | |
| 89 | MATERIALS | |
| 90 | Kits - Screen (6) | 246.00 |
| 91 | Kits - Screen PSA (6) | 98.40 |
| 92 | Kits - Enrolled Visit 5 (6) | 98.40 |
| 93 | Kits - Enrolled Visit 7 (6) | 73.80 |
| 94 | | |
| 95 | | |
| 96 | Project Set Up Fee | 1.00 |
| 97 | Data Management Fee | 1.00 |
| 98 | Monthly Management Fee (10 Months) | 10.00 |
| 99 | Other Contingencies | 1.00 |
| 100 | | |
| 101 | PK lab | |
| 102 | PK Lab | 0.00 |
| 103 | PK Lab | 0.00 |
| 104 | | |

Figure 8C

|     | A | B |
| --- | --- | --- |
| 105 | ENTITY #7 (EKG) | |
| 106 | *INITIAL PAYMENT* | |
| 107 | Project Assurance Services Fee, Project Management, Site Support, Customer Care Center eReporting Services | 10.00 |
| 108 | 12 Lead ECG Analysis Methodology | |
| 109 | Manual Adjudication | 369.00 |
| 110 | 12 Lead ECG Collection and Delivery Equipment | |
| 111 | Mortara ELI -150/200/250 or MAC1200 12-Lead ECG Devea and Support | 108.00 |
| 112 | Standard Electrodes | 4,200 |
| 113 | ECG Paper | 12.00 |
| 114 | Other Contingencies | 1.00 |
| 115 | | |
| 116 | | |
| 117 | ENTITY #1 (Corporation) | |
| 118 | *INITIAL PAYMENT* | |
| 119 | SERVICES: | |
| 120 | Integrations (3 integration) | 12.00 |
| 121 | Portal | 12.00 |
| 122 | Consolidation and Reconciliation | 12.00 |
| 123 | Vendor Management | 12.00 |
| 124 | Medical Monitoring Support | 0.00 |
| 125 | Patient Diaries - Printing Shipping, QC and Logistics tracking | 0.00 |
| 126 | | |
| 127 | CLINICAL PROFESSIONAL SERVICES: | |
| 128 | Startup Regulatory, and Site Management Activities | 0.00 |
| 129 | Monitoring Activities | 0.00 |
| 130 | Project Management Activities (PM) | 12.00 |
| 131 | Data Management Activities (DM) | 8,612.00 |
| 132 | Monthly Management Fee | 0.00 |
| 133 | Safety, Medical &Scientific Activities | 12.00 |
| 134 | Biostatistics & Medical Writing Activities | 0.00 |
| 135 | Labeling Regulatory Input | 0.00 |
| 136 | | |
| 137 | SYSTEMS AND TOOLS: | |
| 138 | Screening and Enrollment Tools | 12.00 |
| 139 | Site Compliance Tools | 12.00 |
| 140 | Reporting Tools | 12.00 |
| 141 | Monitoring System | 12.00 |
| 142 | Safety System | 12.00 |
| 143 | Supplies System | 12.00 |
| 144 | IVRS System | 12.00 |
| 145 | | |
| 146 | SAFETY MEDICAL & SCIENTIFIC SERVICES | |
| 147 | SAFETY MEDICAL & SCIENTIFIC SERVICES (SCIENTIFIC WRITING) | |
| 148 | | |
| 149 | TOTAL PROFESSIONAL FEES | |
| 150 | | |
| 151 | CREDIT | 15 |
| 152 | | |
| 153 | TOTAL PROFESSIONAL FEES AFTER CREDIT | |
| 154 | | |
| 155 | ENTITY #2 (CRO) | |

Figure 8D

| A | B |
|---|---|
| 156 INITIAL PAYMENT | |
| 157 INVESTIGATOR MEETING (Travel and expenses) | 1.00 |
| 158 CLINICAL TRIAL MATERIAL COORDINATION | 12.00 |
| 159 GRANTS | 123.00 |
| 160 TRAVEL MONITOR | 96.00 |
| 161 REGULATORY (CENTRAL IRB COSTS) | 12.00 |
| 162 ADVERTISING | 1.00 |
| 163 Other (Contingencies) | 0.00 |
| 164 PURCHASE OF 13 SCALES ( $ 1300 each) | 12.00 |
| 165 PURCHASE OF 26 CALIBRATION WEIGHTS | 0.00 |
| 166 | |
| 167 ENTITY #5 (Supplies) | |
| 168 INITIAL PAYMENT | |
| 169 Distribution to Clinical Site | 20.00 |
| 170 Shipment | 12.00 |
| 171 | |
| 172 ENTITY #6 (Labs) | |
| 173 INITIAL PAYMENT | |
| 174 Estimated Transportation Costs: | |
| 175 Outbound (7) | 12.00 |
| 176 Inbound RT -Screen | 246.00 |
| 177 Inbound RT -Screen Cooled | 80.00 |
| 178 Inbound RT - Enrolled - Visit 7 | 100.00 |
| 179 | |
| 180 ENTITY #7 (EKG) | |
| 181 INITIAL PAYMENT | |
| 182 Pass Through/Courier Shipments | 24.00 |
| 183 | |
| 184 ENTITY #1 (Corporation) | |
| 185 INITIAL PAYMENT | |
| 186 Travel to Client Meetings | 3.00 |
| 187 Travel for Audit Visits | 1.00 |
| 188 Meetings and Teleconferences | 53.76 |
| 189 Printing, Shipping and Other | 1.00 |
| 190 IVRS Expenses | 12.00 |
| 191 Translation | 1.00 |
| 192 Advertising | 1.00 |
| 193 OTHER CONTINGENCIES | 1.00 |
| 194 | |
| 195 CREDIT | |
| 196 | |
| 197 TOTAL ESTIMATED PASS THROUGH EXPENSES | |
| 198 | |
| 199 ENTITY #4 (CRO) | |
| 200 ENTITY #5 (Supplies) | |
| 201 ENTITY #6 (Lab) | |
| 202 ENTITY #7 (EKG) | |
| 203 ENTITY #1 (Corporation) | |
| 204 | |
| 205 TOTAL PROFESSIONAL FEES AND PASS THROUGH EXPENSES | |
| 206 | |
| 207 FACILITIES MANAGEMENT | |
| 208 | |

Figure 8E

| | C | D | E | F | G | H |
|---|---|---|---|---|---|---|
| 1 | | | | | | |
| 2 | | | | | | |
| 3 | | | | | | |
| 4 | | | | | | |
| 5 | | | | | | |
| 6 | | | | | | |
| 7 | PROJECT BUDGET | | | TOTAL INVOICED | | |
| 8 | Unit Price | Total | | Unit | % Completed | Total |
| 9 | | 529,883.92 | | | 0.00% | - |
| 10 | | | | | | - |
| 11 | | 90,586.00 | | | | - |
| 12 | 945.00 | 11,340.00 | | 0.0 | 0.00% | - |
| 13 | 1,421.00 | 17,052.00 | | 0.0 | 0.00% | - |
| 14 | 1,539.00 | 18,468.00 | | 0.0 | 0.00% | - |
| 15 | - | - | | 0.0 | N/A | - |
| 16 | 26,514.00 | 26,514.00 | | 0.0 | 0.00% | - |
| 17 | - | N/A | | 0.0 | N/A | - |
| 18 | 4,328.00 | 4,328.00 | | 0.0 | 0.00% | - |
| 19 | 12,884.00 | 12,884.00 | | 0.0 | 0.00% | - |
| 20 | - | N/A | | 0.0 | N/A | - |
| 21 | | | | | | |
| 22 | | 105,462.00 | | | | - |
| 23 | 7,065.00 | 84,780.00 | | 0.0 | 0.00% | - |
| 24 | 744.34 | 8,932.08 | | 0.0 | 0.00% | - |
| 25 | 328.04 | 7,872.96 | | 0.0 | 0.00% | - |
| 26 | 323.08 | 3,876.96 | | 0.0 | 0.00% | - |
| 27 | - | N/A | | 0.0 | N/A | - |
| 28 | - | N/A | | 0.0 | N/A | - |
| 29 | - | N/A | | 0.0 | N/A | - |
| 30 | | | | | | |
| 31 | | 205,695.96 | | | | - |
| 32 | 1,527.33 | 18,327.96 | | 0.0 | 0.00% | - |
| 33 | 2,129.68 | 153,336.96 | | 0.0 | 0.00% | - |
| 34 | 1,580.42 | 18,965.04 | | 0.0 | 0.00% | - |
| 35 | 283.50 | 3,402.00 | | 0.0 | 0.00% | - |
| 36 | 972.00 | 11,664.00 | | 0.0 | 0.00% | - |
| 37 | - | N/A | | 0.0 | N/A | - |
| 38 | - | N/A | | 0.0 | N/A | - |
| 39 | - | N/A | | 0.0 | N/A | - |
| 40 | - | N/A | | 0.0 | N/A | - |
| 41 | - | N/A | | 0.0 | N/A | - |
| 42 | | | | | | |
| 43 | | 37,047.96 | | | | - |
| 44 | 3,087.33 | 37,047.96 | | 0.0 | 0.00% | - |
| 45 | 3,087.33 | N/A | | 0.0 | N/A | - |
| 46 | - | N/A | | 0.0 | N/A | - |
| 47 | | | | | | |
| 48 | | 84,072.00 | | | | - |
| 49 | 738.00 | 8,856.00 | | 0.0 | 0.00% | - |
| 50 | 12,160.00 | 12,160.00 | | 0.0 | 0.00% | - |
| 51 | 54,888.00 | 54,888.00 | | 0.0 | 0.00% | - |
| 52 | 6,732.00 | 6,732.00 | | 0.0 | 0.00% | - |

Figure 8F

| | C | D | E | F | G | H |
|---|---|---|---|---|---|---|
| 53 | 1,436.00 | 1,436.00 | | 0.0 | 0.00% | - |
| 54 | | | | | | |
| 55 | | 7,020.00 | | | | - |
| 56 | - | - | | 0.0 | | - |
| 57 | 585.00 | 7,020.00 | | 0.0 | 0.00% | - |
| 58 | | | | | | |
| 59 | | | | | | - |
| 60 | | | | | | |
| 61 | | 31,902.20 | | | 0.00% | - |
| 62 | | | | | | |
| 63 | | 31,902.20 | | | | - |
| 64 | 500.00 | 500.00 | | 0.0 | 0.00% | - |
| 65 | 3,000.00 | 3,000.00 | | 0.0 | 0.00% | - |
| 66 | 1.25 | 2,500.00 | | 0.0 | 0.00% | - |
| 67 | 1,167.00 | 3,501.00 | | 0.0 | 0.00% | - |
| 68 | 3.60 | 2,401.20 | | 0.0 | 0.00% | - |
| 69 | 2,500.00 | 2,500.00 | | 0.0 | 0.00% | - |
| 70 | 17,500.00 | 17,500.00 | | 0.0 | 0.00% | - |
| 71 | - | N/A | | 0.0 | N/A | - |
| 72 | | | | | | |
| 73 | | 48,149.00 | | | 0.00% | - |
| 74 | | | | | | |
| 75 | | 15,280.04 | | | | - |
| 76 | 12.00 | 2,952.00 | | 0.0 | 0.00% | - |
| 77 | 9.00 | 2,214.00 | | 0.0 | 0.00% | - |
| 78 | 9.00 | 2,214.00 | | 0.0 | 0.00% | - |
| 79 | 19.98 | 1,474.52 | | 0.0 | 0.00% | - |
| 80 | 18.62 | 4,580.52 | | 0.0 | 0.00% | - |
| 81 | 15.00 | 1,845.00 | | 0.0 | 0.00% | - |
| 82 | | | | | | |
| 83 | | 4,428.00 | | | | - |
| 84 | 12.00 | 1,180.80 | | 0.0 | 0.00% | - |
| 85 | 9.00 | 885.60 | | 0.0 | 0.00% | - |
| 86 | 9.00 | 885.60 | | 0.0 | 0.00% | - |
| 87 | 15.00 | 1,476.00 | | 0.0 | 0.00% | - |
| 88 | | | | | | |
| 89 | | 3,419.40 | | | | - |
| 90 | 7.00 | 1,722.00 | | 0.0 | 0.00% | - |
| 91 | 5.00 | 492.00 | | 0.0 | 0.00% | - |
| 92 | 7.00 | 688.80 | | 0.0 | 0.00% | - |
| 93 | 7.00 | 516.60 | | 0.0 | 0.00% | - |
| 94 | | | | | | |
| 95 | | 25,021.56 | | | | - |
| 96 | 4,000.00 | 4,000.00 | | 0.0 | 0.00% | - |
| 97 | 3,000.00 | 3,000.00 | | 0.0 | 0.00% | - |
| 98 | 170.00 | 1,700.00 | | 0.0 | 0.00% | - |
| 99 | 16,321.56 | 16,321.56 | | 0.0 | 0.00% | - |
| 100 | | | | | | |
| 101 | | - | | | | - |
| 102 | - | N/A | | 0.0 | N/A | - |
| 103 | - | N/A | | 0.0 | N/A | - |
| 104 | | | | | | |

Figure 8G

|     | C | D | E | F | G | H |
|-----|---|---|---|---|---|---|
| 105 |   | 42,896.00 |   |   | 0.00% | - |
| 106 |   |   |   |   |   |   |
| 107 | 347.85 | 3,478.50 |   | 0.0 | 0.00% | - |
| 108 |   | 16,605.00 |   |   | N/A | - |
| 109 | 45.00 | 16,605.00 |   | 0.0 | 0.00% | - |
| 110 |   | 22,812.50 |   |   | N/A | - |
| 111 | 150.00 | 16,200.00 |   | 0.0 | 0.00% | - |
| 112 | 0.40 | 1,680.00 |   | 0.0 | 0.00% | - |
| 113 | 25.00 | 300.00 |   | 0.0 | 0.00% | - |
| 114 | 4,632.50 | 4,632.50 |   | 0.0 | 0.00% | - |
| 115 |   |   |   |   |   |   |
| 116 |   |   |   |   |   |   |
| 117 |   | 691,468.00 |   |   | 0.00% | - |
| 118 |   |   |   |   |   |   |
| 119 |   | 154,833.00 |   |   |   | - |
| 120 | 2,447.00 | 29,364.00 |   | 0.0 | 0.00% | - |
| 121 | 2,371.58 | 28,459.00 |   | 0.0 | 0.00% | - |
| 122 | 3,167.50 | 38,010.00 |   | 0.0 | 0.00% | - |
| 123 | 4,916.67 | 59,000.00 |   | 0.0 | 0.00% | - |
| 124 | - | N/A |   | 0.0 | N/A | - |
| 125 | - | N/A |   | 0.0 | N/A | - |
| 126 |   |   |   |   |   |   |
| 127 |   | 317,674.00 |   |   |   | - |
| 128 | - | N/A |   | 0.0 | N/A | - |
| 129 | - | N/A |   | 0.0 | N/A | - |
| 130 | 5,731.33 | 68,776.00 |   | 0.0 | 0.00% | - |
| 131 | 25.15 | 216,585.00 |   | 0.0 | 0.00% | - |
| 132 | - | N/A |   | 0.0 | N/A | - |
| 133 | 2,692.75 | 32,313.00 |   | 0.0 | 0.00% | - |
| 134 | - | N/A |   | 0.0 | N/A | - |
| 135 | - | N/A |   | 0.0 | N/A | - |
| 136 |   |   |   |   |   |   |
| 137 |   | 218,961.00 |   |   |   | - |
| 138 | 1,972.58 | 23,671.00 |   | 0.0 | 0.00% | - |
| 139 | 2,337.25 | 28,047.00 |   | 0.0 | 0.00% | - |
| 140 | 2,268.50 | 27,222.00 |   | 0.0 | 0.00% | - |
| 141 | 2,400.75 | 28,809.00 |   | 0.0 | 0.00% | - |
| 142 | 2,392.92 | 28,715.00 |   | 0.0 | 0.00% | - |
| 143 | 1,448.17 | 17,378.00 |   | 0.0 | 0.00% | - |
| 144 | 5,426.58 | 65,119.00 |   | 0.0 | 0.00% | - |
| 145 |   |   |   |   |   |   |
| 146 |   | - |   |   |   | - |
| 147 |   | N/A |   | 0.0 | N/A |   |
| 148 |   |   |   |   |   |   |
| 149 |   | 1,344,299.12 |   |   | 0.00% | - |
| 150 |   |   |   |   |   |   |
| 151 |   |   |   |   |   | - |
| 152 |   |   |   |   |   |   |
| 153 |   | 1,344,299.12 |   |   | 0.00% | - |
| 154 |   |   |   |   |   |   |
| 155 |   | 831,105.00 |   |   | 0.00% | - |

Figure 8H

| | C | D | E | F | G | H |
|---|---|---|---|---|---|---|
| 156 | | | | | | |
| 157 | 57,600.00 | 57,600.00 | | | 0.00% | - |
| 158 | 833.75 | 10,005.00 | | | 0.00% | - |
| 159 | 5,100.00 | 627,300.00 | | | 0.00% | - |
| 160 | 868.75 | 83,400.00 | | | 0.00% | - |
| 161 | 2,000.00 | 24,000.00 | | | 0.00% | - |
| 162 | - | - | | | #DIV/0! | - |
| 163 | - | N/A | | | N/A | - |
| 164 | 2,400.00 | 28,800.00 | | | 0.00% | - |
| 165 | - | N/A | | | N/A | - |
| 166 | | | | | | |
| 167 | | 8,400.04 | | | 0.00% | - |
| 168 | | | | | | |
| 169 | 350.00 | 7,000.00 | | | 0.00% | - |
| 170 | 116.67 | 1,400.04 | | | 0.00% | - |
| 171 | | | | | | |
| 172 | | 6,108.00 | | | 0.00% | - |
| 173 | | | | | | |
| 174 | | 6,108.00 | | | 0.00% | - |
| 175 | 63.00 | 756.00 | | | 0.00% | - |
| 176 | 12.00 | 2,952.00 | | | 0.00% | - |
| 177 | 15.00 | 1,200.00 | | | 0.00% | - |
| 178 | 12.00 | 1,200.00 | | | 0.00% | - |
| 179 | | | | | | |
| 180 | | 1,152.00 | | | 0.00% | - |
| 181 | | | | | | |
| 182 | 48.00 | 1,152.00 | | | 0.00% | - |
| 183 | | | | | | |
| 184 | | 38,032.00 | | | 0.00% | - |
| 185 | | | | | | |
| 186 | 1,000.00 | 3,000.00 | | | 0.00% | - |
| 187 | - | - | | | #DIV/0! | - |
| 188 | 150.00 | 8,064.00 | | | 0.00% | - |
| 189 | - | - | | | #DIV/0! | - |
| 190 | 164.00 | 1,968.00 | | | 0.00% | - |
| 191 | - | - | | | #DIV/0! | - |
| 192 | - | - | | | #DIV/0! | - |
| 193 | 25,000.00 | 25,000.00 | | | 0.00% | - |
| 194 | | | | | | |
| 195 | | | | | | - |
| 196 | | | | | | |
| 197 | | 884,797.04 | | | 0.00% | - |
| 198 | | | | | | |
| 199 | | 1,360,988.92 | | | 0.00% | - |
| 200 | | 40,302.24 | | | 0.00% | - |
| 201 | | 54,257.00 | | | 0.00% | - |
| 202 | | 44,048.00 | | | 0.00% | - |
| 203 | | 729,500.00 | | | 0.00% | - |
| 204 | | | | | | |
| 205 | | 2,229,096.16 | | | 0.00% | - |
| 206 | | | | | | |
| 207 | | (268,859.82) | | | 0.00% | - |
| 208 | | | | | | |

Figure 8I

| | I | J | K | L | M | N | O | P |
|---|---|---|---|---|---|---|---|---|
| 1 | | | | | | | | |
| 2 | | | | | | | | |
| 3 | Invoice Date | | | | Invoice Date | | | |
| 4 | Due Date | | | | Due Date | | | |
| 5 | Invoice # | | | | Invoice # | | | |
| 6 | | | | | | | | |
| 7 | | 1st | Month 01 | | | Month | | |
| 8 | | Unit | Unit Price | Total | | Unit | Unit Price | Total |
| 9 | | | | - | | | | - |
| 10 | | | | | | | | |
| 11 | | | | - | | | | - |
| 12 | | | - | - | | | - | - |
| 13 | | | - | - | | | - | - |
| 14 | | | - | - | | | - | - |
| 15 | | | - | - | | | - | - |
| 16 | | | - | - | | | - | - |
| 17 | | | - | - | | | - | - |
| 18 | | | - | - | | | - | - |
| 19 | | | - | - | | | - | - |
| 20 | | | - | - | | | - | - |
| 21 | | | | | | | | |
| 22 | | | | - | | | | - |
| 23 | | | - | - | | | - | - |
| 24 | | | - | - | | | - | - |
| 25 | | | - | - | | | - | - |
| 26 | | | - | - | | | - | - |
| 27 | | | - | - | | | - | - |
| 28 | | | - | - | | | - | - |
| 29 | | | - | - | | | - | - |
| 30 | | | | | | | | |
| 31 | | | | - | | | | - |
| 32 | | | - | - | | | - | - |
| 33 | | | - | - | | | - | - |
| 34 | | | - | - | | | - | - |
| 35 | | | - | - | | | - | - |
| 36 | | | - | - | | | - | - |
| 37 | | | - | - | | | - | - |
| 38 | | | - | - | | | - | - |
| 39 | | | - | - | | | - | - |
| 40 | | | - | - | | | - | - |
| 41 | | | - | - | | | - | - |
| 42 | | | | | | | | |
| 43 | | | | - | | | | - |
| 44 | | | - | - | | | - | - |
| 45 | | | - | - | | | - | - |
| 46 | | | - | - | | | - | - |
| 47 | | | | | | | | |
| 48 | | | | - | | | | - |
| 49 | | | - | - | | | - | - |
| 50 | | | - | - | | | - | - |
| 51 | | | - | - | | | - | - |
| 52 | | | - | - | | | - | - |

Figure 8J

| | I | J | K | L | M | N | O | P |
|---|---|---|---|---|---|---|---|---|
| 53 | | | - | - | | | - | - |
| 54 | | | | | | | | |
| 55 | | | | - | | | - | - |
| 56 | | | - | - | | | - | - |
| 57 | | | - | - | | | - | - |
| 58 | | | | | | | | |
| 59 | | | | - | | | - | - |
| 60 | | | | | | | | |
| 61 | | | | - | | | | |
| 62 | | | | | | | | |
| 63 | | | | - | | | | - |
| 64 | | | - | - | | | - | - |
| 65 | | | - | - | | | - | - |
| 66 | | | - | - | | | - | - |
| 67 | | | - | - | | | - | - |
| 68 | | | - | - | | | - | - |
| 69 | | | - | - | | | - | - |
| 70 | | | - | - | | | - | - |
| 71 | | | - | - | | | - | - |
| 72 | | | | | | | | |
| 73 | | | | - | | | | - |
| 74 | | | | | | | | |
| 75 | | | | - | | | | - |
| 76 | | | - | - | | | - | - |
| 77 | | | - | - | | | - | - |
| 78 | | | - | - | | | - | - |
| 79 | | | - | - | | | - | - |
| 80 | | | - | - | | | - | - |
| 81 | | | - | - | | | - | - |
| 82 | | | | | | | | |
| 83 | | | | - | | | | - |
| 84 | | | - | - | | | - | - |
| 85 | | | - | - | | | - | - |
| 86 | | | - | - | | | - | - |
| 87 | | | - | - | | | - | - |
| 88 | | | | | | | | |
| 89 | | | | - | | | | - |
| 90 | | | - | - | | | - | - |
| 91 | | | - | - | | | - | - |
| 92 | | | - | - | | | - | - |
| 93 | | | - | - | | | - | - |
| 94 | | | | | | | | |
| 95 | | | | - | | | | - |
| 96 | | | - | - | | | - | - |
| 97 | | | - | - | | | - | - |
| 98 | | | - | - | | | - | - |
| 99 | | | - | - | | | - | - |
| 100 | | | | | | | | |
| 101 | | | | - | | | | - |
| 102 | | | - | - | | | - | - |
| 103 | | | - | - | | | - | - |
| 104 | | | | | | | | |

Figure 8K

| | I | J | K | L | M | N | O | P |
|---|---|---|---|---|---|---|---|---|
| 105 | | | | - | | | | - |
| 106 | | | | | | | | 15,305.00 |
| 107 | | | | - | | | | - |
| 108 | | | | - | | | | - |
| 109 | | | - | - | | | - | - |
| 110 | | | | - | | | | - |
| 111 | | | - | - | | | - | - |
| 112 | | | - | - | | | - | - |
| 113 | | | - | - | | | | - |
| 114 | | | - | - | | | | |
| 115 | | | | | | | | |
| 116 | | | | | | | | |
| 117 | | | | - | | | | - |
| 118 | | | | | | | | |
| 119 | | | | - | | | | - |
| 120 | | | - | - | | | - | - |
| 121 | | | - | - | | | - | - |
| 122 | | | - | - | | | - | - |
| 123 | | | - | - | | | - | - |
| 124 | | | - | - | | | - | - |
| 125 | | | - | - | | | - | - |
| 126 | | | | | | | | |
| 127 | | | | - | | | | - |
| 128 | | | - | - | | | - | - |
| 129 | | | - | - | | | - | - |
| 130 | | | - | - | | | - | - |
| 131 | | | - | - | | | - | - |
| 132 | | | - | - | | | - | - |
| 133 | | | - | - | | | - | - |
| 134 | | | - | - | | | - | - |
| 135 | | | - | - | | | - | - |
| 136 | | | | | | | | |
| 137 | | | | - | | | | - |
| 138 | | | - | - | | | - | - |
| 139 | | | - | - | | | - | - |
| 140 | | | - | - | | | - | - |
| 141 | | | - | - | | | - | - |
| 142 | | | - | - | | | - | - |
| 143 | | | - | - | | | - | - |
| 144 | | | - | - | | | - | - |
| 145 | | | | | | | | |
| 146 | | | | - | | | - | - |
| 147 | | | - | - | | | - | - |
| 148 | | | | | | | | |
| 149 | | | | - | | | | - |
| 150 | | | | | | | | |
| 151 | | | - | - | | | - | - |
| 152 | | | | | | | | |
| 153 | | | | - | | | | - |
| 154 | | | | | | | | |
| 155 | | | | - | | | | - |

Figure 8L

| | I | J | K | L | M | N | O | P |
|---|---|---|---|---|---|---|---|---|
| 156 | | | | | | | | |
| 157 | | | - | - | | | - | - |
| 158 | | | - | - | | | - | - |
| 159 | | | - | - | | | - | - |
| 160 | | | - | - | | | - | - |
| 161 | | | - | - | | | - | - |
| 162 | | | - | - | | | - | - |
| 163 | | | - | - | | | - | - |
| 164 | | | - | - | | | - | - |
| 165 | | | - | - | | | - | - |
| 166 | | | | | | | | |
| 167 | | | | - | | | | - |
| 168 | | | | | | | | |
| 169 | | | - | - | | | - | - |
| 170 | | | - | - | | | - | - |
| 171 | | | | | | | | |
| 172 | | | | - | | | | - |
| 173 | | | | | | | | |
| 174 | | | | - | | | | - |
| 175 | | | - | - | | | - | - |
| 176 | | | - | - | | | - | - |
| 177 | | | - | - | | | - | - |
| 178 | | | - | - | | | - | - |
| 179 | | | | - | | | | |
| 180 | | | | - | | | | - |
| 181 | | | | | | | | |
| 182 | | | - | - | | | - | - |
| 183 | | | | | | | | |
| 184 | | | | - | | | | - |
| 185 | | | | | | | | |
| 186 | | | - | - | | | - | - |
| 187 | | | - | - | | | - | - |
| 188 | | | - | - | | | - | - |
| 189 | | | - | - | | | - | - |
| 190 | | | - | - | | | - | - |
| 191 | | | - | - | | | - | - |
| 192 | | | - | - | | | - | - |
| 193 | | | - | - | | | - | - |
| 194 | | | | | | | | |
| 195 | | | | | | | | |
| 196 | | | | | | | | |
| 197 | | | | - | | | | - |
| 198 | | | | | | | | |
| 199 | | | | - | | | | - |
| 200 | | | | - | | | | - |
| 201 | | | | - | | | | - |
| 202 | | | | - | | | | - |
| 203 | | | | - | | | | - |
| 204 | | | | | | | | |
| 205 | | | | - | | | | - |
| 206 | | | | | | | | |
| 207 | | | | - | | | | - |
| 208 | | | | | | | | |

Figure 8M

| | BM | BN | BO | BP | BQ | BR | BS |
|---|---|---|---|---|---|---|---|
| 1 | | | | | | | |
| 2 | | | | | | | |
| 3 | nvoice | | | | | | |
| 4 | | Due Date | | | | | |
| 5 | | Invoice # | | | | | |
| 6 | | | | | | | |
| 7 | | | Month 15 | | | | |
| 8 | | Unit | Unit Price | Total | | Reconciliation | |
| 9 | | | | - | | | |
| 10 | | | | | | | |
| 11 | | | | - | | OK | |
| 12 | | | - | - | | OK | |
| 13 | | | - | - | | OK | |
| 14 | | | - | - | | OK | |
| 15 | | | - | - | | OVER | |
| 16 | | | - | - | | OK | |
| 17 | | | - | - | | OK | |
| 18 | | | - | - | | OK | |
| 19 | | | - | - | | OK | |
| 20 | | | - | - | | OK | |
| 21 | | | | | | | |
| 22 | | | | - | | OK | |
| 23 | | | - | - | | OK | |
| 24 | | | - | - | | OK | |
| 25 | | | - | - | | OK | |
| 26 | | | - | - | | OK | |
| 27 | | | - | - | | OK | |
| 28 | | | - | - | | OK | |
| 29 | | | - | - | | OK | |
| 30 | | | | | | | |
| 31 | | | | - | | OK | |
| 32 | | | - | - | | OK | |
| 33 | | | - | - | | OK | |
| 34 | | | - | - | | OK | |
| 35 | | | - | - | | OK | |
| 36 | | | - | - | | OK | |
| 37 | | | - | - | | OK | |
| 38 | | | - | - | | OK | |
| 39 | | | - | - | | OK | |
| 40 | | | - | - | | OK | |
| 41 | | | - | - | | OK | |
| 42 | | | | | | | |
| 43 | | | | - | | OK | |
| 44 | | | - | - | | OK | |
| 45 | | | - | - | | OK | |
| 46 | | | - | - | | OK | |
| 47 | | | | | | | |
| 48 | | | | - | | OK | |
| 49 | | | - | - | | OK | |
| 50 | | | - | - | | OK | |
| 51 | | | - | - | | OK | |
| 52 | | | - | - | | OK | |

Figure 8N

|     | BM | BN | BO | BP | BQ | BR   | BS |
|-----|----|----|----|----|----|------|----|
| 53  |    |    | -  | -  |    | OK   |    |
| 54  |    |    |    |    |    |      |    |
| 55  |    |    | -  | -  |    | OK   |    |
| 56  |    |    | -  | -  |    | OVER |    |
| 57  |    |    | -  | -  |    | OK   |    |
| 58  |    |    |    |    |    |      |    |
| 59  |    |    | -  | -  |    | OVER |    |
| 60  |    |    |    |    |    |      |    |
| 61  |    |    |    |    |    |      |    |
| 62  |    |    |    |    |    |      |    |
| 63  |    |    |    | -  |    | OK   |    |
| 64  |    |    | -  | -  |    | OK   |    |
| 65  |    |    | -  | -  |    | OK   |    |
| 66  |    |    | -  | -  |    | OK   |    |
| 67  |    |    | -  | -  |    | OK   |    |
| 68  |    |    | -  | -  |    | OK   |    |
| 69  |    |    | -  | -  |    | OK   |    |
| 70  |    |    | -  | -  |    | OK   |    |
| 71  |    |    | -  | -  |    | OK   |    |
| 72  |    |    |    |    |    |      |    |
| 73  |    |    |    | -  |    |      |    |
| 74  |    |    |    |    |    |      |    |
| 75  |    |    |    | -  |    | OK   |    |
| 76  |    |    | -  | -  |    | OK   |    |
| 77  |    |    | -  | -  |    | OK   |    |
| 78  |    |    | -  | -  |    | OK   |    |
| 79  |    |    | -  | -  |    | OK   |    |
| 80  |    |    | -  | -  |    | OK   |    |
| 81  |    |    | -  | -  |    | OK   |    |
| 82  |    |    |    |    |    |      |    |
| 83  |    |    |    | -  |    | OK   |    |
| 84  |    |    | -  | -  |    | OK   |    |
| 85  |    |    | -  | -  |    | OK   |    |
| 86  |    |    | -  | -  |    | OK   |    |
| 87  |    |    | -  | -  |    | OK   |    |
| 88  |    |    |    |    |    |      |    |
| 89  |    |    |    | -  |    | OK   |    |
| 90  |    |    | -  | -  |    | OK   |    |
| 91  |    |    | -  | -  |    | OK   |    |
| 92  |    |    | -  | -  |    | OK   |    |
| 93  |    |    | -  | -  |    | OK   |    |
| 94  |    |    |    |    |    |      |    |
| 95  |    |    |    | -  |    | OK   |    |
| 96  |    |    | -  | -  |    | OK   |    |
| 97  |    |    | -  | -  |    | OK   |    |
| 98  |    |    | -  | -  |    | OK   |    |
| 99  |    |    | -  | -  |    | OK   |    |
| 100 |    |    |    |    |    |      |    |
| 101 |    |    | -  | -  |    |      |    |
| 102 |    |    | -  | -  |    | OK   |    |
| 103 |    |    | -  | -  |    | OK   |    |
| 104 |    |    |    |    |    |      |    |

Figure 8O

| | BM | BN | BO | BP | BQ | BR | BS |
|---|---|---|---|---|---|---|---|
| 105 | | | | - | | | |
| 106 | | | | | | | |
| 107 | | | | - | | OK | |
| 108 | | | | - | | OK | |
| 109 | | | - | - | | OK | |
| 110 | | | | - | | OK | |
| 111 | | | - | - | | OK | |
| 112 | | | - | - | | OK | |
| 113 | | | - | - | | OK | |
| 114 | | | - | - | | OK | |
| 115 | | | - | - | | | |
| 116 | | | | | | | |
| 117 | | | | - | | | |
| 118 | | | | | | | |
| 119 | | | | - | | OK | |
| 120 | | | - | - | | OK | |
| 121 | | | - | - | | OK | |
| 122 | | | - | - | | OK | |
| 123 | | | - | - | | OK | |
| 124 | | | - | - | | OK | |
| 125 | | | - | - | | OK | |
| 126 | | | | | | | |
| 127 | | | | - | | OK | |
| 128 | | | - | - | | OK | |
| 129 | | | - | - | | OK | |
| 130 | | | - | - | | OK | |
| 131 | | | - | - | | OK | |
| 132 | | | - | - | | OK | |
| 133 | | | - | - | | OK | |
| 134 | | | - | - | | OK | |
| 135 | | | - | - | | OK | |
| 136 | | | | | | | |
| 137 | | | | - | | OK | |
| 138 | | | - | - | | OK | |
| 139 | | | - | - | | OK | |
| 140 | | | - | - | | OK | |
| 141 | | | - | - | | OK | |
| 142 | | | - | - | | OK | |
| 143 | | | - | - | | OK | |
| 144 | | | - | - | | OK | |
| 145 | | | | | | | |
| 146 | | | - | - | | OVER | |
| 147 | | | - | - | | OK | |
| 148 | | | | | | | |
| 149 | | | | - | | OK | |
| 150 | | | | | | | |
| 151 | | | - | - | | | |
| 152 | | | | | | | |
| 153 | | | | - | | OK | |
| 154 | | | | | | | |
| 155 | | | | - | | | |

Figure 8P

|     | BM | BN | BO | BP | BQ | BR | BS |
|-----|----|----|----|----|----|----|----|
| 156 |    |    |    |    |    |    |    |
| 157 |    |    | -  | -  |    | OK |    |
| 158 |    |    | -  | -  |    | OK |    |
| 159 |    |    | -  | -  |    | OK |    |
| 160 |    |    | -  | -  |    | OK |    |
| 161 |    |    | -  | -  |    | OK |    |
| 162 |    |    | -  | -  |    | OVER |  |
| 163 |    |    | -  | -  |    | OK |    |
| 164 |    |    | -  | -  |    | OK |    |
| 165 |    |    | -  | -  |    | OK |    |
| 166 |    |    |    |    |    |    |    |
| 167 |    |    |    | -  |    |    |    |
| 168 |    |    |    |    |    |    |    |
| 169 |    |    | -  | -  |    | OK |    |
| 170 |    |    | -  | -  |    | OK |    |
| 171 |    |    |    |    |    |    |    |
| 172 |    |    |    | -  |    |    |    |
| 173 |    |    |    |    |    |    |    |
| 174 |    |    |    | -  |    | OK |    |
| 175 |    |    | -  | -  |    | OK |    |
| 176 |    |    | -  | -  |    | OK |    |
| 177 |    |    | -  | -  |    | OK |    |
| 178 |    |    | -  | -  |    | OK |    |
| 179 |    |    |    |    |    |    |    |
| 180 |    |    |    | -  |    |    |    |
| 181 |    |    |    |    |    |    |    |
| 182 |    |    | -  | -  |    | OK |    |
| 183 |    |    |    |    |    |    |    |
| 184 |    |    |    | -  |    |    |    |
| 185 |    |    |    |    |    |    |    |
| 186 |    |    | -  | -  |    | OK |    |
| 187 |    |    | -  | -  |    | OVER |  |
| 188 |    |    | -  | -  |    | OK |    |
| 189 |    |    | -  | -  |    | OVER |  |
| 190 |    |    | -  | -  |    | OK |    |
| 191 |    |    | -  | -  |    | OVER |  |
| 192 |    |    | -  | -  |    | OVER |  |
| 193 |    |    | -  | -  |    | OK |    |
| 194 |    |    |    |    |    |    |    |
| 195 |    |    |    |    |    |    |    |
| 196 |    |    |    |    |    |    |    |
| 197 |    |    |    | -  |    | OK |    |
| 198 |    |    |    |    |    |    |    |
| 199 |    |    |    | -  |    |    |    |
| 200 |    |    |    | -  |    |    |    |
| 201 |    |    |    | -  |    |    |    |
| 202 |    |    |    | -  |    |    |    |
| 203 |    |    |    | -  |    |    |    |
| 204 |    |    |    |    |    |    |    |
| 205 |    |    |    | -  |    | OK |    |
| 206 |    |    |    |    |    |    |    |
| 207 |    |    |    | -  |    | OK |    |
| 208 |    |    |    |    |    |    |    |

Figure 9A

Budget Summary

| | General Contract | | |
|---|---|---|---|
| | Contract Value | | Trial actual Invoices |
| Integration SERVICES | | | |
| Integrations (2 integrations) | $ | 29,364 | $ - |
| Portal | | 28,459 | $ - |
| Consolidation and Reconciliation | | 38,010 | $ - |
| Vendor Management: | | 59,000 | $ - |
| CLINICAL PROFESSIONAL SERVICES: | | - | |
| Start up, Regulatory, and Site Management Activities | | 134,654 | $ - |
| Monitoring Activities | | 205,696 | $ - |
| Project Management Activities (PM) | | 174,238 | $ - |
| Data Management Activities (DM) | | 216,585 | $ - |
| Safety, Medical & Scientific Services Activities | | 32,313 | $ - |
| Biostatistics & Medical Writing Activities | | 84,073 | $ - |
| SUBTOTAL PROFESSIONAL FEES | $ | 1,002,392 | $ - |
| | | | |
| SYSTEMS AND TOOLS: | | | |
| Screening and Enrollment Tools | | 23,671 | $ - |
| Site Compliance Tools | | 28,047 | $ - |
| Reporting Tools | | 27,222 | $ - |
| Monitoring System | | 28,809 | $ - |
| Safety | | 28,715 | $ - |
| Supplies | | 17,378 | $ - |

Figure 9B

| | B | J | K | AM | AN | AO |
|---|---|---|---|---|---|---|
| 24 | IVRS System | | 65,119 | | | |
| 25 | SUBTOTAL SYSTEMS AND REPORTING TOOLS | $ | 218,961 | $ | | |
| 26 | | | | | | |
| 27 | TOTAL SERVICES, INTEGRATIONS, PROFESSIONAL FEES, AND SYSTEMS AND TOOLS | $ | 1,221,353 | $ | | |
| 28 | | | | | | |
| 29 | | | | | | |
| 30 | VALUE ADDED SUPPLIER ITEMS | | | | | |
| 31 | Drug Labeling | | 31,902 | $ | | |
| 32 | Diagnostic Services: | | - | | | |
| 33 | Labs | | 48,149 | $ | | |
| 34 | ECG | | 42,896 | $ | | |
| 35 | Investigator Grants | | 627,300 | $ | | |
| 36 | Investigator Meeting Travel | | 57,600 | $ | | |
| 37 | Monitor Travel | | 83,400 | $ | | |
| 38 | Other Meals and Travel | | 3,000 | $ | | |
| 39 | Meetings and Teleconferences | | 8,064 | $ | | |
| 40 | IVRS Expenses | | 1,968 | $ | | |
| 41 | Shipping, Printing, and Other | | 15,660 | $ | | |
| 42 | Weight Scales | | 28,800 | $ | | |
| 43 | Other (contingencies) | | 35,005 | $ | | |
| 44 | | | | | | |
| 45 | | | | | | |
| 46 | Central IRB Cost | | 24,000 | $ | | |
| 47 | TOTAL ESTIMATED PASS THROUGH COSTS | $ | 1,007,744 | $ | | |
| 48 | | | | | | |
| 49 | | | | | | |
| 50 | TOTAL PROJECT BUDGET | $ | 2,229,097 | $ | | |

Figure 9C

| | AP | AQ | AT | AU | AV | AW | AX | BA | BB | BC |
|---|---|---|---|---|---|---|---|---|---|---|
| 1 | | | % Completed Until 31/05/2007 | Total Completed Until 05/31/2007 | | | | % Completed Until 06/30/2007 | Total Completed Until 06/30/2007 | |
| 2 | | Projected Work - Month 01 | Total % to date | Total $ to date | | | Projected Work - Month 02 | Total % to date | Total $ to date | |
| 3 | | | | | | | | | | |
| 4 | 70.0% | $ 20,554.80 | 70.0% | $ 20,554.80 | | 10.0% | $ 2,936.40 | 80.0% | $ 23,491.20 | |
| 5 | 70.0% | $ 19,921.30 | 70.0% | $ 19,921.30 | | 10.0% | $ 2,845.90 | 80.0% | $ 22,767.20 | |
| 6 | 20.0% | $ 7,602.00 | 20.0% | $ 7,602.00 | | 20.0% | $ 7,602.00 | 40.0% | $ 15,204.00 | |
| 7 | 30.0% | $ 17,700.00 | 30.0% | $ 17,700.00 | | 30.0% | $ 17,700.00 | 60.0% | $ 35,400.00 | |
| 8 | | | | | | | | | | |
| 9 | 20.0% | $ 26,930.79 | 20.0% | $ 26,930.79 | | 20.0% | $ 26,930.79 | 40.0% | $ 53,861.58 | |
| 10 | 5.0% | $ 10,284.80 | 5.0% | $ 10,284.80 | | 5.0% | $ 10,284.80 | 10.0% | $ 20,569.60 | |
| 11 | 10.0% | $ 17,423.80 | 10.0% | $ 17,423.80 | | 10.0% | $ 17,423.80 | 20.0% | $ 34,847.60 | |
| 12 | 10.0% | $ 21,658.50 | 10.0% | $ 21,658.50 | | 10.0% | $ 21,658.50 | 20.0% | $ 43,317.00 | |
| 13 | 5.0% | $ 1,615.65 | 5.0% | $ 1,615.65 | | 5.0% | $ 1,615.65 | 10.0% | $ 3,231.30 | |
| 14 | 10.0% | $ 8,407.30 | 10.0% | $ 8,407.30 | | 10.0% | $ 8,407.30 | 20.0% | $ 16,814.60 | |
| 15 | | $ 152,099 | | $ 152,099 | | | $ 117,405 | | $ 269,504 | |
| 16 | | | | | | | | | | |
| 17 | | | | | | | | | | |
| 18 | 70.0% | $ 16,569.70 | 70.0% | $ 16,569.70 | | 10.0% | $ 2,367.10 | 80.0% | $ 18,936.80 | |
| 19 | 70.0% | $ 19,632.90 | 70.0% | $ 19,632.90 | | 10.0% | $ 2,804.70 | 80.0% | $ 22,437.60 | |
| 20 | 70.0% | $ 19,055.40 | 70.0% | $ 19,055.40 | | 10.0% | $ 2,722.20 | 80.0% | $ 21,777.60 | |
| 21 | 70.0% | $ 20,166.30 | 70.0% | $ 20,166.30 | | 10.0% | $ 2,880.90 | 80.0% | $ 23,047.20 | |
| 22 | 70.0% | $ 20,100.50 | 70.0% | $ 20,100.50 | | 10.0% | $ 2,871.50 | 80.0% | $ 22,972.00 | |
| 23 | 70.0% | $ 12,164.60 | 70.0% | $ 12,164.60 | | 10.0% | $ 1,737.80 | 80.0% | $ 13,902.40 | |

Figure 9D

| | AP | AQ | AT | AU | AV | AW | AX | BA | BB | BC |
|---|---|---|---|---|---|---|---|---|---|---|
| 24 | 70.0% | $ 45,583.30 | 70.0% | $ 45,583.30 | | 10.0% | $ 6,511.90 | 80.0% | $ 52,095.20 | |
| 25 | | $ 153,273 | | $ 153,273 | | | $ 21,896 | | $ 175,169 | |
| 26 | | | | | | | | | | |
| 27 | | $ 305,372 | | $ 305,372 | | | $ 139,301 | | $ 444,673 | |
| 28 | | | | | | | | | | |
| 29 | | | | | | | | | | |
| 30 | | | | | | | | | | |
| 31 | 50.0% | $ 15,951.10 | 50.0% | $ 15,951.10 | | 50.0% | $ 15,951.10 | 100.0% | $ 31,902.20 | |
| 32 | 0.0% | $ - | 0.0% | $ - | | 0.0% | | 0.0% | $ - | |
| 33 | 0.0% | $ - | 0.0% | $ - | | 0.0% | $ - | 0.0% | $ - | |
| 34 | 0.0% | $ - | 0.0% | $ - | | 0. % | $ - | 0.0% | $ - | |
| 35 | 0.0% | $ - | 0.0% | $ - | | 0.0% | | 0.0% | $ - | |
| 36 | 100.0% | $ 57,600.00 | 100.0% | $ 57,600.00 | | 0.0% | $ - | 100.0% | $ 57,600.00 | |
| 37 | 100.0% | $ 83,400.00 | 100.0% | $ 83,400.00 | | 0.0% | $ - | 100.0% | $ 83,400.00 | |
| 38 | 0.0% | $ - | 0.0% | $ - | | 0.0% | $ - | 0.0% | $ - | |
| 39 | 33.3% | $ 2,687.73 | 33.3% | $ 2,687.73 | | 33.3% | $ 2,687.73 | 66.7% | $ 5,375.46 | |
| 40 | 25.0% | $ 492.00 | 25.0% | $ 492.00 | | 6.8% | $ 134.22 | 31.8% | $ 626.22 | |
| 41 | 30.0% | $ 4,698.01 | 30.0% | $ 4,698.01 | | 10.0% | $ 1,566.00 | 40.0% | $ 6,264.02 | |
| 42 | 10.0% | $ 2,880.00 | 10.0% | $ 2,880.00 | | 10.0% | $ 2,880.00 | 20.0% | $ 5,760.00 | |
| 43 | 0.0% | $ - | 0.0% | $ - | | 100.0% | $ 35,005.00 | 100.0% | $ 35,005.00 | |
| 44 | 8.3% | $ - | 8.3% | $ - | | 8.3% | | 16.7% | $ - | |
| 45 | 70.0% | $ - | 70.0% | $ - | | 0.0% | | 70.0% | $ - | |
| 46 | 0.0% | $ - | 0.0% | $ - | | 0.0% | $ - | 0.0% | $ - | |
| 47 | | $ 167,709 | | $ 167,709 | | | $ 58,224 | | $ 225,933 | |
| 48 | | | | | | | | | | |
| 49 | | | | | | | | | | |
| 50 | | $ 473,080 | | $ 473,080 | | | $ 197,525 | | $ 670,606 | |

Figure 9E

| | BD | BE | BH | BI | BJ | BK | BL | BO | BP | BQ |
|---|---|---|---|---|---|---|---|---|---|---|
| 1 | | | | Total Completed Until 07/31/2007 | | | | | Total Completed Until 08/30/2007 | |
| 2 | Projected Work - Month 03 | | % Completed Until 07/31/2007 | Total $ to date | | Projected Work - Month 04 | | % Completed Until 08/30/2007 | Total $ to date | |
| 3 | | | Total % to date | | | | | Total % to date | | |
| 4 | 2.0% | $ 587.28 | 82.0% | $ 24,078.48 | | 2.0% | $ 587.28 | 84.0% | $ 24,665.76 | |
| 5 | 2.0% | $ 569.18 | 82.0% | $ 23,336.38 | | 2.0% | $ 569.18 | 84.0% | $ 23,905.56 | |
| 6 | 20.0% | $ 7,602.00 | 60.0% | $ 22,806.00 | | 4.4% | $ 1,687.64 | 64.4% | $ 24,493.64 | |
| 7 | 4.0% | $ 2,360.00 | 64.0% | $ 37,760.00 | | 4.0% | $ 2,360.00 | 68.0% | $ 40,120.00 | |
| 8 | | | | | | | | | | |
| 9 | 20.0% | $ 26,930.79 | 60.0% | $ 80,792.38 | | 4.4% | $ 5,978.64 | 64.4% | $ 86,771.01 | |
| 10 | 10.0% | $ 20,569.60 | 20.0% | $ 41,139.19 | | 11.4% | $ 23,511.05 | 31.4% | $ 64,650.24 | |
| 11 | 10.0% | $ 17,423.80 | 30.0% | $ 52,271.40 | | 7.8% | $ 13,555.72 | 37.8% | $ 65,827.12 | |
| 12 | 10.0% | $ 21,658.50 | 30.0% | $ 64,975.50 | | 7.8% | $ 16,850.31 | 37.8% | $ 81,825.81 | |
| 13 | 5.0% | $ 1,615.65 | 15.0% | $ 4,846.95 | | 9.4% | $ 3,050.35 | 24.4% | $ 7,897.30 | |
| 14 | 10.0% | $ 8,407.30 | 30.0% | $ 25,221.90 | | 0.0% | $ - | 30.0% | $ 25,221.90 | |
| 15 | | $ 107,724 | | $ 377,228 | | | $ 68,150 | | $ 445,378 | |
| 16 | | $ - | | | | | $ - | | | |
| 17 | | | | | | | | | | |
| 18 | 2.0% | $ 473.42 | 82.0% | $ 19,410.22 | | 2.0% | $ 473.42 | 84.0% | $ 19,883.64 | |
| 19 | 2.0% | $ 560.94 | 82.0% | $ 22,998.54 | | 2.0% | $ 560.94 | 84.0% | $ 23,559.48 | |
| 20 | 2.0% | $ 544.44 | 82.0% | $ 22,322.04 | | 2.0% | $ 544.44 | 84.0% | $ 22,866.48 | |
| 21 | 2.0% | $ 576.18 | 82.0% | $ 23,623.38 | | 2.0% | $ 576.18 | 84.0% | $ 24,199.56 | |
| 22 | 2.0% | $ 574.30 | 82.0% | $ 23,546.30 | | 2.0% | $ 574.30 | 84.0% | $ 24,120.60 | |
| 23 | 2.0% | $ 347.56 | 82.0% | $ 14,249.96 | | 2.0% | $ 347.56 | 84.0% | $ 14,597.52 | |

Figure 9F

| | BD | BE | BH | BI | BJ | BK | BL | BO | BP | BQ |
|---|---|---|---|---|---|---|---|---|---|---|
| 24 | 2.0% | $ 1,302.38 | 82.0% | $ 53,397.58 | | 2.0% | $ 1,302.38 | 84.0% | $ 54,699.96 | |
| 25 | | $ 4,379 | | $ 179,548 | | | $ 4,379 | | $ 183,927 | |
| 26 | | | | | | | | | | |
| 27 | | $ 112,103 | | $ 556,776 | | | $ 72,529 | | $ 629,306 | |
| 28 | | | | | | | | | | |
| 29 | | | | | | | | | | |
| 30 | | | | | | | | | | |
| 31 | 0.0% | $ - | 100.0% | $ 31,902.20 | | 0.0% | $ - | 100.0% | $ 31,902.20 | |
| 32 | 0.0% | | 0.0% | $ - | | 0.0% | | 0.0% | $ - | |
| 33 | 16.7% | $ 8,026.44 | 16.7% | $ 8,026.44 | | 16.7% | $ 8,026.44 | 33.3% | $ 16,052.88 | |
| 34 | 15.0% | $ 6,434.40 | 15.0% | $ 6,434.40 | | 17.0% | $ 7,292.32 | 32.0% | $ 13,726.72 | |
| 35 | 16.7% | $ 104,570.91 | 16.7% | $ 104,570.91 | | 16.7% | $ 104,570.91 | 33.3% | $ 209,141.82 | |
| 36 | 0.0% | $ - | 100.0% | $ 57,600.00 | | 0.0% | $ - | 100.0% | $ 57,600.00 | |
| 37 | 0.0% | $ - | 100.0% | $ 83,400.00 | | 0.0% | $ - | 100.0% | $ 83,400.00 | |
| 38 | 0.0% | $ - | 0.0% | $ - | | 20.0% | $ 600.00 | 20.0% | $ 600.00 | |
| 39 | 33.3% | $ 2,687.73 | 100.0% | $ 8,063.19 | | 0.0% | $ - | 100.0% | $ 8,063.19 | |
| 40 | 6.8% | $ 134.22 | 38.6% | $ 760.44 | | 6.8% | $ 134.22 | 45.5% | $ 894.65 | |
| 41 | 8.6% | $ 1,342.07 | 48.6% | $ 7,606.08 | | 8.6% | $ 1,342.07 | 57.1% | $ 8,948.15 | |
| 42 | 30.0% | $ 8,640.00 | 50.0% | $ 14,400.00 | | 5.6% | $ 1,601.28 | 55.6% | $ 16,001.28 | |
| 43 | 0.0% | $ - | 100.0% | $ 35,005.00 | | 0.0% | | 100.0% | $ 35,005.00 | |
| 44 | 8.3% | $ - | 25.0% | $ - | | 8.3% | | 0.0% | $ - | |
| 45 | 0.0% | $ - | 70.0% | $ - | | 0.0% | | 0.0% | $ - | |
| 46 | 0.0% | $ - | 0.0% | $ - | | 33.3% | $ 7,999.20 | 33.3% | $ 7,999.20 | |
| 47 | | $ 131,836 | | $ 357,769 | | | $ 131,566 | | $ 489,335 | |
| 48 | | | | | | | | | | |
| 49 | | | | | | | | | | |
| 50 | | $ 243,939 | | $ 914,545 | | | $ 204,096 | | $ 1,118,641 | |

Figure 9G

| | BR | BS | BV | BW | BX | BY | BZ | CC | CD | CE |
|---|---|---|---|---|---|---|---|---|---|---|
| 1 | | | % Completed Until XX/XX/2008 | Total Completed Until XX/XX/08 | | | | % Completed Until XX/XX/2008 | Total Completed Until XX/XX/08 | |
| 2 | Projected Work - Month 5 | | Total % to date | Total $ to date | | Projected Work - Month 06 | | Total % to date | Total $ to date | |
| 3 | | | | | | | | | | |
| 4 | 2.0% | $ 587.28 | 86.0% | $ 25,253.04 | | 2.0% | $ 587.28 | 88.0% | $ 25,840.32 | |
| 5 | 2.0% | $ 569.18 | 86.0% | $ 24,474.74 | | 2.0% | $ 569.18 | 88.0% | $ 25,043.92 | |
| 6 | 4.4% | $ 1,687.64 | 68.9% | $ 26,181.29 | | 4.4% | $ 1,687.64 | 73.3% | $ 27,868.93 | |
| 7 | 4.0% | $ 2,360.00 | 72.0% | $ 42,480.00 | | 4.0% | $ 2,360.00 | 76.0% | $ 44,840.00 | |
| 8 | | | | | | | | | | |
| 9 | 4.4% | $ 5,978.64 | 68.9% | $ 92,749.65 | | 4.4% | $ 5,978.64 | 73.3% | $ 98,728.28 | |
| 10 | 11.4% | $ 23,511.05 | 42.9% | $ 88,161.29 | | 11.4% | $ 23,511.05 | 54.3% | $ 111,672.34 | |
| 11 | 7.8% | $ 13,555.72 | 45.6% | $ 79,382.83 | | 7.8% | $ 13,555.72 | 53.3% | $ 92,938.55 | |
| 12 | 7.8% | $ 16,850.31 | 45.6% | $ 98,676.13 | | 7.8% | $ 16,850.31 | 53.3% | $ 115,526.44 | |
| 13 | 9.4% | $ 3,050.35 | 33.9% | $ 10,947.64 | | 9.4% | $ 3,050.35 | 43.3% | $ 13,997.99 | |
| 14 | 0.0% | $ - | 30.0% | $ 25,221.90 | | 0.0% | $ - | 30.0% | $ 25,221.90 | |
| 15 | | $ 68,150 | | $ 513,529 | | | $ 68,150 | | $ 581,679 | |
| 16 | | $ - | | | | | $ - | | | |
| 17 | | | | | | | | | | |
| 18 | 2.0% | $ 473.42 | 86.0% | $ 20,357.06 | | 2.0% | $ 473.42 | 88.0% | $ 20,830.48 | |
| 19 | 2.0% | $ 560.94 | 86.0% | $ 24,120.42 | | 2.0% | $ 560.94 | 88.0% | $ 24,681.36 | |
| 20 | 2.0% | $ 544.44 | 86.0% | $ 23,410.92 | | 2.0% | $ 544.44 | 88.0% | $ 23,955.36 | |
| 21 | 2.0% | $ 576.18 | 86.0% | $ 24,775.74 | | 2.0% | $ 576.18 | 88.0% | $ 25,351.92 | |
| 22 | 2.0% | $ 574.30 | 86.0% | $ 24,694.90 | | 2.0% | $ 574.30 | 88.0% | $ 25,269.20 | |
| 23 | 2.0% | $ 347.56 | 86.0% | $ 14,945.08 | | 2.0% | $ 347.56 | 88.0% | $ 15,292.64 | |

Figure 9H

| | BR | BS | | BV | BW | | BX | BY | BZ | | CC | CD | | CE |
|---|---|---|---|---|---|---|---|---|---|---|---|---|---|---|
| 24 | 2.0% | $ | 1,302.38 | 86.0% | $ | 56,002.34 | | 2.0% | $ | 1,302.38 | 88.0% | $ | 57,304.72 | |
| 25 | | $ | 4,379 | | $ | 188,306 | | | $ | 4,379 | | $ | 192,686 | |
| 26 | | | | | | | | | | | | | | |
| 27 | | $ | 72,529 | | $ | 701,835 | | | $ | 72,529 | | $ | 774,364 | |
| 28 | | | | | | | | | | | | | | |
| 29 | | | | | | | | | | | | | | |
| 30 | | | | | | | | | | | | | | |
| 31 | 0.0% | $ | - | 100.0% | $ | 31,902.20 | | 0.0% | $ | - | 100.0% | $ | 31,902.20 | |
| 32 | 0.0% | | | 0.0% | $ | - | | 0.0% | | | 0.0% | $ | - | |
| 33 | 16.7% | $ | 8,026.44 | 50.0% | $ | 24,079.32 | | 16.7% | $ | 8,026.44 | 66.7% | $ | 32,105.76 | |
| 34 | 17.0% | $ | 7,292.32 | 49.0% | $ | 21,019.04 | | 17.0% | $ | 7,292.32 | 66.0% | $ | 28,311.36 | |
| 35 | 16.7% | $ | 104,570.91 | 50.0% | $ | 313,712.73 | | 16.7% | $ | 104,570.91 | 66.7% | $ | 418,283.64 | |
| 36 | 0.0% | $ | - | 100.0% | $ | 57,600.00 | | 0.0% | $ | - | 100.0% | $ | 57,600.00 | |
| 37 | 0.0% | $ | - | 100.0% | $ | 83,400.00 | | 0.0% | $ | - | 100.0% | $ | 83,400.00 | |
| 38 | 20.0% | $ | 600.00 | 40.0% | $ | 1,200.00 | | 20.0% | $ | 600.00 | 60.0% | $ | 1,800.00 | |
| 39 | 0.0% | $ | - | 100.0% | $ | 8,063.19 | | 0.0% | $ | - | 100.0% | $ | 8,063.19 | |
| 40 | 6.8% | $ | 134.22 | 52.3% | $ | 1,028.87 | | 6.8% | $ | 134.22 | 59.1% | $ | 1,163.09 | |
| 41 | 8.6% | $ | 1,342.07 | 65.7% | $ | 10,290.21 | | 8.6% | $ | 1,342.07 | 74.3% | $ | 11,632.28 | |
| 42 | 5.6% | $ | 1,601.28 | 61.1% | $ | 17,602.56 | | 5.6% | $ | 1,601.28 | 66.7% | $ | 19,203.84 | |
| 43 | 0.0% | $ | - | 100.0% | $ | 35,005.00 | | 0.0% | $ | - | 100.0% | $ | 35,005.00 | |
| 44 | 8.3% | | | 0.0% | $ | - | | 8.3% | | | 0.0% | $ | - | |
| 45 | 0.0% | | | 0.0% | $ | - | | 20.0% | | | 0.0% | $ | - | |
| 46 | 33.3% | $ | 7,999.20 | 66.7% | $ | 15,998.40 | | 33.3% | $ | 7,999.20 | 100.0% | $ | 23,997.60 | |
| 47 | | $ | 131,566 | | $ | 620,902 | | | $ | 131,566 | | $ | 752,468 | |
| 48 | | | | | | | | | | | | | | |
| 49 | | | | | | | | | | | | | | |
| 50 | | $ | 204,096 | | $ | 1,322,736 | | | $ | 204,096 | | $ | 1,526,832 | |

Figure 9I

| | CF | CG | | CJ | CK | | CL | CM | CN | | CQ | CR | | CS |
|---|---|---|---|---|---|---|---|---|---|---|---|---|---|---|
| 1 | | | | | | | | | | | | | | |
| 2 | Projected Work - Month 07 | | | % Completed Until XX/XX/20 08 | Total Completed Until XX/XX/08 | | | Projected Work - Month 08 | | | % Completed Until XX/XX/20 08 | Total Completed Until XX/XX/08 | | |
| 3 | | | | Total % to date | Total $ to date | | | | | | Total % to date | Total $ to date | | |
| 4 | 2.0% | $ | 587.28 | 90.0% | $ | 26,427.60 | | 2.0% | $ | 587.28 | 92.0% | $ | 27,014.88 | |
| 5 | 2.0% | $ | 569.18 | 90.0% | $ | 25,613.10 | | 2.0% | $ | 569.18 | 92.0% | $ | 26,182.28 | |
| 6 | 4.4% | $ | 1,687.64 | 77.8% | $ | 29,556.58 | | 4.4% | $ | 1,687.64 | 82.2% | $ | 31,244.22 | |
| 7 | 4.0% | $ | 2,360.00 | 80.0% | $ | 47,200.00 | | 4.0% | $ | 2,360.00 | 84.0% | $ | 49,560.00 | |
| 8 | | | | | | | | | | | | | | |
| 9 | 4.4% | $ | 5,978.64 | 77.8% | $ | 104,706.92 | | 4.4% | $ | 5,978.64 | 82.2% | $ | 110,685.56 | |
| 10 | 11.4% | $ | 23,511.05 | 65.7% | $ | 135,183.38 | | 11.4% | $ | 23,511.05 | 77.2% | $ | 158,694.43 | |
| 11 | 7.8% | $ | 13,555.72 | 61.1% | $ | 106,494.27 | | 7.8% | $ | 13,555.72 | 68.9% | $ | 120,049.98 | |
| 12 | 7.8% | $ | 16,850.31 | 61.1% | $ | 132,376.75 | | 7.8% | $ | 16,850.31 | 68.9% | $ | 149,227.07 | |
| 13 | 9.4% | $ | 3,050.35 | 52.8% | $ | 17,048.34 | | 9.4% | $ | 3,050.35 | 62.2% | $ | 20,098.69 | |
| 14 | 0.0% | $ | - | 30.0% | $ | 25,221.90 | | 0.0% | $ | - | 30.0% | $ | 25,221.90 | |
| 15 | | $ | 68,150 | | $ | 649,829 | | | $ | 68,150 | | $ | 717,979 | |
| 16 | | $ | - | | | | | | $ | - | | | | |
| 17 | | | | | | | | | | | | | | |
| 18 | 2.0% | $ | 473.42 | 90.0% | $ | 21,303.90 | | 2.0% | $ | 473.42 | 92.0% | $ | 21,777.32 | |
| 19 | 2.0% | $ | 560.94 | 90.0% | $ | 25,242.30 | | 2.0% | $ | 560.94 | 92.0% | $ | 25,803.24 | |
| 20 | 2.0% | $ | 544.44 | 90.0% | $ | 24,499.80 | | 2.0% | $ | 544.44 | 92.0% | $ | 25,044.24 | |
| 21 | 2.0% | $ | 576.18 | 90.0% | $ | 25,928.10 | | 2.0% | $ | 576.18 | 92.0% | $ | 26,504.28 | |
| 22 | 2.0% | $ | 574.30 | 90.0% | $ | 25,843.50 | | 2.0% | $ | 574.30 | 92.0% | $ | 26,417.80 | |
| 23 | 2.0% | $ | 347.56 | 90.0% | $ | 15,640.20 | | 2.0% | $ | 347.56 | 92.0% | $ | 15,987.76 | |

Figure 9J

| | CF | CG | | CJ | CK | | CL | CM | CN | | CQ | CR | | CS |
|---|---|---|---|---|---|---|---|---|---|---|---|---|---|---|
| 24 | 2.0% | 1,302.38 | $ | 90.0% | 58,607.10 | $ | | 2.0% | 1,302.38 | $ | 92.0% | 59,909.48 | $ | |
| 25 | | 4,379 | $ | | 197,065 | $ | | | 4,379 | $ | | 201,444 | $ | |
| 26 | | | | | | | | | | | | | | |
| 27 | | 72,529 | $ | | 846,894 | $ | | | 72,529 | $ | | 919,423 | | |
| 28 | | | | | | | | | | | | | | |
| 29 | | | | | | | | | | | | | | |
| 30 | | | | | | | | | | | | | | |
| 31 | 0.0% | - | $ | 100.0% | 31,902.20 | $ | | 0.0% | - | $ | 100.0% | 31,902.20 | $ | |
| 32 | 0.0% | | | 0.0% | - | | | 0.0% | | | 0.0% | - | | |
| 33 | 16.7% | 8,026.44 | $ | 83.4% | 40,132.19 | $ | | 16.7% | 8,021.62 | $ | 100.0% | 48,153.82 | $ | |
| 34 | 17.0% | 7,292.32 | $ | 83.0% | 35,603.68 | $ | | 17.0% | 7,292.32 | $ | 100.0% | 42,896.00 | $ | |
| 35 | 16.7% | 104,570.91 | $ | 83.4% | 522,854.55 | $ | | 16.7% | 104,570.91 | $ | 100.0% | 627,425.46 | $ | |
| 36 | 0.0% | - | $ | 100.0% | 57,600.00 | $ | | 0.0% | - | $ | 100.0% | 57,600.00 | $ | |
| 37 | 0.0% | - | $ | 100.0% | 83,400.00 | $ | | 0.0% | - | $ | 100.0% | 83,400.00 | $ | |
| 38 | 20.0% | 600.00 | $ | 80.0% | 2,400.00 | $ | | 20.0% | 600.00 | $ | 100.0% | 3,000.00 | $ | |
| 39 | 0.0% | - | $ | 100.0% | 8,063.19 | $ | | 0.0% | - | $ | 100.0% | 8,063.19 | $ | |
| 40 | 6.8% | 134.22 | $ | 65.9% | 1,297.31 | $ | | 6.8% | 134.22 | $ | 72.7% | 1,431.52 | $ | |
| 41 | 8.6% | 1,342.07 | $ | 82.9% | 12,974.34 | $ | | 8.6% | 1,342.07 | $ | 91.4% | 14,316.41 | $ | |
| 42 | 5.6% | 1,601.28 | $ | 72.2% | 20,805.12 | $ | | 5.6% | 1,601.28 | $ | 77.8% | 22,406.40 | $ | |
| 43 | 0.0% | - | $ | 100.0% | 35,005.00 | $ | | 0.0% | - | $ | 100.0% | 35,005.00 | $ | |
| 44 | 8.3% | | | 0.0% | - | $ | | 8.3% | | | 0.0% | - | | |
| 45 | 0.0% | | | 0.0% | - | $ | | 0.0% | | | 0.0% | - | | |
| 46 | 0.0% | - | $ | 100.0% | 23,997.60 | $ | | 0.0% | - | $ | 100.0% | 23,997.60 | $ | |
| 47 | | 123,567 | $ | | 876,035 | $ | | | 123,562 | $ | | 999,598 | $ | |
| 48 | | | | | | | | | | | | | | |
| 49 | | | | | | | | | | | | | | |
| 50 | | 196,097 | $ | | 1,722,929 | $ | | | 196,092 | $ | | 1,919,021 | $ | |

Figure 9K

| | CT | CU | | CX | CY | | CZ | DA | DB | | DE | DF | |
|---|---|---|---|---|---|---|---|---|---|---|---|---|---|
| 1 | | | | % Completed Until XX/XX/20 08 | Total Completed Until XX/XX/08 | | | | | | % Completed Until XX/XX/20 08 | Total Completed Until XX/XX/08 | |
| 2 | Projected Work - Month 09 | | | Total % to date | Total $ to date | | | Projected Work - Month 10 | | | Total % to date | Total $ to date | |
| 3 | | | | | | | | | | | | | |
| 4 | 2.0% | $ | 587.28 | 94.0% | $ | 27,602.16 | | 2.0% | $ | 587.28 | 96.0% | $ | 28,189.44 |
| 5 | 2.0% | $ | 569.18 | 94.0% | $ | 26,751.46 | | 2.0% | $ | 569.18 | 96.0% | $ | 27,320.64 |
| 6 | 4.4% | $ | 1,687.64 | 86.6% | $ | 32,931.86 | | 4.4% | $ | 1,687.64 | 91.1% | $ | 34,619.51 |
| 7 | 4.0% | $ | 2,360.00 | 88.0% | $ | 51,920.00 | | 4.0% | $ | 2,360.00 | 92.0% | $ | 54,280.00 |
| 8 | | | | | | | | | | | | | |
| 9 | 4.4% | $ | 5,978.64 | 86.6% | $ | 116,664.19 | | 4.4% | $ | 5,978.64 | 91.1% | $ | 122,642.83 |
| 10 | 11.4% | $ | 23,511.05 | 88.6% | $ | 182,205.48 | | 11.4% | $ | 23,511.05 | 100.0% | $ | 205,716.53 |
| 11 | 7.8% | $ | 13,555.72 | 76.7% | $ | 133,605.70 | | 7.8% | $ | 13,555.72 | 84.5% | $ | 147,161.41 |
| 12 | 7.8% | $ | 16,850.31 | 76.7% | $ | 166,077.38 | | 7.8% | $ | 16,850.31 | 84.5% | $ | 182,927.69 |
| 13 | 9.4% | $ | 3,050.35 | 71.6% | $ | 23,149.03 | | 9.4% | $ | 3,050.35 | 81.1% | $ | 26,199.38 |
| 14 | 0.0% | $ | - | 30.0% | $ | 25,221.90 | | 23.3% | $ | 19,614.23 | 53.3% | $ | 44,836.13 |
| 15 | | $ | 68,150 | | $ | 786,129 | | | $ | 87,764 | | $ | 873,894 |
| 16 | | $ | - | | | | | | $ | - | | | |
| 17 | | | | | | | | | | | | | |
| 18 | 2.0% | $ | 473.42 | 94.0% | $ | 22,250.74 | | 2.0% | $ | 473.42 | 96.0% | $ | 22,724.16 |
| 19 | 2.0% | $ | 560.94 | 94.0% | $ | 26,364.18 | | 2.0% | $ | 560.94 | 96.0% | $ | 26,925.12 |
| 20 | 2.0% | $ | 544.44 | 94.0% | $ | 25,588.68 | | 2.0% | $ | 544.44 | 96.0% | $ | 26,133.12 |
| 21 | 2.0% | $ | 576.18 | 94.0% | $ | 27,080.46 | | 2.0% | $ | 576.18 | 96.0% | $ | 27,656.64 |
| 22 | 2.0% | $ | 574.30 | 94.0% | $ | 26,992.10 | | 2.0% | $ | 574.30 | 96.0% | $ | 27,566.40 |
| 23 | 2.0% | $ | 347.56 | 94.0% | $ | 16,335.32 | | 2.0% | $ | 347.56 | 96.0% | $ | 16,682.88 |

Figure 9L

| | CT | CU | | CX | CY | | CZ | DA | DB | | DE | DF | |
|---|---|---|---|---|---|---|---|---|---|---|---|---|---|
| 24 | 2.0% | 1,302.38 | $ | 94.0% | 61,211.86 | $ | | 2.0% | 1,302.38 | $ | 96.0% | 62,514.24 | $ |
| 25 | | 4,379 | $ | | 205,823 | $ | | | 4,379 | $ | | 210,203 | $ |
| 26 | | | | | | | | | | | | | |
| 27 | | 72,529 | $ | | 991,953 | $ | | | 92,144 | $ | | 1,084,096 | $ |
| 28 | | | | | | | | | | | | | |
| 29 | | | | | | | | | | | | | |
| 30 | | | | | | | | | | | | | |
| 31 | 0.0% | - | $ | 100.0% | 31,902.20 | $ | | 0.0% | - | $ | 100.0% | 31,902.20 | $ |
| 32 | 0.0% | | $ | 0.0% | - | $ | | 0.0% | | $ | 0.0% | - | $ |
| 33 | 0.0% | - | $ | 100.0% | 48,153.82 | $ | | 0.0% | - | $ | 100.0% | 48,153.82 | $ |
| 34 | 0.0% | - | $ | 100.0% | 42,896.00 | $ | | 0.% | - | $ | 100.0% | 42,896.00 | $ |
| 35 | 0.0% | - | $ | 100.0% | 627,425.46 | $ | | 0.0% | - | $ | 100.0% | 627,425.46 | $ |
| 36 | 0.0% | - | $ | 100.0% | 57,600.00 | $ | | 0.0% | - | $ | 100.0% | 57,600.00 | $ |
| 37 | 0.0% | - | $ | 100.0% | 83,400.00 | $ | | 0.0% | - | $ | 100.0% | 83,400.00 | $ |
| 38 | 0.0% | - | $ | 100.0% | 3,000.00 | $ | | 0.0% | - | $ | 100.0% | 3,000.00 | $ |
| 39 | 0.0% | - | $ | 100.0% | 8,063.19 | $ | | 0.0% | - | $ | 100.0% | 8,063.19 | $ |
| 40 | 6.8% | 134.22 | $ | 79.6% | 1,565.74 | $ | | 6.8% | 134.22 | $ | 86.4% | 1,699.96 | $ |
| 41 | 8.6% | 1,342.07 | $ | 100.0% | 15,658.47 | $ | | 0.0% | - | $ | 100.0% | 15,658.47 | $ |
| 42 | 5.6% | 1,601.28 | $ | 83.4% | 24,007.68 | $ | | 5.6% | 1,601.28 | $ | 88.9% | 25,608.96 | $ |
| 43 | 0.0% | - | $ | 100.0% | 35,005.00 | $ | | 0.0% | - | $ | 100.0% | 35,005.00 | $ |
| 44 | 8.3% | | | 0.0% | - | $ | | 8.3% | | | 0.0% | - | $ |
| 45 | 10.0% | | | 0.0% | - | $ | | | | | 0.0% | - | $ |
| 46 | 0.0% | - | $ | 100.0% | 23,997.60 | $ | | 0.0% | - | $ | 100.0% | 23,997.60 | $ |
| 47 | | 3,078 | $ | | 1,002,675 | $ | | | 1,735 | $ | | 1,004,411 | $ |
| 48 | | | | | | | | | | | | | |
| 49 | | | | | | | | | | | | | |
| 50 | | 75,607 | $ | | 1,994,628 | $ | | | 93,879 | $ | | 2,088,507 | $ |

Figure 9M

| | DG | DH | DI | DL | DM | DN | DO | DP | DS | DT |
|---|---|---|---|---|---|---|---|---|---|---|
| 1 | | | | | Total Completed Until XX/XX/08 | | | | | Total Completed Until XX/XX/08 |
| 2 | | Projected Work - Month 11 | | % Completed Until XX/XX/2008 | Total $ to date | | Projected Work - Month 12 | | % Completed Until XX/XX/2008 | Total $ to date |
| 3 | | | | Total % to date | | | | | Total % to date | |
| 4 | | 2.0% | $ 587.28 | 98.0% | $ 28,776.72 | | 2.0% | $ 587.28 | 100.0% | $ 29,364.00 |
| 5 | | 2.0% | $ 569.18 | 98.0% | $ 27,889.82 | | 2.0% | $ 569.18 | 100.0% | $ 28,459.00 |
| 6 | | 4.4% | $ 1,687.64 | 95.5% | $ 36,307.15 | | 4.4% | $ 1,687.64 | 100.0% | $ 37,994.80 |
| 7 | | 4.0% | $ 2,360.00 | 96.0% | $ 56,640.00 | | 4.0% | $ 2,360.00 | 100.0% | $ 59,000.00 |
| 8 | | | | | | | | | | |
| 9 | | 4.4% | $ 5,978.64 | 95.5% | $ 128,621.46 | | 4.4% | $ 5,978.64 | 100.0% | $ 134,600.10 |
| 10 | | 0.0% | $ - | 100.0% | $ 205,716.53 | | 0.0% | $ - | 100.0% | $ 205,716.53 |
| 11 | | 7.8% | $ 13,555.72 | 92.2% | $ 160,717.13 | | 7.8% | $ 13,555.72 | 100.0% | $ 174,272.85 |
| 12 | | 7.8% | $ 16,850.31 | 92.2% | $ 199,778.00 | | 7.8% | $ 16,850.31 | 100.0% | $ 216,628.32 |
| 13 | | 9.4% | $ 3,050.35 | 90.5% | $ 29,249.73 | | 9.4% | $ 3,050.35 | 100.0% | $ 32,300.07 |
| 14 | | 23.3% | $ 19,614.23 | 76.7% | $ 64,450.36 | | 23.3% | $ 19,614.23 | 100.0% | $ 84,064.59 |
| 15 | | | $ 64,253 | | $ 938,147 | | | $ 64,253 | | $ 1,002,400 |
| 16 | | | $ - | | | | | $ - | | |
| 17 | | | | | | | | | | |
| 18 | | 2.0% | $ 473.42 | 98.0% | $ 23,197.58 | | 2.0% | $ 473.42 | 100.0% | $ 23,671.00 |
| 19 | | 2.0% | $ 560.94 | 98.0% | $ 27,486.06 | | 2.0% | $ 560.94 | 100.0% | $ 28,047.00 |
| 20 | | 2.0% | $ 544.44 | 98.0% | $ 26,677.56 | | 2.0% | $ 544.44 | 100.0% | $ 27,222.00 |
| 21 | | 2.0% | $ 576.18 | 98.0% | $ 28,232.82 | | 2.0% | $ 576.18 | 100.0% | $ 28,809.00 |
| 22 | | 2.0% | $ 574.30 | 98.0% | $ 28,140.70 | | 2.0% | $ 574.30 | 100.0% | $ 28,715.00 |
| 23 | | 2.0% | $ 347.56 | 98.0% | $ 17,030.44 | | 2.0% | $ 347.56 | 100.0% | $ 17,378.00 |

Figure 9N

| | DG | DH | DI | DL | DM | DN | DO | DP | DS | DT |
|---|---|---|---|---|---|---|---|---|---|---|
| 24 | | 2.0% | $ 1,302.38 | 98.0% | $ 63,816.62 | | 2.0% | $ 1,302.38 | 100.0% | $ 65,119.00 |
| 25 | | | $ 4,379 | | $ 214,582 | | | $ 4,379 | | $ 218,961 |
| 26 | | | | | | | | | | |
| 27 | | | $ 68,633 | | $ 1,152,729 | | | $ 68,633 | | $ 1,221,361 |
| 28 | | | | | | | | | | |
| 29 | | | | | | | | | | |
| 30 | | | | | | | | | | |
| 31 | | 0.0% | $ - | 100.0% | $ 31,902.20 | | 0.0% | $ - | 100.0% | $ 31,902.20 |
| 32 | | 0.0% | | 0.0% | | | 0.0% | | 0.0% | - |
| 33 | | 0.0% | $ - | 100.0% | $ 48,153.82 | | 0.0% | $ - | 100.0% | $ 48,153.82 |
| 34 | | 0.0% | $ - | 100.0% | $ 42,896.00 | | 0.0% | $ - | 100.0% | $ 42,896.00 |
| 35 | | 0.0% | $ - | 100.0% | $ 627,425.46 | | 0.0% | $ - | 100.0% | $ 627,425.46 |
| 36 | | 0.0% | $ - | 100.0% | $ 57,600.00 | | 0.0% | $ - | 100.0% | $ 57,600.00 |
| 37 | | 0.0% | $ - | 100.0% | $ 83,400.00 | | 0.0% | $ - | 100.0% | $ 83,400.00 |
| 38 | | 0.0% | $ - | 100.0% | $ 3,000.00 | | 0.0% | $ - | 100.0% | $ 3,000.00 |
| 39 | | 0.0% | $ - | 100.0% | $ 8,063.19 | | 0.0% | $ - | 100.0% | $ 8,063.19 |
| 40 | | 6.8% | $ 134.22 | 93.2% | $ 1,834.18 | | 6.8% | $ 134.22 | 100.0% | $ 1,968.39 |
| 41 | | 0.0% | $ - | 100.0% | $ 15,658.47 | | 0.0% | $ - | 100.0% | $ 15,658.47 |
| 42 | | 5.6% | $ 1,601.28 | 94.5% | $ 27,210.24 | | 5.6% | $ 1,601.28 | 100.0% | $ 28,811.52 |
| 43 | | 0.0% | $ - | 100.0% | $ 35,005.00 | | 0.0% | $ - | 100.0% | $ 35,005.00 |
| 44 | | 8.3% | | 0.0% | - | | 8.3% | | 0.0% | - |
| 45 | | 0.0% | | 0.0% | | | 0.0% | | 0.0% | |
| 46 | | 0.0% | $ - | 100.0% | $ 23,997.60 | | 0.0% | $ - | 100.0% | $ 23,997.60 |
| 47 | | | $ 1,735 | | $ 1,006,146 | | | $ 1,735 | | $ 1,007,882 |
| 48 | | | | | | | | | | |
| 49 | | | | | | | | | | |
| 50 | | | $ 70,368 | | $ 2,158,875 | | | $ 70,368 | | $ 2,229,243 |

Figure 10A

| | B | C | D | E | F | G | H | I | J | K | L | N |
|---|---|---|---|---|---|---|---|---|---|---|---|---|
| 3 | | | | | | Numoda | ENTITY#1 | | | ENTITY#4 | | |
| 4 | Type | Date | | Payments | | Portion received | Paid | Left | | Portion received | Paid | |
| 5 | LOI | 4/18/2007 | | 25,000 | | 25,000 | 25,000 | - | | | | |
| 6 | CS | 6/1/2007 | | 233,590 | | 103,720 | 103,720 | - | | 121,038 | 53,000 | |
| 7 | 1st | 6/18/2007 | | 181,410 | | 53,432 | 53,432 | - | | 112,723 | 9,569 | |
| 8 | 2nd | 7/16/2007 | | 181,410 | | 53,432 | 53,432 | - | | 112,723 | 25,200 | |
| 9 | 3rd | 8/15/2007 | | 181,410 | | 53,432 | 53,432 | - | | 112,723 | 9,600 | |
| 10 | 4th | 10/4/2007 | | 181,410 | | 53,432 | 53,432 | - | | 112,723 | 26,822 | |
| 11 | 5th | 10/17/2007 | | 181,410 | | 53,432 | 53,432 | - | | 112,723 | 34,530 | |
| 12 | 6th | 12/27/2007 | | 181,410 | | 53,432 | 53,432 | - | | 112,723 | 35,424 | |
| 13 | 7th | 12/27/2007 | | 181,410 | | 53,432 | 53,432 | - | | 112,723 | 47,665 | |
| 14 | 8th | 4/4/2008 | | 181,410 | | 53,432 | 53,432 | - | | 112,723 | 65,597 | |
| 15 | 9th | 4/4/2008 | | 181,410 | | 53,432 | 53,432 | - | | 112,723 | 17,221 | |
| 16 | 10th | 4/4/2008 | | 181,410 | | 53,432 | 53,432 | - | | 112,723 | 8,019 | |
| 17 | 11th | | | | | 53,432 | 53,432 | - | | | 15,353 | |
| 18 | 12th | | | | | | | - | | | 103,230 | |
| 19 | 13th | | | | | | | - | | | 48,128 | |
| 20 | 14th | | | | | | | - | | | 52,943 | |
| 21 | 15th | | | | | | | - | | | 1,374 | |
| 22 | 16th | | | | | | | - | | | 15,815 | |
| 23 | | | | | | | | - | | | 26,569 | |
| 24 | | | | | | | | - | | | 28,334 | |
| 25 | | | | | | | | - | | | 7,227 | |
| 26 | | | | | | | | - | | | 73,142 | |
| 27 | | | | | | | | - | | | 42,294 | |
| 28 | | | | | | | | - | | | 83,951 | |
| 29 | | | | | | | | - | | | 53,881 | |
| 30 | | | | | | | | - | | | 16,708 | |
| 39 | | | | 2,047,690 | | 716,470 | 716,470 | - | | 1,248,269 | 901,597 | |

Figure 10B

| | Change Order | | | | | Numoda | ENTITY#1 | | | ENTITY#4 | |
|---|---|---|---|---|---|---|---|---|---|---|---|
| | Type | Date | | Payments | | Portion received | Paid | Left | | Portion received | Paid |
| | CO#1 | Paid | | 27,930 | | 11,220 | 11,220 | - | | 16,710 | 16,710 |
| | CO#2 | sent | | 34,100 | | | | - | | 34,100 | |
| | CNF#01 | sent | | 11,250 | | 7,500 | 7,500 | - | | 3,700 | |
| | CNF#02 | Aproved | | 43,701 | | 36,900 | 36,900 | - | | 6,851 | |
| | CNF#04 | Invoiced | | 44,700 | | 5,237 | 2,683 | 2,554 | | 39,463 | |
| | CO #04 | Sent/not App | | 326,375 | | 234,590 | | 237,144 | | | |
| | CNF#06 | | | 97,650 | | | - | 237,144 | | | |
| | CNF#07 | | | | | | - | 237,144 | | | |
| | CNF#08 | | | | | | - | 237,144 | | | |
| | CNF#09 | | | | | | - | 237,144 | | | |
| | CNF#10 | | | | | | - | 237,144 | | | |
| | CNF#11 | | | | | | - | 237,144 | | | |
| | | | | 585,706 | - | 295,447 | 58,303 | | - | 100,824 | 16,710 |
| | | | | | | | | | | | |
| | | | | | | TOTAL BUDGET | | 2,229,097 | | | |
| | | | | | | TOTAL NUMODA BUDGET | | 958,915 | | | |
| | | | | | | TOTAL VENDORS BUDGET | | 1,270,182 | | | |
| | | | 2,074,690 | | | TOTAL RECEIVED | | 2,047,690 | | | |
| | | | | | | TOTAL RECEIVED TO NUMODA | | 716,470 | | | |
| | | | | | | TOTAL RECEIVED TO VENDORS | | 1,331,220 | | | |
| | | | | | | | | | | | |
| | | | | | | TOTAL PAID TO VENDORS | | 1,035,528 | | | |
| | | | | | | CASH RESERVED TO VENDORS | | 295,692 | | | 295,692 |
| | | | | | | CASH RESERVED TO SPONSOR | | 25,000 | | | |

Figure 10C

| | O | P | Q | R | S | T | U | V | W | X | Y | Z |
|---|---|---|---|---|---|---|---|---|---|---|---|---|
| 3 | | Entity#5 | | | | ENTITY#7 | | | | ENTITY#6 | | |
| 4 | Portion received | Paid | Left | | Portion received | Paid | Left | | Portion received | Paid | Left | |
| 5 | | | | | | | | | | | | |
| 6 | 2,015 | | 2,015 | | 2,202 | | 2,202 | | 2,713 | | 2,713 | |
| 7 | 3,480 | 31,900 | (26,405) | | 3,804 | 15,305 | (11,501) | | 4,686 | 7,550 | (151) | |
| 8 | 3,480 | 5,914 | (28,838) | | 3,804 | 348 | 3,456 | | 4,686 | 331 | 4,204 | |
| 9 | 3,480 | 429 | (25,787) | | 3,804 | 2,025 | 1,779 | | 4,686 | 3,961 | 4,929 | |
| 10 | 3,480 | 504 | (22,810) | | 3,804 | 2,545 | 1,260 | | 4,686 | 2,786 | 6,829 | |
| 11 | 3,480 | 350 | (19,679) | | 3,804 | 2,541 | 1,263 | | 4,686 | 2,257 | 9,257 | |
| 12 | 3,480 | 428 | (16,627) | | 3,804 | 2,276 | 1,528 | | 4,686 | 4,543 | 9,400 | |
| 13 | 3,480 | 515 | (13,662) | | 3,804 | 2,453 | 1,352 | | 4,686 | 4,608 | 9,478 | |
| 14 | 3,480 | 439 | (10,621) | | 3,804 | 2,168 | 1,636 | | 4,686 | 3,595 | 10,568 | |
| 15 | 3,480 | 1,417 | (8,558) | | 3,804 | 2,268 | 1,537 | | 4,686 | 3,272 | 11,982 | |
| 16 | 3,480 | 2,338 | (7,415) | | 3,804 | 2,317 | 1,488 | | 4,686 | | 16,668 | |
| 17 | 3,480 | | (3,934) | | 3,804 | 2,272 | 1,532 | | 4,686 | | 21,353 | |
| 18 | | | (3,934) | | | | - | | | | 21,353 | |
| 19 | | | (3,934) | | | | - | | | | 21,353 | |
| 20 | | | (3,934) | | | | - | | | | 21,353 | |
| 21 | | | (3,934) | | | | - | | | | 21,353 | |
| 22 | | | (3,934) | | | | - | | | | 21,353 | |
| 23 | | | (3,934) | | | | - | | | | 21,353 | |
| 24 | | | (3,934) | | | | - | | | | 21,353 | |
| 25 | | | (3,934) | | | | - | | | | 21,353 | |
| 26 | | | (3,934) | | | | - | | | | 21,353 | |
| 27 | | | (3,934) | | | | - | | | | 21,353 | |
| 28 | | | (3,934) | | | | - | | | | 21,353 | |
| 29 | | | (3,934) | | | | - | | | | 21,353 | |
| 30 | | | (3,934) | | | | - | | | | 21,353 | |
| 31 | | | (3,934) | | | | - | | | | 21,353 | |
| 32 | | | (3,934) | | | | - | | | | 21,353 | |
| 33 | | | (3,934) | | | | - | | | | 21,353 | |
| 34 | | | (3,934) | | | | - | | | | 21,353 | |
| 35 | | | (3,934) | | | | - | | | | 21,353 | |
| 36 | | | (3,934) | | | | - | | | | 21,353 | |
| 37 | | | (3,934) | | | | - | | | | 21,353 | |
| 39 | 40,300 | 44,234 | (261,010) | | 44,048 | 36,517 | | | 54,257 | 32,904 | | - |

Figure 10D

| | O | P | Q | R | S | T | U | V | W | X | Y | Z |
|---|---|---|---|---|---|---|---|---|---|---|---|---|
| 40 | | | | | | | | | | | 6,620 | |
| 41 | | | | | | | | | | | | |
| 42 | | ENTITY#5 | | | | ENTITY#7 | | | | ENTITY#6 | | |
| 43 | Portion received | Paid | Left | | Portion received | Paid | Left | | Portion received | Paid | Left | |
| 44 | | | | | | | | | | | | |
| 45 | | | - | | | | - | | | | - | |
| 46 | | | - | | | | - | | | | - | |
| 47 | | | - | | | | - | | | | - | |
| 48 | | | - | | | | - | | | | - | |
| 49 | | | - | | | | - | | | | - | |
| 50 | 727 | | 727 | | 9,316 | | 9,316 | | | 1,697 | (1,697) | |
| 51 | | | 727 | | | | 9,316 | | | | (1,697) | |
| 52 | | | 727 | | | | 9,316 | | | | (1,697) | |
| 53 | | | 727 | | | | 9,316 | | | | (1,697) | |
| 54 | | | 727 | | | | 9,316 | | | | (1,697) | |
| 55 | | | 727 | | | | 9,316 | | | | (1,697) | |
| 56 | | | 727 | | | | 9,316 | | | | (1,697) | |
| 57 | | | | | | | | | | | | |
| 58 | 727 | - | | | 9,316 | - | | | | - | 1,697 | |
| 59 | | | | | | | | | | | | |
| 60 | | | 181,410 | | January, 08 | Payment | | | | | | |
| 61 | | | 181,410 | | February, 08 | Payment | | | | | | |
| 62 | | | 181,410 | | March, 08 | Payment | | | | | | |
| 63 | | | 44,700 | | March, 08 | CO # 4 Recrutment Program | | | | | | |
| 64 | | | | | | | | | | | | |
| 65 | TOTAL DUE NOT PAID | | 588,930 | | | | | | | | | |
| 66 | | | | | | | | | | | | |
| 67 | | | | | | | | | | | | |
| 68 | | | | | | | | | | | | |
| 69 | | | | | | | | | | | | |
| 70 | | | | | | | | | | | | |
| 71 | | | | | | | | | | | | |

Figure 10E

| | AA | AB | AC | AD | AE | AF | AG | AH |
|---|---|---|---|---|---|---|---|---|
| | | OTHERS | | | | SUBTOTAL 1 | | |
| 3 | Portion received | Paid | Left | | Portion received | Paid | Left | |
| 4 | | | | | | | | |
| 5 | | | | | 25,000 | 25,000 | - | |
| 6 | 1,902 | | 1,902 | | 233,590 | 156,720 | 76,870 | |
| 7 | 3,285 | 1,378 | 3,808 | | 181,410 | 119,134 | 68,905 | |
| 8 | 3,285 | 6,423 | 669 | | 181,410 | 91,647 | 67,015 | |
| 9 | 3,285 | 543 | 3,411 | | 181,410 | 69,990 | 87,455 | |
| 10 | 3,285 | 1,918 | 4,777 | | 181,410 | 88,006 | 75,957 | 53,432 |
| 11 | 3,285 | 675 | 7,387 | | 181,410 | 93,785 | 76,420 | |
| 12 | 3,285 | 5,400 | 5,271 | | 181,410 | #REF! | 76,871 | |
| 13 | 3,285 | 3,939 | 4,617 | | 181,410 | 114,073 | 66,842 | |
| 14 | 3,285 | | 7,902 | | 181,410 | 125,232 | 56,611 | |
| 15 | 3,285 | | 11,186 | | 181,410 | 77,610 | 111,649 | |
| 16 | 3,285 | | 14,471 | | 181,410 | 66,105 | 129,915 | |
| 17 | 3,285 | | 17,756 | | 68,687 | 71,057 | 21,353 | |
| 18 | | | 17,756 | | | 103,230 | (68,056) | |
| 19 | | | 17,756 | | | 48,128 | (12,954) | |
| 20 | | | 17,756 | | | 52,943 | (17,769) | |
| 21 | | | 17,756 | | | 1,374 | 33,801 | |
| 22 | | | | | | | 1,604 | |
| 23 | | | | | | | (9,150) | |
| 24 | | | | | | | (10,916) | |
| 25 | | | | | | | 10,192 | |
| 26 | | | | | | | (55,723) | |
| 27 | | | | | | | (24,875) | |
| 28 | | | | | | | | |
| 29 | | | | | | | | |
| 30 | | | | | | | | |
| 31 | | | | | | | | |
| 32 | | | | | | | | |
| 33 | | | | | | | | |
| 34 | | | | | | | | |
| 35 | | | | | | | | |
| 36 | | | | | | | 17,419 | |
| 37 | | | | | | | | |
| 38 | | | | | - | | | |
| 39 | 38,032 | 20,276 | 17,756 | | 2,116,376 | #REF! | 33,801 | |

Figure 10F

| | AA | AB | AC | AD | AE | AF | AG | AH |
|---|---|---|---|---|---|---|---|---|
| | ENTITY#6 | other | | | SUBTOTAL 2 | | | |
| | Portion received | Paid | Left | | Portion received | Paid | Left | |
| 40 | | | | | | | | |
| 41 | | | | | | | | |
| 42 | | | | | | | | |
| 43 | | | | | | | | |
| 44 | | | | | | | | |
| 45 | | | | | 27,930 | 27,930 | - | |
| 46 | | | | | 34,100 | - | 34,100 | |
| 47 | | | | | 11,200 | 7,500 | 37,800 | |
| 48 | | | | | 43,751 | 36,900 | 44,651 | |
| 49 | | | | | 44,700 | 2,683 | 86,668 | |
| 50 | 1,236 | | 1,236 | | 245,868 | 1,697 | 330,840 | |
| 51 | | | 1,236 | | - | - | 330,840 | |
| 52 | | | 1,236 | | - | - | 330,840 | |
| 53 | | | 1,236 | | - | - | 330,840 | |
| 54 | | | 1,236 | | - | - | 330,840 | |
| 55 | | | 1,236 | | - | - | 330,840 | |
| 56 | | | 1,236 | | - | - | 330,840 | |
| 57 | | | | | | | | |
| 58 | 1,236 | - | | | 407,549 | 76,710 | | |
| 59 | | | | | | | | |
| 60 | | | | | | | | |
| 61 | | | | | | | | |
| 62 | | | | | | | | |
| 63 | | | | | | | | |
| 64 | | | | | | | | |
| 65 | | | | | | | | |
| 66 | | | | | | | | |
| 67 | | | | | | | | |
| 68 | | | | | | | | |
| 69 | | | | | | | | |
| 70 | | | | | | | | |
| 71 | | | | | | | | |

Figure 12B

| | | | | | | | Visit | | | | | | | eCRF Status | | | |
|---|---|---|---|---|---|---|---|---|---|---|---|---|---|---|---|---|---|
| PatientID | Initials | Current Status | Date Randomi zed/ (Screened) | Date Disc'ned | Drug Dispensed | V1 - Screening | V2 - Baseline | V3 - Randomization | V4 - Treatment Period | V5 - Treatment Period | V6 - Treatment Period | V7 - Treatment Period | | C | L | I/P | Q |
| 10001 | PLR | C | 26 Nov 2007 | | Y | 10/30/2007 | 11/07/2007 | 11/26/2007 | 12/12/2007 | 12/24/2007 | 01/22/2008 | 02/19/2008 | | 70 | 68 | 0 | 1 |
| 10002 | J-P | D | 15 Nov 2007 | 11/15/2007 | Y | 10/30/2007 | 11/09/2007 | 11/15/2007 | | | | 11/29/2007 | | 43 | 42 | 0 | 0 |
| 10003 | LCS | C | 13 Nov 2007 | | Y | 10/30/2007 | 11/07/2007 | 11/13/2007 | 11/27/2007 | 12/12/2007 | 01/11/2008 | 02/15/2008 | | 70 | 68 | 0 | 2 |
| 10004 | SAT | C | 21 Dec 2007 | | Y | 12/07/2007 | 12/14/2007 | 12/21/2007 | 01/04/2008 | 01/18/2008 | 02/15/2008 | 03/14/2008 | | 70 | 67 | 0 | 2 |
| 10005 | CRK | C | 24 Jan 2008 | | Y | 01/09/2008 | 01/17/2008 | 01/24/2008 | 02/08/2008 | 02/21/2008 | 03/20/2008 | 04/18/2008 | | 70 | 66 | 0 | 2 |
| 10006 | N-R | C | 24 Jan 2008 | | Y | 01/11/2008 | 01/17/2008 | 01/24/2008 | 02/08/2008 | 02/25/2008 | 03/27/2008 | 04/24/2008 | | 70 | 64 | 0 | 4 |
| 10007 | TMB | C | 01 Feb 2008 | | Y | 01/14/2008 | 01/24/2008 | 02/01/2008 | 02/15/2008 | 02/29/2008 | 03/27/2008 | 04/23/2008 | | 70 | 66 | 0 | 4 |
| 10008 | LMS | C | 12 Feb 2008 | | Y | 01/28/2008 | 02/04/2008 | 02/12/2008 | 02/26/2008 | 03/12/2008 | 04/09/2008 | 05/07/2008 | | 70 | 54 | 0 | 0 |
| 10009 | BLA | SF | (05 Feb 2008) | | N | 02/05/2008 | 02/12/2008 | | | | | | | 21 | 20 | 0 | 0 |
| 10010 | J-M | SF | (12 Feb 2008) | | N | 02/12/2008 | | | | | | | | 13 | 12 | 0 | 0 |

Screening and Enrollment Reporting Tools
Early Safety Signal Detection System
Monitoring System
Real-Time Reporting Tools
Document Management System
Log Off

Figure 18A

|    | A |
|----|---|
| 1  | XXXXXXX |
| 2  | Enrolled Patients |
| 3  | Evaluable Patients |
| 4  | Sites |
| 5  | Total CRF Pages |
| 6  | Study Duration |
| 7  | |
| 8  | |
| 9  | ENTITY #4 |
| 10 | *INITIAL PAYMENT* |
| 11 | STUDY SETUP AND REGULATORY |
| 12 | INVESTIGATOR SELECTION |
| 13 | QUALIFICATION SITE ASSESSMENT VISIT |
| 14 | COLLECTION AND PROCESSING OF REGULATORY DOCUMENTATION |
| 15 | KICK OF MEETING |
| 16 | INVESTIGATOR MTG (Atendance & Participation) |
| 17 | INVESTIGATOR MTG (Coordination) |
| 18 | TRAINING MTG |
| 19 | NEGOTIATION & ADMINISTRATION OF INVESTIGATOR CONTRACTS |
| 20 | NEGOTIATION OF INVESTIGATOR CONTRACTS |
| 21 | |
| 22 | PROJECT MANAGEMENT |
| 23 | PROJECT COORDINATION (12 Months) |
| 24 | PROJECT MEETINGS |
| 25 | CONFERENCE CALLS |
| 26 | NEWSLETTERS |
| 27 | STATUS REPORTS |
| 28 | Scale and Calibration Weight Coordination |
| 29 | PROTOCOL AMENDMENT # 01 (Review) |
| 30 | |
| 31 | CLINICAL MONITORING AND MEDICAL SUPPORT |
| 32 | INITIATION VISITS |
| 33 | INTERIM MONITORING VISITS |
| 34 | CLOSEOUT VISITS |
| 35 | STATUS REPORTS |
| 36 | ADMINISTRATION |
| 37 | PROTOCOLA AMENDMENT #01 (Cordination for 12 Sites) |
| 38 | MEDICAL MANAGEMENT |
| 39 | SAE Management (SET-UP) |
| 40 | SAE Management (01 SAE) |
| 41 | SAE Narratives (01 Narrative) |
| 42 | |
| 43 | SITE MANAGEMENT |
| 44 | SITE MANAGEMENT |
| 45 | PROJECT MEETINGS |
| 46 | STATUS REPORTS |
| 47 | |
| 48 | BIOSTATISTICAL SERVICES |
| 49 | ='\\Numodanas1\sales\Sales Share\Ann\Patent CPAC\source documents 1\[Bu |
| 50 | ='\\Numodanas1\sales\Sales Share\Ann\Patent CPAC\source documents 1\[Bu |
| 51 | ='\\Numodanas1\sales\Sales Share\Ann\Patent CPAC\source documents 1\[Bu |
| 52 | ='\\Numodanas1\sales\Sales Share\Ann\Patent CPAC\source documents 1\[Bu |
| 53 | ='\\Numodanas1\sales\Sales Share\Ann\Patent CPAC\source documents 1\[Bu |
| 54 | |
| 55 | SAFETY MEDICAL & SCIENTIFIC SERVICES |

Figure 18B

| | A |
|---|---|
| 56 | SAFETY MEDICAL & SCIENTIFIC SERVICES (SCIENTIFIC WRITING) |
| 57 | IN HOUSE MEDICAL SUPPORT |
| 58 | |
| 59 | CREDIT |
| 60 | |
| 61 | ENTITY #5 |
| 62 | *INITIAL PAYMENT* |
| 63 | STUDY SETUP AND REGULATORY |
| 64 | GENERATION OF RANDOMIZATION CODE |
| 65 | GENERATION/REVISION OF LABELING RECORD |
| 66 | Acquisition of single Panel Labels to be applied to the bottles (2000 units) |
| 67 | Acquisition of three panel labels to be applied to the boxes (667 units) |
| 68 | Acquisiton of boxes (667 units) |
| 69 | Approvals of labels according to the Randomization Code |
| 70 | Labeling of Bottled Gels and Packaging into boxes |
| 71 | Release of Clinically Labeled Product ( Included) |
| 72 | |
| 73 | ENTITY #6 |
| 74 | *INITIAL PAYMENT* |
| 75 | TESTING: SCREEN |
| 76 | Chemistry Panel(1) |
| 77 | Hematology Panel(2) |
| 78 | Urinalysis |
| 79 | PSA( cooled) |
| 80 | Hemoglobin A1C |
| 81 | Serum Pregnancy (5) |
| 82 | |
| 83 | TESTING: ENROLLED - VISIT 7 |
| 84 | Chemistry Panel(1) |
| 85 | Hematology Panel(2) |
| 86 | Urinalysis |
| 87 | Serum Pregnancy (5) |
| 88 | |
| 89 | MATERIALS |
| 90 | Kits - Screen (6) |
| 91 | Kits - Screen  PSA (6) |
| 92 | Kits - Enrolled Visit 5 (6) |
| 93 | Kits - Enrolled Visit 7 (6) |
| 94 | |
| 95 | |
| 96 | Project Set Up Fee |
| 97 | Data Management Fee |
| 98 | Monthly Management Fee   (10 Months) |
| 99 | Other Contingencies |
| 100 | |
| 101 | PK lab |
| 102 | ='\\Numodanas1\sales\Sales Share\Ann\Patent CPAC\source documents 1\[Bu |
| 103 | ='\\Numodanas1\sales\Sales Share\Ann\Patent CPAC\source documents 1\[Bu |
| 104 | |
| 105 | ENTITY #7 |
| 106 | *INITIAL PAYMENT* |
| 107 | Project Assurance Services Fee, Project Management , Site Support, Customer Care Center eReporting Services |

Figure 18C

| | A |
|---|---|
| 108 | 12 Lead ECG Analysis Methodology |
| 109 | Manual Adjudication |
| 110 | 12 Lead ECG Collection and Delivery Equipment |
| 111 | Mortara ELI -150/200/250 or MAC1200 12-Lead ECG Devea and Support |
| 112 | Standard Electrodes |
| 113 | ECG Paper |
| 114 | Other Contingencies |
| 115 | |
| 116 | |
| 117 | ENTITY #1 |
| 118 | *INITIAL PAYMENT* |
| 119 | Services |
| 120 | Integrations (3) |
| 121 | Portal |
| 122 | Consolidation and Reconciliation |
| 123 | Vendor Management: |
| 124 | Ongoing Medical Monitoring Support Services |
| 125 | Patient Diaries - Printing Shipping, QC and Logistics tracking |
| 126 | |
| 127 | CLINICAL PROFESSIONAL SERVICES: |
| 128 | Startup Regulatory, and Stie Management Activities |
| 129 | Monitoring Activities |
| 130 | Project Management Activities (PM) |
| 131 | Data Management Activities (DM) |
| 132 | Monthly Management Fee |
| 133 | Safety, Medical &Scientific Activities |
| 134 | Biostatistics & Medical Writing Activites |
| 135 | Labeling Regulatory Input |
| 136 | |
| 137 | Systems and Tools |
| 138 | Screening and Enrollment Tools |
| 139 | Site Compliance Tools |
| 140 | Reporting Tools |
| 141 | Monitoring System |
| 142 | Safety |
| 143 | Supplies |
| 144 | IVRS System |
| 145 | |
| 146 | SAFETY MEDICAL & SCIENTIFIC SERVICES |
| 147 | SAFETY MEDICAL & SCIENTIFIC SERVICES (SCIENTIFIC WRITING) |
| 148 | |
| 149 | TOTAL PROFESSIONAL FEES |
| 150 | |
| 151 | CREDIT |
| 152 | |
| 153 | TOTAL PROFESSIONAL FEES AFTER CREDIT |
| 154 | |
| 155 | ENTITY #4 |
| 156 | *INITIAL PAYMENT* |
| 157 | INVESTIGATOR MEETING (Travel and expenses) |
| 158 | CLINICAL TRIAL MATERIAL COORDINATION |
| 159 | GRANTS |
| 160 | TRAVEL MONITOR |

Figure 18D

| | A |
|---|---|
| 161 | REGULATORY (CENTRAL IRB COSTS) |
| 162 | ADVERTISING |
| 163 | Other (Contingencies) |
| 164 | PURCHASE OF 13 SCALES ( $ 1300 each) |
| 165 | PURCHASE OF 26 CALIBRATION WEIGHTS |
| 166 | |
| 167 | ENTITY #5 |
| 168 | *INITIAL PAYMENT* |
| 169 | Distribution to Clinical Site |
| 170 | Shipment |
| 171 | |
| 172 | ENTITY #6 |
| 173 | *INITIAL PAYMENT* |
| 174 | Estimated Transportation Costs: |
| 175 | Outbound (7) |
| 176 | Inbound RT -Screen |
| 177 | Inbound RT -Screen Cooled |
| 178 | Inbound RT - Enrolled - Visit 7 |
| 179 | |
| 180 | ENTITY #7 |
| 181 | *INITIAL PAYMENT* |
| 182 | Pass Through/Courier Shipments |
| 183 | |
| 184 | ENTITY #1 |
| 185 | *INITIAL PAYMENT* |
| 186 | Travel to Client Meetings |
| 187 | Travel for Audit Visits |
| 188 | Meetings and Teleconferences |
| 189 | Printing, Shipping and Other |
| 190 | IVRS Expenses |
| 191 | Translation |
| 192 | Advertising |
| 193 | OTHER CONTINGENCIES |
| 194 | |
| 195 | CREDIT |
| 196 | |
| 197 | TOTAL ESTIMATED PASS THROUGH EXPENSES |
| 198 | |
| 199 | =A155 |
| 200 | =A167 |
| 201 | =A172 |
| 202 | =A180 |
| 203 | =A184 |
| 204 | |
| 205 | TOTAL PROFESSIONAL FEES AND PASS THROUGH EXPENSES |
| 206 | |
| 207 | FACILITIES MANAGEMENT |
| 208 | |

Figure 18E

| | B |
|---|---|
| 1 | |
| 2 | 246 |
| 3 | 123 |
| 4 | 12 |
| 5 | |
| 6 | 12 |
| 7 | |
| 8 | Unit |
| 9 | |
| 10 | |
| 11 | |
| 12 | ='\\Numodanas1\sales\Sales Share\Ann\Patent CPAC\source documents 1\[Budget Tracking Template1 3G to A\ |
| 13 | ='\\Numodanas1\sales\Sales Share\Ann\Patent CPAC\source documents 1\[Budget Tracking Template1 3G to A\ |
| 14 | ='\\Numodanas1\sales\Sales Share\Ann\Patent CPAC\source documents 1\[Budget Tracking Template1 3G to A\ |
| 15 | ='\\Numodanas1\sales\Sales Share\Ann\Patent CPAC\source documents 1\[Budget Tracking Template1 3G to A\ |
| 16 | ='\\Numodanas1\sales\Sales Share\Ann\Patent CPAC\source documents 1\[Budget Tracking Template1 3G to A\ |
| 17 | ='\\Numodanas1\sales\Sales Share\Ann\Patent CPAC\source documents 1\[Budget Tracking Template1 3G to A\ |
| 18 | ='\\Numodanas1\sales\Sales Share\Ann\Patent CPAC\source documents 1\[Budget Tracking Template1 3G to A\ |
| 19 | ='\\Numodanas1\sales\Sales Share\Ann\Patent CPAC\source documents 1\[Budget Tracking Template1 3G to A\ |
| 20 | ='\\Numodanas1\sales\Sales Share\Ann\Patent CPAC\source documents 1\[Budget Tracking Template1 3G to A\ |
| 21 | |
| 22 | |
| 23 | ='\\Numodanas1\sales\Sales Share\Ann\Patent CPAC\source documents 1\[Budget Tracking Template1 3G to A\ |
| 24 | ='\\Numodanas1\sales\Sales Share\Ann\Patent CPAC\source documents 1\[Budget Tracking Template1 3G to A\ |
| 25 | ='\\Numodanas1\sales\Sales Share\Ann\Patent CPAC\source documents 1\[Budget Tracking Template1 3G to A\ |
| 26 | ='\\Numodanas1\sales\Sales Share\Ann\Patent CPAC\source documents 1\[Budget Tracking Template1 3G to A\ |
| 27 | ='\\Numodanas1\sales\Sales Share\Ann\Patent CPAC\source documents 1\[Budget Tracking Template1 3G to A\ |
| 28 | ='\\Numodanas1\sales\Sales Share\Ann\Patent CPAC\source documents 1\[Budget Tracking Template1 3G to A\ |
| 29 | ='\\Numodanas1\sales\Sales Share\Ann\Patent CPAC\source documents 1\[Budget Tracking Template1 3G to A\ |
| 30 | |
| 31 | |
| 32 | ='\\Numodanas1\sales\Sales Share\Ann\Patent CPAC\source documents 1\[Budget Tracking Template1 3G to A\ |
| 33 | ='\\Numodanas1\sales\Sales Share\Ann\Patent CPAC\source documents 1\[Budget Tracking Template1 3G to A\ |
| 34 | ='\\Numodanas1\sales\Sales Share\Ann\Patent CPAC\source documents 1\[Budget Tracking Template1 3G to A\ |
| 35 | ='\\Numodanas1\sales\Sales Share\Ann\Patent CPAC\source documents 1\[Budget Tracking Template1 3G to A\ |
| 36 | ='\\Numodanas1\sales\Sales Share\Ann\Patent CPAC\source documents 1\[Budget Tracking Template1 3G to A\ |
| 37 | ='\\Numodanas1\sales\Sales Share\Ann\Patent CPAC\source documents 1\[Budget Tracking Template1 3G to A\ |
| 38 | ='\\Numodanas1\sales\Sales Share\Ann\Patent CPAC\source documents 1\[Budget Tracking Template1 3G to A\ |
| 39 | ='\\Numodanas1\sales\Sales Share\Ann\Patent CPAC\source documents 1\[Budget Tracking Template1 3G to A\ |
| 40 | ='\\Numodanas1\sales\Sales Share\Ann\Patent CPAC\source documents 1\[Budget Tracking Template1 3G to A\ |
| 41 | ='\\Numodanas1\sales\Sales Share\Ann\Patent CPAC\source documents 1\[Budget Tracking Template1 3G to A\ |
| 42 | |
| 43 | |
| 44 | ='\\Numodanas1\sales\Sales Share\Ann\Patent CPAC\source documents 1\[Budget Tracking Template1 3G to A\ |
| 45 | ='\\Numodanas1\sales\Sales Share\Ann\Patent CPAC\source documents 1\[Budget Tracking Template1 3G to A\ |
| 46 | ='\\Numodanas1\sales\Sales Share\Ann\Patent CPAC\source documents 1\[Budget Tracking Template1 3G to A\ |
| 47 | |
| 48 | |
| 49 | ='\\Numodanas1\sales\Sales Share\Ann\Patent CPAC\source documents 1\[Budget Tracking Template1 3G to A\ |
| 50 | ='\\Numodanas1\sales\Sales Share\Ann\Patent CPAC\source documents 1\[Budget Tracking Template1 3G to A\ |
| 51 | ='\\Numodanas1\sales\Sales Share\Ann\Patent CPAC\source documents 1\[Budget Tracking Template1 3G to A\ |
| 52 | ='\\Numodanas1\sales\Sales Share\Ann\Patent CPAC\source documents 1\[Budget Tracking Template1 3G to A\ |
| 53 | ='\\Numodanas1\sales\Sales Share\Ann\Patent CPAC\source documents 1\[Budget Tracking Template1 3G to A\ |
| 54 | |
| 55 | |

Figure 18F

| | B |
|---|---|
| 56 | ="\\Numodanas1\sales\Sales Share\Ann\Patent CPAC\source documents 1\[Budget Tracking Template1 3G to A\ |
| 57 | ="\\Numodanas1\sales\Sales Share\Ann\Patent CPAC\source documents 1\[Budget Tracking Template1 3G to A\ |
| 58 | |
| 59 | |
| 60 | |
| 61 | |
| 62 | |
| 63 | |
| 64 | ="\\Numodanas1\sales\Sales Share\Ann\Patent CPAC\source documents 1\[Budget Tracking Template1 3G to A\ |
| 65 | ="\\Numodanas1\sales\Sales Share\Ann\Patent CPAC\source documents 1\[Budget Tracking Template1 3G to A\ |
| 66 | ="\\Numodanas1\sales\Sales Share\Ann\Patent CPAC\source documents 1\[Budget Tracking Template1 3G to A\ |
| 67 | ="\\Numodanas1\sales\Sales Share\Ann\Patent CPAC\source documents 1\[Budget Tracking Template1 3G to A\ |
| 68 | ="\\Numodanas1\sales\Sales Share\Ann\Patent CPAC\source documents 1\[Budget Tracking Template1 3G to A\ |
| 69 | ="\\Numodanas1\sales\Sales Share\Ann\Patent CPAC\source documents 1\[Budget Tracking Template1 3G to A\ |
| 70 | ="\\Numodanas1\sales\Sales Share\Ann\Patent CPAC\source documents 1\[Budget Tracking Template1 3G to A\ |
| 71 | ="\\Numodanas1\sales\Sales Share\Ann\Patent CPAC\source documents 1\[Budget Tracking Template1 3G to A\ |
| 72 | |
| 73 | |
| 74 | |
| 75 | |
| 76 | ="\\Numodanas1\sales\Sales Share\Ann\Patent CPAC\source documents 1\[Budget Tracking Template1 3G to A\ |
| 77 | ="\\Numodanas1\sales\Sales Share\Ann\Patent CPAC\source documents 1\[Budget Tracking Template1 3G to A\ |
| 78 | ="\\Numodanas1\sales\Sales Share\Ann\Patent CPAC\source documents 1\[Budget Tracking Template1 3G to A\ |
| 79 | ="\\Numodanas1\sales\Sales Share\Ann\Patent CPAC\source documents 1\[Budget Tracking Template1 3G to A\ |
| 80 | ="\\Numodanas1\sales\Sales Share\Ann\Patent CPAC\source documents 1\[Budget Tracking Template1 3G to A\ |
| 81 | ="\\Numodanas1\sales\Sales Share\Ann\Patent CPAC\source documents 1\[Budget Tracking Template1 3G to A\ |
| 82 | |
| 83 | |
| 84 | ="\\Numodanas1\sales\Sales Share\Ann\Patent CPAC\source documents 1\[Budget Tracking Template1 3G to A\ |
| 85 | ="\\Numodanas1\sales\Sales Share\Ann\Patent CPAC\source documents 1\[Budget Tracking Template1 3G to A\ |
| 86 | ="\\Numodanas1\sales\Sales Share\Ann\Patent CPAC\source documents 1\[Budget Tracking Template1 3G to A\ |
| 87 | ="\\Numodanas1\sales\Sales Share\Ann\Patent CPAC\source documents 1\[Budget Tracking Template1 3G to A\ |
| 88 | |
| 89 | |
| 90 | ="\\Numodanas1\sales\Sales Share\Ann\Patent CPAC\source documents 1\[Budget Tracking Template1 3G to A\ |
| 91 | ="\\Numodanas1\sales\Sales Share\Ann\Patent CPAC\source documents 1\[Budget Tracking Template1 3G to A\ |
| 92 | ="\\Numodanas1\sales\Sales Share\Ann\Patent CPAC\source documents 1\[Budget Tracking Template1 3G to A\ |
| 93 | ="\\Numodanas1\sales\Sales Share\Ann\Patent CPAC\source documents 1\[Budget Tracking Template1 3G to A\ |
| 94 | |
| 95 | |
| 96 | ="\\Numodanas1\sales\Sales Share\Ann\Patent CPAC\source documents 1\[Budget Tracking Template1 3G to A\ |
| 97 | ="\\Numodanas1\sales\Sales Share\Ann\Patent CPAC\source documents 1\[Budget Tracking Template1 3G to A\ |
| 98 | ="\\Numodanas1\sales\Sales Share\Ann\Patent CPAC\source documents 1\[Budget Tracking Template1 3G to A\ |
| 99 | ="\\Numodanas1\sales\Sales Share\Ann\Patent CPAC\source documents 1\[Budget Tracking Template1 3G to A\ |
| 100 | |
| 101 | |
| 102 | ="\\Numodanas1\sales\Sales Share\Ann\Patent CPAC\source documents 1\[Budget Tracking Template1 3G to A\ |
| 103 | ="\\Numodanas1\sales\Sales Share\Ann\Patent CPAC\source documents 1\[Budget Tracking Template1 3G to A\ |
| 104 | |
| 105 | |
| 106 | |
| 107 | ="\\Numodanas1\sales\Sales Share\Ann\Patent CPAC\source documents 1\[Budget Tracking Template1 3G |

Figure 18G

| | B |
|---|---|
| 108 | |
| 109 | ='\\Numodanas1\sales\Sales Share\Ann\Patent CPAC\source documents 1\[Budget Tracking Template1 3G to A` |
| 110 | |
| 111 | ='\\Numodanas1\sales\Sales Share\Ann\Patent CPAC\source documents 1\[Budget Tracking Template1 3G to A` |
| 112 | ='\\Numodanas1\sales\Sales Share\Ann\Patent CPAC\source documents 1\[Budget Tracking Template1 3G to A` |
| 113 | ='\\Numodanas1\sales\Sales Share\Ann\Patent CPAC\source documents 1\[Budget Tracking Template1 3G to A` |
| 114 | ='\\Numodanas1\sales\Sales Share\Ann\Patent CPAC\source documents 1\[Budget Tracking Template1 3G to A` |
| 115 | |
| 116 | |
| 117 | |
| 118 | |
| 119 | |
| 120 | ='\\Numodanas1\sales\Sales Share\Ann\Patent CPAC\source documents 1\[Budget Tracking Template1 3G to A` |
| 121 | ='\\Numodanas1\sales\Sales Share\Ann\Patent CPAC\source documents 1\[Budget Tracking Template1 3G to A` |
| 122 | ='\\Numodanas1\sales\Sales Share\Ann\Patent CPAC\source documents 1\[Budget Tracking Template1 3G to A` |
| 123 | ='\\Numodanas1\sales\Sales Share\Ann\Patent CPAC\source documents 1\[Budget Tracking Template1 3G to A` |
| 124 | ='\\Numodanas1\sales\Sales Share\Ann\Patent CPAC\source documents 1\[Budget Tracking Template1 3G to A` |
| 125 | ='\\Numodanas1\sales\Sales Share\Ann\Patent CPAC\source documents 1\[Budget Tracking Template1 3G to A` |
| 126 | |
| 127 | |
| 128 | ='\\Numodanas1\sales\Sales Share\Ann\Patent CPAC\source documents 1\[Budget Tracking Template1 3G to A` |
| 129 | ='\\Numodanas1\sales\Sales Share\Ann\Patent CPAC\source documents 1\[Budget Tracking Template1 3G to A` |
| 130 | ='\\Numodanas1\sales\Sales Share\Ann\Patent CPAC\source documents 1\[Budget Tracking Template1 3G to A` |
| 131 | ='\\Numodanas1\sales\Sales Share\Ann\Patent CPAC\source documents 1\[Budget Tracking Template1 3G to A` |
| 132 | ='\\Numodanas1\sales\Sales Share\Ann\Patent CPAC\source documents 1\[Budget Tracking Template1 3G to A` |
| 133 | ='\\Numodanas1\sales\Sales Share\Ann\Patent CPAC\source documents 1\[Budget Tracking Template1 3G to A` |
| 134 | ='\\Numodanas1\sales\Sales Share\Ann\Patent CPAC\source documents 1\[Budget Tracking Template1 3G to A` |
| 135 | ='\\Numodanas1\sales\Sales Share\Ann\Patent CPAC\source documents 1\[Budget Tracking Template1 3G to A` |
| 136 | |
| 137 | |
| 138 | ='\\Numodanas1\sales\Sales Share\Ann\Patent CPAC\source documents 1\[Budget Tracking Template1 3G to A` |
| 139 | ='\\Numodanas1\sales\Sales Share\Ann\Patent CPAC\source documents 1\[Budget Tracking Template1 3G to A` |
| 140 | ='\\Numodanas1\sales\Sales Share\Ann\Patent CPAC\source documents 1\[Budget Tracking Template1 3G to A` |
| 141 | ='\\Numodanas1\sales\Sales Share\Ann\Patent CPAC\source documents 1\[Budget Tracking Template1 3G to A` |
| 142 | ='\\Numodanas1\sales\Sales Share\Ann\Patent CPAC\source documents 1\[Budget Tracking Template1 3G to A` |
| 143 | ='\\Numodanas1\sales\Sales Share\Ann\Patent CPAC\source documents 1\[Budget Tracking Template1 3G to A` |
| 144 | ='\\Numodanas1\sales\Sales Share\Ann\Patent CPAC\source documents 1\[Budget Tracking Template1 3G to A` |
| 145 | |
| 146 | |
| 147 | |
| 148 | |
| 149 | |
| 150 | |
| 151 | 15 |
| 152 | |
| 153 | |
| 154 | |
| 155 | |
| 156 | |
| 157 | ='\\Numodanas1\sales\Sales Share\Ann\Patent CPAC\source documents 1\[Budget Tracking Template1 3G to A` |
| 158 | ='\\Numodanas1\sales\Sales Share\Ann\Patent CPAC\source documents 1\[Budget Tracking Template1 3G to A` |
| 159 | ='\\Numodanas1\sales\Sales Share\Ann\Patent CPAC\source documents 1\[Budget Tracking Template1 3G to A` |
| 160 | ='\\Numodanas1\sales\Sales Share\Ann\Patent CPAC\source documents 1\[Budget Tracking Template1 3G to A` |

Figure 18H

| | B |
|---|---|
| 161 | ='\\Numodanas1\sales\Sales Share\Ann\Patent CPAC\source documents 1\[Budget Tracking Template1 3G to A\ |
| 162 | 1 |
| 163 | ='\\Numodanas1\sales\Sales Share\Ann\Patent CPAC\source documents 1\[Budget Tracking Template1 3G to A\ |
| 164 | ='\\Numodanas1\sales\Sales Share\Ann\Patent CPAC\source documents 1\[Budget Tracking Template1 3G to A\ |
| 165 | ='\\Numodanas1\sales\Sales Share\Ann\Patent CPAC\source documents 1\[Budget Tracking Template1 3G to A\ |
| 166 | |
| 167 | |
| 168 | |
| 169 | ='\\Numodanas1\sales\Sales Share\Ann\Patent CPAC\source documents 1\[Budget Tracking Template1 3( |
| 170 | ='\\Numodanas1\sales\Sales Share\Ann\Patent CPAC\source documents 1\[Budget Tracking Template1 3( |
| 171 | |
| 172 | |
| 173 | |
| 174 | |
| 175 | ='\\Numodanas1\sales\Sales Share\Ann\Patent CPAC\source documents 1\[Budget Tracking Template1 3G to A\ |
| 176 | ='\\Numodanas1\sales\Sales Share\Ann\Patent CPAC\source documents 1\[Budget Tracking Template1 3G to A\ |
| 177 | ='\\Numodanas1\sales\Sales Share\Ann\Patent CPAC\source documents 1\[Budget Tracking Template1 3G to A\ |
| 178 | ='\\Numodanas1\sales\Sales Share\Ann\Patent CPAC\source documents 1\[Budget Tracking Template1 3G to A\ |
| 179 | |
| 180 | |
| 181 | |
| 182 | ='\\Numodanas1\sales\Sales Share\Ann\Patent CPAC\source documents 1\[Budget Tracking Template1 3( |
| 183 | |
| 184 | |
| 185 | |
| 186 | ='\\Numodanas1\sales\Sales Share\Ann\Patent CPAC\source documents 1\[Budget Tracking Template1 3G to A\ |
| 187 | ='\\Numodanas1\sales\Sales Share\Ann\Patent CPAC\source documents 1\[Budget Tracking Template1 3G to A\ |
| 188 | ='\\Numodanas1\sales\Sales Share\Ann\Patent CPAC\source documents 1\[Budget Tracking Template1 3G to A\ |
| 189 | ='\\Numodanas1\sales\Sales Share\Ann\Patent CPAC\source documents 1\[Budget Tracking Template1 3G to A\ |
| 190 | ='\\Numodanas1\sales\Sales Share\Ann\Patent CPAC\source documents 1\[Budget Tracking Template1 3G to A\ |
| 191 | ='\\Numodanas1\sales\Sales Share\Ann\Patent CPAC\source documents 1\[Budget Tracking Template1 3G to A\ |
| 192 | ='\\Numodanas1\sales\Sales Share\Ann\Patent CPAC\source documents 1\[Budget Tracking Template1 3G to A\ |
| 193 | ='\\Numodanas1\sales\Sales Share\Ann\Patent CPAC\source documents 1\[Budget Tracking Template1 3G to A\ |
| 194 | |
| 195 | |
| 196 | |
| 197 | |
| 198 | |
| 199 | |
| 200 | |
| 201 | |
| 202 | |
| 203 | |
| 204 | |
| 205 | |
| 206 | |
| 207 | |
| 208 | |

Figure 18I

| | C |
|---|---|
| 1 | |
| 2 | |
| 3 | |
| 4 | |
| 5 | |
| 6 | |
| 7 | PROJECT BUDGET |
| 8 | Unit Price |
| 9 | |
| 10 | |
| 11 | |
| 12 | ='\\Numodanas1\sales\Sales Share\Ann\Patent CPAC\source documents 1\[Budget Tracking Template1 3G to A\ |
| 13 | ='\\Numodanas1\sales\Sales Share\Ann\Patent CPAC\source documents 1\[Budget Tracking Template1 3G to A\ |
| 14 | ='\\Numodanas1\sales\Sales Share\Ann\Patent CPAC\source documents 1\[Budget Tracking Template1 3G to A\ |
| 15 | ='\\Numodanas1\sales\Sales Share\Ann\Patent CPAC\source documents 1\[Budget Tracking Template1 3G to A\ |
| 16 | ='\\Numodanas1\sales\Sales Share\Ann\Patent CPAC\source documents 1\[Budget Tracking Template1 3G to A\ |
| 17 | ='\\Numodanas1\sales\Sales Share\Ann\Patent CPAC\source documents 1\[Budget Tracking Template1 3G to A\ |
| 18 | ='\\Numodanas1\sales\Sales Share\Ann\Patent CPAC\source documents 1\[Budget Tracking Template1 3G to A\ |
| 19 | ='\\Numodanas1\sales\Sales Share\Ann\Patent CPAC\source documents 1\[Budget Tracking Template1 3G to A\ |
| 20 | ='\\Numodanas1\sales\Sales Share\Ann\Patent CPAC\source documents 1\[Budget Tracking Template1 3G to A\ |
| 21 | |
| 22 | |
| 23 | ='\\Numodanas1\sales\Sales Share\Ann\Patent CPAC\source documents 1\[Budget Tracking Template1 3G to A\ |
| 24 | ='\\Numodanas1\sales\Sales Share\Ann\Patent CPAC\source documents 1\[Budget Tracking Template1 3G to A\ |
| 25 | ='\\Numodanas1\sales\Sales Share\Ann\Patent CPAC\source documents 1\[Budget Tracking Template1 3G to A\ |
| 26 | ='\\Numodanas1\sales\Sales Share\Ann\Patent CPAC\source documents 1\[Budget Tracking Template1 3G to A\ |
| 27 | ='\\Numodanas1\sales\Sales Share\Ann\Patent CPAC\source documents 1\[Budget Tracking Template1 3G to A\ |
| 28 | ='\\Numodanas1\sales\Sales Share\Ann\Patent CPAC\source documents 1\[Budget Tracking Template1 3G to A\ |
| 29 | ='\\Numodanas1\sales\Sales Share\Ann\Patent CPAC\source documents 1\[Budget Tracking Template1 3G to A\ |
| 30 | |
| 31 | |
| 32 | ='\\Numodanas1\sales\Sales Share\Ann\Patent CPAC\source documents 1\[Budget Tracking Template1 3G to A\ |
| 33 | ='\\Numodanas1\sales\Sales Share\Ann\Patent CPAC\source documents 1\[Budget Tracking Template1 3G to A\ |
| 34 | ='\\Numodanas1\sales\Sales Share\Ann\Patent CPAC\source documents 1\[Budget Tracking Template1 3G to A\ |
| 35 | ='\\Numodanas1\sales\Sales Share\Ann\Patent CPAC\source documents 1\[Budget Tracking Template1 3G to A\ |
| 36 | ='\\Numodanas1\sales\Sales Share\Ann\Patent CPAC\source documents 1\[Budget Tracking Template1 3G to A\ |
| 37 | ='\\Numodanas1\sales\Sales Share\Ann\Patent CPAC\source documents 1\[Budget Tracking Template1 3G to A\ |
| 38 | ='\\Numodanas1\sales\Sales Share\Ann\Patent CPAC\source documents 1\[Budget Tracking Template1 3G to A\ |
| 39 | ='\\Numodanas1\sales\Sales Share\Ann\Patent CPAC\source documents 1\[Budget Tracking Template1 3G to A\ |
| 40 | ='\\Numodanas1\sales\Sales Share\Ann\Patent CPAC\source documents 1\[Budget Tracking Template1 3G to A\ |
| 41 | ='\\Numodanas1\sales\Sales Share\Ann\Patent CPAC\source documents 1\[Budget Tracking Template1 3G to A\ |
| 42 | |
| 43 | |
| 44 | ='\\Numodanas1\sales\Sales Share\Ann\Patent CPAC\source documents 1\[Budget Tracking Template1 3G to A\ |
| 45 | ='\\Numodanas1\sales\Sales Share\Ann\Patent CPAC\source documents 1\[Budget Tracking Template1 3G to A\ |
| 46 | ='\\Numodanas1\sales\Sales Share\Ann\Patent CPAC\source documents 1\[Budget Tracking Template1 3G to A\ |
| 47 | |
| 48 | |
| 49 | ='\\Numodanas1\sales\Sales Share\Ann\Patent CPAC\source documents 1\[Budget Tracking Template1 3G to A\ |
| 50 | ='\\Numodanas1\sales\Sales Share\Ann\Patent CPAC\source documents 1\[Budget Tracking Template1 3G to A\ |
| 51 | ='\\Numodanas1\sales\Sales Share\Ann\Patent CPAC\source documents 1\[Budget Tracking Template1 3G to A\ |
| 52 | ='\\Numodanas1\sales\Sales Share\Ann\Patent CPAC\source documents 1\[Budget Tracking Template1 3G to A\ |
| 53 | ='\\Numodanas1\sales\Sales Share\Ann\Patent CPAC\source documents 1\[Budget Tracking Template1 3G to A\ |
| 54 | |
| 55 | |

Figure 18J

| | C |
|---|---|
| 56 | ="\\Numodanas1\sales\Sales Share\Ann\Patent CPAC\source documents 1\[Budget Tracking Template1 3G to A\ |
| 57 | ="\\Numodanas1\sales\Sales Share\Ann\Patent CPAC\source documents 1\[Budget Tracking Template1 3G to A\ |
| 58 | |
| 59 | |
| 60 | |
| 61 | |
| 62 | |
| 63 | |
| 64 | ="\\Numodanas1\sales\Sales Share\Ann\Patent CPAC\source documents 1\[Budget Tracking Template1 3G to A\ |
| 65 | ="\\Numodanas1\sales\Sales Share\Ann\Patent CPAC\source documents 1\[Budget Tracking Template1 3G to A\ |
| 66 | ="\\Numodanas1\sales\Sales Share\Ann\Patent CPAC\source documents 1\[Budget Tracking Template1 3G to A\ |
| 67 | ="\\Numodanas1\sales\Sales Share\Ann\Patent CPAC\source documents 1\[Budget Tracking Template1 3G to A\ |
| 68 | ="\\Numodanas1\sales\Sales Share\Ann\Patent CPAC\source documents 1\[Budget Tracking Template1 3G to A\ |
| 69 | ="\\Numodanas1\sales\Sales Share\Ann\Patent CPAC\source documents 1\[Budget Tracking Template1 3G to A\ |
| 70 | ="\\Numodanas1\sales\Sales Share\Ann\Patent CPAC\source documents 1\[Budget Tracking Template1 3G to A\ |
| 71 | ="\\Numodanas1\sales\Sales Share\Ann\Patent CPAC\source documents 1\[Budget Tracking Template1 3G to A\ |
| 72 | |
| 73 | |
| 74 | |
| 75 | |
| 76 | ="\\Numodanas1\sales\Sales Share\Ann\Patent CPAC\source documents 1\[Budget Tracking Template1 3G to A\ |
| 77 | ="\\Numodanas1\sales\Sales Share\Ann\Patent CPAC\source documents 1\[Budget Tracking Template1 3G to A\ |
| 78 | ="\\Numodanas1\sales\Sales Share\Ann\Patent CPAC\source documents 1\[Budget Tracking Template1 3G to A\ |
| 79 | ="\\Numodanas1\sales\Sales Share\Ann\Patent CPAC\source documents 1\[Budget Tracking Template1 3G to A\ |
| 80 | ="\\Numodanas1\sales\Sales Share\Ann\Patent CPAC\source documents 1\[Budget Tracking Template1 3G to A\ |
| 81 | ="\\Numodanas1\sales\Sales Share\Ann\Patent CPAC\source documents 1\[Budget Tracking Template1 3G to A\ |
| 82 | |
| 83 | |
| 84 | ="\\Numodanas1\sales\Sales Share\Ann\Patent CPAC\source documents 1\[Budget Tracking Template1 3G to A\ |
| 85 | ="\\Numodanas1\sales\Sales Share\Ann\Patent CPAC\source documents 1\[Budget Tracking Template1 3G to A\ |
| 86 | ="\\Numodanas1\sales\Sales Share\Ann\Patent CPAC\source documents 1\[Budget Tracking Template1 3G to A\ |
| 87 | ="\\Numodanas1\sales\Sales Share\Ann\Patent CPAC\source documents 1\[Budget Tracking Template1 3G to A\ |
| 88 | |
| 89 | |
| 90 | ="\\Numodanas1\sales\Sales Share\Ann\Patent CPAC\source documents 1\[Budget Tracking Template1 3G to A\ |
| 91 | ="\\Numodanas1\sales\Sales Share\Ann\Patent CPAC\source documents 1\[Budget Tracking Template1 3G to A\ |
| 92 | ="\\Numodanas1\sales\Sales Share\Ann\Patent CPAC\source documents 1\[Budget Tracking Template1 3G to A\ |
| 93 | ="\\Numodanas1\sales\Sales Share\Ann\Patent CPAC\source documents 1\[Budget Tracking Template1 3G to A\ |
| 94 | |
| 95 | |
| 96 | ="\\Numodanas1\sales\Sales Share\Ann\Patent CPAC\source documents 1\[Budget Tracking Template1 3G to A\ |
| 97 | ="\\Numodanas1\sales\Sales Share\Ann\Patent CPAC\source documents 1\[Budget Tracking Template1 3G to A\ |
| 98 | ="\\Numodanas1\sales\Sales Share\Ann\Patent CPAC\source documents 1\[Budget Tracking Template1 3G to A\ |
| 99 | ="\\Numodanas1\sales\Sales Share\Ann\Patent CPAC\source documents 1\[Budget Tracking Template1 3G to A\ |
| 100 | |
| 101 | |
| 102 | ="\\Numodanas1\sales\Sales Share\Ann\Patent CPAC\source documents 1\[Budget Tracking Template1 3G to A\ |
| 103 | ="\\Numodanas1\sales\Sales Share\Ann\Patent CPAC\source documents 1\[Budget Tracking Template1 3G to A\ |
| 104 | |
| 105 | |
| 106 | |
| 107 | ="\\Numodanas1\sales\Sales Share\Ann\Patent CPAC\source documents 1\[Budget Tracking Template1 3G |

Figure 18K

| | C |
|---|---|
| 108 | |
| 109 | ='\\Numodanas1\sales\Sales Share\Ann\Patent CPAC\source documents 1\[Budget Tracking Template1 3G to A\ |
| 110 | |
| 111 | ='\\Numodanas1\sales\Sales Share\Ann\Patent CPAC\source documents 1\[Budget Tracking Template1 3G to A\ |
| 112 | ='\\Numodanas1\sales\Sales Share\Ann\Patent CPAC\source documents 1\[Budget Tracking Template1 3G to A\ |
| 113 | ='\\Numodanas1\sales\Sales Share\Ann\Patent CPAC\source documents 1\[Budget Tracking Template1 3G to A\ |
| 114 | ='\\Numodanas1\sales\Sales Share\Ann\Patent CPAC\source documents 1\[Budget Tracking Template1 3G to A\ |
| 115 | |
| 116 | |
| 117 | |
| 118 | |
| 119 | |
| 120 | ='\\Numodanas1\sales\Sales Share\Ann\Patent CPAC\source documents 1\[Budget Tracking Template1 3G to A\ |
| 121 | ='\\Numodanas1\sales\Sales Share\Ann\Patent CPAC\source documents 1\[Budget Tracking Template1 3G to A\ |
| 122 | ='\\Numodanas1\sales\Sales Share\Ann\Patent CPAC\source documents 1\[Budget Tracking Template1 3G to A\ |
| 123 | ='\\Numodanas1\sales\Sales Share\Ann\Patent CPAC\source documents 1\[Budget Tracking Template1 3G to A\ |
| 124 | ='\\Numodanas1\sales\Sales Share\Ann\Patent CPAC\source documents 1\[Budget Tracking Template1 3G to A\ |
| 125 | ='\\Numodanas1\sales\Sales Share\Ann\Patent CPAC\source documents 1\[Budget Tracking Template1 3G to A\ |
| 126 | |
| 127 | |
| 128 | ='\\Numodanas1\sales\Sales Share\Ann\Patent CPAC\source documents 1\[Budget Tracking Template1 3G to A\ |
| 129 | ='\\Numodanas1\sales\Sales Share\Ann\Patent CPAC\source documents 1\[Budget Tracking Template1 3G to A\ |
| 130 | ='\\Numodanas1\sales\Sales Share\Ann\Patent CPAC\source documents 1\[Budget Tracking Template1 3G to A\ |
| 131 | ='\\Numodanas1\sales\Sales Share\Ann\Patent CPAC\source documents 1\[Budget Tracking Template1 3G to A\ |
| 132 | ='\\Numodanas1\sales\Sales Share\Ann\Patent CPAC\source documents 1\[Budget Tracking Template1 3G to A\ |
| 133 | ='\\Numodanas1\sales\Sales Share\Ann\Patent CPAC\source documents 1\[Budget Tracking Template1 3G to A\ |
| 134 | ='\\Numodanas1\sales\Sales Share\Ann\Patent CPAC\source documents 1\[Budget Tracking Template1 3G to A\ |
| 135 | ='\\Numodanas1\sales\Sales Share\Ann\Patent CPAC\source documents 1\[Budget Tracking Template1 3G to A\ |
| 136 | |
| 137 | |
| 138 | ='\\Numodanas1\sales\Sales Share\Ann\Patent CPAC\source documents 1\[Budget Tracking Template1 3G to A\ |
| 139 | ='\\Numodanas1\sales\Sales Share\Ann\Patent CPAC\source documents 1\[Budget Tracking Template1 3G to A\ |
| 140 | ='\\Numodanas1\sales\Sales Share\Ann\Patent CPAC\source documents 1\[Budget Tracking Template1 3G to A\ |
| 141 | ='\\Numodanas1\sales\Sales Share\Ann\Patent CPAC\source documents 1\[Budget Tracking Template1 3G to A\ |
| 142 | ='\\Numodanas1\sales\Sales Share\Ann\Patent CPAC\source documents 1\[Budget Tracking Template1 3G to A\ |
| 143 | ='\\Numodanas1\sales\Sales Share\Ann\Patent CPAC\source documents 1\[Budget Tracking Template1 3G to A\ |
| 144 | ='\\Numodanas1\sales\Sales Share\Ann\Patent CPAC\source documents 1\[Budget Tracking Template1 3G to A\ |
| 145 | |
| 146 | |
| 147 | |
| 148 | |
| 149 | |
| 150 | |
| 151 | |
| 152 | |
| 153 | |
| 154 | |
| 155 | |
| 156 | |
| 157 | ='\\Numodanas1\sales\Sales Share\Ann\Patent CPAC\source documents 1\[Budget Tracking Template1 3G to A\ |
| 158 | ='\\Numodanas1\sales\Sales Share\Ann\Patent CPAC\source documents 1\[Budget Tracking Template1 3G to A\ |
| 159 | ='\\Numodanas1\sales\Sales Share\Ann\Patent CPAC\source documents 1\[Budget Tracking Template1 3G to A\ |
| 160 | ='\\Numodanas1\sales\Sales Share\Ann\Patent CPAC\source documents 1\[Budget Tracking Template1 3G to A\ |

Figure 18L

| | C |
|---|---|
| 161 | ='\\Numodanas1\sales\Sales Share\Ann\Patent CPAC\source documents 1\[Budget Tracking Template1 3G to A\ |
| 162 | ='\\Numodanas1\sales\Sales Share\Ann\Patent CPAC\source documents 1\[Budget Tracking Template1 3G to A\ |
| 163 | ='\\Numodanas1\sales\Sales Share\Ann\Patent CPAC\source documents 1\[Budget Tracking Template1 3G to A\ |
| 164 | ='\\Numodanas1\sales\Sales Share\Ann\Patent CPAC\source documents 1\[Budget Tracking Template1 3G to A\ |
| 165 | ='\\Numodanas1\sales\Sales Share\Ann\Patent CPAC\source documents 1\[Budget Tracking Template1 3G to A\ |
| 166 | |
| 167 | |
| 168 | |
| 169 | ='\\Numodanas1\sales\Sales Share\Ann\Patent CPAC\source documents 1\[Budget Tracking Template1 3G to A\ |
| 170 | ='\\Numodanas1\sales\Sales Share\Ann\Patent CPAC\source documents 1\[Budget Tracking Template1 3G to A\ |
| 171 | |
| 172 | |
| 173 | |
| 174 | |
| 175 | ='\\Numodanas1\sales\Sales Share\Ann\Patent CPAC\source documents 1\[Budget Tracking Template1 3G to A\ |
| 176 | ='\\Numodanas1\sales\Sales Share\Ann\Patent CPAC\source documents 1\[Budget Tracking Template1 3G to A\ |
| 177 | ='\\Numodanas1\sales\Sales Share\Ann\Patent CPAC\source documents 1\[Budget Tracking Template1 3G to A\ |
| 178 | ='\\Numodanas1\sales\Sales Share\Ann\Patent CPAC\source documents 1\[Budget Tracking Template1 3G to A\ |
| 179 | |
| 180 | |
| 181 | |
| 182 | ='\\Numodanas1\sales\Sales Share\Ann\Patent CPAC\source documents 1\[Budget Tracking Template1 3( |
| 183 | |
| 184 | |
| 185 | |
| 186 | ='\\Numodanas1\sales\Sales Share\Ann\Patent CPAC\source documents 1\[Budget Tracking Template1 3G to A\ |
| 187 | ='\\Numodanas1\sales\Sales Share\Ann\Patent CPAC\source documents 1\[Budget Tracking Template1 3G to A\ |
| 188 | ='\\Numodanas1\sales\Sales Share\Ann\Patent CPAC\source documents 1\[Budget Tracking Template1 3G to A\ |
| 189 | ='\\Numodanas1\sales\Sales Share\Ann\Patent CPAC\source documents 1\[Budget Tracking Template1 3G to A\ |
| 190 | ='\\Numodanas1\sales\Sales Share\Ann\Patent CPAC\source documents 1\[Budget Tracking Template1 3G to A\ |
| 191 | ='\\Numodanas1\sales\Sales Share\Ann\Patent CPAC\source documents 1\[Budget Tracking Template1 3G to A\ |
| 192 | ='\\Numodanas1\sales\Sales Share\Ann\Patent CPAC\source documents 1\[Budget Tracking Template1 3G to A\ |
| 193 | ='\\Numodanas1\sales\Sales Share\Ann\Patent CPAC\source documents 1\[Budget Tracking Template1 3G to A\ |
| 194 | |
| 195 | |
| 196 | |
| 197 | |
| 198 | |
| 199 | |
| 200 | |
| 201 | |
| 202 | |
| 203 | |
| 204 | |
| 205 | |
| 206 | |
| 207 | |
| 208 | |

Figure 18M

| | D | E |
|---|---|---|
| 1 | | |
| 2 | | |
| 3 | | |
| 4 | | |
| 5 | | |
| 6 | | |
| 7 | | |
| 8 | Total | |
| 9 | =SUBTOTAL(9,D11,D22,D43,D31,D48,D55,D59,D10) | |
| 10 | | |
| 11 | =SUM(D12:D20) | |
| 12 | =IF(B12>0,B12*C12,"N/A ") | |
| 13 | =IF(B13>0,B13*C13,"N/A ") | |
| 14 | =IF(B14>0,B14*C14,"N/A ") | |
| 15 | =B15*C15 | |
| 16 | =IF(B16>0,B16*C16,"N/A ") | |
| 17 | =IF(B17>0,B17*C17,"N/A ") | |
| 18 | =IF(B18>0,B18*C18,"N/A ") | |
| 19 | =IF(B19>0,B19*C19,"N/A ") | |
| 20 | =IF(B20>0,B20*C20,"N/A ") | |
| 21 | | |
| 22 | =SUM(D23:D29) | |
| 23 | =IF(B23>0,B23*C23,"N/A ") | |
| 24 | =IF(B24>0,B24*C24,"N/A ") | |
| 25 | =IF(B25>0,B25*C25,"N/A ") | |
| 26 | =IF(B26>0,B26*C26,"N/A ") | |
| 27 | =IF(B27>0,B27*C27,"N/A ") | |
| 28 | =IF(B28>0,B28*C28,"N/A ") | |
| 29 | =IF(B29>0,B29*C29,"N/A ") | |
| 30 | | |
| 31 | =SUM(D32:D41) | |
| 32 | =IF(B32>0,B32*C32,"N/A ") | |
| 33 | =IF(B33>0,B33*C33,"N/A ") | |
| 34 | =IF(B34>0,B34*C34,"N/A ") | |
| 35 | =IF(B35>0,B35*C35,"N/A ") | |
| 36 | =IF(B36>0,B36*C36,"N/A ") | |
| 37 | =IF(B37>0,B37*C37,"N/A ") | |
| 38 | =IF(B38>0,B38*C38,"N/A ") | |
| 39 | =IF(B39>0,B39*C39,"N/A ") | |
| 40 | =IF(B40>0,B40*C40,"N/A ") | |
| 41 | =IF(B41>0,B41*C41,"N/A ") | |
| 42 | | |
| 43 | =SUM(D44:D46) | |
| 44 | =IF(B44>0,B44*C44,"N/A ") | |
| 45 | =IF(B45>0,B45*C45,"N/A ") | |
| 46 | =IF(B46>0,B46*C46,"N/A ") | |
| 47 | | |
| 48 | =SUM(D49:D53) | |
| 49 | =IF(B49>0,B49*C49,"N/A ") | |
| 50 | =IF(B50>0,B50*C50,"N/A ") | |
| 51 | =IF(B51>0,B51*C51,"N/A ") | |
| 52 | =IF(B52>0,B52*C52,"N/A ") | |
| 53 | =IF(B53>0,B53*C53,"N/A ") | |
| 54 | | |
| 55 | =SUM(D56:D57) | |

Figure 18N

|     | D | E |
| --- | --- | --- |
| 56 | =IF(B56>0,B56*C56,"N/A ") | |
| 57 | =IF(B57>0,B57*C57,"N/A ") | |
| 58 | | |
| 59 | | |
| 60 | | |
| 61 | =SUBTOTAL(9,D63) | |
| 62 | | |
| 63 | =SUM(D64:D71) | |
| 64 | =IF(B64>0,B64*C64,"N/A ") | |
| 65 | =IF(B65>0,B65*C65,"N/A ") | |
| 66 | =IF(B66>0,B66*C66,"N/A ") | |
| 67 | =IF(B67>0,B67*C67,"N/A ") | |
| 68 | =IF(B68>0,B68*C68,"N/A ") | |
| 69 | =IF(B69>0,B69*C69,"N/A ") | |
| 70 | =IF(B70>0,B70*C70,"N/A ") | |
| 71 | =IF(B71>0,B71*C71,"N/A ") | |
| 72 | | |
| 73 | =SUBTOTAL(9,D75,D83,D89,D95,D101) | |
| 74 | | |
| 75 | =SUM(D76:D81) | |
| 76 | =IF(B76>0,B76*C76,"N/A ") | |
| 77 | =IF(B77>0,B77*C77,"N/A ") | |
| 78 | =IF(B78>0,B78*C78,"N/A ") | |
| 79 | =IF(B79>0,B79*C79,"N/A ") | |
| 80 | =IF(B80>0,B80*C80,"N/A ") | |
| 81 | =IF(B81>0,B81*C81,"N/A ") | |
| 82 | | |
| 83 | =SUM(D84:D87) | |
| 84 | =IF(B84>0,B84*C84,"N/A ") | |
| 85 | =IF(B85>0,B85*C85,"N/A ") | |
| 86 | =IF(B86>0,B86*C86,"N/A ") | |
| 87 | =IF(B87>0,B87*C87,"N/A ") | |
| 88 | | |
| 89 | =SUM(D90:D93) | |
| 90 | =IF(B90>0,B90*C90,"N/A ") | |
| 91 | =IF(B91>0,B91*C91,"N/A ") | |
| 92 | =IF(B92>0,B92*C92,"N/A ") | |
| 93 | =IF(B93>0,B93*C93,"N/A ") | |
| 94 | | |
| 95 | =SUM(D96:D99) | |
| 96 | =IF(B96>0,B96*C96,"N/A ") | |
| 97 | =IF(B97>0,B97*C97,"N/A ") | |
| 98 | =IF(B98>0,B98*C98,"N/A ") | |
| 99 | =IF(B99>0,B99*C99,"N/A ") | |
| 100 | | |
| 101 | =SUM(D102:D103) | |
| 102 | =IF(B102>0,B102*C102,"N/A ") | |
| 103 | =IF(B103>0,B103*C103,"N/A ") | |
| 104 | | |
| 105 | =SUBTOTAL(9,D107,D108,D110) | |
| 106 | | |
| 107 | =B107*C107 | |

Figure 18O

| | D | E |
|---|---|---|
| 108 | =SUM(D109) | |
| 109 | =IF(B109>0,B109*C109,"N/A ") | |
| 110 | =SUM(D111:D114) | |
| 111 | =IF(B111>0,B111*C111,"N/A ") | |
| 112 | =IF(B112>0,B112*C112,"N/A ") | |
| 113 | =IF(B113>0,B113*C113,"N/A ") | |
| 114 | =IF(B114>0,B114*C114,"N/A ") | |
| 115 | | |
| 116 | | |
| 117 | =SUBTOTAL(9,D119,D127,D137) | |
| 118 | | |
| 119 | =SUM(D120:D125) | |
| 120 | =IF(B120>0,B120*C120,"N/A ") | |
| 121 | =IF(B121>0,B121*C121,"N/A ") | |
| 122 | =IF(B122>0,B122*C122,"N/A ") | |
| 123 | =IF(B123>0,B123*C123,"N/A ") | |
| 124 | =IF(B124>0,B124*C124,"N/A ") | |
| 125 | =IF(B125>0,B125*C125,"N/A ") | |
| 126 | | |
| 127 | =SUM(D128:D135) | |
| 128 | =IF(B128>0,B128*C128,"N/A ") | |
| 129 | =IF(B129>0,B129*C129,"N/A ") | |
| 130 | =IF(B130>0,B130*C130,"N/A ") | |
| 131 | =IF(B131>0,B131*C131,"N/A ") | |
| 132 | =IF(B132>0,B132*C132,"N/A ") | |
| 133 | =IF(B133>0,B133*C133,"N/A ") | |
| 134 | =IF(B134>0,B134*C134,"N/A ") | |
| 135 | =IF(B135>0,B135*C135,"N/A ") | |
| 136 | | |
| 137 | =SUM(D138:D144) | |
| 138 | =IF(B138>0,B138*C138,"N/A ") | |
| 139 | =IF(B139>0,B139*C139,"N/A ") | |
| 140 | =IF(B140>0,B140*C140,"N/A ") | |
| 141 | =IF(B141>0,B141*C141,"N/A ") | |
| 142 | =IF(B142>0,B142*C142,"N/A ") | |
| 143 | =IF(B143>0,B143*C143,"N/A ") | |
| 144 | =IF(B144>0,B144*C144,"N/A ") | |
| 145 | | |
| 146 | =SUM(D147:D147) | |
| 147 | =IF(B147>0,B147*C147,"N/A ") | |
| 148 | | |
| 149 | =D9+D61+D73+D105+D117 | |
| 150 | | |
| 151 | | |
| 152 | | |
| 153 | =D149+D151 | |
| 154 | | |
| 155 | =SUM(D156:D166) | |
| 156 | | |
| 157 | =IF(B157>0,B157*C157,"N/A ") | |
| 158 | =IF(B158>0,B158*C158,"N/A ") | |
| 159 | =IF(B159>0,B159*C159,"N/A ") | |
| 160 | =IF(B160>0,B160*C160,"N/A ") | |

Figure 18P

| | D | E |
|---|---|---|
| 161 | =IF(B161>0,B161*C161,"N/A ") | |
| 162 | =IF(B162>0,B162*C162,"N/A ") | |
| 163 | =IF(B163>0,B163*C163,"N/A ") | |
| 164 | =IF(B164>0,B164*C164,"N/A ") | |
| 165 | =IF(B165>0,B165*C165,"N/A ") | |
| 166 | | |
| 167 | =SUM(D168:D170) | |
| 168 | | |
| 169 | =IF(B169>0,B169*C169,"N/A ") | |
| 170 | =IF(B170>0,B170*C170,"N/A ") | |
| 171 | | |
| 172 | =SUM(D173:D174) | |
| 173 | | |
| 174 | =SUM(D175:D179) | |
| 175 | =B175*C175 | |
| 176 | =B176*C176 | |
| 177 | =B177*C177 | |
| 178 | =B178*C178 | |
| 179 | | |
| 180 | =SUM(D181:D183) | |
| 181 | | |
| 182 | =B182*C182 | |
| 183 | | |
| 184 | =SUM(D185:D193) | |
| 185 | | |
| 186 | =B186*C186 | |
| 187 | =B187*C187 | |
| 188 | =B188*C188 | |
| 189 | =B189*C189 | |
| 190 | =B190*C190 | |
| 191 | =B191*C191 | |
| 192 | =B192*C192 | |
| 193 | =B193*C193 | |
| 194 | | |
| 195 | | |
| 196 | | |
| 197 | =D155+D167+D172+D180+D184+D195 | |
| 198 | | |
| 199 | =D9+D155 | |
| 200 | =D61+D167 | |
| 201 | =D73+D172 | |
| 202 | =D105+D180 | |
| 203 | =D117+D184 | |
| 204 | | |
| 205 | =D153+D197 | |
| 206 | | |
| 207 | =D153*(-0.2) | |
| 208 | | |

Figure 18Q

| | F |
|---|---|
| 1 | |
| 2 | |
| 3 | |
| 4 | |
| 5 | |
| 6 | |
| 7 | |
| 8 | Unit |
| 9 | |
| 10 | |
| 11 | |
| 12 | =J12+N12+R12+V12+Z12+AD12+AH12+AL12+AP12+AT12+AX12+BB12+BF12+BJ12+BN12 |
| 13 | =J13+N13+R13+V13+Z13+AD13+AH13+AL13+AP13+AT13+AX13+BB13+BF13+BJ13+BN13 |
| 14 | =J14+N14+R14+V14+Z14+AD14+AH14+AL14+AP14+AT14+AX14+BB14+BF14+BJ14+BN14 |
| 15 | =J15+N15+R15+V15+Z15+AD15+AH15+AL15+AP15+AT15+AX15+BB15+BF15+BJ15+BN15 |
| 16 | =J16+N16+R16+V16+Z16+AD16+AH16+AL16+AP16+AT16+AX16+BB16+BF16+BJ16+BN16 |
| 17 | =J17+N17+R17+V17+Z17+AD17+AH17+AL17+AP17+AT17+AX17+BB17+BF17+BJ17+BN17 |
| 18 | =J18+N18+R18+V18+Z18+AD18+AH18+AL18+AP18+AT18+AX18+BB18+BF18+BJ18+BN18 |
| 19 | =J19+N19+R19+V19+Z19+AD19+AH19+AL19+AP19+AT19+AX19+BB19+BF19+BJ19+BN19 |
| 20 | =J20+N20+R20+V20+Z20+AD20+AH20+AL20+AP20+AT20+AX20+BB20+BF20+BJ20+BN20 |
| 21 | |
| 22 | |
| 23 | =J23+N23+R23+V23+Z23+AD23+AH23+AL23+AP23+AT23+AX23+BB23+BF23+BJ23+BN23 |
| 24 | =J24+N24+R24+V24+Z24+AD24+AH24+AL24+AP24+AT24+AX24+BB24+BF24+BJ24+BN24 |
| 25 | =J25+N25+R25+V25+Z25+AD25+AH25+AL25+AP25+AT25+AX25+BB25+BF25+BJ25+BN25 |
| 26 | =J26+N26+R26+V26+Z26+AD26+AH26+AL26+AP26+AT26+AX26+BB26+BF26+BJ26+BN26 |
| 27 | =J27+N27+R27+V27+Z27+AD27+AH27+AL27+AP27+AT27+AX27+BB27+BF27+BJ27+BN27 |
| 28 | =J28+N28+R28+V28+Z28+AD28+AH28+AL28+AP28+AT28+AX28+BB28+BF28+BJ28+BN28 |
| 29 | =J29+N29+R29+V29+Z29+AD29+AH29+AL29+AP29+AT29+AX29+BB29+BF29+BJ29+BN29 |
| 30 | |
| 31 | |
| 32 | =J32+N32+R32+V32+Z32+AD32+AH32+AL32+AP32+AT32+AX32+BB32+BF32+BJ32+BN32 |
| 33 | =J33+N33+R33+V33+Z33+AD33+AH33+AL33+AP33+AT33+AX33+BB33+BF33+BJ33+BN33 |
| 34 | =J34+N34+R34+V34+Z34+AD34+AH34+AL34+AP34+AT34+AX34+BB34+BF34+BJ34+BN34 |
| 35 | =J35+N35+R35+V35+Z35+AD35+AH35+AL35+AP35+AT35+AX35+BB35+BF35+BJ35+BN35 |
| 36 | =J36+N36+R36+V36+Z36+AD36+AH36+AL36+AP36+AT36+AX36+BB36+BF36+BJ36+BN36 |
| 37 | =J37+N37+R37+V37+Z37+AD37+AH37+AL37+AP37+AT37+AX37+BB37+BF37+BJ37+BN37 |
| 38 | =J38+N38+R38+V38+Z38+AD38+AH38+AL38+AP38+AT38+AX38+BB38+BF38+BJ38+BN38 |
| 39 | =J39+N39+R39+V39+Z39+AD39+AH39+AL39+AP39+AT39+AX39+BB39+BF39+BJ39+BN39 |
| 40 | =J40+N40+R40+V40+Z40+AD40+AH40+AL40+AP40+AT40+AX40+BB40+BF40+BJ40+BN40 |
| 41 | =J41+N41+R41+V41+Z41+AD41+AH41+AL41+AP41+AT41+AX41+BB41+BF41+BJ41+BN41 |
| 42 | |
| 43 | |
| 44 | =J44+N44+R44+V44+Z44+AD44+AH44+AL44+AP44+AT44+AX44+BB44+BF44+BJ44+BN44 |
| 45 | =J45+N45+R45+V45+Z45+AD45+AH45+AL45+AP45+AT45+AX45+BB45+BF45+BJ45+BN45 |
| 46 | =J46+N46+R46+V46+Z46+AD46+AH46+AL46+AP46+AT46+AX46+BB46+BF46+BJ46+BN46 |
| 47 | |
| 48 | |
| 49 | =J49+N49+R49+V49+Z49+AD49+AH49+AL49+AP49+AT49+AX49+BB49+BF49+BJ49+BN49 |
| 50 | =J50+N50+R50+V50+Z50+AD50+AH50+AL50+AP50+AT50+AX50+BB50+BF50+BJ50+BN50 |
| 51 | =J51+N51+R51+V51+Z51+AD51+AH51+AL51+AP51+AT51+AX51+BB51+BF51+BJ51+BN51 |
| 52 | =J52+N52+R52+V52+Z52+AD52+AH52+AL52+AP52+AT52+AX52+BB52+BF52+BJ52+BN52 |
| 53 | =J53+N53+R53+V53+Z53+AD53+AH53+AL53+AP53+AT53+AX53+BB53+BF53+BJ53+BN53 |
| 54 | |
| 55 | |

Figure 18R

| | F |
|---|---|
| 56 | =J56+N56+R56+V56+Z56+AD56+AH56+AL56+AP56+AT56+AX56+BB56+BF56+BJ56+BN56 |
| 57 | =J57+N57+R57+V57+Z57+AD57+AH57+AL57+AP57+AT57+AX57+BB57+BF57+BJ57+BN57 |
| 58 | |
| 59 | |
| 60 | |
| 61 | |
| 62 | |
| 63 | |
| 64 | =J64+N64+R64+V64+Z64+AD64+AH64+AL64+AP64+AT64+AX64+BB64+BF64+BJ64+BN64 |
| 65 | =J65+N65+R65+V65+Z65+AD65+AH65+AL65+AP65+AT65+AX65+BB65+BF65+BJ65+BN65 |
| 66 | =J66+N66+R66+V66+Z66+AD66+AH66+AL66+AP66+AT66+AX66+BB66+BF66+BJ66+BN66 |
| 67 | =J67+N67+R67+V67+Z67+AD67+AH67+AL67+AP67+AT67+AX67+BB67+BF67+BJ67+BN67 |
| 68 | =J68+N68+R68+V68+Z68+AD68+AH68+AL68+AP68+AT68+AX68+BB68+BF68+BJ68+BN68 |
| 69 | =J69+N69+R69+V69+Z69+AD69+AH69+AL69+AP69+AT69+AX69+BB69+BF69+BJ69+BN69 |
| 70 | =J70+N70+R70+V70+Z70+AD70+AH70+AL70+AP70+AT70+AX70+BB70+BF70+BJ70+BN70 |
| 71 | =J71+N71+R71+V71+Z71+AD71+AH71+AL71+AP71+AT71+AX71+BB71+BF71+BJ71+BN71 |
| 72 | |
| 73 | |
| 74 | |
| 75 | |
| 76 | =J76+N76+R76+V76+Z76+AD76+AH76+AL76+AP76+AT76+AX76+BB76+BF76+BJ76+BN76 |
| 77 | =J77+N77+R77+V77+Z77+AD77+AH77+AL77+AP77+AT77+AX77+BB77+BF77+BJ77+BN77 |
| 78 | =J78+N78+R78+V78+Z78+AD78+AH78+AL78+AP78+AT78+AX78+BB78+BF78+BJ78+BN78 |
| 79 | =J79+N79+R79+V79+Z79+AD79+AH79+AL79+AP79+AT79+AX79+BB79+BF79+BJ79+BN79 |
| 80 | =J80+N80+R80+V80+Z80+AD80+AH80+AL80+AP80+AT80+AX80+BB80+BF80+BJ80+BN80 |
| 81 | =J81+N81+R81+V81+Z81+AD81+AH81+AL81+AP81+AT81+AX81+BB81+BF81+BJ81+BN81 |
| 82 | |
| 83 | |
| 84 | =J84+N84+R84+V84+Z84+AD84+AH84+AL84+AP84+AT84+AX84+BB84+BF84+BJ84+BN84 |
| 85 | =J85+N85+R85+V85+Z85+AD85+AH85+AL85+AP85+AT85+AX85+BB85+BF85+BJ85+BN85 |
| 86 | =J86+N86+R86+V86+Z86+AD86+AH86+AL86+AP86+AT86+AX86+BB86+BF86+BJ86+BN86 |
| 87 | =J87+N87+R87+V87+Z87+AD87+AH87+AL87+AP87+AT87+AX87+BB87+BF87+BJ87+BN87 |
| 88 | |
| 89 | |
| 90 | =J90+N90+R90+V90+Z90+AD90+AH90+AL90+AP90+AT90+AX90+BB90+BF90+BJ90+BN90 |
| 91 | =J91+N91+R91+V91+Z91+AD91+AH91+AL91+AP91+AT91+AX91+BB91+BF91+BJ91+BN91 |
| 92 | =J92+N92+R92+V92+Z92+AD92+AH92+AL92+AP92+AT92+AX92+BB92+BF92+BJ92+BN92 |
| 93 | =J93+N93+R93+V93+Z93+AD93+AH93+AL93+AP93+AT93+AX93+BB93+BF93+BJ93+BN93 |
| 94 | |
| 95 | |
| 96 | =J96+N96+R96+V96+Z96+AD96+AH96+AL96+AP96+AT96+AX96+BB96+BF96+BJ96+BN96 |
| 97 | =J97+N97+R97+V97+Z97+AD97+AH97+AL97+AP97+AT97+AX97+BB97+BF97+BJ97+BN97 |
| 98 | =J98+N98+R98+V98+Z98+AD98+AH98+AL98+AP98+AT98+AX98+BB98+BF98+BJ98+BN98 |
| 99 | =J99+N99+R99+V99+Z99+AD99+AH99+AL99+AP99+AT99+AX99+BB99+BF99+BJ99+BN99 |
| 100 | |
| 101 | |
| 102 | =J102+N102+R102+V102+Z102+AD102+AH102+AL102+AP102+AT102+AX102+BB102+BF102+BJ102+BN102 |
| 103 | =J103+N103+R103+V103+Z103+AD103+AH103+AL103+AP103+AT103+AX103+BB103+BF103+BJ103+BN103 |
| 104 | |
| 105 | |
| 106 | |
| 107 | =J107+N107+R107+V107+Z107+AD107+AH107+AL107+AP107+AT107+AX107+BB107+BF107+BJ107+BN1 |

Figure 18S

| | F |
|---|---|
| 108 | |
| 109 | =J109+N109+R109+V109+Z109+AD109+AH109+AL109+AP109+AT109+AX109+BB109+BF109+BJ109+BN109 |
| 110 | |
| 111 | =J111+N111+R111+V111+Z111+AD111+AH111+AL111+AP111+AT111+AX111+BB111+BF111+BJ111+BN111 |
| 112 | =J112+N112+R112+V112+Z112+AD112+AH112+AL112+AP112+AT112+AX112+BB112+BF112+BJ112+BN112 |
| 113 | =J113+N113+R113+V113+Z113+AD113+AH113+AL113+AP113+AT113+AX113+BB113+BF113+BJ113+BN113 |
| 114 | =J114+N114+R114+V114+Z114+AD114+AH114+AL114+AP114+AT114+AX114+BB114+BF114+BJ114+BN114 |
| 115 | |
| 116 | |
| 117 | |
| 118 | |
| 119 | |
| 120 | =J120+N120+R120+V120+Z120+AD120+AH120+AL120+AP120+AT120+AX120+BB120+BF120+BJ120+BN120 |
| 121 | =J121+N121+R121+V121+Z121+AD121+AH121+AL121+AP121+AT121+AX121+BB121+BF121+BJ121+BN121 |
| 122 | =J122+N122+R122+V122+Z122+AD122+AH122+AL122+AP122+AT122+AX122+BB122+BF122+BJ122+BN122 |
| 123 | =J123+N123+R123+V123+Z123+AD123+AH123+AL123+AP123+AT123+AX123+BB123+BF123+BJ123+BN123 |
| 124 | =J124+N124+R124+V124+Z124+AD124+AH124+AL124+AP124+AT124+AX124+BB124+BF124+BJ124+BN124 |
| 125 | =J125+N125+R125+V125+Z125+AD125+AH125+AL125+AP125+AT125+AX125+BB125+BF125+BJ125+BN125 |
| 126 | |
| 127 | |
| 128 | =J128+N128+R128+V128+Z128+AD128+AH128+AL128+AP128+AT128+AX128+BB128+BF128+BJ128+BN128 |
| 129 | =J129+N129+R129+V129+Z129+AD129+AH129+AL129+AP129+AT129+AX129+BB129+BF129+BJ129+BN129 |
| 130 | =J130+N130+R130+V130+Z130+AD130+AH130+AL130+AP130+AT130+AX130+BB130+BF130+BJ130+BN130 |
| 131 | =J131+N131+R131+V131+Z131+AD131+AH131+AL131+AP131+AT131+AX131+BB131+BF131+BJ131+BN131 |
| 132 | =J132+N132+R132+V132+Z132+AD132+AH132+AL132+AP132+AT132+AX132+BB132+BF132+BJ132+BN132 |
| 133 | =J133+N133+R133+V133+Z133+AD133+AH133+AL133+AP133+AT133+AX133+BB133+BF133+BJ133+BN133 |
| 134 | =J134+N134+R134+V134+Z134+AD134+AH134+AL134+AP134+AT134+AX134+BB134+BF134+BJ134+BN134 |
| 135 | =J135+N135+R135+V135+Z135+AD135+AH135+AL135+AP135+AT135+AX135+BB135+BF135+BJ135+BN135 |
| 136 | |
| 137 | |
| 138 | =J138+N138+R138+V138+Z138+AD138+AH138+AL138+AP138+AT138+AX138+BB138+BF138+BJ138+BN138 |
| 139 | =J139+N139+R139+V139+Z139+AD139+AH139+AL139+AP139+AT139+AX139+BB139+BF139+BJ139+BN139 |
| 140 | =J140+N140+R140+V140+Z140+AD140+AH140+AL140+AP140+AT140+AX140+BB140+BF140+BJ140+BN140 |
| 141 | =J141+N141+R141+V141+Z141+AD141+AH141+AL141+AP141+AT141+AX141+BB141+BF141+BJ141+BN141 |
| 142 | =J142+N142+R142+V142+Z142+AD142+AH142+AL142+AP142+AT142+AX142+BB142+BF142+BJ142+BN142 |
| 143 | =J143+N143+R143+V143+Z143+AD143+AH143+AL143+AP143+AT143+AX143+BB143+BF143+BJ143+BN143 |
| 144 | =J144+N144+R144+V144+Z144+AD144+AH144+AL144+AP144+AT144+AX144+BB144+BF144+BJ144+BN144 |
| 145 | |
| 146 | |
| 147 | =J147+N147+R147+V147+Z147+AD147+AH147+AL147+AP147+AT147+AX147+BB147+BF147+BJ147+BN147 |
| 148 | |
| 149 | |
| 150 | |
| 151 | |
| 152 | |
| 153 | |
| 154 | |
| 155 | |
| 156 | |
| 157 | |
| 158 | |
| 159 | |
| 160 | |

Figure 18T

| | F |
|---|---|
| 161 | |
| 162 | |
| 163 | |
| 164 | |
| 165 | |
| 166 | |
| 167 | |
| 168 | |
| 169 | |
| 170 | |
| 171 | |
| 172 | |
| 173 | |
| 174 | |
| 175 | |
| 176 | |
| 177 | |
| 178 | |
| 179 | |
| 180 | |
| 181 | |
| 182 | |
| 183 | |
| 184 | |
| 185 | |
| 186 | |
| 187 | |
| 188 | |
| 189 | |
| 190 | |
| 191 | |
| 192 | |
| 193 | |
| 194 | |
| 195 | |
| 196 | |
| 197 | |
| 198 | |
| 199 | |
| 200 | |
| 201 | |
| 202 | |
| 203 | |
| 204 | |
| 205 | |
| 206 | |
| 207 | |
| 208 | |

Figure 18U

| | G |
|---|---|
| 1 | |
| 2 | |
| 3 | |
| 4 | |
| 5 | |
| 6 | |
| 7 | TOTAL INVOICED |
| 8 | % Completed |
| 9 | =H9/D9 |
| 10 | |
| 11 | |
| 12 | =IF(B12>0,H12/D12,"N/A") |
| 13 | =IF(B13>0,H13/D13,"N/A") |
| 14 | =IF(B14>0,H14/D14,"N/A") |
| 15 | =IF(B15>0,H15/D15,"N/A") |
| 16 | =IF(B16>0,H16/D16,"N/A") |
| 17 | =IF(B17>0,H17/D17,"N/A") |
| 18 | =IF(B18>0,H18/D18,"N/A") |
| 19 | =IF(B19>0,H19/D19,"N/A") |
| 20 | =IF(B20>0,H20/D20,"N/A") |
| 21 | |
| 22 | |
| 23 | =IF(B23>0,H23/D23,"N/A") |
| 24 | =IF(B24>0,H24/D24,"N/A") |
| 25 | =IF(B25>0,H25/D25,"N/A") |
| 26 | =IF(B26>0,H26/D26,"N/A") |
| 27 | =IF(B27>0,H27/D27,"N/A") |
| 28 | =IF(B28>0,H28/D28,"N/A") |
| 29 | =IF(B29>0,H29/D29,"N/A") |
| 30 | |
| 31 | |
| 32 | =IF(B32>0,H32/D32,"N/A") |
| 33 | =IF(B33>0,H33/D33,"N/A") |
| 34 | =IF(B34>0,H34/D34,"N/A") |
| 35 | =IF(B35>0,H35/D35,"N/A") |
| 36 | =IF(B36>0,H36/D36,"N/A") |
| 37 | =IF(B37>0,H37/D37,"N/A") |
| 38 | =IF(B38>0,H38/D38,"N/A") |
| 39 | =IF(B39>0,H39/D39,"N/A") |
| 40 | =IF(B40>0,H40/D40,"N/A") |
| 41 | =IF(B41>0,H41/D41,"N/A") |
| 42 | |
| 43 | |
| 44 | =IF(B44>0,H44/D44,"N/A") |
| 45 | =IF(B45>0,H45/D45,"N/A") |
| 46 | =IF(B46>0,H46/D46,"N/A") |
| 47 | |
| 48 | |
| 49 | =IF(B49>0,H49/D49,"N/A") |
| 50 | =IF(B50>0,H50/D50,"N/A") |
| 51 | =IF(B51>0,H51/D51,"N/A") |
| 52 | =IF(B52>0,H52/D52,"N/A") |
| 53 | =IF(B53>0,H53/D53,"N/A") |
| 54 | |
| 55 | |

Figure 18V

| | G |
|---|---|
| 56 | =IF(B56>0,H56/D56,"N/A") |
| 57 | =IF(B57>0,H57/D57,"N/A") |
| 58 | |
| 59 | |
| 60 | |
| 61 | =H61/D61 |
| 62 | |
| 63 | |
| 64 | =IF(B64>0,H64/D64,"N/A") |
| 65 | =IF(B65>0,H65/D65,"N/A") |
| 66 | =IF(B66>0,H66/D66,"N/A") |
| 67 | =IF(B67>0,H67/D67,"N/A") |
| 68 | =IF(B68>0,H68/D68,"N/A") |
| 69 | =IF(B69>0,H69/D69,"N/A") |
| 70 | =IF(B70>0,H70/D70,"N/A") |
| 71 | =IF(B71>0,H71/D71,"N/A") |
| 72 | |
| 73 | =H73/D73 |
| 74 | |
| 75 | |
| 76 | =IF(B76>0,H76/D76,"N/A") |
| 77 | =IF(B77>0,H77/D77,"N/A") |
| 78 | =IF(B78>0,H78/D78,"N/A") |
| 79 | =IF(B79>0,H79/D79,"N/A") |
| 80 | =IF(B80>0,H80/D80,"N/A") |
| 81 | =IF(B81>0,H81/D81,"N/A") |
| 82 | |
| 83 | |
| 84 | =IF(B84>0,H84/D84,"N/A") |
| 85 | =IF(B85>0,H85/D85,"N/A") |
| 86 | =IF(B86>0,H86/D86,"N/A") |
| 87 | =IF(B87>0,H87/D87,"N/A") |
| 88 | |
| 89 | |
| 90 | =IF(B90>0,H90/D90,"N/A") |
| 91 | =IF(B91>0,H91/D91,"N/A") |
| 92 | =IF(B92>0,H92/D92,"N/A") |
| 93 | =IF(B93>0,H93/D93,"N/A") |
| 94 | |
| 95 | |
| 96 | =IF(B96>0,H96/D96,"N/A") |
| 97 | =IF(B97>0,H97/D97,"N/A") |
| 98 | =IF(B98>0,H98/D98,"N/A") |
| 99 | =IF(B99>0,H99/D99,"N/A") |
| 100 | |
| 101 | |
| 102 | =IF(B102>0,H102/D102,"N/A") |
| 103 | =IF(B103>0,H103/D103,"N/A") |
| 104 | |
| 105 | =H105/D105 |
| 106 | |
| 107 | =IF(B107>0,H107/D107,"N/A") |

Figure 18W

| | G |
|---|---|
| 108 | =IF(B108>0,H108/D108,"N/A") |
| 109 | =IF(B109>0,H109/D109,"N/A") |
| 110 | =IF(B110>0,H110/D110,"N/A") |
| 111 | =IF(B111>0,H111/D111,"N/A") |
| 112 | =IF(B112>0,H112/D112,"N/A") |
| 113 | =IF(B113>0,H113/D113,"N/A") |
| 114 | =IF(B114>0,H114/D114,"N/A") |
| 115 | |
| 116 | |
| 117 | =H117/D117 |
| 118 | |
| 119 | |
| 120 | =IF(B120>0,H120/D120,"N/A") |
| 121 | =IF(B121>0,H121/D121,"N/A") |
| 122 | =IF(B122>0,H122/D122,"N/A") |
| 123 | =IF(B123>0,H123/D123,"N/A") |
| 124 | =IF(B124>0,H124/D124,"N/A") |
| 125 | =IF(B125>0,H125/D125,"N/A") |
| 126 | |
| 127 | |
| 128 | =IF(B128>0,H128/D128,"N/A") |
| 129 | =IF(B129>0,H129/D129,"N/A") |
| 130 | =IF(B130>0,H130/D130,"N/A") |
| 131 | =IF(B131>0,H131/D131,"N/A") |
| 132 | =IF(B132>0,H132/D132,"N/A") |
| 133 | =IF(B133>0,H133/D133,"N/A") |
| 134 | =IF(B134>0,H134/D134,"N/A") |
| 135 | =IF(B135>0,H135/D135,"N/A") |
| 136 | |
| 137 | |
| 138 | =IF(B138>0,H138/D138,"N/A") |
| 139 | =IF(B139>0,H139/D139,"N/A") |
| 140 | =IF(B140>0,H140/D140,"N/A") |
| 141 | =IF(B141>0,H141/D141,"N/A") |
| 142 | =IF(B142>0,H142/D142,"N/A") |
| 143 | =IF(B143>0,H143/D143,"N/A") |
| 144 | =IF(B144>0,H144/D144,"N/A") |
| 145 | |
| 146 | |
| 147 | =IF(B147>0,H147/D147,"N/A") |
| 148 | |
| 149 | =H149/D149 |
| 150 | |
| 151 | |
| 152 | |
| 153 | =H153/D153 |
| 154 | |
| 155 | =H155/D155 |
| 156 | |
| 157 | =IF(B157>0,H157/D157,"N/A") |
| 158 | =IF(B158>0,H158/D158,"N/A") |
| 159 | =IF(B159>0,H159/D159,"N/A") |
| 160 | =IF(B160>0,H160/D160,"N/A") |

Figure 18X

| | G |
|---|---|
| 161 | =IF(B161>0,H161/D161,"N/A") |
| 162 | =IF(B162>0,H162/D162,"N/A") |
| 163 | =IF(B163>0,H163/D163,"N/A") |
| 164 | =IF(B164>0,H164/D164,"N/A") |
| 165 | =IF(B165>0,H165/D165,"N/A") |
| 166 | |
| 167 | =H167/D167 |
| 168 | |
| 169 | =IF(B169>0,H169/D169,"N/A") |
| 170 | =IF(B170>0,H170/D170,"N/A") |
| 171 | |
| 172 | =H172/D172 |
| 173 | |
| 174 | =H174/D174 |
| 175 | =IF(B175>0,H175/D175,"N/A") |
| 176 | =IF(B176>0,H176/D176,"N/A") |
| 177 | =IF(B177>0,H177/D177,"N/A") |
| 178 | =IF(B178>0,H178/D178,"N/A") |
| 179 | |
| 180 | =H180/D180 |
| 181 | |
| 182 | =IF(B182>0,H182/D182,"N/A") |
| 183 | |
| 184 | =H184/D184 |
| 185 | |
| 186 | =IF(B186>0,H186/D186,"N/A") |
| 187 | =IF(B187>0,H187/D187,"N/A") |
| 188 | =IF(B188>0,H188/D188,"N/A") |
| 189 | =IF(B189>0,H189/D189,"N/A") |
| 190 | =IF(B190>0,H190/D190,"N/A") |
| 191 | =IF(B191>0,H191/D191,"N/A") |
| 192 | =IF(B192>0,H192/D192,"N/A") |
| 193 | =IF(B193>0,H193/D193,"N/A") |
| 194 | |
| 195 | |
| 196 | |
| 197 | =H197/D197 |
| 198 | |
| 199 | =H199/D199 |
| 200 | =H200/D200 |
| 201 | =H201/D201 |
| 202 | =H202/D202 |
| 203 | =H203/D203 |
| 204 | |
| 205 | =H205/D205 |
| 206 | |
| 207 | =H207/D207 |
| 208 | |

Figure 18Y

| | H |
|---|---|
| 1 | |
| 2 | |
| 3 | |
| 4 | |
| 5 | |
| 6 | |
| 7 | |
| 8 | Total |
| 9 | =SUBTOTAL(9,H11,H22,H43,H31,H48,H55,H59,H10) |
| 10 | =L10+P10+T10+X10+AB10+AF10+AJ10+AN10+AR10+AV10+AZ10+BD10+BH10+BL10+BP10 |
| 11 | =SUM(H12:H20) |
| 12 | =L12+P12+T12+X12+AB12+AF12+AJ12+AN12+AR12+AV12+AZ12+BD12+BH12+BL12+BP12 |
| 13 | =L13+P13+T13+X13+AB13+AF13+AJ13+AN13+AR13+AV13+AZ13+BD13+BH13+BL13+BP13 |
| 14 | =L14+P14+T14+X14+AB14+AF14+AJ14+AN14+AR14+AV14+AZ14+BD14+BH14+BL14+BP14 |
| 15 | =L15+P15+T15+X15+AB15+AF15+AJ15+AN15+AR15+AV15+AZ15+BD15+BH15+BL15+BP15 |
| 16 | =L16+P16+T16+X16+AB16+AF16+AJ16+AN16+AR16+AV16+AZ16+BD16+BH16+BL16+BP16 |
| 17 | =L17+P17+T17+X17+AB17+AF17+AJ17+AN17+AR17+AV17+AZ17+BD17+BH17+BL17+BP17 |
| 18 | =L18+P18+T18+X18+AB18+AF18+AJ18+AN18+AR18+AV18+AZ18+BD18+BH18+BL18+BP18 |
| 19 | =L19+P19+T19+X19+AB19+AF19+AJ19+AN19+AR19+AV19+AZ19+BD19+BH19+BL19+BP19 |
| 20 | =L20+P20+T20+X20+AB20+AF20+AJ20+AN20+AR20+AV20+AZ20+BD20+BH20+BL20+BP20 |
| 21 | |
| 22 | =SUM(H23:H29) |
| 23 | =L23+P23+T23+X23+AB23+AF23+AJ23+AN23+AR23+AV23+AZ23+BD23+BH23+BL23+BP23 |
| 24 | =L24+P24+T24+X24+AB24+AF24+AJ24+AN24+AR24+AV24+AZ24+BD24+BH24+BL24+BP24 |
| 25 | =L25+P25+T25+X25+AB25+AF25+AJ25+AN25+AR25+AV25+AZ25+BD25+BH25+BL25+BP25 |
| 26 | =L26+P26+T26+X26+AB26+AF26+AJ26+AN26+AR26+AV26+AZ26+BD26+BH26+BL26+BP26 |
| 27 | =L27+P27+T27+X27+AB27+AF27+AJ27+AN27+AR27+AV27+AZ27+BD27+BH27+BL27+BP27 |
| 28 | =L28+P28+T28+X28+AB28+AF28+AJ28+AN28+AR28+AV28+AZ28+BD28+BH28+BL28+BP28 |
| 29 | =L29+P29+T29+X29+AB29+AF29+AJ29+AN29+AR29+AV29+AZ29+BD29+BH29+BL29+BP29 |
| 30 | |
| 31 | =SUM(H32:H41) |
| 32 | =L32+P32+T32+X32+AB32+AF32+AJ32+AN32+AR32+AV32+AZ32+BD32+BH32+BL32+BP32 |
| 33 | =L33+P33+T33+X33+AB33+AF33+AJ33+AN33+AR33+AV33+AZ33+BD33+BH33+BL33+BP33 |
| 34 | =L34+P34+T34+X34+AB34+AF34+AJ34+AN34+AR34+AV34+AZ34+BD34+BH34+BL34+BP34 |
| 35 | =L35+P35+T35+X35+AB35+AF35+AJ35+AN35+AR35+AV35+AZ35+BD35+BH35+BL35+BP35 |
| 36 | =L36+P36+T36+X36+AB36+AF36+AJ36+AN36+AR36+AV36+AZ36+BD36+BH36+BL36+BP36 |
| 37 | =L37+P37+T37+X37+AB37+AF37+AJ37+AN37+AR37+AV37+AZ37+BD37+BH37+BL37+BP37 |
| 38 | =L38+P38+T38+X38+AB38+AF38+AJ38+AN38+AR38+AV38+AZ38+BD38+BH38+BL38+BP38 |
| 39 | =L39+P39+T39+X39+AB39+AF39+AJ39+AN39+AR39+AV39+AZ39+BD39+BH39+BL39+BP39 |
| 40 | =L40+P40+T40+X40+AB40+AF40+AJ40+AN40+AR40+AV40+AZ40+BD40+BH40+BL40+BP40 |
| 41 | =L41+P41+T41+X41+AB41+AF41+AJ41+AN41+AR41+AV41+AZ41+BD41+BH41+BL41+BP41 |
| 42 | |
| 43 | =SUM(H44:H46) |
| 44 | =L44+P44+T44+X44+AB44+AF44+AJ44+AN44+AR44+AV44+AZ44+BD44+BH44+BL44+BP44 |
| 45 | =L45+P45+T45+X45+AB45+AF45+AJ45+AN45+AR45+AV45+AZ45+BD45+BH45+BL45+BP45 |
| 46 | =L46+P46+T46+X46+AB46+AF46+AJ46+AN46+AR46+AV46+AZ46+BD46+BH46+BL46+BP46 |
| 47 | |
| 48 | =SUM(H49:H53) |
| 49 | =L49+P49+T49+X49+AB49+AF49+AJ49+AN49+AR49+AV49+AZ49+BD49+BH49+BL49+BP49 |
| 50 | =L50+P50+T50+X50+AB50+AF50+AJ50+AN50+AR50+AV50+AZ50+BD50+BH50+BL50+BP50 |
| 51 | =L51+P51+T51+X51+AB51+AF51+AJ51+AN51+AR51+AV51+AZ51+BD51+BH51+BL51+BP51 |
| 52 | =L52+P52+T52+X52+AB52+AF52+AJ52+AN52+AR52+AV52+AZ52+BD52+BH52+BL52+BP52 |
| 53 | =L53+P53+T53+X53+AB53+AF53+AJ53+AN53+AR53+AV53+AZ53+BD53+BH53+BL53+BP53 |
| 54 | |
| 55 | =SUM(H56:H57) |

Figure 18Z

| | H |
|---|---|
| 56 | =L56+P56+T56+X56+AB56+AF56+AJ56+AN56+AR56+AV56+AZ56+BD56+BH56+BL56+BP56 |
| 57 | =L57+P57+T57+X57+AB57+AF57+AJ57+AN57+AR57+AV57+AZ57+BD57+BH57+BL57+BP57 |
| 58 | |
| 59 | =L59+P59+T59+X59+AB59+AF59+AJ59+AN59+AR59+AV59+AZ59+BD59+BH59+BL59+BP59 |
| 60 | |
| 61 | =SUBTOTAL(9,H63) |
| 62 | |
| 63 | =SUM(H64:H71) |
| 64 | =L64+P64+T64+X64+AB64+AF64+AJ64+AN64+AR64+AV64+AZ64+BD64+BH64+BL64+BP64 |
| 65 | =L65+P65+T65+X65+AB65+AF65+AJ65+AN65+AR65+AV65+AZ65+BD65+BH65+BL65+BP65 |
| 66 | =L66+P66+T66+X66+AB66+AF66+AJ66+AN66+AR66+AV66+AZ66+BD66+BH66+BL66+BP66 |
| 67 | =L67+P67+T67+X67+AB67+AF67+AJ67+AN67+AR67+AV67+AZ67+BD67+BH67+BL67+BP67 |
| 68 | =L68+P68+T68+X68+AB68+AF68+AJ68+AN68+AR68+AV68+AZ68+BD68+BH68+BL68+BP68 |
| 69 | =L69+P69+T69+X69+AB69+AF69+AJ69+AN69+AR69+AV69+AZ69+BD69+BH69+BL69+BP69 |
| 70 | =L70+P70+T70+X70+AB70+AF70+AJ70+AN70+AR70+AV70+AZ70+BD70+BH70+BL70+BP70 |
| 71 | =L71+P71+T71+X71+AB71+AF71+AJ71+AN71+AR71+AV71+AZ71+BD71+BH71+BL71+BP71 |
| 72 | |
| 73 | =SUBTOTAL(9,H75,H83,H89,H95,H101) |
| 74 | |
| 75 | =SUM(H76:H81) |
| 76 | =L76+P76+T76+X76+AB76+AF76+AJ76+AN76+AR76+AV76+AZ76+BD76+BH76+BL76+BP76 |
| 77 | =L77+P77+T77+X77+AB77+AF77+AJ77+AN77+AR77+AV77+AZ77+BD77+BH77+BL77+BP77 |
| 78 | =L78+P78+T78+X78+AB78+AF78+AJ78+AN78+AR78+AV78+AZ78+BD78+BH78+BL78+BP78 |
| 79 | =L79+P79+T79+X79+AB79+AF79+AJ79+AN79+AR79+AV79+AZ79+BD79+BH79+BL79+BP79 |
| 80 | =L80+P80+T80+X80+AB80+AF80+AJ80+AN80+AR80+AV80+AZ80+BD80+BH80+BL80+BP80 |
| 81 | =L81+P81+T81+X81+AB81+AF81+AJ81+AN81+AR81+AV81+AZ81+BD81+BH81+BL81+BP81 |
| 82 | |
| 83 | =SUM(H84:H87) |
| 84 | =L84+P84+T84+X84+AB84+AF84+AJ84+AN84+AR84+AV84+AZ84+BD84+BH84+BL84+BP84 |
| 85 | =L85+P85+T85+X85+AB85+AF85+AJ85+AN85+AR85+AV85+AZ85+BD85+BH85+BL85+BP85 |
| 86 | =L86+P86+T86+X86+AB86+AF86+AJ86+AN86+AR86+AV86+AZ86+BD86+BH86+BL86+BP86 |
| 87 | =L87+P87+T87+X87+AB87+AF87+AJ87+AN87+AR87+AV87+AZ87+BD87+BH87+BL87+BP87 |
| 88 | |
| 89 | =SUM(H90:H93) |
| 90 | =L90+P90+T90+X90+AB90+AF90+AJ90+AN90+AR90+AV90+AZ90+BD90+BH90+BL90+BP90 |
| 91 | =L91+P91+T91+X91+AB91+AF91+AJ91+AN91+AR91+AV91+AZ91+BD91+BH91+BL91+BP91 |
| 92 | =L92+P92+T92+X92+AB92+AF92+AJ92+AN92+AR92+AV92+AZ92+BD92+BH92+BL92+BP92 |
| 93 | =L93+P93+T93+X93+AB93+AF93+AJ93+AN93+AR93+AV93+AZ93+BD93+BH93+BL93+BP93 |
| 94 | |
| 95 | =SUM(H96:H99) |
| 96 | =L96+P96+T96+X96+AB96+AF96+AJ96+AN96+AR96+AV96+AZ96+BD96+BH96+BL96+BP96 |
| 97 | =L97+P97+T97+X97+AB97+AF97+AJ97+AN97+AR97+AV97+AZ97+BD97+BH97+BL97+BP97 |
| 98 | =L98+P98+T98+X98+AB98+AF98+AJ98+AN98+AR98+AV98+AZ98+BD98+BH98+BL98+BP98 |
| 99 | =L99+P99+T99+X99+AB99+AF99+AJ99+AN99+AR99+AV99+AZ99+BD99+BH99+BL99+BP99 |
| 100 | |
| 101 | =SUM(H102:H103) |
| 102 | =L102+P102+T102+X102+AB102+AF102+AJ102+AN102+AR102+AV102+AZ102+BD102+BH102+BL102+BP10 |
| 103 | =L103+P103+T103+X103+AB103+AF103+AJ103+AN103+AR103+AV103+AZ103+BD103+BH103+BL103+BP10 |
| 104 | |
| 105 | =SUBTOTAL(9,H107,H108,H110) |
| 106 | |
| 107 | =L107+P107+T107+X107+AB107+AF107+AJ107+AN107+AR107+AV107+AZ107+BD107+BH107+BL107+BP |

Figure 18AA

| | H |
|---|---|
| 108 | =SUM(H109) |
| 109 | =L109+P109+T109+X109+AB109+AF109+AJ109+AN109+AR109+AV109+AZ109+BD109+BH109+BL109+BP1( |
| 110 | =SUM(H111:H114) |
| 111 | =L111+P111+T111+X111+AB111+AF111+AJ111+AN111+AR111+AV111+AZ111+BD111+BH111+BL111+BP1 |
| 112 | =L112+P112+T112+X112+AB112+AF112+AJ112+AN112+AR112+AV112+AZ112+BD112+BH112+BL112+BP1 |
| 113 | =L113+P113+T113+X113+AB113+AF113+AJ113+AN113+AR113+AV113+AZ113+BD113+BH113+BL113+BP1 |
| 114 | =L114+P114+T114+X114+AB114+AF114+AJ114+AN114+AR114+AV114+AZ114+BD114+BH114+BL114+BP1 |
| 115 | |
| 116 | |
| 117 | =SUBTOTAL(9,H119,H127,H137) |
| 118 | |
| 119 | =SUM(H120:H125) |
| 120 | =L120+P120+T120+X120+AB120+AF120+AJ120+AN120+AR120+AV120+AZ120+BD120+BH120+BL120+BP1 |
| 121 | =L121+P121+T121+X121+AB121+AF121+AJ121+AN121+AR121+AV121+AZ121+BD121+BH121+BL121+BP1 |
| 122 | =L122+P122+T122+X122+AB122+AF122+AJ122+AN122+AR122+AV122+AZ122+BD122+BH122+BL122+BP1 |
| 123 | =L123+P123+T123+X123+AB123+AF123+AJ123+AN123+AR123+AV123+AZ123+BD123+BH123+BL123+BP1 |
| 124 | =L124+P124+T124+X124+AB124+AF124+AJ124+AN124+AR124+AV124+AZ124+BD124+BH124+BL124+BP1 |
| 125 | =L125+P125+T125+X125+AB125+AF125+AJ125+AN125+AR125+AV125+AZ125+BD125+BH125+BL125+BP1 |
| 126 | |
| 127 | =SUM(H128:H135) |
| 128 | =L128+P128+T128+X128+AB128+AF128+AJ128+AN128+AR128+AV128+AZ128+BD128+BH128+BL128+BP1 |
| 129 | =L129+P129+T129+X129+AB129+AF129+AJ129+AN129+AR129+AV129+AZ129+BD129+BH129+BL129+BP1 |
| 130 | =L130+P130+T130+X130+AB130+AF130+AJ130+AN130+AR130+AV130+AZ130+BD130+BH130+BL130+BP1 |
| 131 | =L131+P131+T131+X131+AB131+AF131+AJ131+AN131+AR131+AV131+AZ131+BD131+BH131+BL131+BP1 |
| 132 | =L132+P132+T132+X132+AB132+AF132+AJ132+AN132+AR132+AV132+AZ132+BD132+BH132+BL132+BP1 |
| 133 | =L133+P133+T133+X133+AB133+AF133+AJ133+AN133+AR133+AV133+AZ133+BD133+BH133+BL133+BP1 |
| 134 | =L134+P134+T134+X134+AB134+AF134+AJ134+AN134+AR134+AV134+AZ134+BD134+BH134+BL134+BP1 |
| 135 | =L135+P135+T135+X135+AB135+AF135+AJ135+AN135+AR135+AV135+AZ135+BD135+BH135+BL135+BP1 |
| 136 | |
| 137 | =SUM(H138:H144) |
| 138 | =L138+P138+T138+X138+AB138+AF138+AJ138+AN138+AR138+AV138+AZ138+BD138+BH138+BL138+BP1 |
| 139 | =L139+P139+T139+X139+AB139+AF139+AJ139+AN139+AR139+AV139+AZ139+BD139+BH139+BL139+BP1 |
| 140 | =L140+P140+T140+X140+AB140+AF140+AJ140+AN140+AR140+AV140+AZ140+BD140+BH140+BL140+BP1 |
| 141 | =L141+P141+T141+X141+AB141+AF141+AJ141+AN141+AR141+AV141+AZ141+BD141+BH141+BL141+BP1 |
| 142 | =L142+P142+T142+X142+AB142+AF142+AJ142+AN142+AR142+AV142+AZ142+BD142+BH142+BL142+BP1 |
| 143 | =L143+P143+T143+X143+AB143+AF143+AJ143+AN143+AR143+AV143+AZ143+BD143+BH143+BL143+BP1 |
| 144 | =L144+P144+T144+X144+AB144+AF144+AJ144+AN144+AR144+AV144+AZ144+BD144+BH144+BL144+BP1 |
| 145 | |
| 146 | =SUM(H147:H147) |
| 147 | =L147+P147+T147+X147+AB147+AF147+AJ147+AN147+AR147+AV147+AZ147+BD147+BH147+BL147+BP1 |
| 148 | |
| 149 | =H9+H61+H73+H105+H117 |
| 150 | |
| 151 | =L151+P151+T151+X151+AB151+AF151+AJ151+AN151+AR151+AV151+AZ151+BD151+BH151+BL151+BP |
| 152 | |
| 153 | =H149+H151 |
| 154 | |
| 155 | =SUM(H156:H166) |
| 156 | |
| 157 | =L157+P157+T157+X157+AB157+AF157+AJ157+AN157+AR157+AV157+AZ157+BD157+BH157+BL157+BP1 |
| 158 | =L158+P158+T158+X158+AB158+AF158+AJ158+AN158+AR158+AV158+AZ158+BD158+BH158+BL158+BP1 |
| 159 | =L159+P159+T159+X159+AB159+AF159+AJ159+AN159+AR159+AV159+AZ159+BD159+BH159+BL159+BP1 |
| 160 | =L160+P160+T160+X160+AB160+AF160+AJ160+AN160+AR160+AV160+AZ160+BD160+BH160+BL160+BP1( |

Figure 18AB

| | H |
|---|---|
| 161 | =L161+P161+T161+X161+AB161+AF161+AJ161+AN161+AR161+AV161+AZ161+BD161+BH161+BL161+BP1( |
| 162 | =L162+P162+T162+X162+AB162+AF162+AJ162+AN162+AR162+AV162+AZ162+BD162+BH162+BL162+BP1( |
| 163 | =L163+P163+T163+X163+AB163+AF163+AJ163+AN163+AR163+AV163+AZ163+BD163+BH163+BL163+BP1( |
| 164 | =L164+P164+T164+X164+AB164+AF164+AJ164+AN164+AR164+AV164+AZ164+BD164+BH164+BL164+BP1( |
| 165 | =L165+P165+T165+X165+AB165+AF165+AJ165+AN165+AR165+AV165+AZ165+BD165+BH165+BL165+BP1( |
| 166 | |
| 167 | =SUM(H168:H170) |
| 168 | |
| 169 | =L169+P169+T169+X169+AB169+AF169+AJ169+AN169+AR169+AV169+AZ169+BD169+BH169+BL169+BP1( |
| 170 | =L170+P170+T170+X170+AB170+AF170+AJ170+AN170+AR170+AV170+AZ170+BD170+BH170+BL170+BP1 |
| 171 | |
| 172 | =SUM(H173:H174) |
| 173 | |
| 174 | =SUM(H175:H179) |
| 175 | =L175+P175+T175+X175+AB175+AF175+AJ175+AN175+AR175+AV175+AZ175+BD175+BH175+BL175+BP1 |
| 176 | =L176+P176+T176+X176+AB176+AF176+AJ176+AN176+AR176+AV176+AZ176+BD176+BH176+BL176+BP1 |
| 177 | =L177+P177+T177+X177+AB177+AF177+AJ177+AN177+AR177+AV177+AZ177+BD177+BH177+BL177+BP1 |
| 178 | =L178+P178+T178+X178+AB178+AF178+AJ178+AN178+AR178+AV178+AZ178+BD178+BH178+BL178+BP1 |
| 179 | |
| 180 | =SUM(H181:H183) |
| 181 | |
| 182 | =L182+P182+T182+X182+AB182+AF182+AJ182+AN182+AR182+AV182+AZ182+BD182+BH182+BL182+BP |
| 183 | |
| 184 | =SUM(H185:H193) |
| 185 | |
| 186 | =L186+P186+T186+X186+AB186+AF186+AJ186+AN186+AR186+AV186+AZ186+BD186+BH186+BL186+BP1( |
| 187 | =L187+P187+T187+X187+AB187+AF187+AJ187+AN187+AR187+AV187+AZ187+BD187+BH187+BL187+BP1( |
| 188 | =L188+P188+T188+X188+AB188+AF188+AJ188+AN188+AR188+AV188+AZ188+BD188+BH188+BL188+BP1( |
| 189 | =L189+P189+T189+X189+AB189+AF189+AJ189+AN189+AR189+AV189+AZ189+BD189+BH189+BL189+BP1( |
| 190 | =L190+P190+T190+X190+AB190+AF190+AJ190+AN190+AR190+AV190+AZ190+BD190+BH190+BL190+BP1( |
| 191 | =L191+P191+T191+X191+AB191+AF191+AJ191+AN191+AR191+AV191+AZ191+BD191+BH191+BL191+BP1( |
| 192 | =L192+P192+T192+X192+AB192+AF192+AJ192+AN192+AR192+AV192+AZ192+BD192+BH192+BL192+BP1( |
| 193 | =L193+P193+T193+X193+AB193+AF193+AJ193+AN193+AR193+AV193+AZ193+BD193+BH193+BL193+BP1( |
| 194 | |
| 195 | =L195+P195+T195+X195+AB195+AF195+AJ195+AN195+AR195+AV195+AZ195+BD195+BH195+BL195+BP |
| 196 | |
| 197 | =H155+H167+H172+H180+H184+H195 |
| 198 | |
| 199 | =H9+H155 |
| 200 | =H61+H167 |
| 201 | =H73+H172 |
| 202 | =H105+H180 |
| 203 | =H117+H184 |
| 204 | |
| 205 | =H153+H197 |
| 206 | |
| 207 | =H153*(-0.2) |
| 208 | |

Figure 18AC

| | I | J | K |
|---|---|---|---|
| 1 | | | |
| 2 | | | |
| 3 | | Invoice Date | |
| 4 | | Due Date | |
| 5 | | Invoice # | |
| 6 | | | |
| 7 | | | 1st Month ---- May, 07 |
| 8 | | Unit | Unit Price |
| 9 | | | |
| 10 | | | |
| 11 | | | |
| 12 | | | =IF(J12>0,$C12,0) |
| 13 | | | =IF(J13>0,$C13,0) |
| 14 | | | =IF(J14>0,$C14,0) |
| 15 | | | =IF(J15>0,$C15,0) |
| 16 | | | =IF(J16>0,$C16,0) |
| 17 | | | =IF(J17>0,$C17,0) |
| 18 | | | =IF(J18>0,$C18,0) |
| 19 | | | =IF(J19>0,$C19,0) |
| 20 | | | =IF(J20>0,$C20,0) |
| 21 | | | |
| 22 | | | |
| 23 | | | =IF(J23>0,$C23,0) |
| 24 | | | =IF(J24>0,$C24,0) |
| 25 | | | =IF(J25>0,$C25,0) |
| 26 | | | =IF(J26>0,$C26,0) |
| 27 | | | =IF(J27>0,$C27,0) |
| 28 | | | =IF(J28>0,$C28,0) |
| 29 | | | =IF(J29>0,$C29,0) |
| 30 | | | |
| 31 | | | |
| 32 | | | =IF(J32>0,$C32,0) |
| 33 | | | =IF(J33>0,$C33,0) |
| 34 | | | =IF(J34>0,$C34,0) |
| 35 | | | =IF(J35>0,$C35,0) |
| 36 | | | =IF(J36>0,$C36,0) |
| 37 | | | =IF(J37>0,$C37,0) |
| 38 | | | =IF(J38>0,$C38,0) |
| 39 | | | =IF(J39>0,$C39,0) |
| 40 | | | =IF(J40>0,$C40,0) |
| 41 | | | =IF(J41>0,$C41,0) |
| 42 | | | |
| 43 | | | |
| 44 | | | =IF(J44>0,$C44,0) |
| 45 | | | =IF(J45>0,$C45,0) |
| 46 | | | =IF(J46>0,$C46,0) |
| 47 | | | |
| 48 | | | |
| 49 | | | =IF(J49>0,$C49,0) |
| 50 | | | =IF(J50>0,$C50,0) |
| 51 | | | =IF(J51>0,$C51,0) |
| 52 | | | =IF(J52>0,$C52,0) |
| 53 | | | =IF(J53>0,$C53,0) |
| 54 | | | |
| 55 | | | |

Figure 18AD

| | I | J | K |
|---|---|---|---|
| 56 | | | =IF(J56>0,$C56,0) |
| 57 | | | =IF(J57>0,$C57,0) |
| 58 | | | |
| 59 | | | |
| 60 | | | |
| 61 | | | |
| 62 | | | |
| 63 | | | |
| 64 | | | =IF(J64>0,$C64,0) |
| 65 | | | =IF(J65>0,$C65,0) |
| 66 | | | =IF(J66>0,$C66,0) |
| 67 | | | =IF(J67>0,$C67,0) |
| 68 | | | =IF(J68>0,$C68,0) |
| 69 | | | =IF(J69>0,$C69,0) |
| 70 | | | =IF(J70>0,$C70,0) |
| 71 | | | =IF(J71>0,$C71,0) |
| 72 | | | |
| 73 | | | |
| 74 | | | |
| 75 | | | |
| 76 | | | =IF(J76>0,$C76,0) |
| 77 | | | =IF(J77>0,$C77,0) |
| 78 | | | =IF(J78>0,$C78,0) |
| 79 | | | =IF(J79>0,$C79,0) |
| 80 | | | =IF(J80>0,$C80,0) |
| 81 | | | =IF(J81>0,$C81,0) |
| 82 | | | |
| 83 | | | |
| 84 | | | =IF(J84>0,$C84,0) |
| 85 | | | =IF(J85>0,$C85,0) |
| 86 | | | =IF(J86>0,$C86,0) |
| 87 | | | =IF(J87>0,$C87,0) |
| 88 | | | |
| 89 | | | |
| 90 | | | =IF(J90>0,$C90,0) |
| 91 | | | =IF(J91>0,$C91,0) |
| 92 | | | =IF(J92>0,$C92,0) |
| 93 | | | =IF(J93>0,$C93,0) |
| 94 | | | |
| 95 | | | |
| 96 | | | =IF(J96>0,$C96,0) |
| 97 | | | =IF(J97>0,$C97,0) |
| 98 | | | =IF(J98>0,$C98,0) |
| 99 | | | =IF(J99>0,$C99,0) |
| 100 | | | |
| 101 | | | |
| 102 | | | =IF(J102>0,$C102,0) |
| 103 | | | =IF(J103>0,$C103,0) |
| 104 | | | |
| 105 | | | |
| 106 | | | |
| 107 | | | |

Figure 18AE

| | I | J | K |
|---|---|---|---|
| 108 | | | |
| 109 | | | =IF(J109>0,$C109,0) |
| 110 | | | |
| 111 | | | =IF(J111>0,$C111,0) |
| 112 | | | =IF(J112>0,$C112,0) |
| 113 | | | =IF(J113>0,$C113,0) |
| 114 | | | =IF(J114>0,$C114,0) |
| 115 | | | |
| 116 | | | |
| 117 | | | |
| 118 | | | |
| 119 | | | |
| 120 | | | =IF(J120>0,$C120,0) |
| 121 | | | =IF(J121>0,$C121,0) |
| 122 | | | =IF(J122>0,$C122,0) |
| 123 | | | =IF(J123>0,$C123,0) |
| 124 | | | =IF(J124>0,$C124,0) |
| 125 | | | =IF(J125>0,$C125,0) |
| 126 | | | |
| 127 | | | |
| 128 | | | =IF(J128>0,$C128,0) |
| 129 | | | =IF(J129>0,$C129,0) |
| 130 | | | =IF(J130>0,$C130,0) |
| 131 | | | =IF(J131>0,$C131,0) |
| 132 | | | =IF(J132>0,$C132,0) |
| 133 | | | =IF(J133>0,$C133,0) |
| 134 | | | =IF(J134>0,$C134,0) |
| 135 | | | =IF(J135>0,$C135,0) |
| 136 | | | |
| 137 | | | |
| 138 | | | =IF(J138>0,$C138,0) |
| 139 | | | =IF(J139>0,$C139,0) |
| 140 | | | =IF(J140>0,$C140,0) |
| 141 | | | =IF(J141>0,$C141,0) |
| 142 | | | =IF(J142>0,$C142,0) |
| 143 | | | =IF(J143>0,$C143,0) |
| 144 | | | =IF(J144>0,$C144,0) |
| 145 | | | |
| 146 | | | |
| 147 | | | =IF(J147>0,$C147,0) |
| 148 | | | |
| 149 | | | |
| 150 | | | |
| 151 | | | =IF(J151>0,$C151,0) |
| 152 | | | |
| 153 | | | |
| 154 | | | |
| 155 | | | |
| 156 | | | |
| 157 | | | =IF(J157>0,$C157,0) |
| 158 | | | =IF(J158>0,$C158,0) |
| 159 | | | =IF(J159>0,$C159,0) |
| 160 | | | =IF(J160>0,$C160,0) |

Figure 18AF

| | I | J | K |
|---|---|---|---|
| 161 | | | =IF(J161>0,$C161,0) |
| 162 | | | =IF(J162>0,$C162,0) |
| 163 | | | =IF(J163>0,$C163,0) |
| 164 | | | =IF(J164>0,$C164,0) |
| 165 | | | =IF(J165>0,$C165,0) |
| 166 | | | |
| 167 | | | |
| 168 | | | |
| 169 | | | =IF(J169>0,$C169,0) |
| 170 | | | =IF(J170>0,$C170,0) |
| 171 | | | |
| 172 | | | |
| 173 | | | |
| 174 | | | |
| 175 | | | =IF(J175>0,$C175,0) |
| 176 | | | =IF(J176>0,$C176,0) |
| 177 | | | =IF(J177>0,$C177,0) |
| 178 | | | =IF(J178>0,$C178,0) |
| 179 | | | |
| 180 | | | |
| 181 | | | |
| 182 | | | =IF(J182>0,$C182,0) |
| 183 | | | |
| 184 | | | |
| 185 | | | |
| 186 | | | =IF(J186>0,$C186,0) |
| 187 | | | =IF(J187>0,$C187,0) |
| 188 | | | =IF(J188>0,$C188,0) |
| 189 | | | =IF(J189>0,$C189,0) |
| 190 | | | =IF(J190>0,$C190,0) |
| 191 | | | =IF(J191>0,$C191,0) |
| 192 | | | =IF(J192>0,$C192,0) |
| 193 | | | =IF(J193>0,$C193,0) |
| 194 | | | |
| 195 | | | |
| 196 | | | |
| 197 | | | |
| 198 | | | |
| 199 | | | |
| 200 | | | |
| 201 | | | |
| 202 | | | |
| 203 | | | |
| 204 | | | |
| 205 | | | |
| 206 | | | |
| 207 | | | |
| 208 | | | |

Figure 18AG

| | L | M | N |
|---|---|---|---|
| 1 | | | |
| 2 | | | |
| 3 | | | Invoice Date |
| 4 | | | Due Date |
| 5 | | | Invoice # |
| 6 | | | |
| 7 | | | |
| 8 | Total | | Unit |
| 9 | =SUBTOTAL(9,L11,L22,L43,L31,L48,L55,L59,L10) | | |
| 10 | | | |
| 11 | =SUM(L12:L20) | | |
| 12 | =$C12*J12 | | |
| 13 | =$C13*J13 | | |
| 14 | =$C14*J14 | | |
| 15 | =$C15*J15 | | |
| 16 | =$C16*J16 | | |
| 17 | =$C17*J17 | | |
| 18 | =$C18*J18 | | |
| 19 | =$C19*J19 | | |
| 20 | =$C20*J20 | | |
| 21 | | | |
| 22 | =SUM(L23:L29) | | |
| 23 | =$C23*J23 | | |
| 24 | =$C24*J24 | | |
| 25 | =$C25*J25 | | |
| 26 | =$C26*J26 | | |
| 27 | =$C27*J27 | | |
| 28 | =$C28*J28 | | |
| 29 | =$C29*J29 | | |
| 30 | | | |
| 31 | =SUM(L32:L41) | | |
| 32 | =$C32*J32 | | |
| 33 | =$C33*J33 | | |
| 34 | =$C34*J34 | | |
| 35 | =$C35*J35 | | |
| 36 | =$C36*J36 | | |
| 37 | =$C37*J37 | | |
| 38 | =$C38*J38 | | |
| 39 | =$C39*J39 | | |
| 40 | =$C40*J40 | | |
| 41 | =$C41*J41 | | |
| 42 | | | |
| 43 | =SUM(L44:L46) | | |
| 44 | =$C44*J44 | | |
| 45 | =$C45*J45 | | |
| 46 | =$C46*J46 | | |
| 47 | | | |
| 48 | =SUM(L49:L53) | | |
| 49 | =J49*K49 | | |
| 50 | =J50*K50 | | |
| 51 | =J51*K51 | | |
| 52 | =J52*K52 | | |
| 53 | =J53*K53 | | |
| 54 | | | |
| 55 | =SUM(L56:L57) | | |

Figure 18AH

| | L | M | N |
|---|---|---|---|
| 56 | =J56*K56 | | |
| 57 | =$C57*J57 | | |
| 58 | | | |
| 59 | =J59*K59 | | |
| 60 | | | |
| 61 | =SUBTOTAL(9,L63) | | |
| 62 | | | |
| 63 | =SUM(L64:L71) | | |
| 64 | =$C64*J64 | | |
| 65 | =$C65*J65 | | |
| 66 | =$C66*J66 | | |
| 67 | =$C67*J67 | | |
| 68 | =$C68*J68 | | |
| 69 | =$C69*J69 | | |
| 70 | =$C70*J70 | | |
| 71 | =$C71*J71 | | |
| 72 | | | |
| 73 | =SUBTOTAL(9,L75,L83,L89,L95,L101) | | |
| 74 | | | |
| 75 | =SUM(L76:L81) | | |
| 76 | =$C76*J76 | | |
| 77 | =$C77*J77 | | |
| 78 | =$C78*J78 | | |
| 79 | =$C79*J79 | | |
| 80 | =$C80*J80 | | |
| 81 | =$C81*J81 | | |
| 82 | | | |
| 83 | =SUM(L84:L87) | | |
| 84 | =$C84*J84 | | |
| 85 | =$C85*J85 | | |
| 86 | =$C86*J86 | | |
| 87 | =$C87*J87 | | |
| 88 | | | |
| 89 | =SUM(L90:L93) | | |
| 90 | =$C90*J90 | | |
| 91 | =$C91*J91 | | |
| 92 | =$C92*J92 | | |
| 93 | =$C93*J93 | | |
| 94 | | | |
| 95 | =SUM(L96:L99) | | |
| 96 | =$C96*J96 | | |
| 97 | =$C97*J97 | | |
| 98 | =$C98*J98 | | |
| 99 | =$C99*J99 | | |
| 100 | | | |
| 101 | =SUM(L102:L103) | | |
| 102 | =$C102*J102 | | |
| 103 | =$C103*J103 | | |
| 104 | | | |
| 105 | =SUBTOTAL(9,L107,L108,L110) | | |
| 106 | | | |
| 107 | =$C107*J107 | | |

Figure 18AI

| | L | M | N |
|---|---|---|---|
| 108 | =SUM(L109) | | |
| 109 | =$C109*J109 | | |
| 110 | =SUM(L111:L114) | | |
| 111 | =$C111*J111 | | |
| 112 | =$C112*J112 | | |
| 113 | =$C113*J113 | | |
| 114 | =$C114*J114 | | |
| 115 | | | |
| 116 | | | |
| 117 | =SUBTOTAL(9,L119,L127,L137) | | |
| 118 | | | |
| 119 | =SUM(L120:L125) | | |
| 120 | =$C120*J120 | | |
| 121 | =$C121*J121 | | |
| 122 | =$C122*J122 | | |
| 123 | =$C123*J123 | | |
| 124 | =$C124*J124 | | |
| 125 | =$C125*J125 | | |
| 126 | | | |
| 127 | =SUM(L128:L135) | | |
| 128 | =$C128*J128 | | |
| 129 | =$C129*J129 | | |
| 130 | =$C130*J130 | | |
| 131 | =$C131*J131 | | |
| 132 | =$C132*J132 | | |
| 133 | =$C133*J133 | | |
| 134 | =$C134*J134 | | |
| 135 | =$C135*J135 | | |
| 136 | | | |
| 137 | =SUM(L138:L144) | | |
| 138 | =$C138*J138 | | |
| 139 | =$C139*J139 | | |
| 140 | =$C140*J140 | | |
| 141 | =$C141*J141 | | |
| 142 | =$C142*J142 | | |
| 143 | =$C143*J143 | | |
| 144 | =$C144*J144 | | |
| 145 | | | |
| 146 | =SUM(L147:L147) | | |
| 147 | =$C147*J147 | | |
| 148 | | | |
| 149 | =L9+L61+L73+L105+L117 | | |
| 150 | | | |
| 151 | =$C151*J151 | | |
| 152 | | | |
| 153 | =L149+L151 | | |
| 154 | | | |
| 155 | =SUM(L156:L166) | | |
| 156 | | | |
| 157 | =$C157*J157 | | |
| 158 | =$C158*J158 | | |
| 159 | =$C159*J159 | | |
| 160 | =$C160*J160 | | |

Figure 18AJ

| | L | M | N |
|---|---|---|---|
| 161 | =$C161*J161 | | |
| 162 | =$C162*J162 | | |
| 163 | =$C163*J163 | | |
| 164 | =$C164*J164 | | |
| 165 | =$C165*J165 | | |
| 166 | | | |
| 167 | =SUM(L168:L170) | | |
| 168 | | | |
| 169 | =$C169*J169 | | |
| 170 | =$C170*J170 | | |
| 171 | | | |
| 172 | =SUM(L173:L174) | | |
| 173 | | | |
| 174 | =SUM(L175:L179) | | |
| 175 | =$C175*J175 | | |
| 176 | =$C176*J176 | | |
| 177 | =$C177*J177 | | |
| 178 | =$C178*J178 | | |
| 179 | =D179 | | |
| 180 | =SUM(L181:L183) | | |
| 181 | | | |
| 182 | =$C182*J182 | | |
| 183 | | | |
| 184 | =SUM(L185:L193) | | |
| 185 | | | |
| 186 | =$C186*J186 | | |
| 187 | =$C187*J187 | | |
| 188 | =$C188*J188 | | |
| 189 | =$C189*J189 | | |
| 190 | =$C190*J190 | | |
| 191 | =$C191*J191 | | |
| 192 | =$C192*J192 | | |
| 193 | =$C193*J193 | | |
| 194 | | | |
| 195 | | | |
| 196 | | | |
| 197 | =L155+L167+L172+L180+L184+L195 | | |
| 198 | | | |
| 199 | =L9+L155 | | |
| 200 | =L61+L167 | | |
| 201 | =L73+L172 | | |
| 202 | =L105+L180 | | |
| 203 | =L117+L184 | | |
| 204 | | | |
| 205 | =L153+L197 | | |
| 206 | | | |
| 207 | =L153*(-0.2) | | |
| 208 | | | |

Figure 18AK

| | O | P |
|---|---|---|
| 1 | | |
| 2 | | |
| 3 | | |
| 4 | | |
| 5 | | |
| 6 | | |
| 7 | Month 02 June, 07 | |
| 8 | Unit Price | Total |
| 9 | | =SUBTOTAL(9,P11,P22,P43,P31,P48,P55,P59,P10) |
| 10 | | |
| 11 | | =SUM(P12:P20) |
| 12 | =IF(N12>0,$C12,0) | =$C12*N12 |
| 13 | =IF(N13>0,$C13,0) | =$C13*N13 |
| 14 | =IF(N14>0,$C14,0) | =$C14*N14 |
| 15 | =IF(N15>0,$C15,0) | =$C15*N15 |
| 16 | =IF(N16>0,$C16,0) | =$C16*N16 |
| 17 | =IF(N17>0,$C17,0) | =$C17*N17 |
| 18 | =IF(N18>0,$C18,0) | =$C18*N18 |
| 19 | =IF(N19>0,$C19,0) | =$C19*N19 |
| 20 | =IF(N20>0,$C20,0) | =$C20*N20 |
| 21 | | |
| 22 | | =SUM(P23:P29) |
| 23 | =IF(N23>0,$C23,0) | =$C23*N23 |
| 24 | =IF(N24>0,$C24,0) | =$C24*N24 |
| 25 | =IF(N25>0,$C25,0) | =$C25*N25 |
| 26 | =IF(N26>0,$C26,0) | =$C26*N26 |
| 27 | =IF(N27>0,$C27,0) | =$C27*N27 |
| 28 | =IF(N28>0,$C28,0) | =$C28*N28 |
| 29 | =IF(N29>0,$C29,0) | =$C29*N29 |
| 30 | | |
| 31 | | =SUM(P32:P41) |
| 32 | =IF(N32>0,$C32,0) | =$C32*N32 |
| 33 | =IF(N33>0,$C33,0) | =$C33*N33 |
| 34 | =IF(N34>0,$C34,0) | =$C34*N34 |
| 35 | =IF(N35>0,$C35,0) | =$C35*N35 |
| 36 | =IF(N36>0,$C36,0) | =$C36*N36 |
| 37 | =IF(N37>0,$C37,0) | =$C37*N37 |
| 38 | =IF(N38>0,$C38,0) | =$C38*N38 |
| 39 | =IF(N39>0,$C39,0) | =$C39*N39 |
| 40 | =IF(N40>0,$C40,0) | =$C40*N40 |
| 41 | =IF(N41>0,$C41,0) | =$C41*N41 |
| 42 | | |
| 43 | | =SUM(P44:P46) |
| 44 | =IF(N44>0,$C44,0) | =$C44*N44 |
| 45 | =IF(N45>0,$C45,0) | =$C45*N45 |
| 46 | =IF(N46>0,$C46,0) | =$C46*N46 |
| 47 | | |
| 48 | | =SUM(P49:P53) |
| 49 | =IF(N49>0,$C49,0) | =$C49*N49 |
| 50 | =IF(N50>0,$C50,0) | =$C50*N50 |
| 51 | =IF(N51>0,$C51,0) | =$C51*N51 |
| 52 | =IF(N52>0,$C52,0) | =$C52*N52 |
| 53 | =IF(N53>0,$C53,0) | =$C53*N53 |
| 54 | | |
| 55 | =IF(N55>0,$C55,0) | =SUM(P56:P57) |

Figure 18AL

| | O | P |
|---|---|---|
| 56 | =IF(N56>0,$C56,0) | =$C56*N56 |
| 57 | =IF(N57>0,$C57,0) | =$C57*N57 |
| 58 | | |
| 59 | =IF(N59>0,$C59,0) | =N59*O59 |
| 60 | | |
| 61 | | |
| 62 | | |
| 63 | | =SUM(P64:P71) |
| 64 | =IF(N64>0,$C64,0) | =$C64*N64 |
| 65 | =IF(N65>0,$C65,0) | =$C65*N65 |
| 66 | =IF(N66>0,$C66,0) | =$C66*N66 |
| 67 | =IF(N67>0,$C67,0) | =$C67*N67 |
| 68 | =IF(N68>0,$C68,0) | =$C68*N68 |
| 69 | =IF(N69>0,$C69,0) | =$C69*N69 |
| 70 | =IF(N70>0,$C70,0) | =$C70*N70 |
| 71 | =IF(N71>0,$C71,0) | =$C71*N71 |
| 72 | | |
| 73 | | =SUBTOTAL(9,P75,P83,P89,P95,P101) |
| 74 | | |
| 75 | | =SUM(P76:P81) |
| 76 | =IF(N76>0,$C76,0) | =$C76*N76 |
| 77 | =IF(N77>0,$C77,0) | =$C77*N77 |
| 78 | =IF(N78>0,$C78,0) | =$C78*N78 |
| 79 | =IF(N79>0,$C79,0) | =$C79*N79 |
| 80 | =IF(N80>0,$C80,0) | =$C80*N80 |
| 81 | =IF(N81>0,$C81,0) | =$C81*N81 |
| 82 | | |
| 83 | | =SUM(P84:P87) |
| 84 | =IF(N84>0,$C84,0) | =$C84*N84 |
| 85 | =IF(N85>0,$C85,0) | =$C85*N85 |
| 86 | =IF(N86>0,$C86,0) | =$C86*N86 |
| 87 | =IF(N87>0,$C87,0) | =$C87*N87 |
| 88 | | |
| 89 | | =SUM(P90:P93) |
| 90 | =IF(N90>0,$C90,0) | =$C90*N90 |
| 91 | =IF(N91>0,$C91,0) | =$C91*N91 |
| 92 | =IF(N92>0,$C92,0) | =$C92*N92 |
| 93 | =IF(N93>0,$C93,0) | =$C93*N93 |
| 94 | | |
| 95 | | =SUM(P96:P99) |
| 96 | =IF(N96>0,$C96,0) | =$C96*N96 |
| 97 | =IF(N97>0,$C97,0) | =$C97*N97 |
| 98 | =IF(N98>0,$C98,0) | =$C98*N98 |
| 99 | =IF(N99>0,$C99,0) | =$C99*N99 |
| 100 | | |
| 101 | | =SUM(P102:P103) |
| 102 | =IF(N102>0,$C102,0) | =$C102*N102 |
| 103 | =IF(N103>0,$C103,0) | =$C103*N103 |
| 104 | | |
| 105 | | =SUBTOTAL(9,P107,P108,P110) |
| 106 | | 15305 |
| 107 | | =$C107*N107 |

Figure 18AM

| | O | P |
|---|---|---|
| 108 | | =SUM(P109) |
| 109 | =IF(N109>0,$C109,0) | =$C109*N109 |
| 110 | | =SUM(P111:P114) |
| 111 | =IF(N111>0,$C111,0) | =$C111*N111 |
| 112 | =IF(N112>0,$C112,0) | =$C112*N112 |
| 113 | =IF(N113>0,$C113,0) | =$C113*N113 |
| 114 | =IF(N114>0,$C114,0) | =$C114*N114 |
| 115 | | |
| 116 | | |
| 117 | | =SUBTOTAL(9,P119,P127,P137) |
| 118 | | |
| 119 | | =SUM(P120:P125) |
| 120 | =IF(N120>0,$C120,0) | =$C120*N120 |
| 121 | =IF(N121>0,$C121,0) | =$C121*N121 |
| 122 | =IF(N122>0,$C122,0) | =$C122*N122 |
| 123 | =IF(N123>0,$C123,0) | =$C123*N123 |
| 124 | =IF(N124>0,$C124,0) | =$C124*N124 |
| 125 | =IF(N125>0,$C125,0) | =$C125*N125 |
| 126 | | |
| 127 | | =SUM(P128:P135) |
| 128 | =IF(N128>0,$C128,0) | =$C128*N128 |
| 129 | =IF(N129>0,$C129,0) | =$C129*N129 |
| 130 | =IF(N130>0,$C130,0) | =$C130*N130 |
| 131 | =IF(N131>0,$C131,0) | =$C131*N131 |
| 132 | =IF(N132>0,$C132,0) | =$C132*N132 |
| 133 | =IF(N133>0,$C133,0) | =$C133*N133 |
| 134 | =IF(N134>0,$C134,0) | =$C134*N134 |
| 135 | =IF(N135>0,$C135,0) | =$C135*N135 |
| 136 | | |
| 137 | | =SUM(P138:P144) |
| 138 | =IF(N138>0,$C138,0) | =$C138*N138 |
| 139 | =IF(N139>0,$C139,0) | =$C139*N139 |
| 140 | =IF(N140>0,$C140,0) | =$C140*N140 |
| 141 | =IF(N141>0,$C141,0) | =$C141*N141 |
| 142 | =IF(N142>0,$C142,0) | =$C142*N142 |
| 143 | =IF(N143>0,$C143,0) | =$C143*N143 |
| 144 | =IF(N144>0,$C144,0) | =$C144*N144 |
| 145 | | |
| 146 | =IF(N146>0,$C146,0) | =SUM(P147:P147) |
| 147 | =IF(N147>0,$C147,0) | =$C147*N147 |
| 148 | | |
| 149 | | =P9+P61+P73+P105+P117 |
| 150 | | |
| 151 | =IF(N151>0,$C151,0) | =$C151*N151 |
| 152 | | |
| 153 | | =P149+P151 |
| 154 | | |
| 155 | | =SUM(P156:P166) |
| 156 | | |
| 157 | =IF(N157>0,$C157,0) | =$C157*N157 |
| 158 | =IF(N158>0,$C158,0) | =$C158*N158 |
| 159 | =IF(N159>0,$C159,0) | =$C159*N159 |
| 160 | =IF(N160>0,$C160,0) | =$C160*N160 |

Figure 18AN

| | O | P |
|---|---|---|
| 161 | =IF(N161>0,$C161,0) | =$C161*N161 |
| 162 | =IF(N162>0,$C162,0) | =$C162*N162 |
| 163 | =IF(N163>0,$C163,0) | =$C163*N163 |
| 164 | =IF(N164>0,$C164,0) | =$C164*N164 |
| 165 | =IF(N165>0,$C165,0) | =$C165*N165 |
| 166 | | |
| 167 | | =SUM(P168:P170) |
| 168 | | |
| 169 | =IF(N169>0,$C169,0) | =$C169*N169 |
| 170 | =IF(N170>0,$C170,0) | =$C170*N170 |
| 171 | | |
| 172 | | =SUM(P173:P174) |
| 173 | | |
| 174 | | =SUM(P175:P179) |
| 175 | =IF(N175>0,$C175,0) | =$C175*N175 |
| 176 | =IF(N176>0,$C176,0) | =$C176*N176 |
| 177 | =IF(N177>0,$C177,0) | =$C177*N177 |
| 178 | =IF(N178>0,$C178,0) | =$C178*N178 |
| 179 | | |
| 180 | | =SUM(P181:P183) |
| 181 | | |
| 182 | =IF(N182>0,$C182,0) | =$C182*N182 |
| 183 | | |
| 184 | | =SUM(P185:P193) |
| 185 | | |
| 186 | =IF(N186>0,$C186,0) | =$C186*N186 |
| 187 | =IF(N187>0,$C187,0) | =$C187*N187 |
| 188 | =IF(N188>0,$C188,0) | =$C188*N188 |
| 189 | =IF(N189>0,$C189,0) | =$C189*N189 |
| 190 | =IF(N190>0,$C190,0) | =$C190*N190 |
| 191 | =IF(N191>0,$C191,0) | =$C191*N191 |
| 192 | =IF(N192>0,$C192,0) | =$C192*N192 |
| 193 | =IF(N193>0,$C193,0) | =$C193*N193 |
| 194 | | |
| 195 | | |
| 196 | | |
| 197 | | =P155+P167+P172+P180+P184+P195 |
| 198 | | |
| 199 | | =P9+P155 |
| 200 | | =P61+P167 |
| 201 | | =P73+P172 |
| 202 | | =P105+P180 |
| 203 | | =P117+P184 |
| 204 | | |
| 205 | | =P153+P197 |
| 206 | | |
| 207 | | =P153*(-0.2) |
| 208 | | |

METHOD AND APPARATUS FOR ACCOUNTING AND CONTRACTING FOR CLINICAL TRIAL STUDIES

CROSS-REFERENCE TO RELATED APPLICATIONS

This application is a continuation of U.S. application Ser. No. 12/165,982 filed Jul. 1, 2008, the entire disclosure of which is incorporated herein by reference.

BACKGROUND OF THE INVENTION

In the life sciences industry, there are pharmaceutical, specialty pharmaceutical, biotechnology, medical device, biopharmaceutical companies and others that are required to perform clinical trials. Clinical trial data and information is submitted to the U.S. Food and Drug Administration and/or a foreign counterpart to gain approval for a new product. This type of product development is complex and expensive because many different suppliers across the globe may be needed to perform even a single trial. The process for managing payments to suppliers for the products and services that are contracted is also complex. Some reasons for the complexity are that the process often requires the life sciences company, known as the "sponsor" of the trial, to use many different suppliers and perhaps their own resources, in combination, and because the supplier billing staff does not know what work has been done by others elsewhere in their company, in other parts of the U.S. or across the globe. There are two major processes that are performed in order to invoice and then pay appropriate invoices for work/deliverables completed. ("Deliverables" refer to the goods and services that need to be provided to perform a clinical trial study. The deliverables include goods and services provided at patient sites, as well as sites remote from the patient sites, such as lab and diagnostic sites, or sites where investigators perform services.)

On the supplier side, there are many issues in connecting the number of billable hours with the activity related to the deliverable that was accomplished. This makes it difficult for a supplier to provide the exact number of deliverables that were completed. Sometimes a supplier cannot distinguish between their own charges that can be invoiced for work completed and the charges of the supplier's subcontractors, known as pass-throughs. This might happen because the supplier does not wish to identify these items and their prices on an invoice. This process is the source of numerous, expensive errors. Bills and invoices that suppliers create often contain duplicate charges, missed charges, and other mistakes that the supplier and their subcontractors may not realize. However, the sponsor of the trial needs to know all details in order to understand several important cash flow matters. For example, a sponsor cannot continue to receive invoices for two years after the trial has been concluded, because it is near impossible to verify these late invoices and deem them as appropriate, long after the project has been performed and completed.

Currently, each supplier is only concerned with their own individual costs and their associated invoices sent to a sponsor. However, the sponsors need to know, for any time period, which remaining invoices will be coming to them or where the current spend is, in comparison to the total budget. They also need to know if the projections for cash requirement have increased or decreased.

On the sponsor side of the process, the sponsor must account for all the money that is spent by all of the suppliers, their subcontractors, and anyone else who is spending money on the clinical trial. The sponsor is responsible to take receipt of, track and manage, and pay appropriate invoices from the right suppliers, for work done in the clinical trial. This process is the source of numerous, expensive errors. Bills and invoices from suppliers may represent duplicates, erroneous charges, and other mistakes that neither the supplier, nor the sponsor may discover. These errors make clinical trials costly and result in higher costs for patients and their families, many of whom cannot afford new medical products.

As a result of the inability to accurately manage invoice payments, pharmaceutical companies often make millions of dollars of erroneous payments each year. Furthermore, without appropriate payments for products and services, valuable vendors might not receive payment for products and services and may no longer be in business to serve the clinical research needs of the life sciences industry. Without appropriate payments, the cost of drug development will continue to rise, making it difficult for people to afford important medications. In addition, the proper accounting of money that is spent on a particular project will provide warning signals that a clinical trial no longer is compliant with the plan for the trial.

Although the biotechnology company and the suppliers may carefully document the activities and the costs associated with the activities, it is difficult and time consuming to decide if an invoice is appropriate for payment. In truth, payment should not be made until it is verified that related deliverables are appropriate for the trial. It is not easy for financial staff to determine appropriateness, because of their lack of clinical knowledge and expertise. Likewise, it is not easy for clinical staff to determine appropriateness because of their lack of financial information about the costs and timing associated with the many different contracts. Since there are multiple suppliers that will deliver services for a clinical trial, and all have different contracts, confusion and payment errors can quickly become expensive if there is no integrated process and/or the integration of appropriate information.

In order to try to reduce the confusion and errors, some biotechnology companies have implemented clinical trial management systems. However, the clinical trial management systems have not been successful in reducing erroneous payments because these systems lack an integrated combination of business rules, formulas and timing knowledge to flag potentially erroneous payments. These clinical trial management systems also lack the near real-time visibility regarding the work and deliverables that have actually been completed. These systems contain only what has been data-entered into the system, making it still necessary to find the data. In addition, these clinical trial management systems do not tie into the objectives of the sponsor to track that the monies spent and activities done actually resulted in the right deliverables.

BRIEF SUMMARY OF THE INVENTION

A clinical trial study is modeled for automatically generating business intelligence information regarding the clinical trial study. The clinical trial study has a total budget amount and a total amount of deliverables. A software application program is provided that has equations and business rules that together define a process, a timeline, and deliverables associated with the clinical trial study. The program is populated with items including entities that have been contracted to provide the deliverables to the clinical trial study, budget items and amounts related to the deliverables for the respective entities that have been contracted to provide the deliverables, and for at least some of the budget items, a time frame in which the budget item is expected to be incurred or paid. Business intelligence information is then automatically generated using the equations and business rules in the program, and the items entered into the program. The business intelligence information includes appropriate invoice payments for the deliverables for the respective entities that have been contracted to provide the deliverables at a specific time frame, an accounting for the clinical trial study, and cash flow needs for the clinical trial study.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings:

FIGS. 1A-1F show a blank Contracted-Budget Summary in accordance with one preferred embodiment of the present invention.

FIGS. 2A-2F shows budget summary formulas in accordance with one preferred embodiment of the present invention.

FIGS. 3A-3F show an actual budget summary for an actual clinical trial project, in accordance with one preferred embodiment of the present invention.

FIGS. 3G-3J show the detail of the individual specifications and assumptions in accordance with one preferred embodiment of the present invention.

FIG. 3K is the payment schedule in accordance with one preferred embodiment of the present invention.

FIG. 3L show CRO assumptions in accordance with one preferred embodiment of the present invention.

FIGS. 3M-3P shows CRO fee and payment schedules in accordance with one preferred embodiment of the present invention.

FIG. 3Q shows lab specifications in accordance with one preferred embodiment of the present invention.

FIG. 3R shows investigator fees in accordance with one preferred embodiment of the present invention.

FIG. 3S shows change orders in accordance with one preferred embodiment of the present invention.

FIGS. 3T-3V show tracking of budget changes in accordance with one preferred embodiment of the present invention.

FIGS. 4A-4H show where each budget item, cost, and the specific rules are entered into a spreadsheet so that it can be seen in a Project Budget Summary.

FIGS. 5A-5D show visit schedules in accordance with one preferred embodiment of the present invention.

FIGS. 6A-6G show patient information in accordance with one preferred embodiment of the present invention.

FIGS. 7A-7E show invoice-related documents in accordance with one preferred embodiment of the present invention.

FIGS. 8A-8P show where each invoice item is entered into the Project Budget and also show how each invoice item is processed in accordance with one preferred embodiment of the present invention.

FIGS. 9A-9N show an accounting of a clinical trial study in accordance with one preferred embodiment of the present invention.

FIGS. 10A-10F show how the values in "work-in-process reports" are calculated using the equations and formulas and the business rules of a "work-in-process report" for specific time frames, in accordance with one preferred embodiment of the present invention.

FIGS. 12A-12B show a portion of the portal database that contains patient status data and patient diagnostic data that are automatically checked as part of the business rules, in accordance with one preferred embodiment of the present invention.

FIGS. 18A-18AN show all of the formulas and business rules in accordance with one preferred embodiment of the present invention.

DETAILED DESCRIPTION OF THE INVENTION

Figure 11:
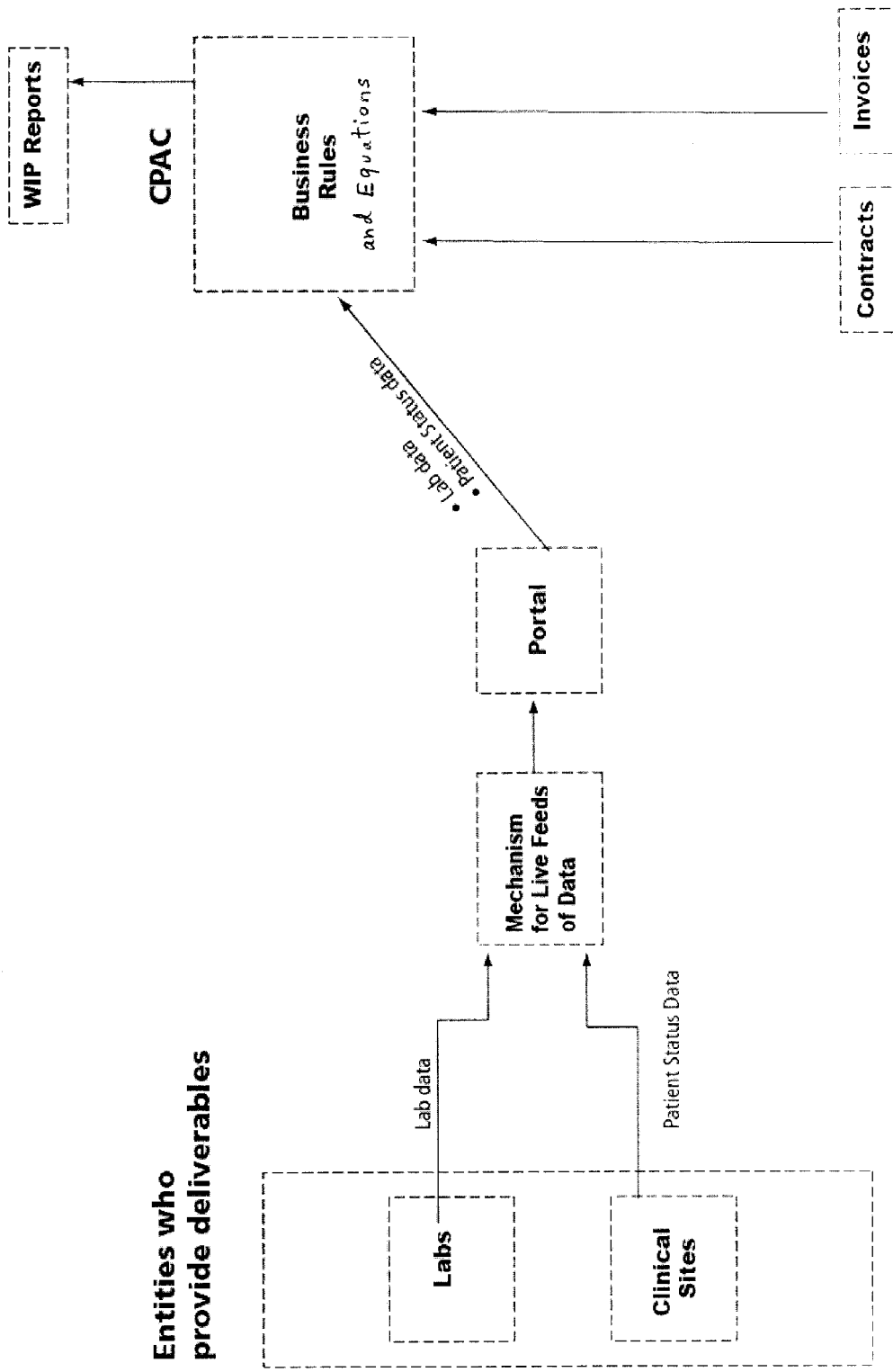
FIG. 11 is a flow diagram that depicts how patient status data and patient diagnostic data is automatically inputted from the entities that have been contracted to provide the deliverables to the clinical trial study, in accordance with one preferred embodiment of the present invention.

For the purposes of explaining the present invention, specific embodiments will be described. These embodiments are exemplary only, and are not intended to limit the scope of the invention.

I. Overview

Preferred embodiments of the present invention overcome the drawbacks of the prior art through a computer-implemented method of calculating appropriate invoice payments to vendors/suppliers who are providing products and services associated with a clinical trial study. In one embodiment, a person who is tasked with calculating appropriate invoice payments is provided with a software application program that has equations, business rules, and formulas that together define, track, calculate and report the process, timeline, and deliverables associated with one or more clinical trial studies. In one embodiment, a person will know when invoice payments are due, what payments are due, and which deliverables and activities/budget items would be part of the payments. This important information protects the original estimates of the clinical trial budget, ensures that overpayments are not being made, reports 'work in process' and expenditures, and allows for one to anticipate the payments due during a particular time period. Preferred embodiments accept the information, process it through a series of steps, and produce reports that make the invoice analysis and payment verification simple and accurate. Various reports can be produced from information, as described below. In one embodiment, invoices, payments, or work-in-process expenses are organized, analyzed, and verified using algorithms that take into account the complexity of clinical trials and the therapeutic area (e.g., cardiology, neurology). Furthermore, the information can be verified against the actual deliverables provided by the vendors, without the need for phone calls, on-site verification, or other costly and less accurate methods of checking/verification.

Preferred embodiments provides a life science company with reports on the accuracy, or inaccuracy of the vendors' financial accounting and reporting for a clinical trial. Life science companies can be armed with financial metrics that help them make good choices. Equations and business rules work together to define a process, a timeline, and deliverables associated with a clinical trial study.

In one preferred embodiment, one or more clinical trial vendors who have been contracted to provide deliverables to the clinical trial are inputted into a computer system, along with budget items, payment terms and amounts related to the deliverables, and a timeframe in which the budget item is expected to be incurred or paid. The budget items may include monitoring activities, biostatistical activities, and the like, that are being conducted during clinical trials. The prices and costs associated with these activities are included. Invoices can be tracked and managed in dollars, pounds, euros, or any other currency.

In one preferred embodiment, reports are produced that compare and reference budget items and their associated costs. Budget items are standardized from libraries of benchmark information, as described in U.S. patent application Ser. No. 12/121,822 filed on May 16, 2008, now U.S. Published Patent Application No. 2008/0288285 (Mancini et al.), which is incorporated herein by reference. The reports may include a series of financial and operational accounting showing the portion of the budget used, and projecting costs on a time basis, and other reports. Reports may also be provided that show where discrepancies exist within any invoice submitted for payment. A portal that links in live feeds of clinical trial information, such as one described in U.S. Published Patent Application No. 2007/0067189 (Boris et al.), which is incorporated by reference herein, will actually calculate and verify without the need to check deliverables completed with the clinical team or a vendor. (The portal is referred to as a "reportal" in U.S. Published Patent Application No. 2007/0067189. A portal is a site designed to act as an entryway to the World Wide Web.) In fact, this type of report may eliminate the need for any invoice to be sent by a vendor, in order for the appropriate payments to be made to vendors.

Figure 13:
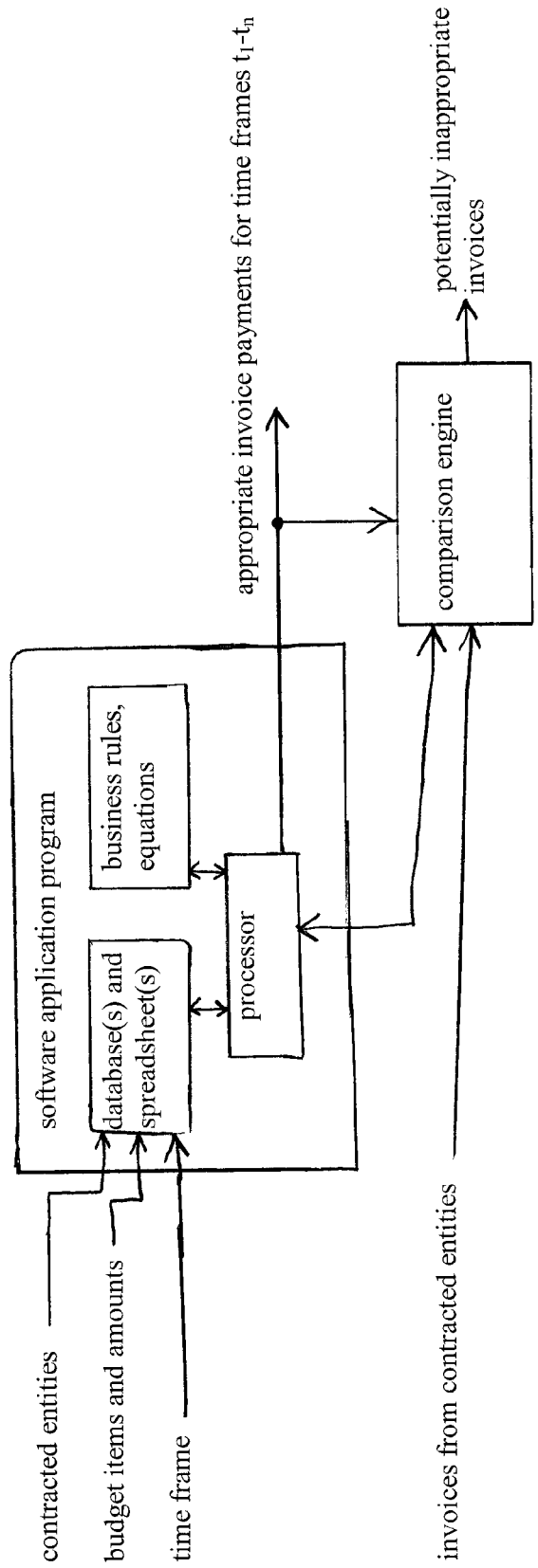
FIGS. 13-17 show schematic block diagrams of apparatus for implementing preferred embodiments of the present invention.

FIG. 13 shows an apparatus for calculating appropriate invoice payments associated with a clinical trial study. Broadly stated, the apparatus of FIG. 13 operates as follows:

1. A software application program is provided that has equations and business rules that together define a process, a timeline, and deliverables associated with a clinical trial study. Some of the equations relate to revenue/cost relationships and the timing thereof, and some of the equations relate to cash inflows and outflows and the timing thereof. The clinical trial study has a plurality of phases, and at least some of the business rules relate to the trial study phases.

2. The following items are entered into the program:
   a. entities that have been contracted to provide the deliverables to the clinical trial study,
   b. budget items and amounts related to the deliverables for the respective entities that have been contracted to provide the deliverables, and
   c. for at least some of the budget items, a time frame in which the budget items are expected to be incurred or paid.

These items are obtained from contracts entered into by the entities contracted to provide the deliverables.

3. Appropriate invoice payments for the deliverables for the respective entities that have been contracted to provide the deliverables at a specific time frame are automatically calculated using the equations and business rules in the program, and the items entered into the program.

One useful purpose of knowing what are the appropriate invoice payments during the course of a study is that reserves may be set aside for the payments without any uncertainly as to whether the reserves are too low or too high.

Optionally, invoices received from the entities at a specific time frame may be compared with the appropriate invoice payments to identify any invoices that may not be appropriate.

Figure 14:
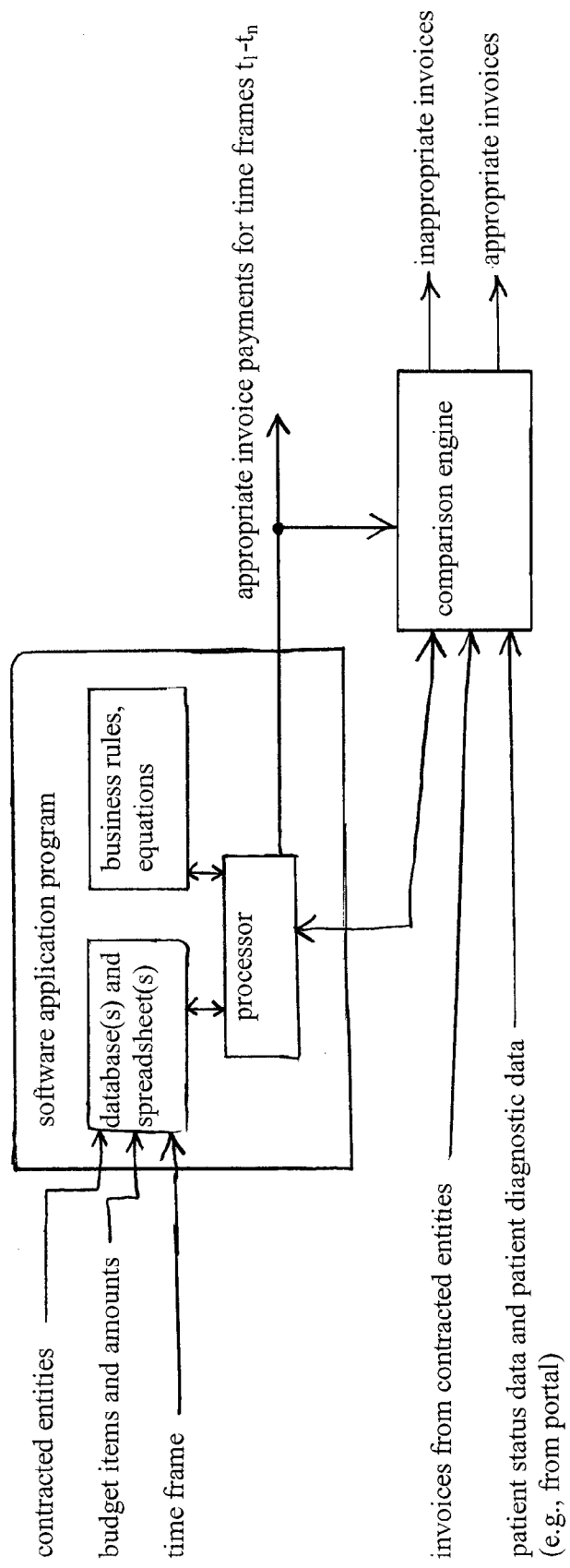

FIG. 14 shows an apparatus for analyzing invoices for a clinical trial study to identify whether invoices are appropriate or not appropriate at a particular time frame in the study. Broadly stated, the apparatus of FIG. 14 operates as follows:

1. A software application program is provided that has equations and business rules that together define a process, a timeline, and deliverables associated with a clinical trial study.

2. The following items are entered into the program:
   a. entities that have been contracted to provide the deliverables to the clinical trial study,
   b. budget items and amounts related to the deliverables for the respective entities that have been contracted to provide the deliverables,
   c. for at least some of the budget items, a time frame in which the budget items are expected to be incurred or paid, and
   d. invoices from the entities that have been contracted to provide the deliverables to the clinical trial study, the invoices including budget items, amounts and a time frame.

3. Patient status data and patient diagnostic data obtained from the entities that have been contracted to provide the deliverables to the clinical trial study are automatically inputted into a comparison engine.

4. The comparison engine automatically identifies invoices that are appropriate and not appropriate at a particular time frame in the study in view of the equations and business rules in the program, the items entered into the program, and the inputted patient status data and patient diagnostic data. Inappropriate invoices, such as those that violate a business rule, preferably cause an "Alert" which would trigger a manual scrutiny of the invoice and additional investigation before the invoice payment is authorized.

When reviewing invoices, the FIG. 14 apparatus provides additional checking capabilities because the invoices are not only being reviewed to determine if they are potentially appropriate in view of the expected deliverables at certain time frames, but actual patient status and diagnostic data provides additional checking capabilities. For example, an invoice might be appropriate at a particular time frame, but the patient status and diagnostic data reveals that the deliverables likely did not occur, and thus the invoice should not be paid.

Figure 15:
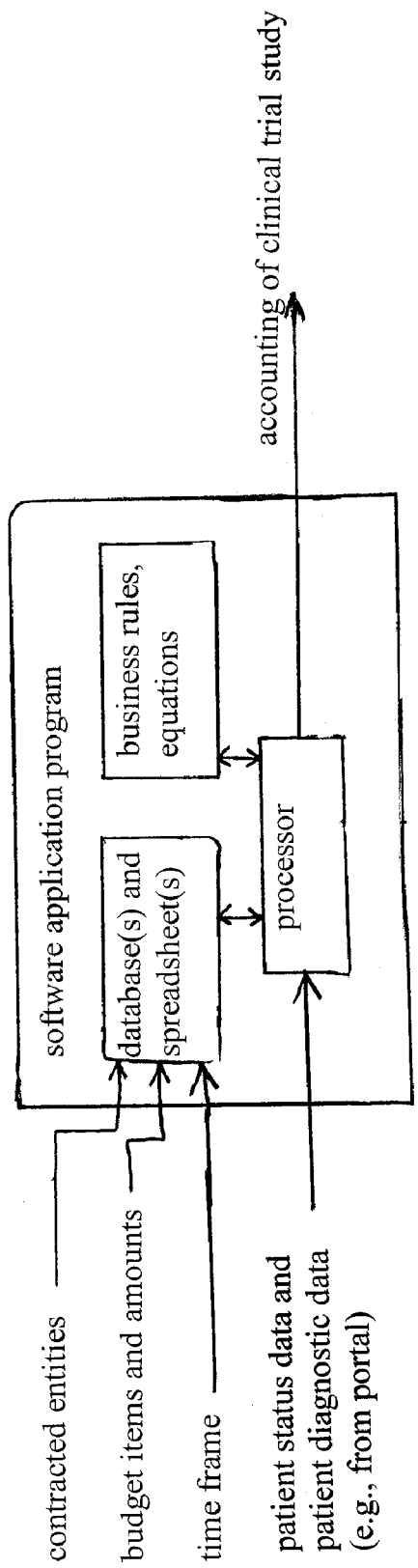

FIG. 15 discloses an apparatus for automatically generating an accounting for a clinical trial study, wherein the clinical trial study has a total budget amount and a total amount of deliverables. Broadly stated, the apparatus of FIG. 15 operates as follows:

1. A software application program is provided that has equations and business rules that together define a process, a timeline, and deliverables associated with a clinical trial study.

2. The following items are entered into the program:
   a. entities that have been contracted to provide the deliverables to the clinical trial study,
   b. budget items and amounts related to the deliverables for the respective entities that have been contracted to provide the deliverables,
   c. for at least some of the budget items, a time frame in which the budget items are expected to be incurred or paid.

3. Patient status data and patient diagnostic data obtained from the entities that have been contracted to provide the deliverables to the clinical trial study are automatically inputted into a processor.

4. The processor automatically generates an accounting of the clinical trial study using the equations and business rules in the program, the items entered into the program, and the inputted patient status data and patient diagnostic data. The accounting is based on a percentage of the deliverables completed and also provides a percentage of the deliverables that are completed. The accounting provides expenses to record for accounting purposes under generally acceptable (accepted) accounting principles.

Figure 16:
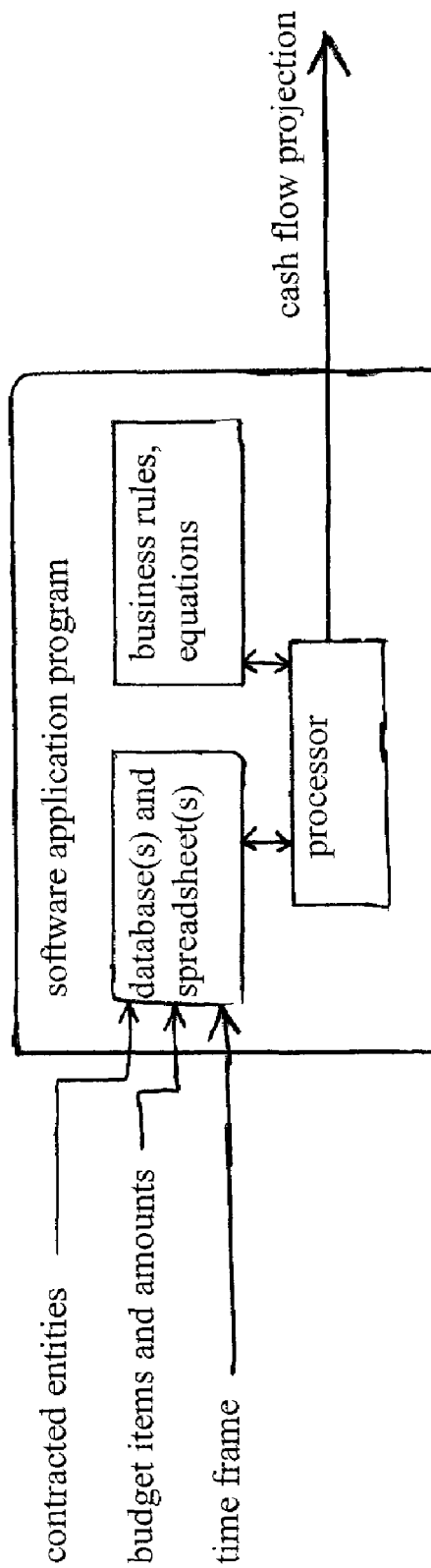

FIG. 16 discloses an apparatus for automatically generating a projection of cash flow needs for a clinical trial study, wherein the clinical trial study has a total budget amount and a total amount of deliverables. Broadly stated, the apparatus of FIG. 16 operates as follows:

1. A software application program is provided that has equations and business rules that together define a process, a timeline, and deliverables associated with a clinical trial study.

2. The following items are entered into the program:
   a. entities that have been contracted to provide the deliverables to the clinical trial study,
   b. budget items and amounts related to the deliverables for the respective entities that have been contracted to provide the deliverables,
   c. for at least some of the budget items, a time frame in which the budget items are expected to be incurred or paid.

4. A projection of cash flow needs of the clinical trial study is automatically generated using the equations and business rules in the program, and the items entered into the program.

Information such as appropriate and inappropriate invoice payments, an accounting for the clinical trial study, and cash flow needs for the clinical trial study can broadly be characterized as business intelligence information. Upon loading the software application program with the items discussed above, the clinical trial study is effectively "modeled." From the model, the various types of business intelligence information can be extracted as needed.

The entities referred to herein include service providers, vendors, subcontractors, and suppliers. The "time frame" referred to herein includes a specific date, or a time window. "Diagnostic data" includes items such as lab data and EKGs/ECGs.

Any conventional database or spreadsheet program may be used in the software application program shown in FIGS. 13-16. Likewise, the processor and comparison engine shown in FIGS. 13-16 may be part of one or multiple general-purpose computers, such as personal computers (PC) that run a Microsoft Windows® or UNIX® operating system. Furthermore, although the disclosed embodiments manage data using spreadsheets, the scope of the present invention includes embodiments that use other forms of software that can perform the equivalent function of managing data via spreadsheets.

II. Detailed Disclosure

The present invention is described in the context of a commercial service offered by Numoda Corporation, Philadelphia, Pa. In the disclosed embodiments, Numoda is a general contractor for a clinical trial study, and thus acts as both a managing entity and a contracted entity (service provider) for the study. However, the scope of the present invention is not limited to this particular implementation of the invention. For example, a pharmaceutical company could directly host and manage the software programs for its own studies.

Figure 1D:
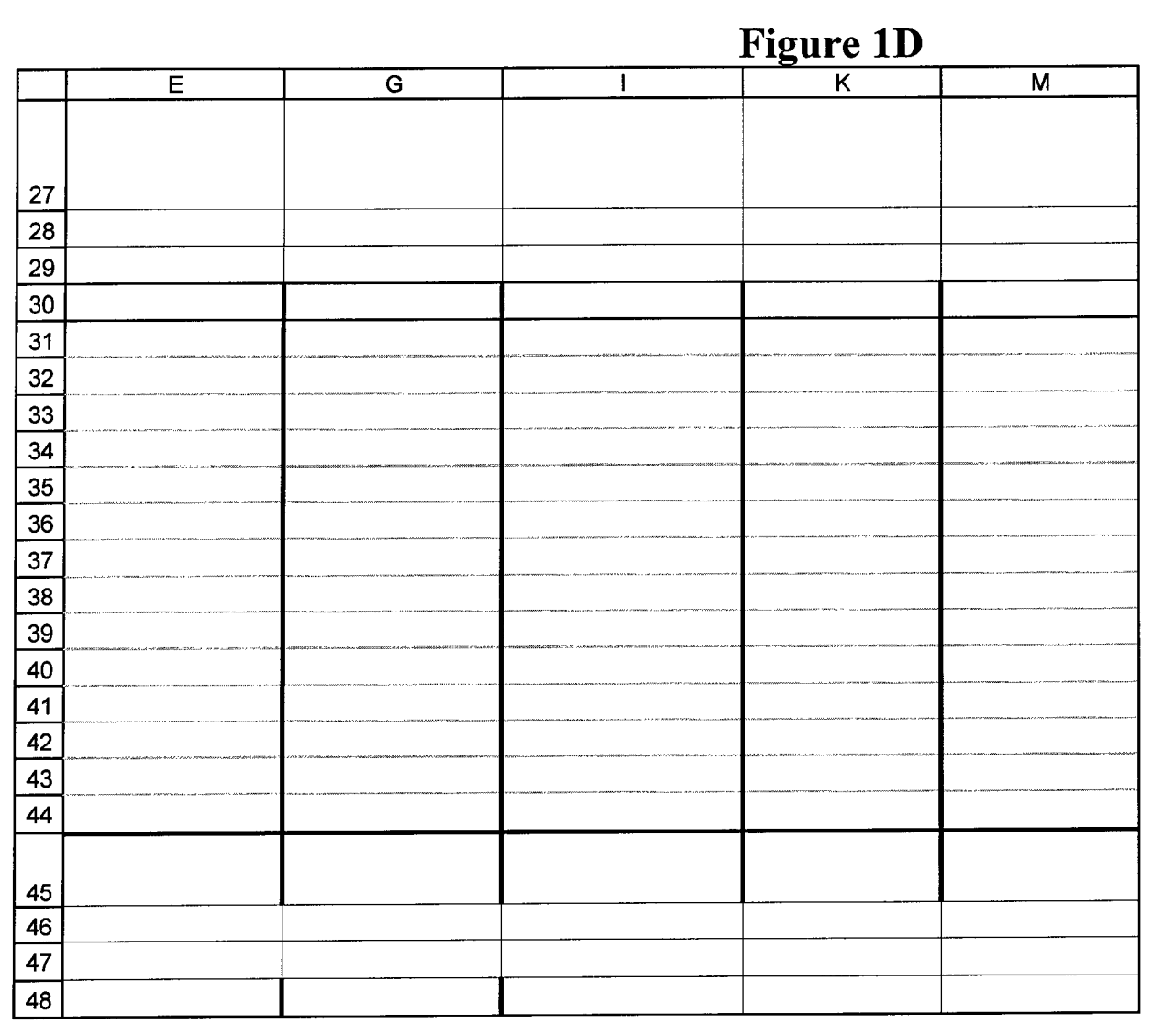

FIGS. 1A-1F show a blank Contracted-Budget Summary. This summary represents the totals across all entities and includes change orders obtained from contracts entered into by the entities contracted to provide the deliverables. Change orders are the updates of costs and budget items that might occur within a project. These change orders can occur at any time and are related to additions or subtractions in the scope of project deliverables and assumptions. Column B shows the list of products and services that are budget items related to the deliverables for a particular clinical trial. There are no limits to the number of clinical trials that can be managed by the system. The system can also be used with clinical programs, which consist of multiple clinical trials combined in a grouping. FIG. 1A, column B, rows 3, 8, 17 and FIG. 1B, column B, row 30 show the classification of types of budget items. Column B uses standard classifications and budget items, similar to the standard classifications discussed in U.S. Published Patent Application No. 2008/028825. The use of standards is not necessary, but may increase the value of the process when used across many trials and clinical programs. There are many products and services provided for clinical trials that are actually standard across the industry, and there is a benefit to using standard terminology.

FIG. 1A, column C shows the corresponding column with the contracted amounts for each of the budget items in each row that are the total across all of the rest of the columns. Column C, rows 15 and row 25 show the subtotal for the budget items in the rows above, in the same column, and row 27 shows a total.

FIG. 1B, column C, rows 45 and 48 show contracted amounts for other budget items and for the total project, respectively. FIGS. 1A and 1B show subtotals of groupings of budget items that are well understood in the industry. These subtotals are on rows 15 and 25 on FIG. 1A and row 45 on FIG. 1B. The grand total is on row 48 of FIG. 1B. FIG. 1C, row 1 is the product and services activities, and row 2, columns E, G, I and K and M show the several different suppliers/entities that will be providing products and services for the clinical trial. FIG. 1C, rows 3-26 shows the place where the costs are entered for the budget items. There is no limit to the number or type of suppliers that can be entered. The lists of groups continue from FIG. 1E, row 1, column O. FIG. 1F, column Q rows 27-48 shows the place where costs are displayed for the budget items. FIG. 1E, column Q, rows 1 and 2 shows the General Contractor value. FIG. 1E, column Q, rows 3-26 shows the total of all entities for budget items. FIG. 1F, column Q, rows 27-48 shows more totals.

Groups are part of the business rules contained in the process. These business rules protect the clinical trial budget by including all necessary groups of products and services that will be required for a successful trial. There is no limitation to the groups, and it is possible to include varying business rules that relate to different types of studies that require different types of services. For example, other diagnostics products and services group can be added. FIG. 1C, row 2, and FIG. 1E, row 2 represent the names of the suppliers/entities that are responsible for the group of products and services. All other rows on FIGS. 1C, 1D, and 1E in column E, G, I, K, M, and O represent costs for individual budget items related to products and services provided by each contract entity. On FIG. 1E, column Q shows the total value.

FIGS. 2A-2F show the summary of the budget in a "formula" view that reveals some of the underlying equations and business rules. These figures also show the link to the formulas related to formulas and equations for change orders associated with the project. There are many business rules related to the timing of the products and services used for a clinical trial project. For example, each clinical trial protocol will detail the clinical rules for the study. Business rules are extrapolated from these protocols. There are rules about the timeline for a study (e.g., how long screening of patients is estimated, treatment time period, closeout). There are rules about the costs associated with a clinical study site performing study protocol procedures for patients. There is no limitation to the amount of rules or the types of rules that can be used.

FIG. 2A, column B shows the budget items, and column C shows the formulas for the cost of the work of managing all of the entities and their payables. Also shown here are the formulas for the integrations, the portal and the ongoing consolidation and reconciliation and entity management that allow for the work shown in rows 3-7, 9-14, and 18-24. FIG. 2B, column C shows the formulas for the cost of the work of managing all of the entities and their payables shown in rows 30-48. FIG. 2C, columns E, G, I, K and M, row 1 shows the groups of activities, and row 2 shows the name of the entities. In the same columns, row 15 and 25 shows the formulas and all other rows show the link to the change order formulas. FIG. 2D, column E, G, I, K and M, rows 27, 45 and 48 show the formulas and all other rows show the links to the change order rules, equations and formulas. There is no limit to the number or type of formulas that can be used. The format shown here can be maintained in any database format. FIG. 2E. column O represents another entity, and column Q shows the formulas for the totals across all columns on FIG. 2A-2E and includes any costs related to change orders. FIG. 2F shows the additional rows for column O and the formulas for the additional rows in column Q, and the link to the formulas, business rules and equations for the change orders. FIG. 2 in its entirety, shows the actual budget at any given point in time, including any or all change orders.

FIGS. 3A-3F show an actual budget summary for an actual clinical trial project that includes the budget items and costs, after all contract information has been entered. Change orders have not been included in these figures. These figures also show a set of contracts from the entities that will be detailed for an actual study. Three entities will be further discussed in this example. One of the entities included in these figures is a diagnostics provider for the trial (in this case, a vendor that provides laboratory analysis). Another entity is a clinical services provider (in this case, a Contract Research Organization, often referred to as a CRO.) FIG. 3A, column B, rows 3-26 and FIG. 3B, column B, rows 27-48 show budget items for Entity #1. Column C in FIGS. 3A and 3B shows the corresponding costs for Entity #1, in the same rows.

FIG. 3C, columns E, G, I, K and M, rows 3-26, FIG. 3D, column E, G, I, K and M, rows 27-48 shows the costs for each of the entities. FIG. 3C, column I, rows 3-26, and FIG. 3D, column I, rows 27-48 represent the costs for the CRO (Entity #4) that will be highlighted later. FIG. 3C, column M, rows 3-26, and FIG. 3D, column M, rows 27-48 represent the costs for the lab provider (Entity #6) that will be highlighted later.

FIG. 3E, column O, rows 3-26, and FIG. 3F, column O, rows 27-48 show the costs for another entity. FIG. 3E, column Q, rows 3-26 and FIG. 3F, column Q, rows 27-48 show the total costs for all entities for each budget item for the original contract, excluding any change order budget items and costs.

FIGS. 3G-3J, column A, all rows, show the detail of the individual specifications and assumptions that were used to decide the necessary budget items for the job, and column B shows the corresponding units. The assumptions in column A come directly from the contract with the sponsor, which contains the entire budget items, units, and costs for all the entities. This is used to determine the business rules for this project.

FIGS. 3H-3J, column A show more detail, and FIGS. 3H-3J, column B show more units. For each contract, the budget items, assumptions, and units identifies items that are then entered.

FIG. 3K is the payment schedule, which will set the rule for the timing of invoices and appropriate payments. This information sets the time frame in which the budget item is expected to be incurred or paid. Also included are the budget items, specifications, units, and costs related to the deliverables for the respective entities who have been contracted to provide the deliverables, and for at least some of the budget items. Also included for each contract, is any other relevant information.

FIG. 3L shows the specifications for Entity #4 (the CRO) and FIGS. 3M-3P show the budget and units for entity # 4 (the CRO), which will establish the rules for the payments to this entity and which will be entered and seen in the budget summary shown in FIGS. 3C and 3D, column I. FIG. 3Q shows the specifications for Entity #6 (the Lab) and shows the unit price for Entity #6 (the Lab), which will establish the rules for the payments to this entity. The total budget will be calculated based on the rules. The summary for this entity is seen in FIGS. 3C and 3D, column M. FIG. 3R shows more specific details of the budget item for the investigator fees/grants as seen in FIG. 3N from the Entity #4 contract. This budget item "Investigator Fees" is reflected in the budget summary shown in FIG. 3D, column I, row 35. This budget item is a significant item in a budget because these funds are used to pay doctors who will enroll patients into the study. Timely and appropriate payments for the investigators can often mean improved results in the enrollment of the trial. Likewise, the ability to see the costs and the payments made to investigators will provide 'intelligence' on whether the doctors are enrolling the right patients, based on the rules.

FIG. 3S shows an example change order for the project that has occurred for this example because medical monitoring was added as a new service to be performed by Entity #4. FIG. 3T, column I, row 13 shows the change in the budget cost for the Entity #4 with the addition of the new services. FIG. 3U, column Q, row 13 shows the change in the total budget for the item. FIG. 3V, column Q, row 48 shows the change in the total budget overall.

The following figures explain how each budget item is processed so that it can be entered into the Project Budget (e.g., units conversion, time frame conversion).

FIGS. 4A-4H show where each budget item, cost, and the specific rules are entered so that it can be seen in the Project Budget Summary.

FIG. 4A, column B, row 3 shows the name of Entity #4, the CRO. Rows 4-13 are the detailed budget items that represent work that will be completed by the entity during study set up. These items come from budget items discussed in U.S. Published Application No. 2008/0288285.

FIG. 4A, column C, row 5 shows the number of investigators for the project that was taken from FIG. 3L, column B, row 4 specifications showing the number of sites. This is an example of the business rules. The business rule is that each site represents a single investigator selection. Therefore, the units are filled in with the number "12." Some of the budget items, unit costs in FIG. 4A, column D, and the original contract cost in column E will be pre-populated in the case where the business analysis process disclosed in U.S. Published Application No. 2008/0288285 (also, referred to below as "the business analysis tool") is used. In these cases, the entity can save tremendous time in proposal writing and is simply given the number of units and the budget in which to work.

In some cases, the budget items, units and costs are calculated based on the timeline. For example, in FIG. 4A, column C, row 24, the budget item "Interim Monitoring Visits" number of units is calculated based on the enrollment and treatment period according to the frequency detailed in the specifications and assumptions. The unit price in FIG. 4A, column D is provided from the business analysis tool. Any budget items, units or unit prices that do not explicitly appear in the contracts from the contracting entities, but which are known to be part of the clinical trial study, are entered in columns A-C of FIGS. 4A-4D so that all costs are accounted for. In some instances, the budget item and unit price already exists, and only the units need to be added. FIG. 4B, column B, row 59 is an example of a budget item entered for Entity #6. FIG. 4B, column C, row 61 shows an example of a combination of how to calculate the total of the patients according to the business rules for the protocol for the clinical trial. In this example, when the assumptions for number of months and the frequency for monitoring visits are provided by the business analysis tool, the process described herein will calculate the number of units, so that it is not necessary to enter the units. Number of units are automatically pre-populated. FIGS. 4C and 4D, column B shows more budget items and columns C and D show the units and unit costs.

FIG. 4C, column B, row 122 shows the investigator meeting budget item and FIG. 4D, column B, row 124 shows the investigator payments (grants). Across the same rows in columns C and D are the units and the unit costs. FIG. 4D, column B, rows 137-142 show the budget items for Entity #6. Columns C and D in the same row show the units and the unit costs. FIGS. 4A-4D, column E, show the original contracted total for each of the budget items. The total of the costs of the budget items for each entity is seen on FIG. 4D, rows 160-164.

FIGS. 4A-4D, columns G, H and I show the place for entry and calculation of the units, unit price, and total for change order #1 (CO#1). In the same figures, columns K, L, and M show the place of entry and calculation for change order #2 (CO#2). There is no limit to the number of change orders or the addition of budget items. FIGS. 4E-4H, column AY shows the total number of units that are calculated for each of the budget items for all of the change orders and the original contract. In the same figures, column AZ shows how to calculate the total of the original contract and the change orders costs for each budget item together. FIGS. 4E-4H, column AZ is linked to the budget summary shown in FIGS. 3A-3F, columns C, E, G, I, K, M and O, lines 3-14, 17-24 and 30-34. It is very important to track and calculate the additional costs of the change orders, as well as to track the changes in units and unit costs of each budget item for each of the entities. Most clinical trials have changes during the trial, and change orders are often difficult to track manually. Conventional industry practice is to simply record that a change order exists and that it has affected the total budget, rather than track and verify that each unit was provided and is appropriate to pay.

FIG. 5A shows how business rules are set for the investigator according to contracts with each of the investigators, an example of which is seen in FIG. 3R. FIG. 5A, column B is the visit schedule according to the business rules set by the protocol of the trial. Column C shows the costs per visit according to the contract with one investigator.

FIG. 6A, column A shows the patient number that will come into this data entry location from the portal. FIG. 6A, column B shows the patient initials. FIG. 6A, column C contains the business rules for the calculation. For example the R in column C, row 5 means that the patient was randomized and so all of the visits are allowed to be paid. In column C, row 6 the D means that the patient was discontinued, and FIG. 6A, column E, row 6 shows the discontinued date. The rule will calculate only the visits during the certain time period until the discontinued date will be appropriate to pay. FIG. 6A, column F shows the drug dispensed Y=yes. If in column F there is a letter N (N=NO) and in column C there is a letter AS (AS=Active screened), this signifies that no further visits costs are to be expected or should be paid for this patient. FIG. 6A, column G, row 4 shows an example of a type of visit following the business rules of the protocol. Column G, row 6 shows the date that visit type occurred.

FIG. 6B, column N, rows 2 and 3 show the status of the completion of certain forms filled out by the investigator. This information is used if the contract with the investigator is based on status of a certain number of forms. Column N, row 4 shows the completed status. Column O, row 4 shows the locked status. These statuses are also used as the business rule to track the status of the work of the clinical monitors in the study and will calculate the appropriate payment for the monitor for the study. The information in these columns and the adjacent columns P and Q comes from the portal.

FIG. 6C, column S, row 5 shows the results of the formula for the date rules for when the investigators are allowed to begin their work. FIG. 6C, column T, row 5 shows the date that will drive how many visits should be paid or rejected as inappropriate at that point in time. This date can be entered as a future date, once the schedule of visits is made so that the cash flow needs will be calculated and reported. Investigator payments will not be allowed to be made outside these date rules. FIG. 6C, column U, row 5 shows either a 0 or a 1 based on the timeline rules set on column S and T. This calculates the right amount to be paid to each investigator at any point in time for any patients, or in total, because FIG. 6A, column A shows the rules for which patient is associated with each investigator. For example, in FIG. 6A, column A, row 5 shows a patient number 10001 with the first two digits signifying the investigator, here, investigator "10." FIG. 6E, column AU, row 5 shows the total of visits for that patient. Other patients in FIG. 6A match respective patients in FIG. 6E having the same row. This is matched against the portal and will allow for cross checking.

FIG. 6D, column U, row 122 is the total for a particular visit type for all patients and all doctors, which is crosschecked against the portal totals and will show an error if not matching.

Now that the rules are in place for the payments to investigators according to the patients that the investigators will treat during the trial, return back to FIG. 5A, column D. This reflects the total of the actual cost and percentage of the work completed at a particular time point, based on the business rules. FIG. 5A, column C, row 8 shows the entry point for any advance payment. Sometimes, the investigator contracts require payment in advance, in which case the system will calculate and subtract from the total to be paid when all the patients are enrolled by the investigator. FIG. 5A, column D, row 13 shows the total projected costs based on the protocol business rules and the contract business rules for this type of visit (visit 1). Row 36 shows the total for the patients with the status 'completed'. In the case where there is a special rule in an investigator contract to pay the investigator for a screen failure patient, row 39 columns C and D will calculate the total to be paid.

FIG. 5A, column H, row 4 will show the actual total number of visit 01 types of visits from the portal. This row shows the link to the business rules, which are directly linked to the portal. Column H, row 13 shows the total cost for visit 01 types based on the individual contracts with the investigators.

Row 39 shows any additional cost to be paid per special contract arrangements and row 41 shows the total for that column.

FIG. 5D, column AV row 41 shows the total costs for all visit types and other costs for work for patients that have completed the study. This example is shown for investigators who are paid under the business rule that they are to be paid by completed patients. Row 43 shows the advance payment that is subtracted for accuracy of total payments to investigators. Row 45 shows the total with the advance payment subtracted. This same type of function is used to track and calculate payments for monitoring visits. These formulas and costs are used for reconciliation purposes against the total budget. For example, the advance payment to the investigators is only reconciled at the end of the study.

FIGS. 3A-F show the completed Project Budget after all contracts have been entered. Tracking the actual invoice and costs for the Entity #4 are explained by the following figures.

FIGS. 7A and 7B is an actual invoice from Entity #4 who has been contracted to provide the deliverables to the clinical trial study. The invoice includes budget items, amounts and a time frame. FIG. 7A is the cover page that comes with an invoice that shows the total cost amount for this invoice. In this example, the relevant information that appears on the invoices which get entered into the Project Budget is the cost for a specific budget item. (Budget items are also discussed in U.S. Publication No. 2008/0288285) The cost is $42,294.13. Often, this information is all the information that is sent to the sponsor, because the agreement with the entity could be based on milestones, invoicing as work is completed, or in another format. FIG. 7B reflects the invoice tracking format to make it easy when the cost is calculated, to see the budget item that was performed, and to see how the cost of this budget item is calculated against the total budget for Entity #4. FIG. 7E, column H, row 47 shows the total amount of this particular invoice, and FIGS. 7D and 7E, column H, rows 2-46 show the subtotal amounts for this particular invoice. This invoice reflects work completed several months ago that is only invoiced now. The invoice and the attached information in these figures provides data to manage accounts payable and current cash flow. However, it does not reflect the actual work done at this point in time, and will not give information about what bills to expect at a later point in time.

FIGS. 8A-8P show where each invoice item is entered into the Project Budget and also show how each invoice item is processed so that it can be entered into the Project Budget (e.g., units conversion, time frame conversion). These figures also include a snapshot of the budget after entry of the invoice.

Each detailed budget item is shown in column A of FIGS. 8A-8D. FIG. 8A, column A, rows 10-57 are the budget items in detail for Entity #4. FIG. 8B, column A, rows 73-103 shows each detailed budget item for Entity #6. FIGS. 8C and 8D, column A shows the detailed budget items for other entities. FIGS. 8A, 8B, 8C, and 8D, column B shows the number of units for each of the detailed budget items. FIGS. 8E, 8F, 8G, 8H, column C shows the unit price for each of the budget items. In the same figures, column D shows the cost associated with each of the budget items and a total for each section that relates to a portion of work that is to be done during a particular time period during the project. For example, in FIG. 8A, row 11-20 are items that are provided during the study set up and regulatory portion of the project, a portion of which occurs within the first few months of the project according to the business rules shown in figures discussed below.

FIGS. 8E-8P are used to verify the appropriateness of an invoice and to accept information from a portal that will confirm that budget items were delivered.

FIGS. 8E-8H shows where the spreadsheet will accept either the unit number on the invoice (column F), or the percent completed (column G), or the total (column H). If the spreadsheet receives the unit number or the percent completed, then it will calculate the other values. This process allows for the freedom to accept information in various formats and to utilize whatever information is most readily available.

FIGS. 8E-8H columns F, G, and H represent the total cost invoiced within a particular time period. The spreadsheet will accept the information from the invoice and will calculate the sum of the invoice for all the periods that are paid. FIGS. 8I-8L, columns J, K and L reflect the units, unit price, and total for the time period of month 01." FIG. 8I-8L, columns N, O and P reflect the units, unit price, and total for the time period of "month 02." FIG. 8M, column BR reflects the automatic reconciliation of the costs, unit, and total for each of the budget items. For example, the budget item for 'Kickoff Meeting' as seen in FIG. 8A, row 15, column B is zero because the number of units allowed for this budget item is zero. Thus, the spreadsheet displays that the cost is 'over' the budget. By doing this automatically, an alert is generated that there is a discrepancy in the invoice. Such discrepancies may also be used when the invoice amount exceeds budget items that are non-zero amounts (e.g., 12 units). If the invoiced amount of work exceeds the budget amount, the portal may be further examined to check and see exactly what work is showing as being actually completed. In some cases, calls should be made to other individuals or other departments about the completion of the work for this budget item. This process is vastly simplified by using the present system because an individual can work on the exceptions rather than call every individual to check every single budget item. The system compares invoices received from the entities at a specific time frame with the appropriate invoice payments and identifies any invoices that are not appropriate and that are appropriate, as calculated by the equations and business rules, as seen in FIG. 8M, column BR. This example has taken a representative sample invoice item, here, 'kick off meeting' and shows the equations and/or business rules that the invoice items are tested against.

FIGS. 18A-18AN show all of the formulas and business rules for one sample clinical trial study. These sets of figures reflect the work related to the entities, budget items, costs, timeframe, and change orders for the study.

The process described herein provides for an accurate, timely, "work in process" accounting. One reason that it is so difficult to account for the work in process and the related 'booked expenses' is because an invoice is often sent by a supplier or contracted entity many months after the expense has been incurred by the sponsor of the clinical development. The sponsor of clinical development is responsible to provide an accounting of all money spent within a certain time frame and to account for the actual expenses incurred during a specific time frame. This type of accounting has become very important since the recent accounting scandals and the new rules established under The Sarbanes-Oxley Act of 2002.

FIGS. 10A-10F show how the values in "work-in-process reports" are calculated using the equations and formulas and the business rules of a "work-in-process report" for specific time frames. These figures show every month, as well as the cumulative values. A specific supplier and a specific budget item will be explained. For example, FIGS. 10A-10F show the budget summary for this project, similar to what has been shown in other figures. However, in this part of the process, FIGS. 10A and 10B, column K displays the original budget cost with the additional cost of the change order calculated together. FIG. 10B, row 50 displays the total project budget that has been calculated and now includes all of the change orders. In this example, only one change order is included to make the example easy to visualize and to understand. There are usually many change orders, making it complicated and nearly impossible to manage using conventional tools.

FIG. 10A, column B, row 14 shows a budget item that contains several detailed budget items for Biostatistics and Medical Writing Activities that will be provided by entity #4, who has been contracted to provide the deliverables to the clinical trial study. The amounts related to the deliverables for the respective entity that has been contracted to provide the deliverables is seen in FIG. 10A in column K, row 14.

The appropriate invoice payments for the deliverables for the respective entities that have been contracted to provide the deliverables will also be automatically calculated for a specific time frame. The time frames in which the budget item is expected to be incurred or paid is shown on FIGS. 9C, 9E, 9G, 9I, 9K and 9M. The timeframe for the budget item can be seen in these figures as well. For example, FIG. 9C, column AP, row 2 shows that this column and the associated amount in column AQ relate to the timeframe for month 01. In the same figure, column AW relates to the timeframe for month 02. This is done using the business rules seen in FIGS. 9C-9N, which display the business rules for the completion of work expected within a particular time frame. FIG. 9C, columns AP and AQ, row 2 identify the projected work percentage to be completed for month 01 for the respective columns. FIG. 9C, column AP, row 4 reflects the business rule for the percentage of work expected to be completed for the integrations budget item (that can be seen in FIG. 9A column B row 4). FIGS. 9C and 9D column AQ in each row provides an accounting of expenses to record for accounting purposes under generally acceptable (accepted) accounting principles related to each budget item and the percentage completion. FIG. 9D, row 50, column AQ provides the total of expenses. This information reflects how expenses should be booked for accounting purposes, which is very different from simply recording the only invoice that has been obtained from supplier, during this time period shown in FIGS. 9C-9N.

The underlying equations relate to revenue/cost relationships and the timing thereof, as well as cash inflows and outflows and the timing thereof. The accounting is based on a percentage of the deliverables completed and the invention provides a percentage of the deliverables that are completed. FIG. 9C, column BA shows an accounting of the percentage of work completed that totals the percentage during each specific time frame to the current date. This is an automatically generated accounting of the clinical trial study using the equations and business rules in the program for all of the tracked items and for items related to the live feed of patient status data and patient diagnostic data.

FIG. 11 is a flow diagram that depicts how patient status data and patient diagnostic data is automatically inputted from the entities that have been contracted to provide the deliverables to the clinical trial study. The inputted patient status data and patient diagnostic data are used with one or more of the business rules as part of the automatic verification of invoices and to manage the work in process expenses.

Figure 12A:
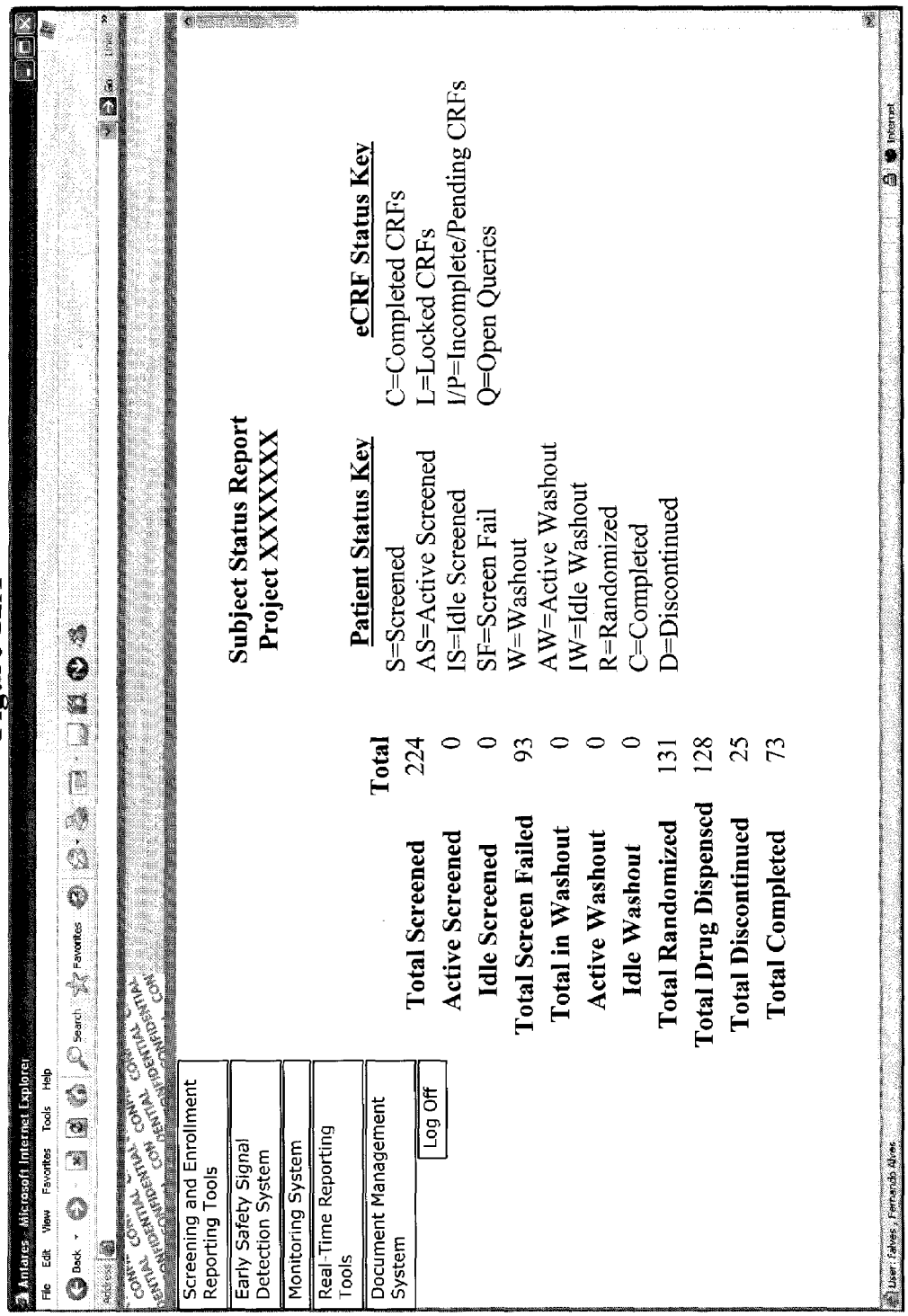

FIGS. 12A-12B show a portion of the portal database that contains patient status data and patient diagnostic data that are automatically checked as part of the business rules described above. This data is available in the portal as the result of a Screening/Enrollment process described in U.S. Published Application No. 2007/0067189, which makes this data readily available to be electronically fed into the system of the present invention, without the need for a person to data enter information. This is a huge advancement over conventional software approaches which typically require data entry and manual checking.

The process described above has many automated components. However, some of the steps in the process may occur manually. For example, some invoices will be manually reviewed against the vendor's contract to convert items into the appropriate units for entry into the software program. In other instances, the software program is programmed to accept the units as they appear on the invoice and convert them automatically into the units that the program needs to perform its calculations. The invoice processing procedures may range from partially automated to fully automated (with OCR capability).

Since the software application program has full knowledge of the status of the clinical trial study at any point in time from both an accounting standpoint and an expected invoice standpoint, the embodiments disclosed in FIGS. 13 and 15 can be combined to provide an apparatus for making automated payments to the contracted entities without even needing to receive or process invoices from the contracted entities.

Figure 17:
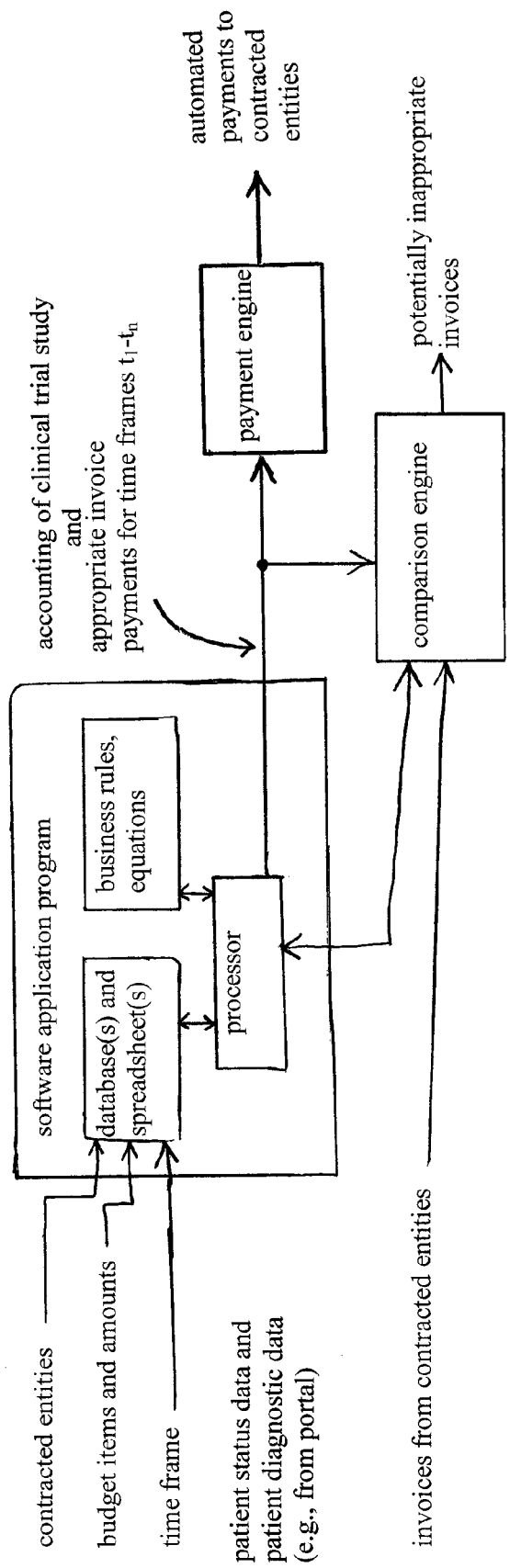

FIG. 17 shows such an embodiment. A payment engine is programmed to periodically make payments to the contracted entities, whether or not the contracted entities have submitted invoices. Incoming invoices may be either kept solely for reconciliation, if necessary, and thus not processed at all in most instances, or may be inputted and checked for potentially inappropriate charges. Alternatively, the allowed invoice amounts may be offset against the previously made or already authorized payments. The embodiment in FIG. 17 allows for a significant reduction in administrative overhead, particularly if the invoices are not processed and maintained only for reconciliation purposes. In an ideal scheme, contracted entities would be instructed to not even send in invoices. The disclosure provided in FIGS. 1-12 includes all of the necessary components to implement the automated payment feature shown in FIG. 17.

The present invention may be implemented with any combination of hardware and software. If implemented as a computer-implemented apparatus, the present invention is implemented using means for performing all of the steps and functions described above.

The present invention can be included in an article of manufacture (e.g., one or more computer program products) having, for instance, computer useable media. The media is encoded with, for instance, computer readable program code means for providing and facilitating the mechanisms of the present invention. The article of manufacture can be included as part of a computer system or sold separately.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention.

What is claimed is:

1. An automated method of calculating appropriate invoice payments associated with a clinical trial study, the method comprising:
   (a) providing a software application program having equations and business rules that together define (i) a process associated with the clinical trial study, (ii) a timeline associated with the clinical trial study, and (iii) deliverables associated with the clinical trial study;
(b) entering into the program:
  (i) entities that have been contracted to provide the deliverables to the clinical trial study,
  (ii) budget items and amounts related to the deliverables for the respective entities that have been contracted to provide the deliverables,
  (iii) for a plurality of the budget items, a time frame in which the budget items are expected to be incurred or paid; and
(c) automatically calculating via a processor appropriate invoice payments for the deliverables for the respective entities that have been contracted to provide the deliverables at a specific time frame, wherein the calculation of the appropriate invoice payments is performed without entering into the program or otherwise using invoices from any of the entities, and is based on:
  (i) the equations and business rules in the program, and
  (ii) the items entered into the program in step (b)(i)-(iii).

2. The method of claim 1 further comprising:
(d) comparing invoices using a comparison engine received from the entities at a specific time frame with the appropriate invoice payments and identifying any invoices that may not be appropriate.

3. The method of claim 1 wherein items (b)(i)-(iii) are obtained from contracts entered into by the entities contracted to provide the deliverables.

4. The method of claim 1 wherein a plurality of the equations relate to revenue/cost relationships and the timing thereof.

5. The method of claim 1 wherein a plurality of the equations relate to cash inflows and outflows and the timing thereof.

6. The method of claim 1 wherein the budget items and amounts include units of the deliverables.

7. The method of claim 1 wherein the clinical trial study has a plurality of phases, and a plurality of the business rules relate to the trial study phases.

8. A method of automatically generating an accounting of expenses to record for booking of expenses for budget items during a time frame of a clinical trial study, the clinical trial study having a total budget amount and a total amount of deliverables, the method comprising:
(a) providing a software application program having equations and business rules that together define (i) a process associated with the clinical trial study, (ii) a timeline associated with the clinical trial study, and (iii) deliverables associated with the clinical trial study;
(b) entering into the program:
  (i) entities that have been contracted to provide the deliverables to the clinical trial study,
  (ii) budget items and amounts related to the deliverables for the respective entities that have been contracted to provide the deliverables, and
  (iii) for a plurality of the budget items, a time frame in which the budget items are expected to be incurred or paid;
(c) automatically inputting patient status data and patient diagnostic data obtained from the entities that have been contracted to provide the deliverables to the clinical trial study into a processor; and
(d) automatically generating via the processor the accounting of expenses to record for booking of expenses for budget items during the time frame of the clinical trial study, wherein the accounting of expensese is generated without entering into the program or otherwise using invoices from any of the entities, and is based on:
  (i) the equations and business rules in the program,
  (ii) the items entered into the program in step (b)(i)-(iii), and
  (iii) the inputted patient status data and patient diagnostic data in step (c).

9. The method of claim 8 wherein the accounting of expenses is based on a percentage of the deliverables completed.

10. The method of claim 8 wherein the accounting of expenses provides a percentage of the deliverables that are completed.

11. The method of claim 8 wherein the accounting of expenses provides expenses to record for accounting purposes under generally accepted accounting principles.

12. A method of automatically generating a projection of cash flow needs for a clinical trial study, the clinical trial study having a total budget amount and a total amount of deliverables, the method comprising:
(a) providing a software application program having equations and business rules that together define (i) a process associated with the clinical trial study, (ii) a timeline associated with the clinical trial study, and (iii) deliverables associated with the clinical trial study;
(b) entering into the program:
  (i) entities that have been contracted to provide the deliverables to the clinical trial study,
  (ii) budget items and amounts related to the deliverables for the respective entities that have been contracted to provide the deliverables,
  (iii) for a plurality of the budget items, a time frame in which the budget item is expected to be incurred or paid; and
(c) automatically generating via a processor the projection of cash flow needs of the clinical trial study, wherein the projection of the cash flow needs is performed without entering into the program or otherwise using invoices from any of the entities, and is based on:
  (i) the equations and business rules in the program, and
  (ii) the items entered into the program in step (b)(i)-(iii).

* * * * *